US012737690B2

(12) United States Patent
Lekivetz et al.

(10) Patent No.: US 12,737,690 B2
(45) Date of Patent: Sep. 15, 2026

(54) GUIDED TESTING REGIME GENERATION AND SELECTION

(71) Applicant: JMP Statistical Discovery LLC, Cary, NC (US)

(72) Inventors: Ryan Adam Lekivetz, Cary, NC (US); Joseph Albert Morgan, Raleigh, NC (US); Jacob Davis Rhyne, Dallas, NC (US)

(73) Assignee: JMP Statistical Discovery LLC, Cary, NC (US)

( * ) Notice: Subject to any disclaimer, the term of this patent is extended or adjusted under 35 U.S.C. 154(b) by 0 days.

(21) Appl. No.: 19/323,063

(22) Filed: Sep. 9, 2025

(65) Prior Publication Data

US 2026/0236842 A1 Aug. 13, 2026

Related U.S. Application Data

(60) Provisional application No. 63/755,845, filed on Feb. 7, 2025, provisional application No. 63/768,469, filed on Mar. 7, 2025.

(51) Int. Cl.
*G06N 20/00* (2019.01)
*G06F 3/0483* (2013.01)
(Continued)

(52) U.S. Cl.
CPC .......... *G06N 20/00* (2019.01); *G06F 3/0483* (2013.01); *G06F 11/3668* (2013.01);
(Continued)

(58) Field of Classification Search
CPC ..... G06F 3/0483; G16H 15/00; G10L 15/063; H04L 61/103; G06N 20/20
See application file for complete search history.

(56) References Cited

U.S. PATENT DOCUMENTS 5,559,728 A 9/1996 Kowalski
6,977,269 B1 12/2005 Saunders
(Continued)

OTHER PUBLICATIONS

Vilar et al, "Prompting PaLM for Translation:Assessing Strategies and Performance", Jul. 2023 , 21 pgs <>.*
(Continued)

*Primary Examiner* — Tuan A Vu
(74) *Attorney, Agent, or Firm* — KDW FIRM PLLC

(57) ABSTRACT

An apparatus includes a processor to: present a prompt to select a first pathway to traverse from among a set including a test-focused pathway of initial test-related parameter prompts followed by subsequent prompts for model-related or term-related parameters, a model-focused pathway of initial model-related parameter prompts followed by subsequent prompts for test-related or term-related parameters, and a term-focused pathway of initial term-related parameter prompts followed by subsequent prompts for test-related or model-related parameters; traverse the first pathway by presenting the initial prompts followed by the subsequent prompts of the first pathway, and receiving initial or subsequent parameter value(s); present a prompt to select a second pathway, different from the first pathway, to traverse from among the set; and traverse the second pathway by presenting the initial prompts followed by the subsequent prompts of the second pathway, and receiving initial or subsequent parameter value(s).

30 Claims, 73 Drawing Sheets

(51) Int. Cl.

| | |
|---|---|
| ***G06F 11/3668*** | (2025.01) |
| *G10L 15/06* | (2013.01) |
| *G16H 15/00* | (2018.01) |
| *H04L 61/103* | (2022.01) |

(52) U.S. Cl.
CPC ............ *G10L 15/063* (2013.01); *G16H 15/00* (2018.01); *H04L 61/103* (2013.01)

(56) References Cited

U.S. PATENT DOCUMENTS

| | | | | |
|---|---|---|---|---|
| 7,451,122 | B2 | 11/2008 | Dietrich | |
| 8,065,132 | B2 | 11/2011 | Chen | |
| 8,306,788 | B2 | 11/2012 | Chen | |
| 8,866,818 | B2 | 10/2014 | Rubin | |
| 10,296,680 | B2 | 5/2019 | Morgan | |
| 10,318,674 | B2 | 6/2019 | Morgan | |
| 10,386,271 | B1 | 8/2019 | King | |
| 10,698,806 | B1 | 6/2020 | Scholz | |
| 10,803,214 | B1 | 10/2020 | Jones | |
| 10,902,162 | B2 | 1/2021 | Morgan | |
| 10,943,407 | B1 | 3/2021 | Morgan | |
| 11,010,285 | B2 | 5/2021 | Hicks | |
| 11,106,567 | B2 | 8/2021 | Hicks | |
| 11,663,374 | B2 | 5/2023 | Lekivetz | |
| 11,699,000 | B2 | 7/2023 | Lekivetz | |
| 2004/0015793 | A1 | 1/2004 | Saxena | |
| 2004/0105495 | A1 | 6/2004 | Lee | |
| 2007/0078553 | A1 | 4/2007 | Miwa | |
| 2007/0239633 | A1 | 10/2007 | Dietrich | |
| 2007/0271352 | A1 | 11/2007 | Khopkar | |
| 2008/0168092 | A1 | 7/2008 | Boggs | |
| 2008/0270333 | A1 | 10/2008 | Jhala | |
| 2009/0083680 | A1 | 3/2009 | McConaghy | |
| 2009/0125270 | A1 | 5/2009 | O'Shea | |
| 2009/0313308 | A1 | 12/2009 | Green | |
| 2011/0178789 | A1 | 7/2011 | Miranda | |
| 2011/0224946 | A1 | 9/2011 | Brayman | |
| 2012/0059641 | A1 | 3/2012 | Castellini | |
| 2012/0079379 | A1 | 3/2012 | Hathaway | |
| 2013/0332132 | A1 | 12/2013 | Mongalvy | |
| 2015/0081596 | A1 | 3/2015 | Maaseidvaag | |
| 2016/0063423 | A1 | 3/2016 | Rao | |
| 2016/0124839 | A1 | 5/2016 | Mordo | |
| 2018/0060469 | A1 | 3/2018 | Morgan | |
| 2018/0137415 | A1 | 5/2018 | Steinberg | |
| 2019/0346297 | A1 | 11/2019 | Lekivetz | |
| 2023/0043370 | A1* | 2/2023 | Ortiz | G06F 3/0483 |
| 2024/0038226 | A1* | 2/2024 | Nouri | G10L 15/063 |
| 2024/0121210 | A1* | 4/2024 | Guedes | H04L 61/103 |
| 2025/0356978 | A1* | 11/2025 | Withrow | G16H 15/00 |
| 2026/0087418 | A1* | 3/2026 | Liersch | G06N 20/20 |

OTHER PUBLICATIONS

Proust, Design of Experiments Guide, 2012, SAS, pp. 1-346 (Year: 2012).

Montevechi et al., Applicaiton of Design of Experimentation on the Simulation of a Process in an Automotive Industry, 2007, IEEE, pp. 1601-1609 (Year: 2007).

Anderson-Cook, et al., "Response surface design evaluation and comparison", Journal of Statistical Planning and Inference, Apr. 12, 2008, 14 pages.

Jones, Bradley, "Discussion of Response surface design evaluation and comparison", Journal of Statistical Planning and Inference, 2009, 3 pages.

Parker, Peter A., "Discussion of Response surface design evaluation and comparison", Journal of Statistical Planning and Inference, 2009, 3 pages.

Khuri, Andre I., "Discussion of Response surface design evaluation and comparison", Journal of Statistical Planning and Inference, 2009, 4 pages.

Borkowski, John J., "Discussion of Response surface design evaluation and comparison", Journal of Statistical Planning and Inference, 2009, 3 pages.

Piepel, Greg F., "Discussion of Response surface design evaluation and comparison", Journal of Statistical Planning and Inference, 2009, 4 pages.

Goos, Peter, "Discussion of Response surface design evaluation and comparison", Journal of Statistical Planning and Inference, 2009, 3 pages.

Lucas, James M., "Discussion of Response surface design evaluation and comparison", Journal of Statistical Planning and Inference, 2009, 2 pages.

Atkinson, Anthony C., "Discussion of Response swface design evaluation and comparison", Journal of Statistical Planning and Inference, 2009, 7 pages.

Robinson, Timothy J., "Discussion of Response surface design evaluation and comparison", Journal of Statistical Planning and Inference, 2009, 2 pages.

Anderson-Cook et ai., Rejoinder for "Discussion of Response surface design evaluation and comparison", Journal of Statistical Planning and Inference, 2009, 3 pages Journal of Statistical Planning and Inference, 2009, 4 pages.

Custom Design Options, SAS Institute, retrieved from <http://www.jmp.com/support/help/Custom_Design_Options.shtml>, Jun. 28, 2017, 8 pages (author unknown).

Minitab® Real-Time SPC Brochure—Minitab®—retrieved Jul. 27, 2021.

MiniTab Workspace® Brochure—Minitab®—retrieved Apr. 5, 2021.

Design-Expert® Software Brochure—Version 13—Stat-Ease, Inc.—retrieved Jan. 25, 2021.

* cited by examiner

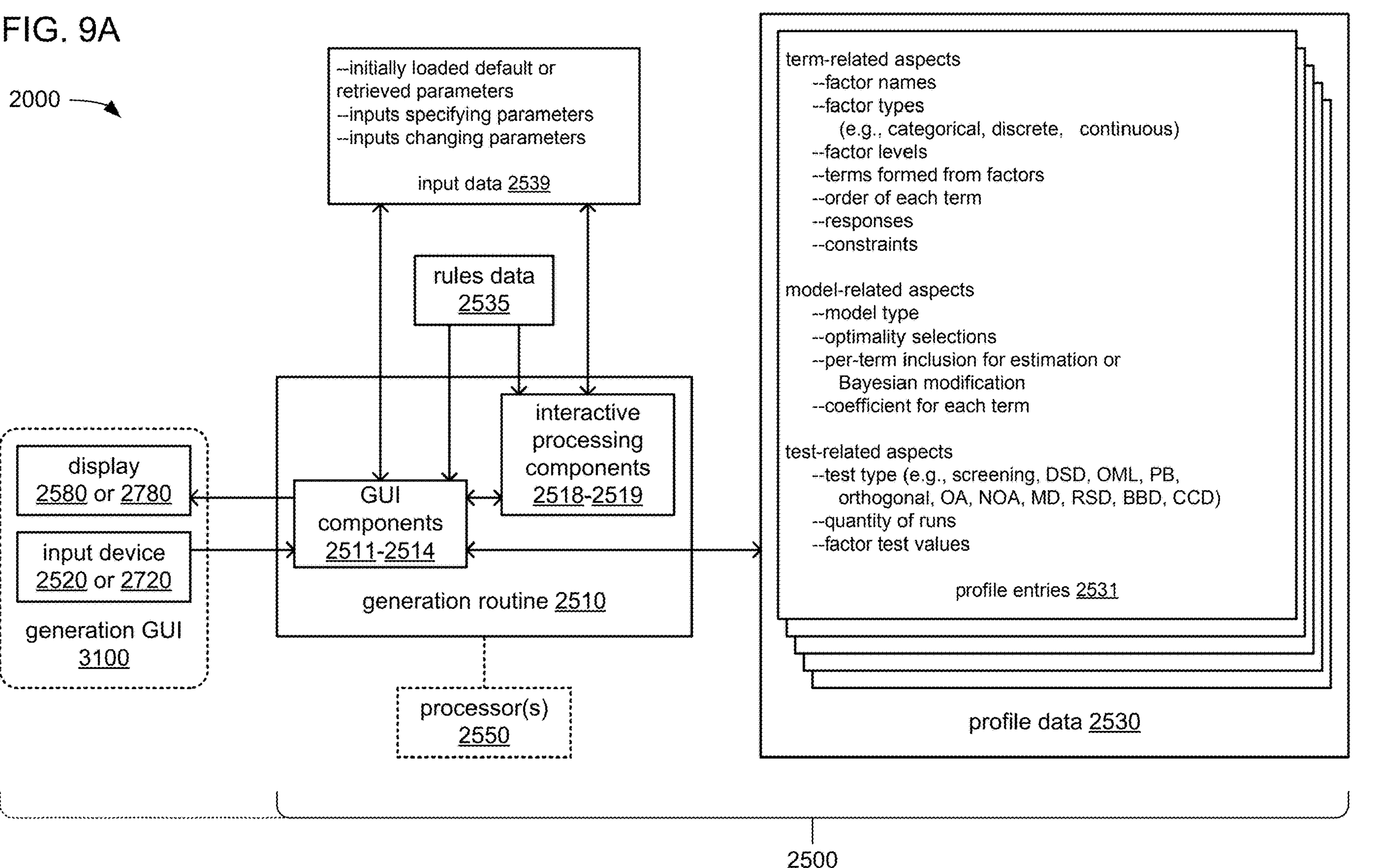
FIG. 9A
2000
--initially loaded default or
retrieved parameters
--inputs specifying parameters
--inputs changing parameters
input data 2539
rules data
2535
display
2580 or 2780
input device
2520 or 2720
generation GUI
3100
GUI
components
2511-2514
interactive
processing
components
2518-2519
generation routine 2510
processor(s)
2550
term-related aspects
--factor names
--factor types
(e.g., categorical, discrete, continuous)
--factor levels
--terms formed from factors
--order of each term
--responses
--constraints
model-related aspects
--model type
--optimality selections
--per-term inclusion for estimation or
Bayesian modification
--coefficient for each term
test-related aspects
--test type (e.g., screening, DSD, OML, PB,
orthogonal, OA, NOA, MD, RSD, BBD, CCD)
--quantity of runs
--factor test values
profile entries 2531
profile data 2530
2500

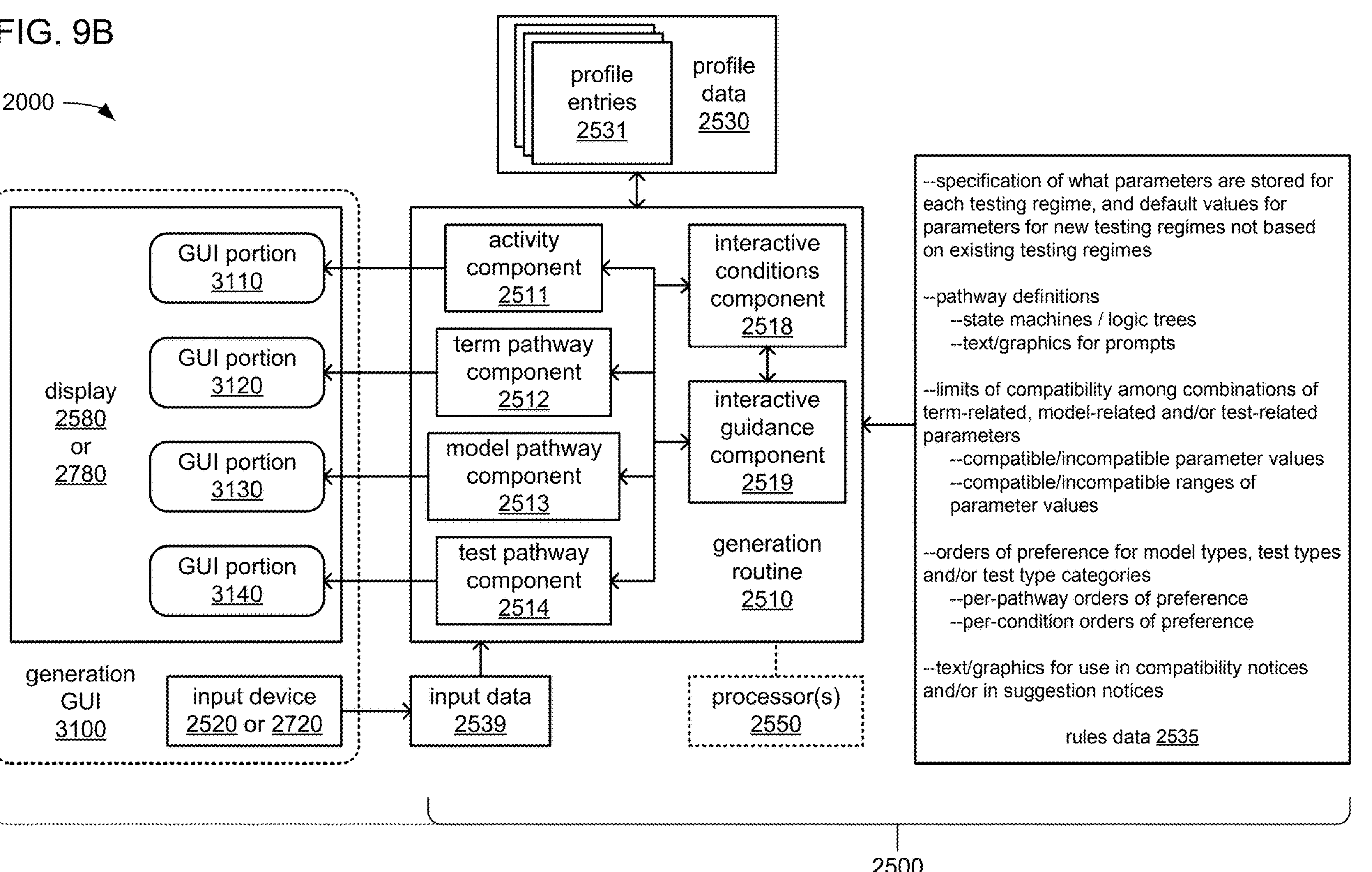
FIG. 9B
2000
profile entries 2531
profile data 2530
GUI portion 3110
GUI portion 3120
GUI portion 3130
GUI portion 3140
display 2580 or 2780
generation GUI 3100
input device 2520 or 2720
activity component 2511
term pathway component 2512
model pathway component 2513
test pathway component 2514
interactive conditions component 2518
interactive guidance component 2519
generation routine 2510
input data 2539
processor(s) 2550
--specification of what parameters are stored for each testing regime, and default values for parameters for new testing regimes not based on existing testing regimes
--pathway definitions
--state machines / logic trees
--text/graphics for prompts
--limits of compatibility among combinations of term-related, model-related and/or test-related parameters
--compatible/incompatible parameter values
--compatible/incompatible ranges of parameter values
--orders of preference for model types, test types and/or test type categories
--per-pathway orders of preference
--per-condition orders of preference
--text/graphics for use in compatibility notices and/or in suggestion notices
rules data 2535
2500

2000
2580
or
2780
3101
3120, 3130,
3140
3106
3107
<< Back
End
Next >>
processor(s)
2550
GUI
component
2512, 2513
or 2514
interactive
processing
components
2518-2519
generation
routine
2510
input data
2539
2500

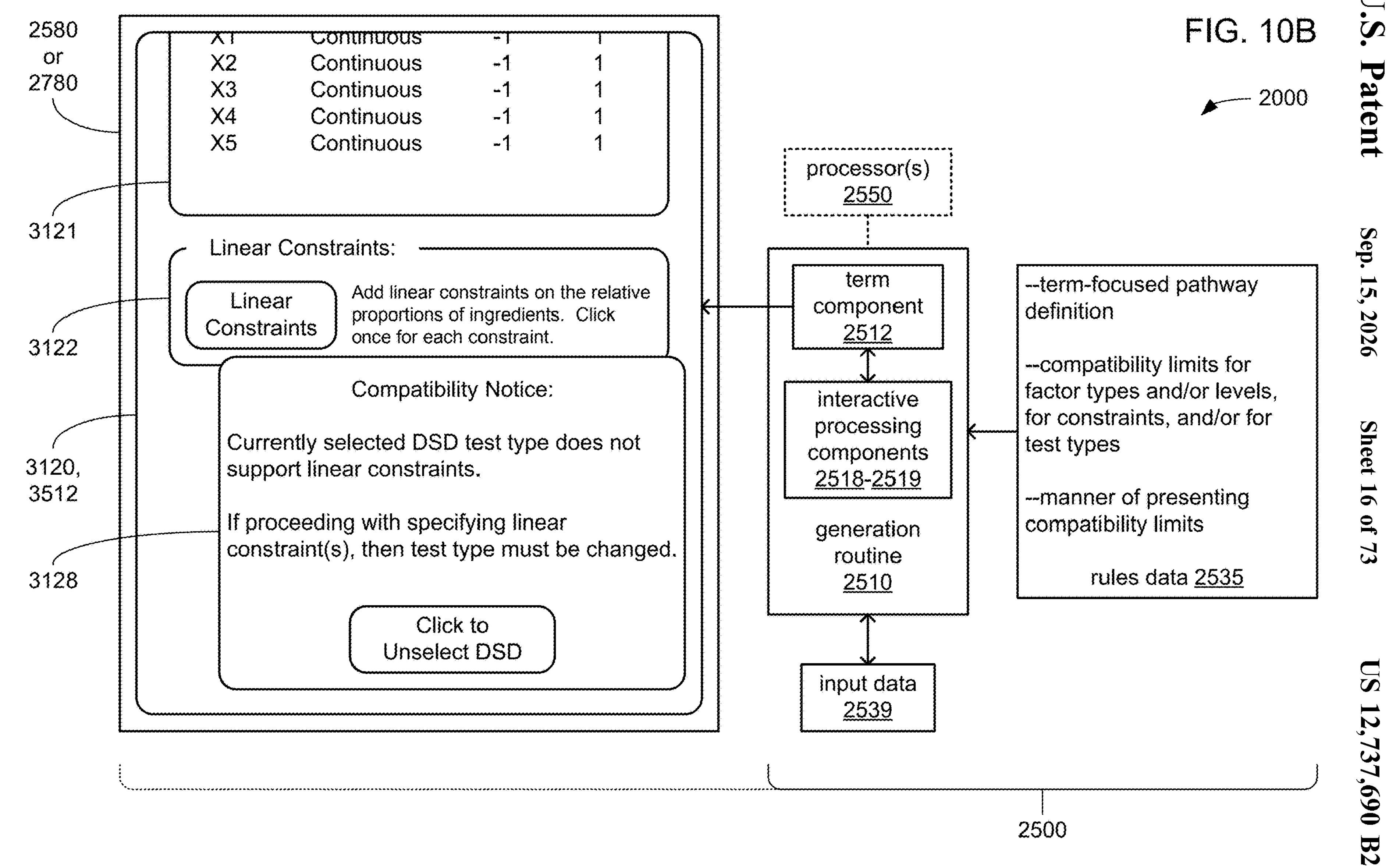
FIG. 10B
2000
2580 or 2780
X1 Continuous -1 1
X2 Continuous -1 1
X3 Continuous -1 1
X4 Continuous -1 1
X5 Continuous -1 1
3121
Linear Constraints:
Linear Constraints
Add linear constraints on the relative proportions of ingredients. Click once for each constraint.
3122
Compatibility Notice:
Currently selected DSD test type does not support linear constraints.
If proceeding with specifying linear constraint(s), then test type must be changed.
Click to Unselect DSD
3120, 3512
3128
processor(s) 2550
term component 2512
interactive processing components 2518-2519
generation routine 2510
input data 2539
--term-focused pathway definition
--compatibility limits for factor types and/or levels, for constraints, and/or for test types
--manner of presenting compatibility limits
rules data 2535
2500

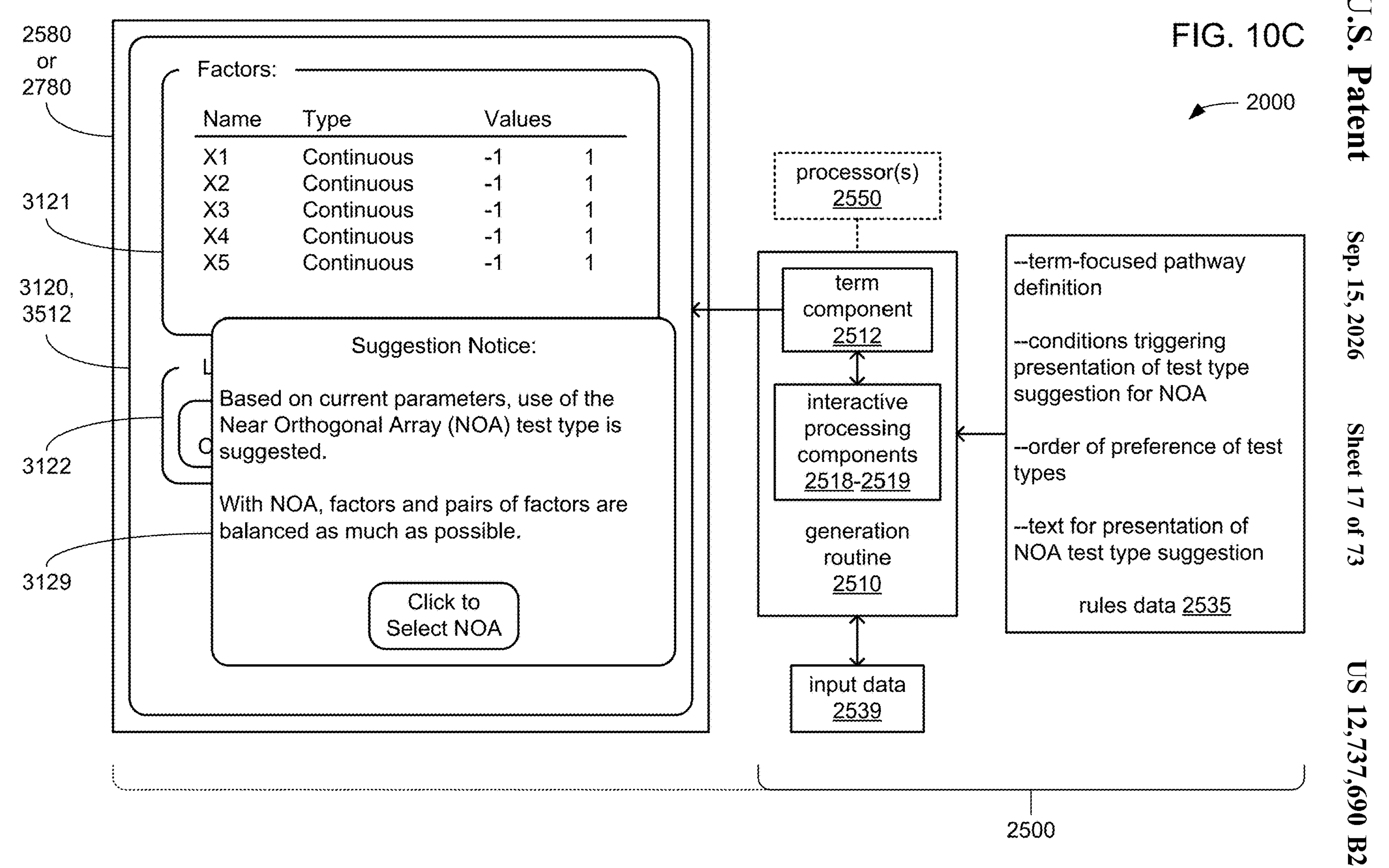
FIG. 10C
2000
2580 or 2780
Factors:
Name
Type
Values
X1
X2
X3
X4
X5
Continuous
Continuous
Continuous
Continuous
Continuous
-1
1
3121
3120, 3512
3122
3129
Suggestion Notice:
Based on current parameters, use of the Near Orthogonal Array (NOA) test type is suggested.
With NOA, factors and pairs of factors are balanced as much as possible.
Click to Select NOA
processor(s) 2550
term component 2512
interactive processing components 2518-2519
generation routine 2510
input data 2539
--term-focused pathway definition
--conditions triggering presentation of test type suggestion for NOA
--order of preference of test types
--text for presentation of NOA test type suggestion
rules data 2535
2500

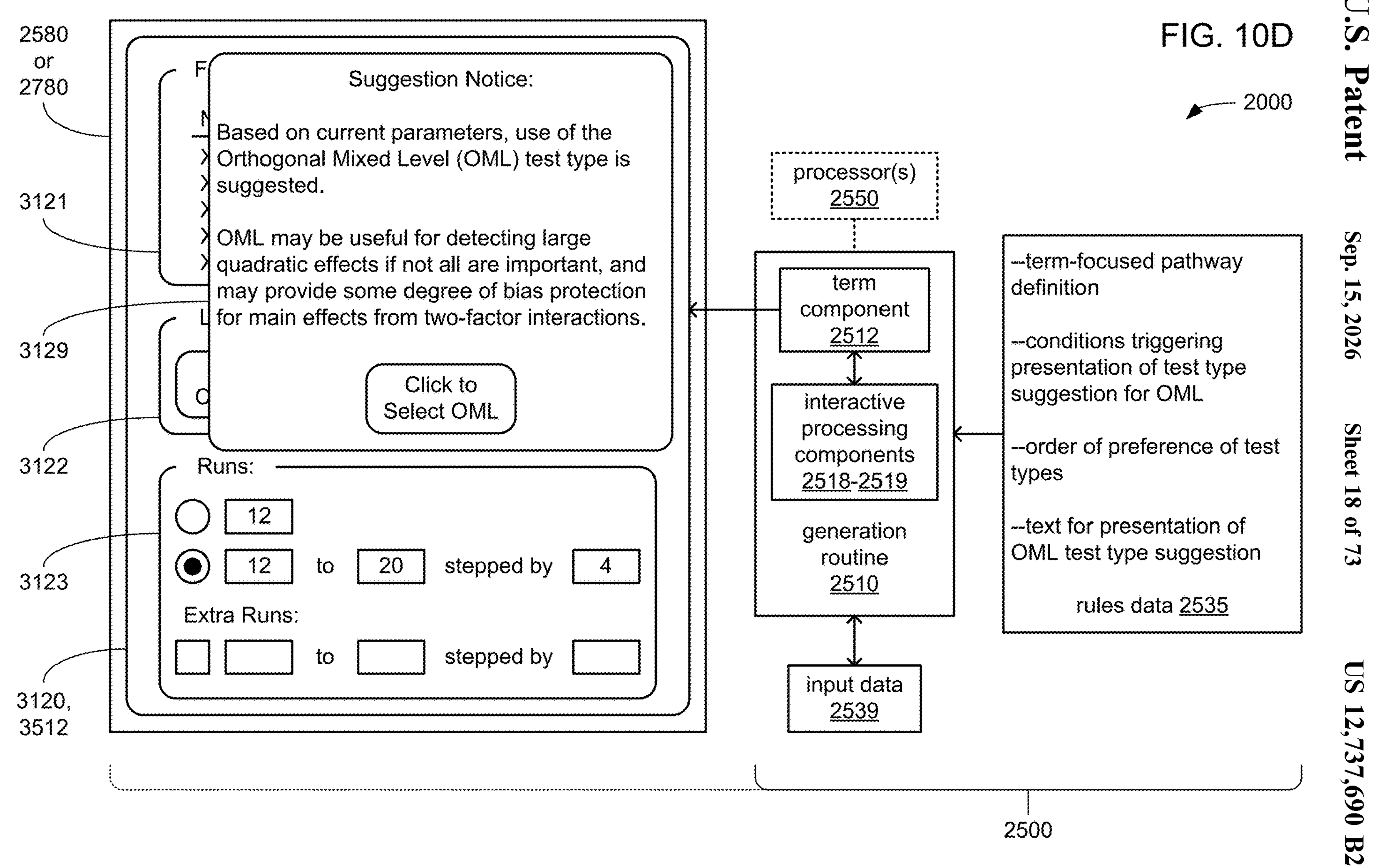
FIG. 10D
2000
2580 or 2780
3121
3129
3122
3123
3120, 3512
Suggestion Notice:
Based on current parameters, use of the Orthogonal Mixed Level (OML) test type is suggested.
OML may be useful for detecting large quadratic effects if not all are important, and may provide some degree of bias protection for main effects from two-factor interactions.
Click to Select OML
Runs:
12
12
to
20
stepped by
4
Extra Runs:
to
stepped by
processor(s) 2550
term component 2512
interactive processing components 2518-2519
generation routine 2510
input data 2539
--term-focused pathway definition
--conditions triggering presentation of test type suggestion for OML
--order of preference of test types
--text for presentation of OML test type suggestion
rules data 2535
2500

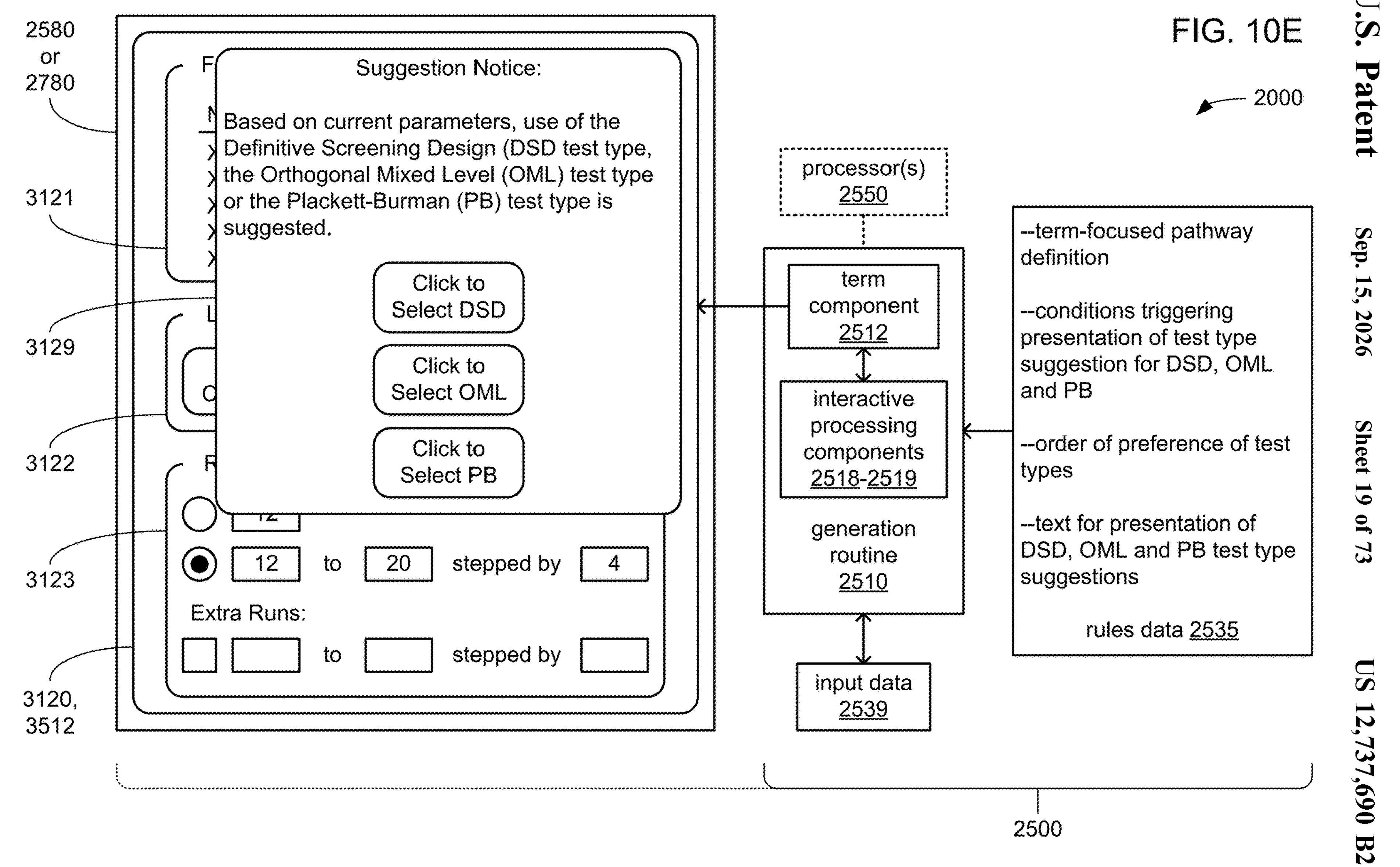
FIG. 10E
2000
2580 or 2780
3121
3129
3122
3123
3120, 3512
Suggestion Notice:
Based on current parameters, use of the Definitive Screening Design (DSD test type, the Orthogonal Mixed Level (OML) test type or the Plackett-Burman (PB) test type is suggested.
Click to Select DSD
Click to Select OML
Click to Select PB
12
to
20
stepped by
4
Extra Runs:
to
stepped by
processor(s) 2550
term component 2512
interactive processing components 2518-2519
generation routine 2510
input data 2539
--term-focused pathway definition
--conditions triggering presentation of test type suggestion for DSD, OML and PB
--order of preference of test types
--text for presentation of DSD, OML and PB test type suggestions
rules data 2535
2500

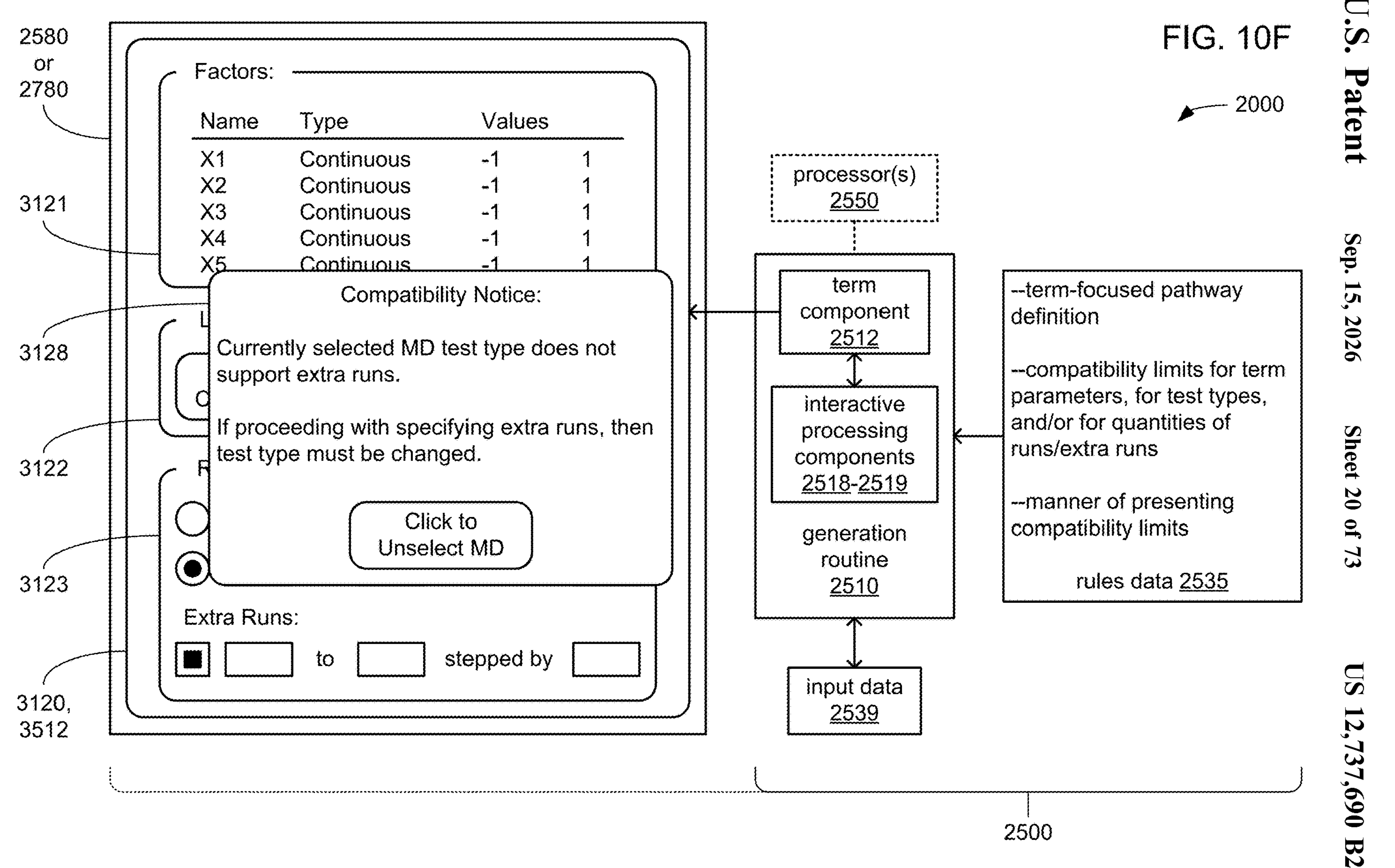
FIG. 10F
2000
2580 or 2780
Factors:
Name Type Values
X1 Continuous -1 1
X2 Continuous -1 1
X3 Continuous -1 1
X4 Continuous -1 1
X5 Continuous -1 1
Compatibility Notice:
Currently selected MD test type does not support extra runs.
If proceeding with specifying extra runs, then test type must be changed.
Click to Unselect MD
Extra Runs:
to
stepped by
3121
3128
3122
3123
3120, 3512
processor(s) 2550
term component 2512
interactive processing components 2518-2519
generation routine 2510
input data 2539
--term-focused pathway definition
--compatibility limits for term parameters, for test types, and/or for quantities of runs/extra runs
--manner of presenting compatibility limits
rules data 2535
2500

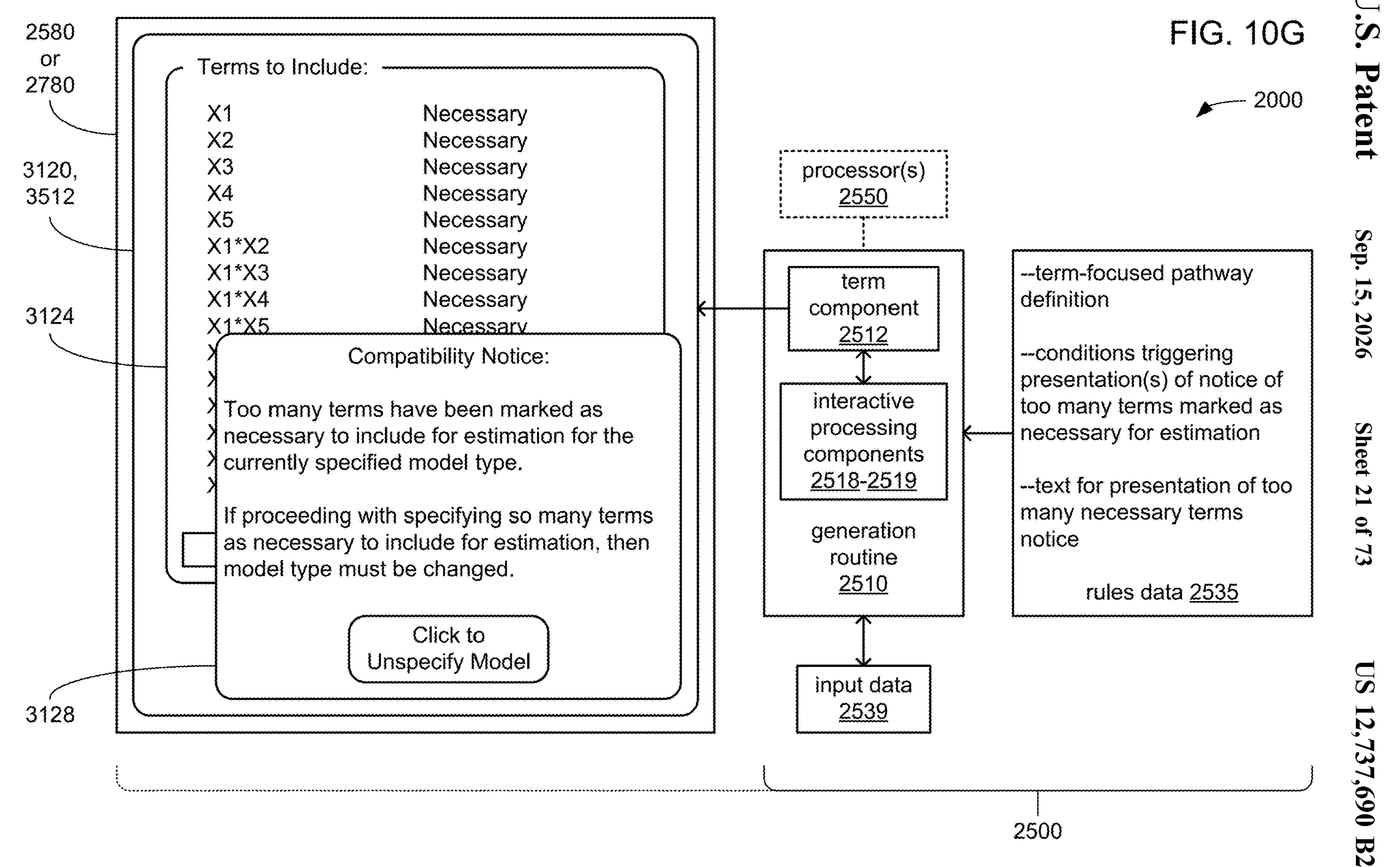

FIG. 10G
2000
2580 or 2780
3120, 3512
3124
3128
Terms to Include:
X1 Necessary
X2 Necessary
X3 Necessary
X4 Necessary
X5 Necessary
X1*X2 Necessary
X1*X3 Necessary
X1*X4 Necessary
X1*X5 Necessary
Compatibility Notice:
Too many terms have been marked as necessary to include for estimation for the currently specified model type.
If proceeding with specifying so many terms as necessary to include for estimation, then model type must be changed.
Click to Unspecify Model
processor(s) 2550
term component 2512
interactive processing components 2518-2519
generation routine 2510
input data 2539
--term-focused pathway definition
--conditions triggering presentation(s) of notice of too many terms marked as necessary for estimation
--text for presentation of too many necessary terms notice
rules data 2535
2500

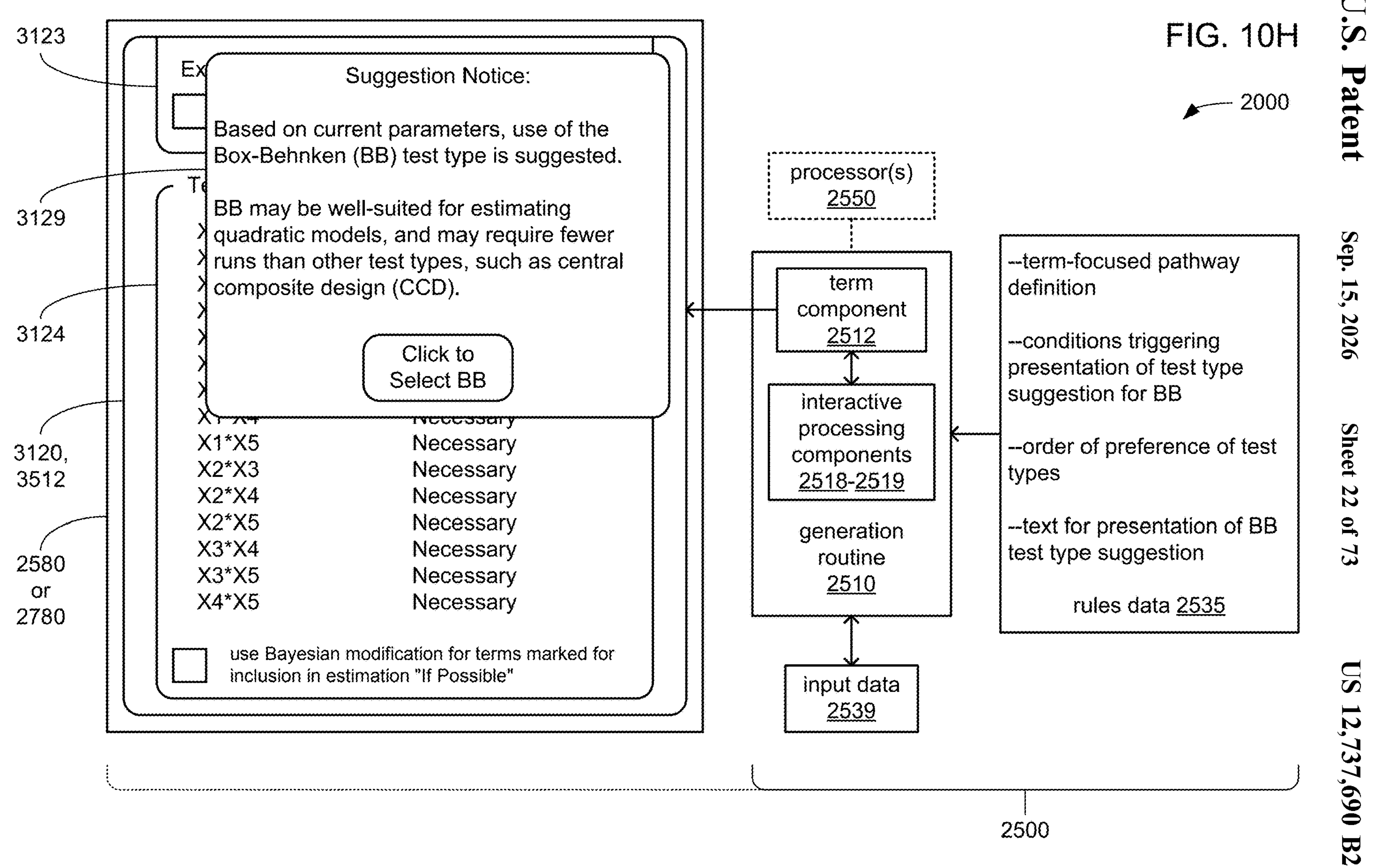

FIG. 10H
2000
3123
Ex
Suggestion Notice:
Based on current parameters, use of the Box-Behnken (BB) test type is suggested.
BB may be well-suited for estimating quadratic models, and may require fewer runs than other test types, such as central composite design (CCD).
Click to Select BB
3129
3124
3120, 3512
2580 or 2780
X1*X5 Necessary
X2*X3 Necessary
X2*X4 Necessary
X2*X5 Necessary
X3*X4 Necessary
X3*X5 Necessary
X4*X5 Necessary
use Bayesian modification for terms marked for inclusion in estimation "If Possible"
processor(s) 2550
term component 2512
interactive processing components 2518-2519
generation routine 2510
input data 2539
--term-focused pathway definition
--conditions triggering presentation of test type suggestion for BB
--order of preference of test types
--text for presentation of BB test type suggestion
rules data 2535
2500

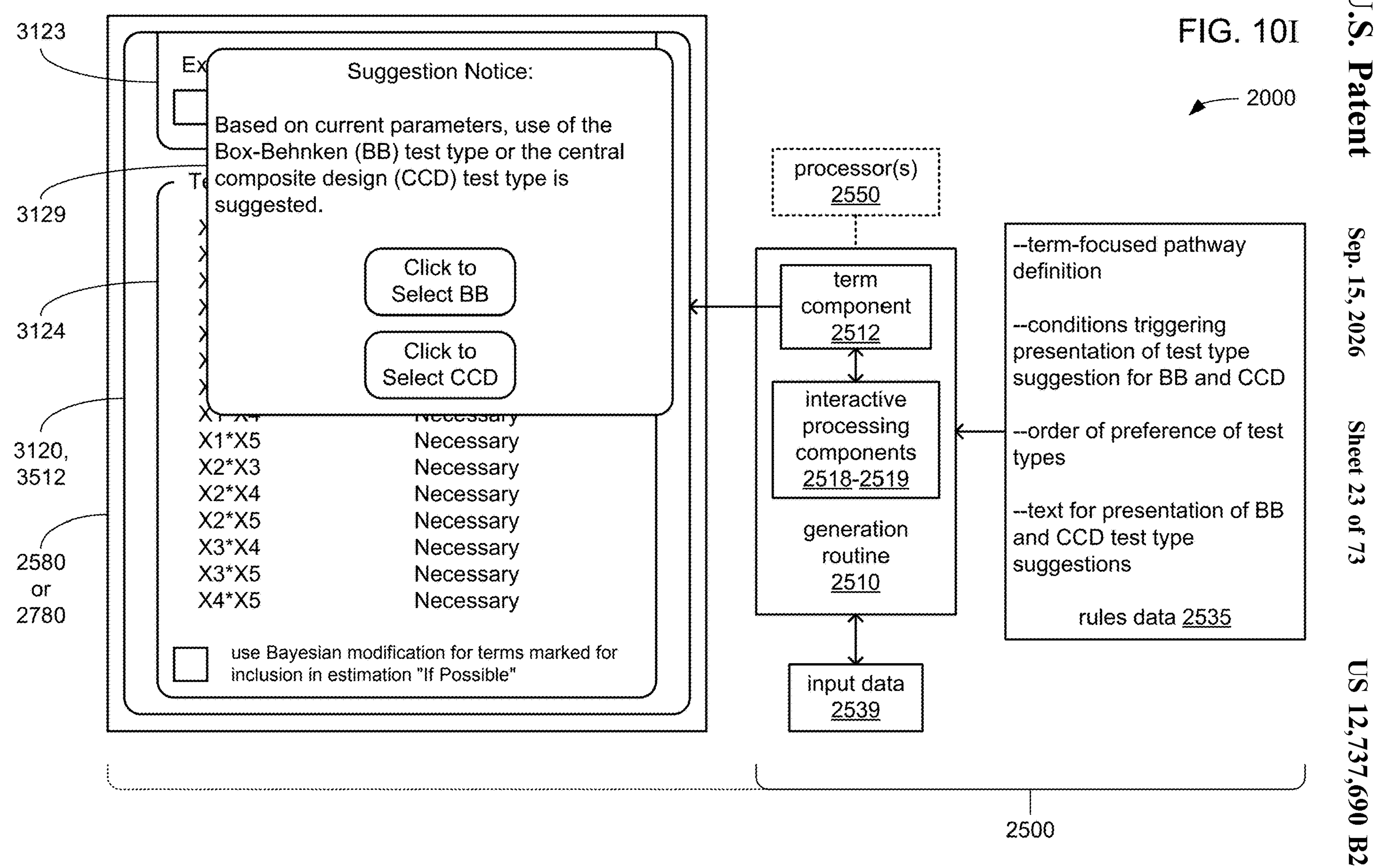

FIG. 10I
2000
3123
Suggestion Notice:
Based on current parameters, use of the Box-Behnken (BB) test type or the central composite design (CCD) test type is suggested.
Click to Select BB
Click to Select CCD
3129
3124
3120, 3512
2580 or 2780
X1*X5 Necessary
X2*X3 Necessary
X2*X4 Necessary
X2*X5 Necessary
X3*X4 Necessary
X3*X5 Necessary
X4*X5 Necessary
use Bayesian modification for terms marked for inclusion in estimation "If Possible"
processor(s) 2550
term component 2512
interactive processing components 2518-2519
generation routine 2510
input data 2539
--term-focused pathway definition
--conditions triggering presentation of test type suggestion for BB and CCD
--order of preference of test types
--text for presentation of BB and CCD test type suggestions
rules data 2535
2500

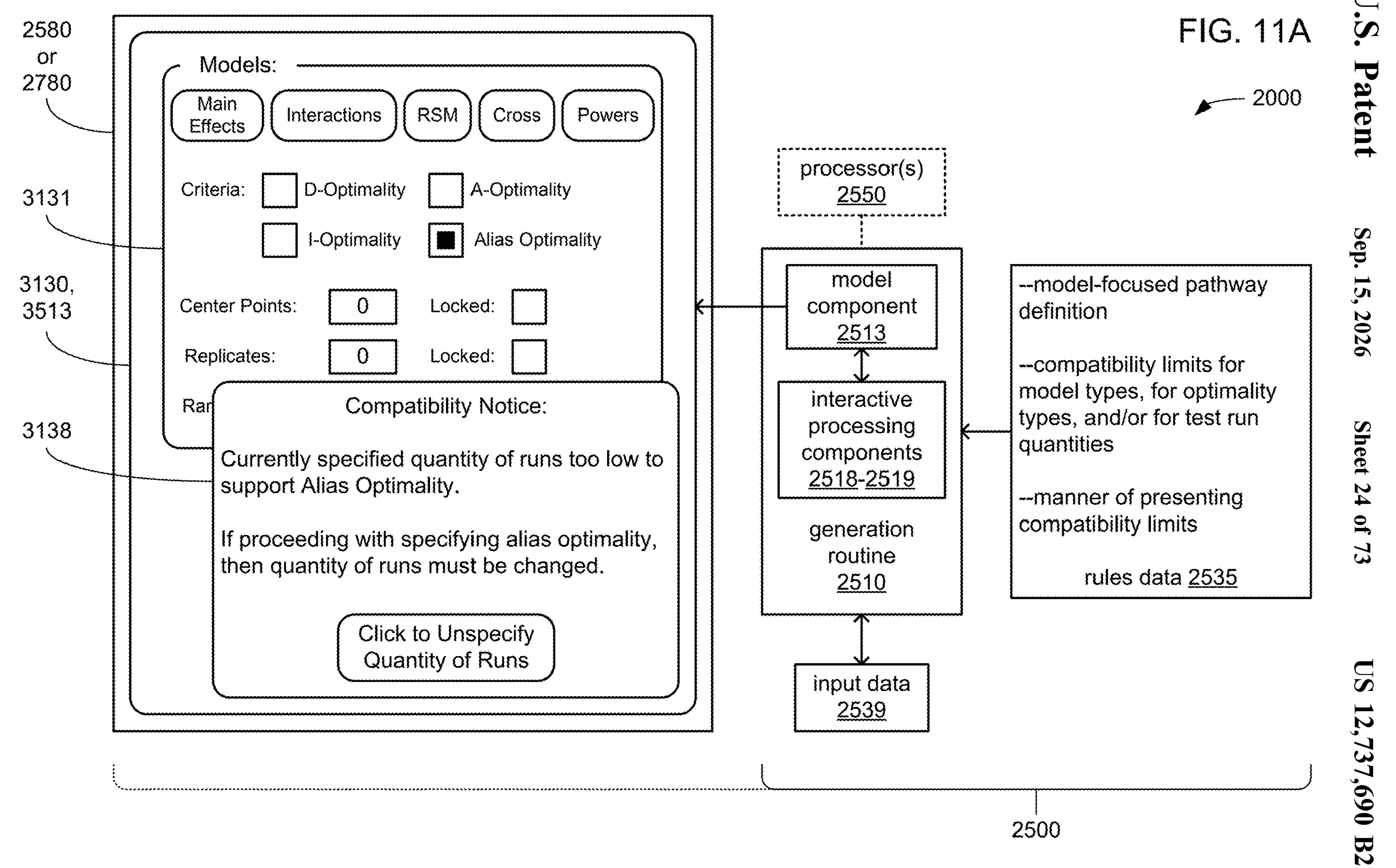
FIG. 11A
2000
2580 or 2780
Models:
Main Effects
Interactions
RSM
Cross
Powers
Criteria:
D-Optimality
A-Optimality
I-Optimality
Alias Optimality
3131
3130, 3513
Center Points:
0
Locked:
Replicates:
0
Locked:
Ra
3138
Compatibility Notice:
Currently specified quantity of runs too low to support Alias Optimality.
If proceeding with specifying alias optimality, then quantity of runs must be changed.
Click to Unspecify Quantity of Runs
processor(s) 2550
model component 2513
interactive processing components 2518-2519
generation routine 2510
input data 2539
--model-focused pathway definition
--compatibility limits for model types, for optimality types, and/or for test run quantities
--manner of presenting compatibility limits
rules data 2535
2500

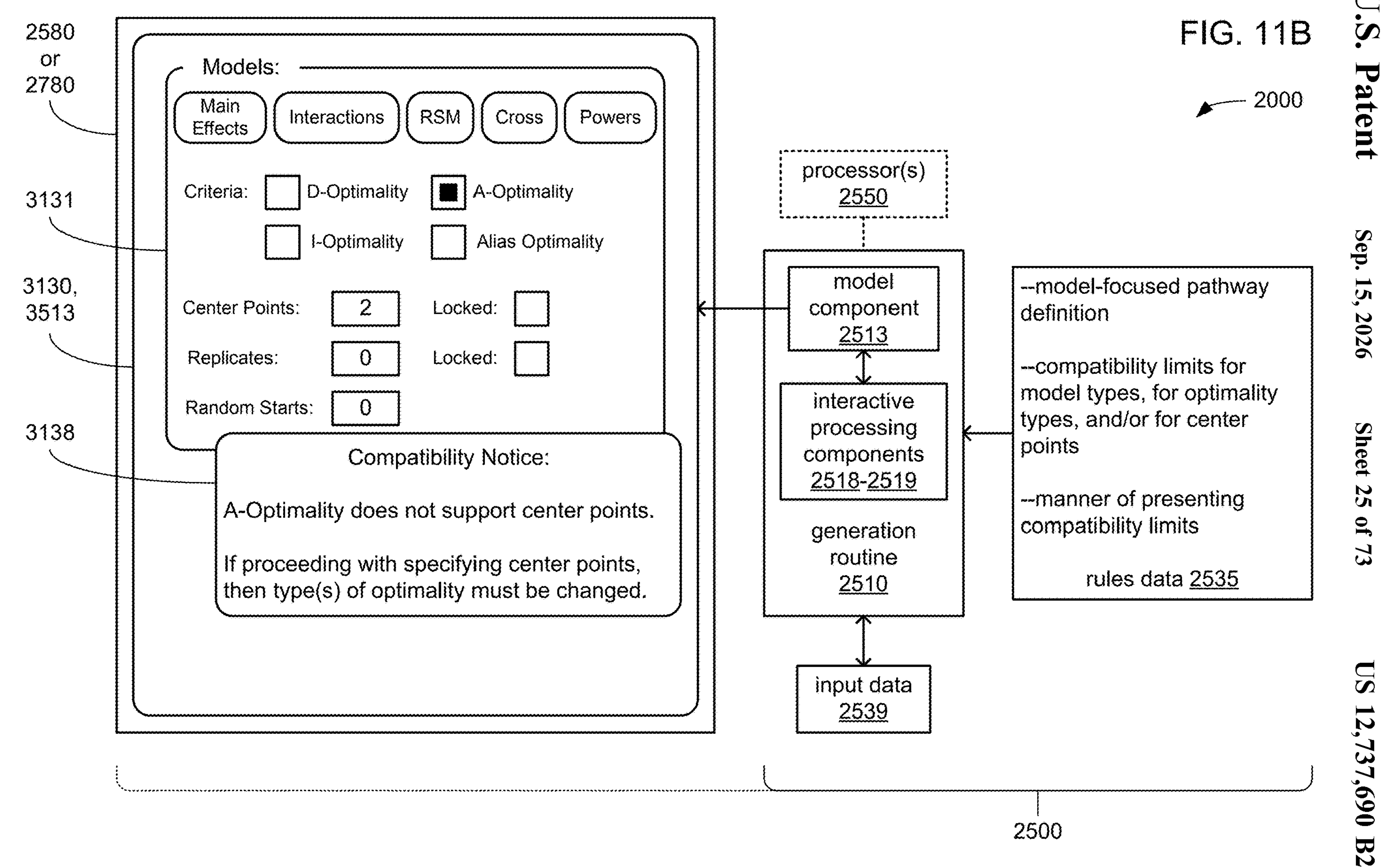
FIG. 11B
2000
2580 or 2780
3131
3130, 3513
3138
Models:
Main Effects
Interactions
RSM
Cross
Powers
Criteria:
D-Optimality
A-Optimality
I-Optimality
Alias Optimality
Center Points:
2
Locked:
Replicates:
0
Locked:
Random Starts:
0
Compatibility Notice:
A-Optimality does not support center points.
If proceeding with specifying center points, then type(s) of optimality must be changed.
processor(s) 2550
model component 2513
interactive processing components 2518-2519
generation routine 2510
input data 2539
--model-focused pathway definition
--compatibility limits for model types, for optimality types, and/or for center points
--manner of presenting compatibility limits
rules data 2535
2500

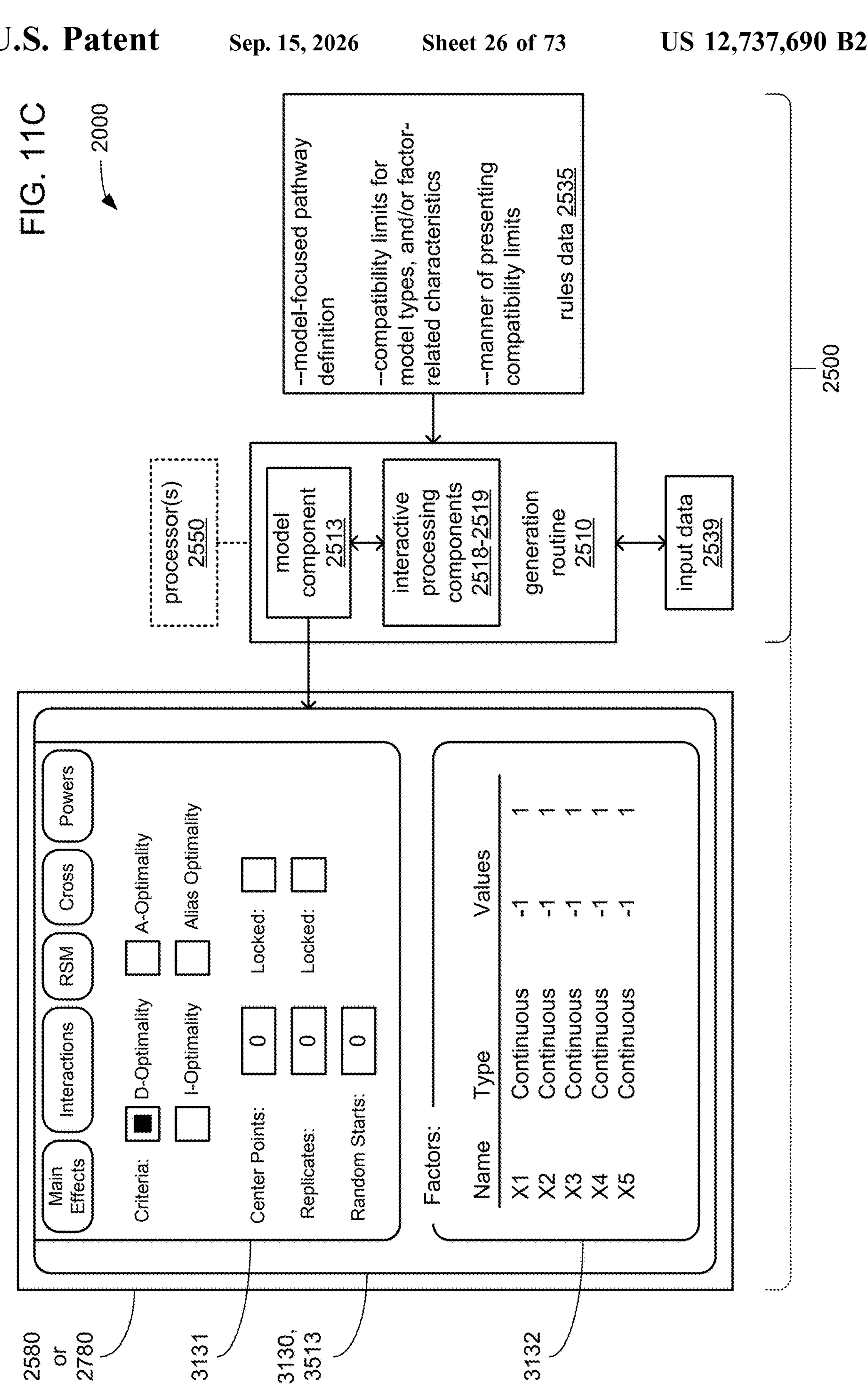
FIG. 11C
2000
--model-focused pathway definition
--compatibility limits for model types, and/or factor-related characteristics
--manner of presenting compatibility limits
rules data 2535
2500
processor(s) 2550
model component 2513
interactive processing components 2518-2519
generation routine 2510
input data 2539
Main Effects
Interactions
RSM
Cross
Powers
Criteria:
D-Optimality
A-Optimality
I-Optimality
Alias Optimality
Center Points:
Replicates:
Random Starts:
0
0
0
Locked:
Locked:
Factors:
Name
Type
Values
X1 Continuous -1 1
X2 Continuous -1 1
X3 Continuous -1 1
X4 Continuous -1 1
X5 Continuous -1 1
2580 or 2780
3131
3130, 3513
3132

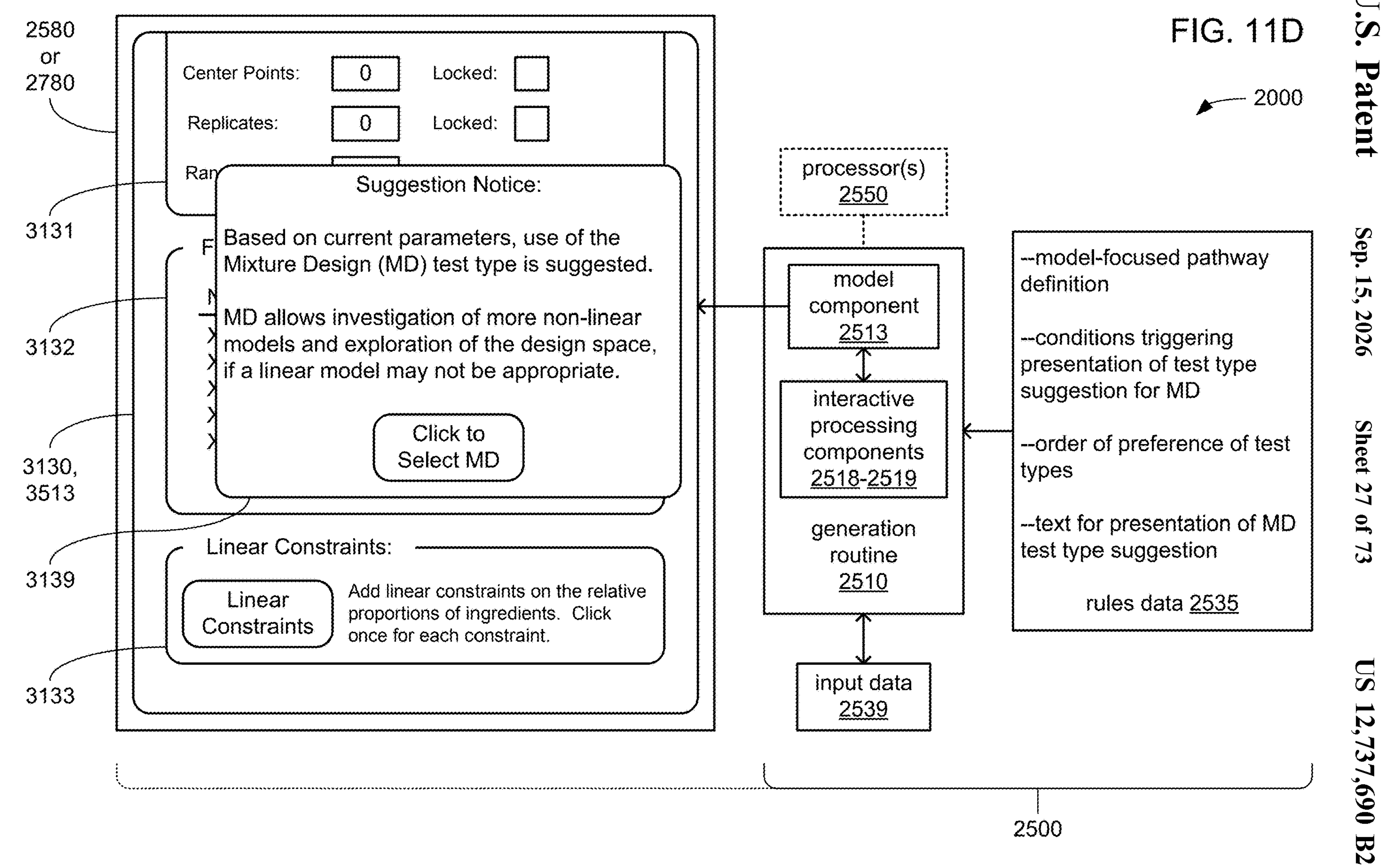
FIG. 11D
2000
2580 or 2780
Center Points:
0
Locked:
Replicates:
0
Locked:
Suggestion Notice:
Based on current parameters, use of the Mixture Design (MD) test type is suggested.
MD allows investigation of more non-linear models and exploration of the design space, if a linear model may not be appropriate.
Click to Select MD
Linear Constraints:
Linear Constraints
Add linear constraints on the relative proportions of ingredients. Click once for each constraint.
3131
3132
3130, 3513
3139
3133
processor(s) 2550
model component 2513
interactive processing components 2518-2519
generation routine 2510
input data 2539
--model-focused pathway definition
--conditions triggering presentation of test type suggestion for MD
--order of preference of test types
--text for presentation of MD test type suggestion
rules data 2535
2500

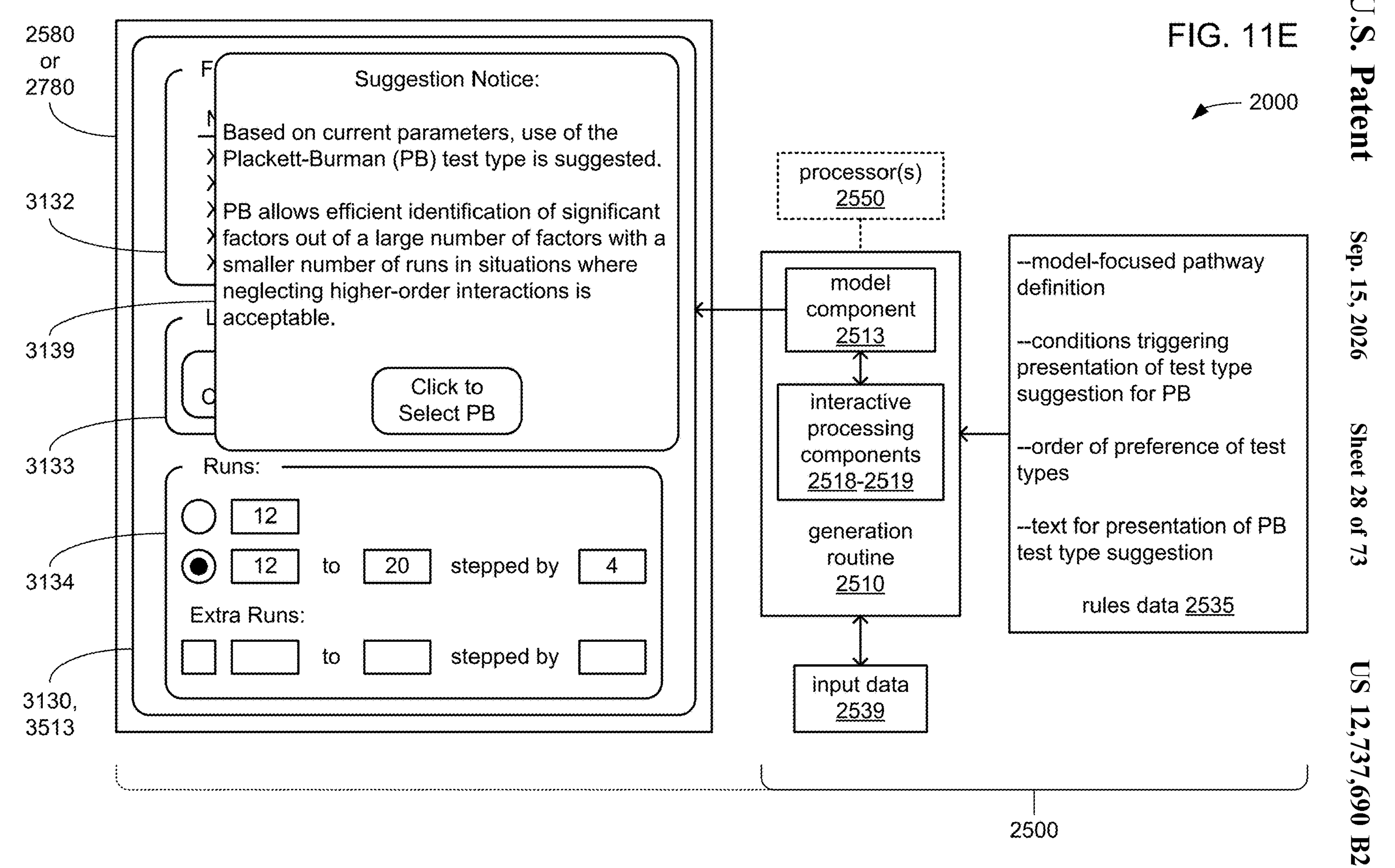
FIG. 11E
2000
Suggestion Notice:
Based on current parameters, use of the Plackett-Burman (PB) test type is suggested.
PB allows efficient identification of significant factors out of a large number of factors with a smaller number of runs in situations where neglecting higher-order interactions is acceptable.
Click to Select PB
Runs:
12
12
to
20
stepped by
4
Extra Runs:
to
stepped by
2580 or 2780
3132
3139
3133
3134
3130, 3513
processor(s) 2550
model component 2513
interactive processing components 2518-2519
generation routine 2510
input data 2539
--model-focused pathway definition
--conditions triggering presentation of test type suggestion for PB
--order of preference of test types
--text for presentation of PB test type suggestion
rules data 2535
2500

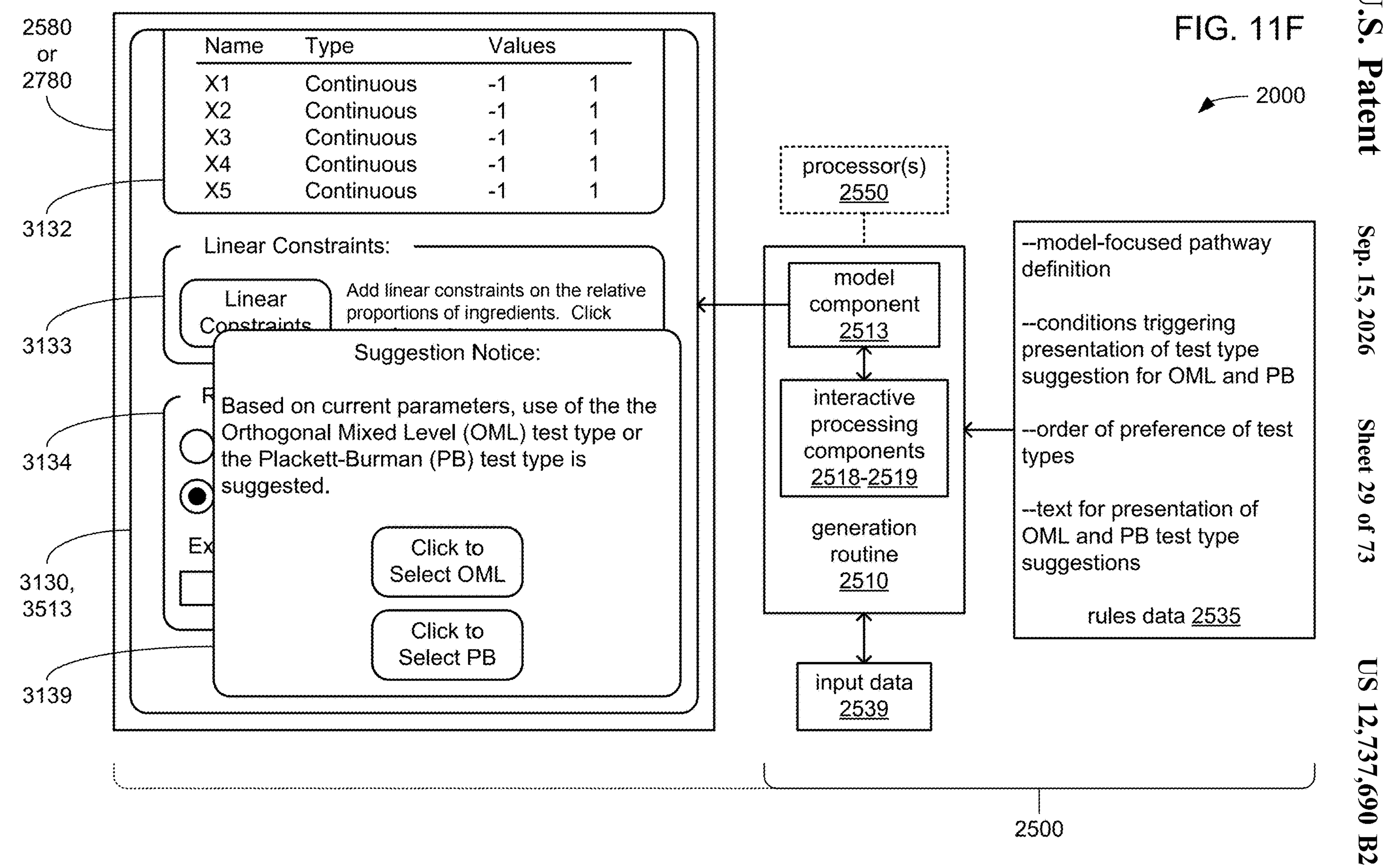
FIG. 11F
2000
2580 or 2780
Name
Type
Values
X1
X2
X3
X4
X5
Continuous
-1
1
3132
Linear Constraints:
Linear Constraints
Add linear constraints on the relative proportions of ingredients. Click
3133
Suggestion Notice:
Based on current parameters, use of the the Orthogonal Mixed Level (OML) test type or the Plackett-Burman (PB) test type is suggested.
Click to Select OML
Click to Select PB
3134
Ex
3130, 3513
3139
processor(s) 2550
model component 2513
interactive processing components 2518-2519
generation routine 2510
input data 2539
--model-focused pathway definition
--conditions triggering presentation of test type suggestion for OML and PB
--order of preference of test types
--text for presentation of OML and PB test type suggestions
rules data 2535
2500

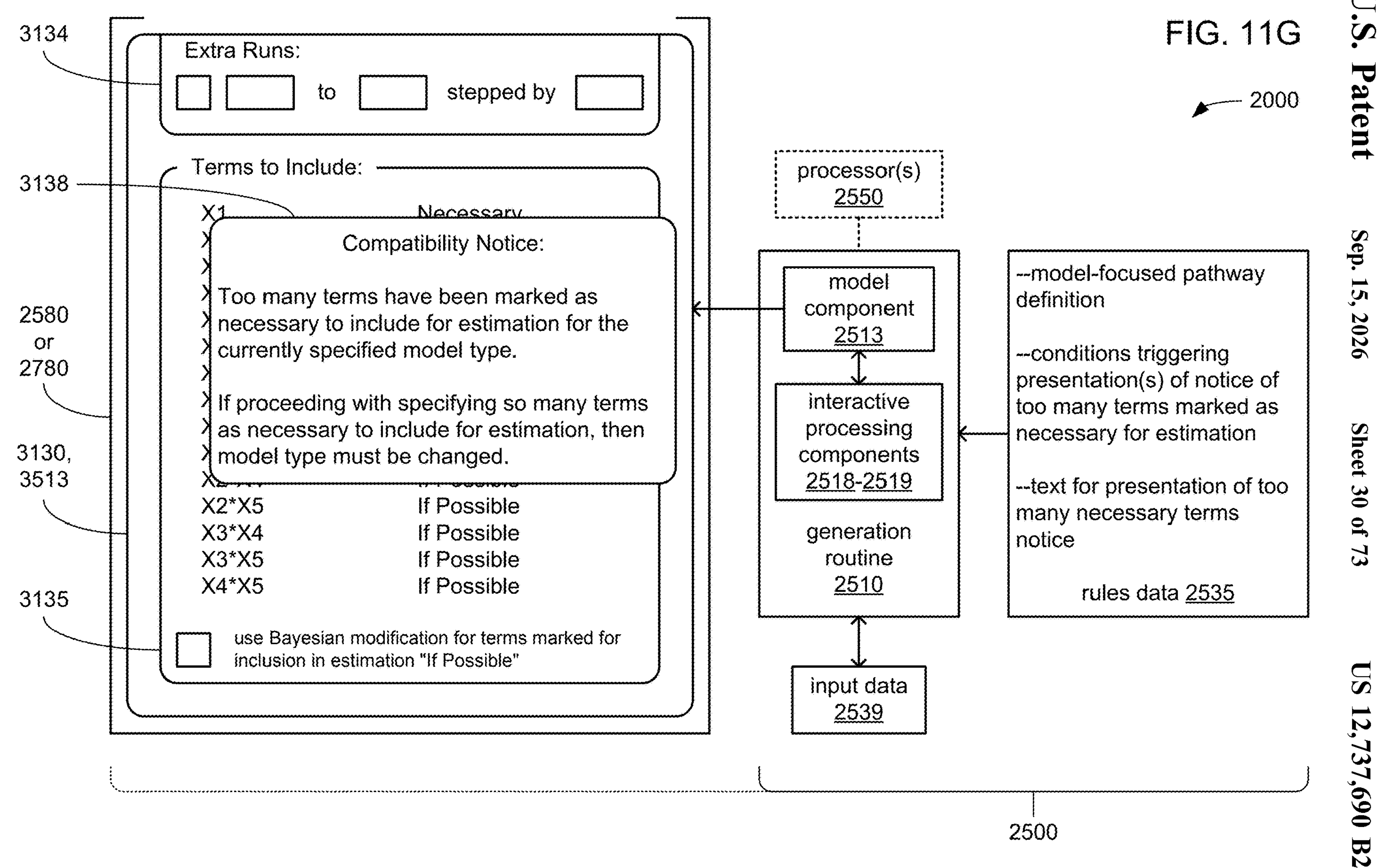
FIG. 11G
2000
3134
Extra Runs:
to
stepped by
3138
Terms to Include:
X1
Necessary
Compatibility Notice:
Too many terms have been marked as necessary to include for estimation for the currently specified model type.
If proceeding with specifying so many terms as necessary to include for estimation, then model type must be changed.
2580 or 2780
3130, 3513
X2*X5
X3*X4
X3*X5
X4*X5
If Possible
If Possible
If Possible
If Possible
3135
use Bayesian modification for terms marked for inclusion in estimation "If Possible"
processor(s) 2550
model component 2513
interactive processing components 2518-2519
generation routine 2510
input data 2539
--model-focused pathway definition
--conditions triggering presentation(s) of notice of too many terms marked as necessary for estimation
--text for presentation of too many necessary terms notice
rules data 2535
2500

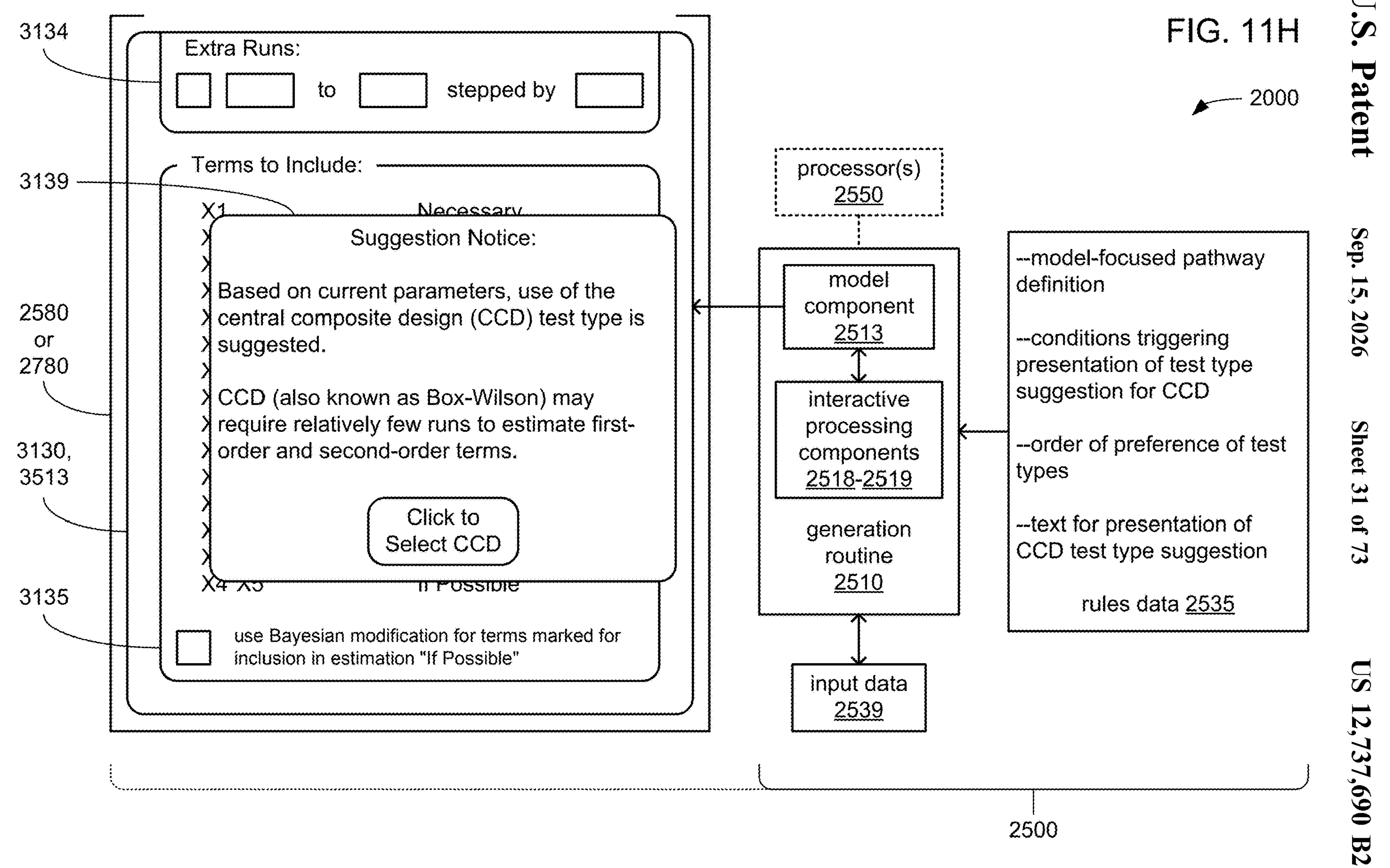
FIG. 11H
2000
3134
Extra Runs:
to
stepped by
3139
Terms to Include:
X1
Necessary
Suggestion Notice:
Based on current parameters, use of the central composite design (CCD) test type is suggested.
CCD (also known as Box-Wilson) may require relatively few runs to estimate first-order and second-order terms.
Click to Select CCD
2580 or 2780
3130, 3513
3135
use Bayesian modification for terms marked for inclusion in estimation "If Possible"
processor(s) 2550
model component 2513
interactive processing components 2518-2519
generation routine 2510
input data 2539
--model-focused pathway definition
--conditions triggering presentation of test type suggestion for CCD
--order of preference of test types
--text for presentation of CCD test type suggestion
rules data 2535
2500

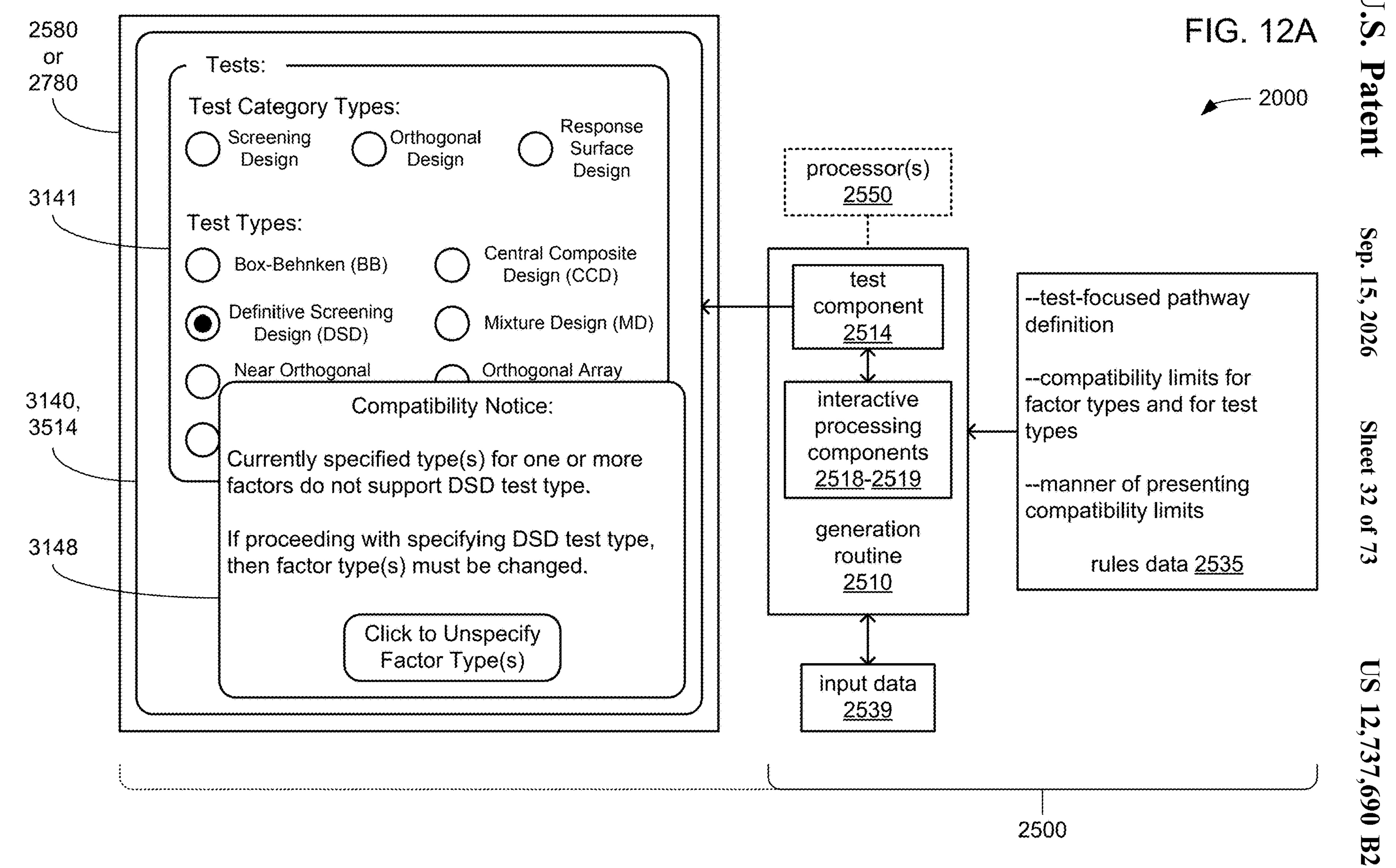
FIG. 12A
2000
--test-focused pathway definition
--compatibility limits for factor types and for test types
--manner of presenting compatibility limits
rules data 2535
processor(s) 2550
test component 2514
interactive processing components 2518-2519
generation routine 2510
input data 2539
2500
Tests:
Test Category Types:
Screening Design
Orthogonal Design
Response Surface Design
Test Types:
Box-Behnken (BB)
Central Composite Design (CCD)
Definitive Screening Design (DSD)
Mixture Design (MD)
Near Orthogonal
Orthogonal Array
Compatibility Notice:
Currently specified type(s) for one or more factors do not support DSD test type.
If proceeding with specifying DSD test type, then factor type(s) must be changed.
Click to Unspecify Factor Type(s)
2580 or 2780
3141
3140, 3514
3148

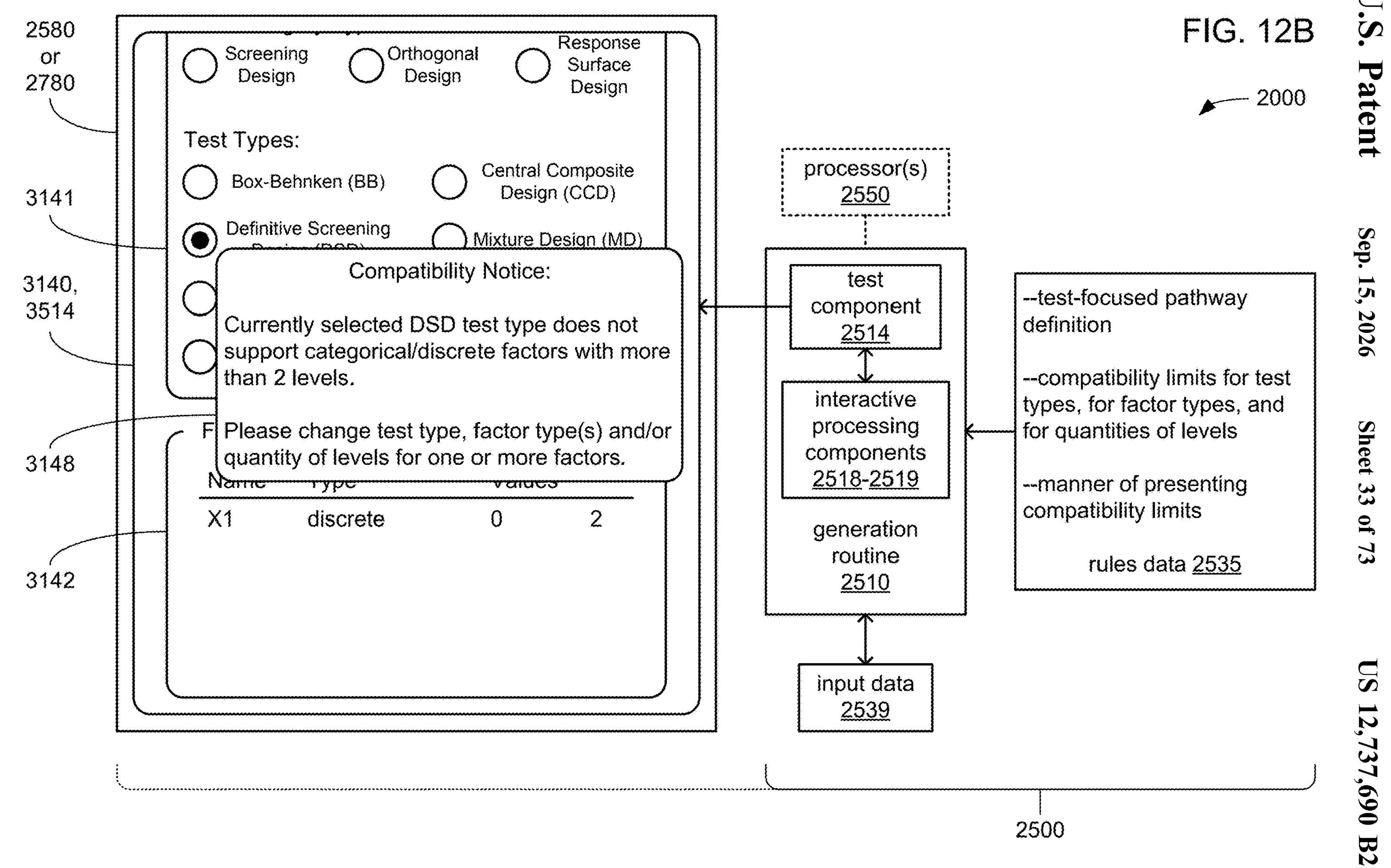
FIG. 12B
2000
2580 or 2780
Screening Design
Orthogonal Design
Response Surface Design
Test Types:
Box-Behnken (BB)
Central Composite Design (CCD)
Definitive Screening
Mixture Design (MD)
3141
3140, 3514
Compatibility Notice:
Currently selected DSD test type does not support categorical/discrete factors with more than 2 levels.
Please change test type, factor type(s) and/or quantity of levels for one or more factors.
3148
X1
discrete
0
2
3142
processor(s) 2550
test component 2514
interactive processing components 2518-2519
generation routine 2510
input data 2539
--test-focused pathway definition
--compatibility limits for test types, for factor types, and for quantities of levels
--manner of presenting compatibility limits
rules data 2535
2500

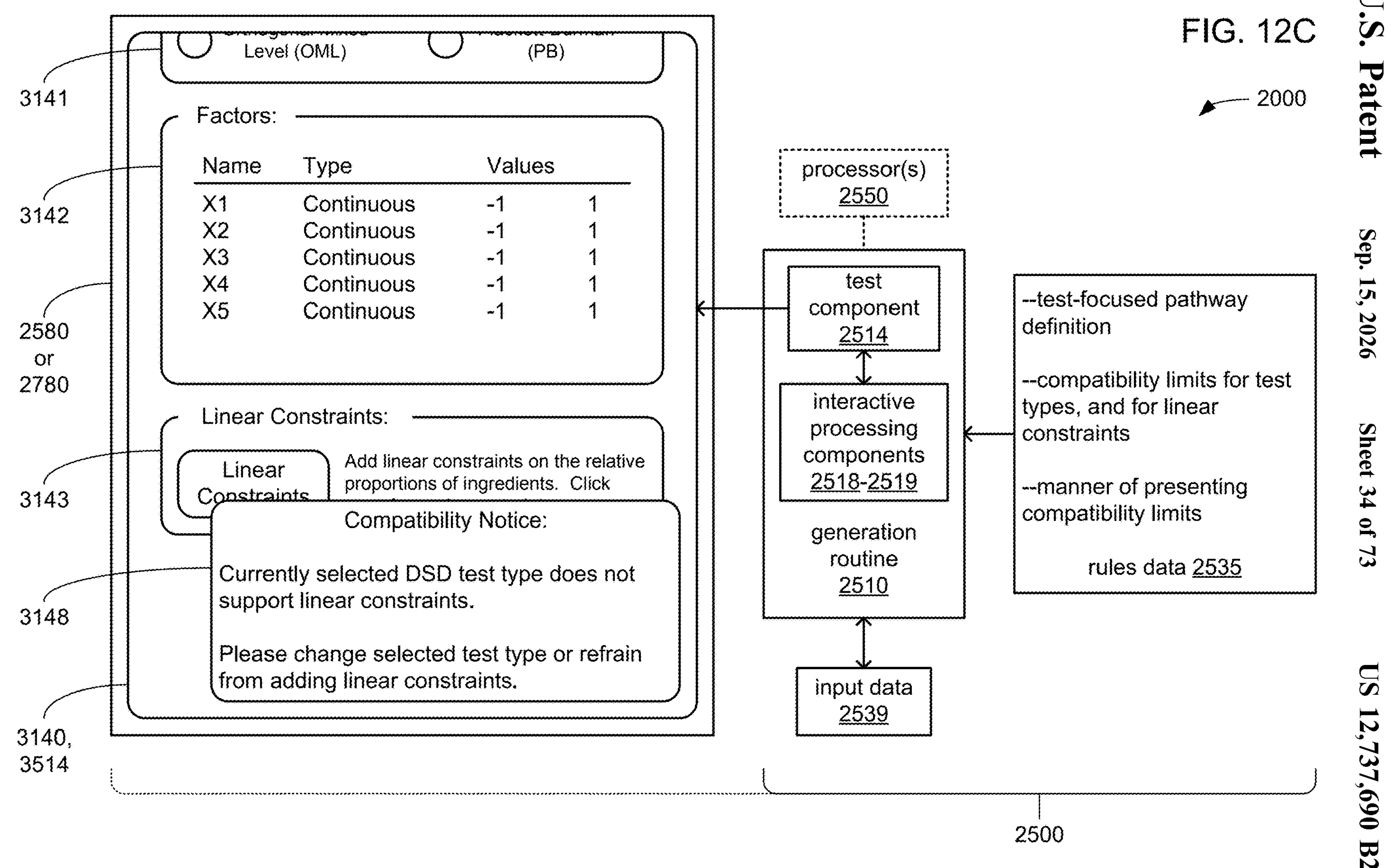
FIG. 12C
2000
Level (OML)
(PB)
Factors:
Name Type Values
X1 Continuous -1 1
X2 Continuous -1 1
X3 Continuous -1 1
X4 Continuous -1 1
X5 Continuous -1 1
Linear Constraints:
Linear Constraints
Add linear constraints on the relative proportions of ingredients. Click
Compatibility Notice:
Currently selected DSD test type does not support linear constraints.
Please change selected test type or refrain from adding linear constraints.
processor(s) 2550
test component 2514
interactive processing components 2518-2519
generation routine 2510
input data 2539
--test-focused pathway definition
--compatibility limits for test types, and for linear constraints
--manner of presenting compatibility limits
rules data 2535
3141
3142
2580 or 2780
3143
3148
3140, 3514
2500

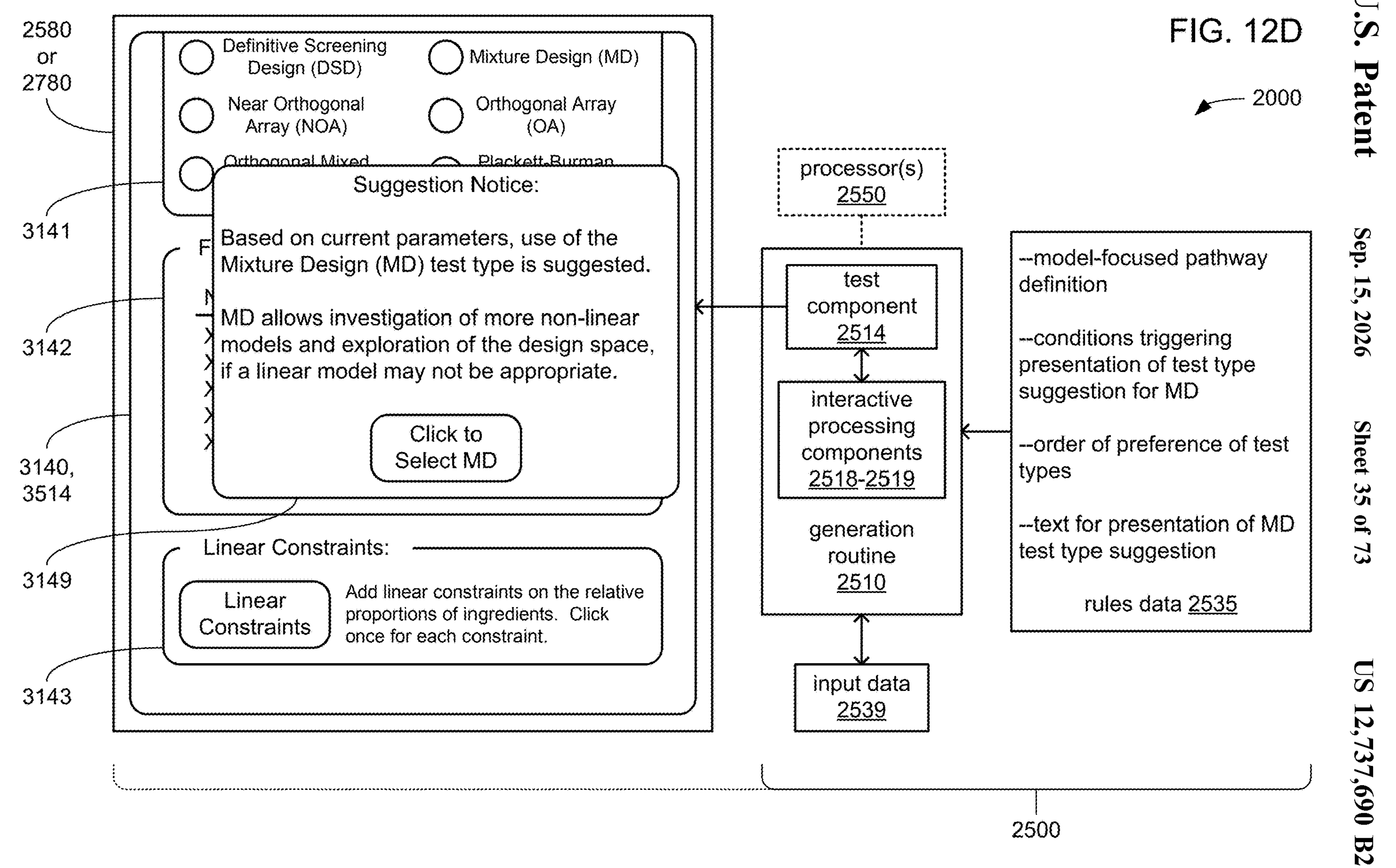
FIG. 12D
2000
2580 or 2780
Definitive Screening Design (DSD)
Mixture Design (MD)
Near Orthogonal Array (NOA)
Orthogonal Array (OA)
Suggestion Notice:
Based on current parameters, use of the Mixture Design (MD) test type is suggested.
MD allows investigation of more non-linear models and exploration of the design space, if a linear model may not be appropriate.
Click to Select MD
Linear Constraints:
Linear Constraints
Add linear constraints on the relative proportions of ingredients. Click once for each constraint.
3141
3142
3140, 3514
3149
3143
processor(s) 2550
test component 2514
interactive processing components 2518-2519
generation routine 2510
input data 2539
--model-focused pathway definition
--conditions triggering presentation of test type suggestion for MD
--order of preference of test types
--text for presentation of MD test type suggestion
rules data 2535
2500

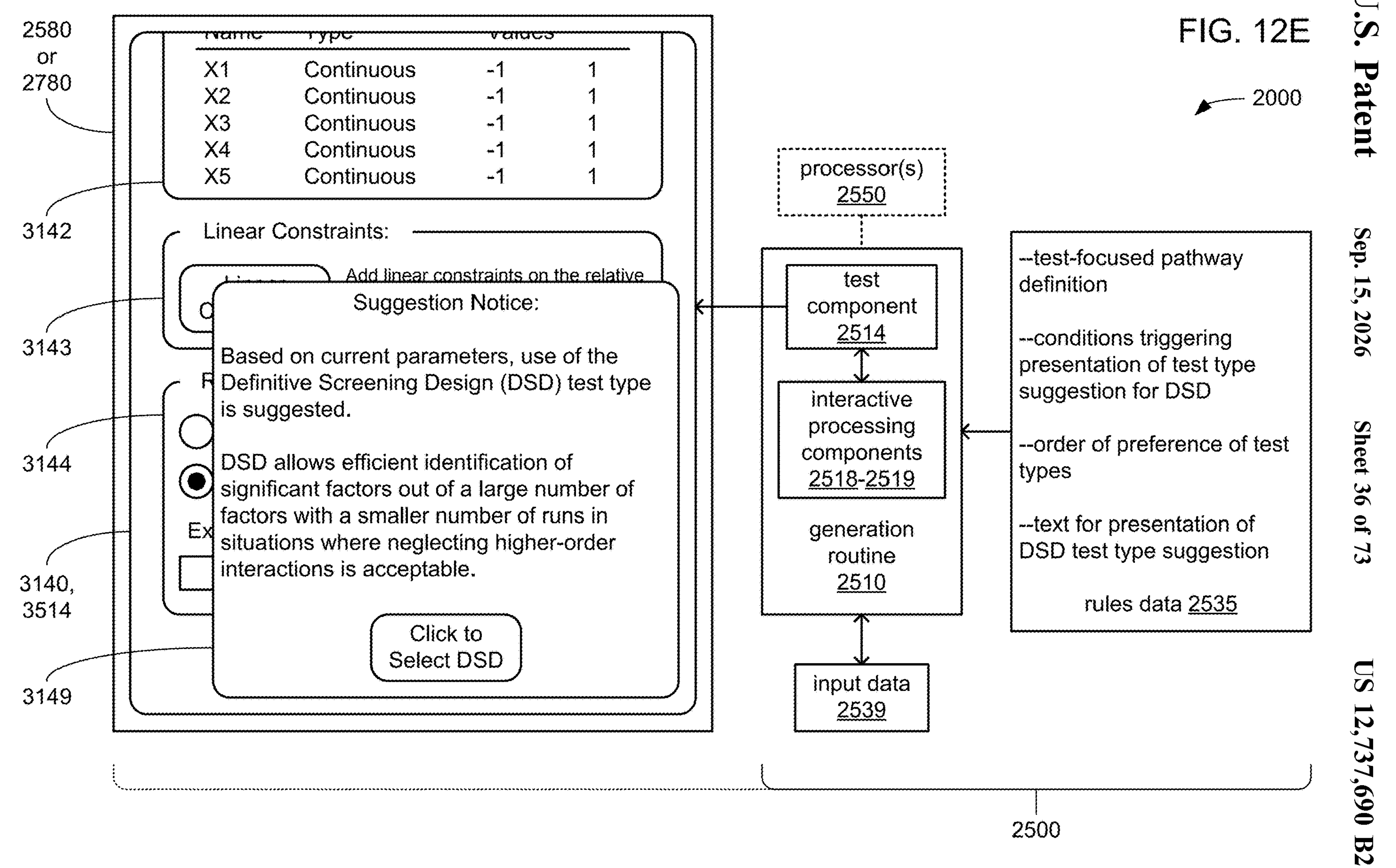
FIG. 12E
2000
2580 or 2780
Name Type Values
X1 Continuous -1 1
X2 Continuous -1 1
X3 Continuous -1 1
X4 Continuous -1 1
X5 Continuous -1 1
Linear Constraints:
Add linear constraints on the relative
Suggestion Notice:
Based on current parameters, use of the Definitive Screening Design (DSD) test type is suggested.
DSD allows efficient identification of significant factors out of a large number of factors with a smaller number of runs in situations where neglecting higher-order interactions is acceptable.
Click to Select DSD
3142
3143
3144
3140, 3514
3149
processor(s) 2550
test component 2514
interactive processing components 2518-2519
generation routine 2510
input data 2539
--test-focused pathway definition
--conditions triggering presentation of test type suggestion for DSD
--order of preference of test types
--text for presentation of DSD test type suggestion
rules data 2535
2500

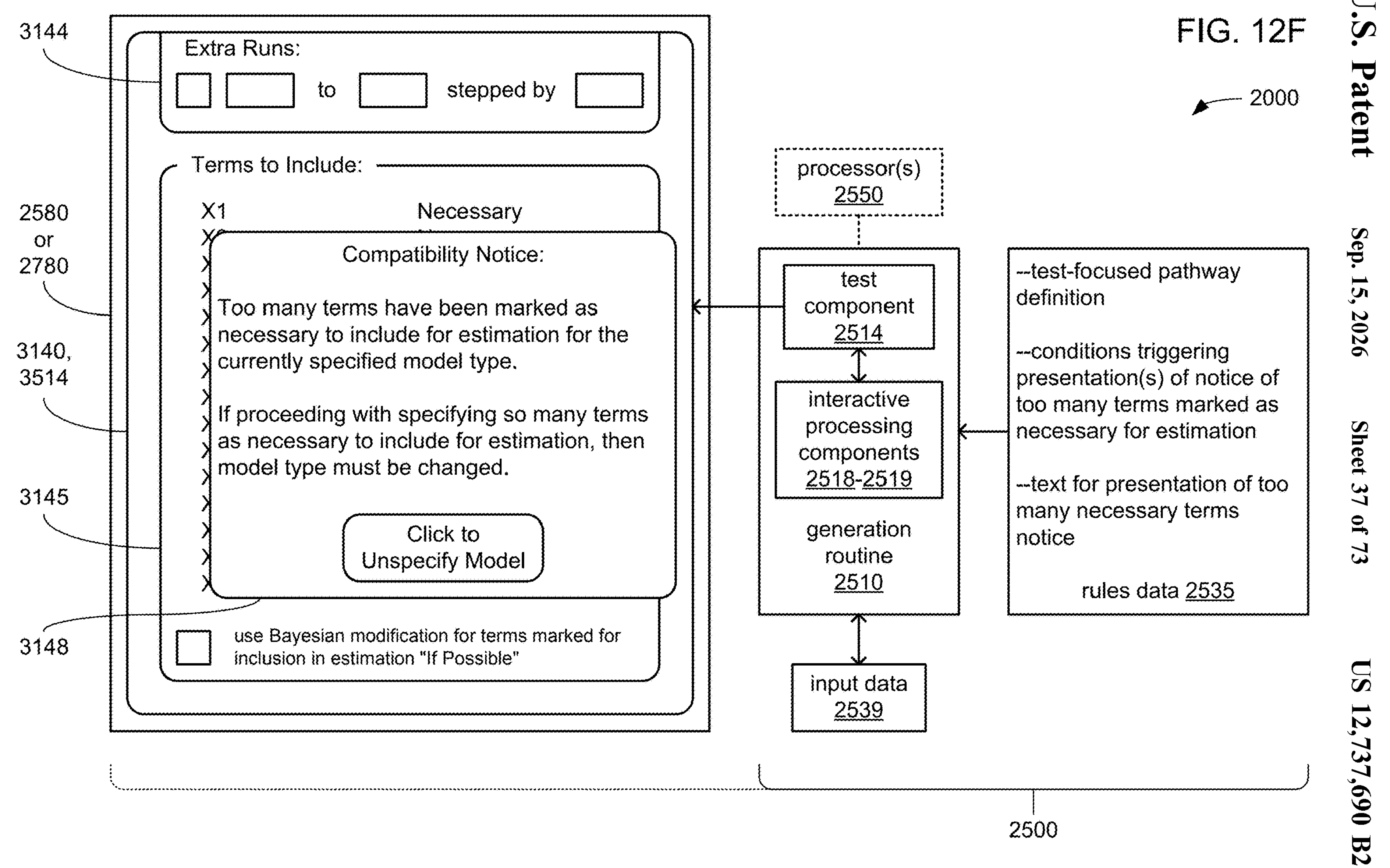
FIG. 12F
2000
Extra Runs:
to
stepped by
Terms to Include:
X1
Necessary
Compatibility Notice:
Too many terms have been marked as necessary to include for estimation for the currently specified model type.
If proceeding with specifying so many terms as necessary to include for estimation, then model type must be changed.
Click to Unspecify Model
use Bayesian modification for terms marked for inclusion in estimation "If Possible"
processor(s) 2550
test component 2514
interactive processing components 2518-2519
generation routine 2510
input data 2539
--test-focused pathway definition
--conditions triggering presentation(s) of notice of too many terms marked as necessary for estimation
--text for presentation of too many necessary terms notice
rules data 2535
3144
2580 or 2780
3140, 3514
3145
3148
2500

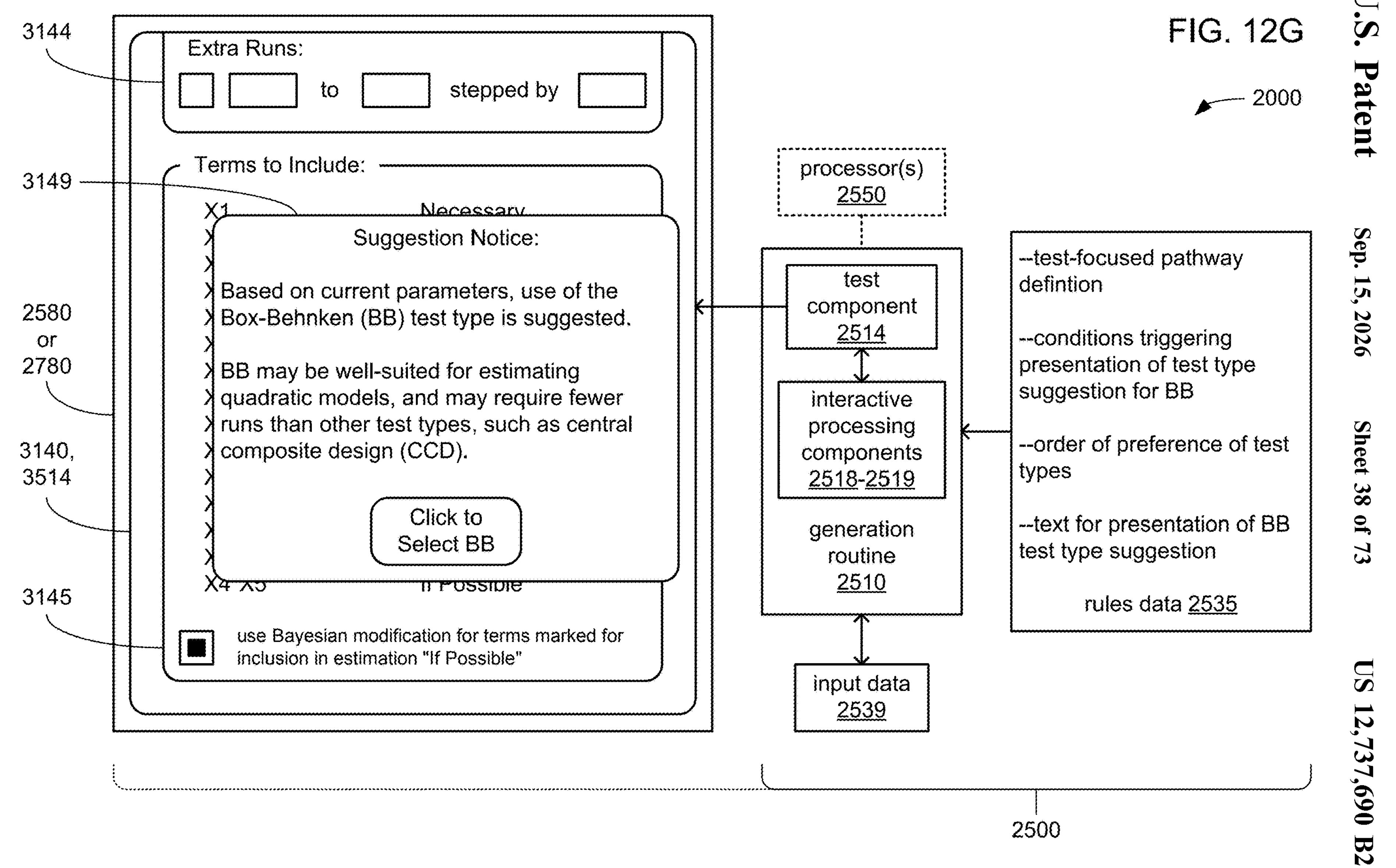
FIG. 12G
2000
3144
Extra Runs:
to
stepped by
3149
Terms to Include:
Suggestion Notice:
Based on current parameters, use of the Box-Behnken (BB) test type is suggested.
BB may be well-suited for estimating quadratic models, and may require fewer runs than other test types, such as central composite design (CCD).
Click to Select BB
2580 or 2780
3140, 3514
3145
use Bayesian modification for terms marked for inclusion in estimation "If Possible"
processor(s) 2550
test component 2514
interactive processing components 2518-2519
generation routine 2510
input data 2539
--test-focused pathway defintion
--conditions triggering presentation of test type suggestion for BB
--order of preference of test types
--text for presentation of BB test type suggestion
rules data 2535
2500

3440
3442
2000

Prediction Variance
OA
DSD
1.0
0.8
0.6
0.4
0.2
0.0
-1.0
-0.5
0
0.5
1.0
A
B
C
D
2580 or 2780
input device
2520 or 2720
candidate profiles
2532
prediction variance component
2544
comparison routine
2540
interactive evaluation component
2549
--graph template for variance per term
rules data
2535

Figure 14E:
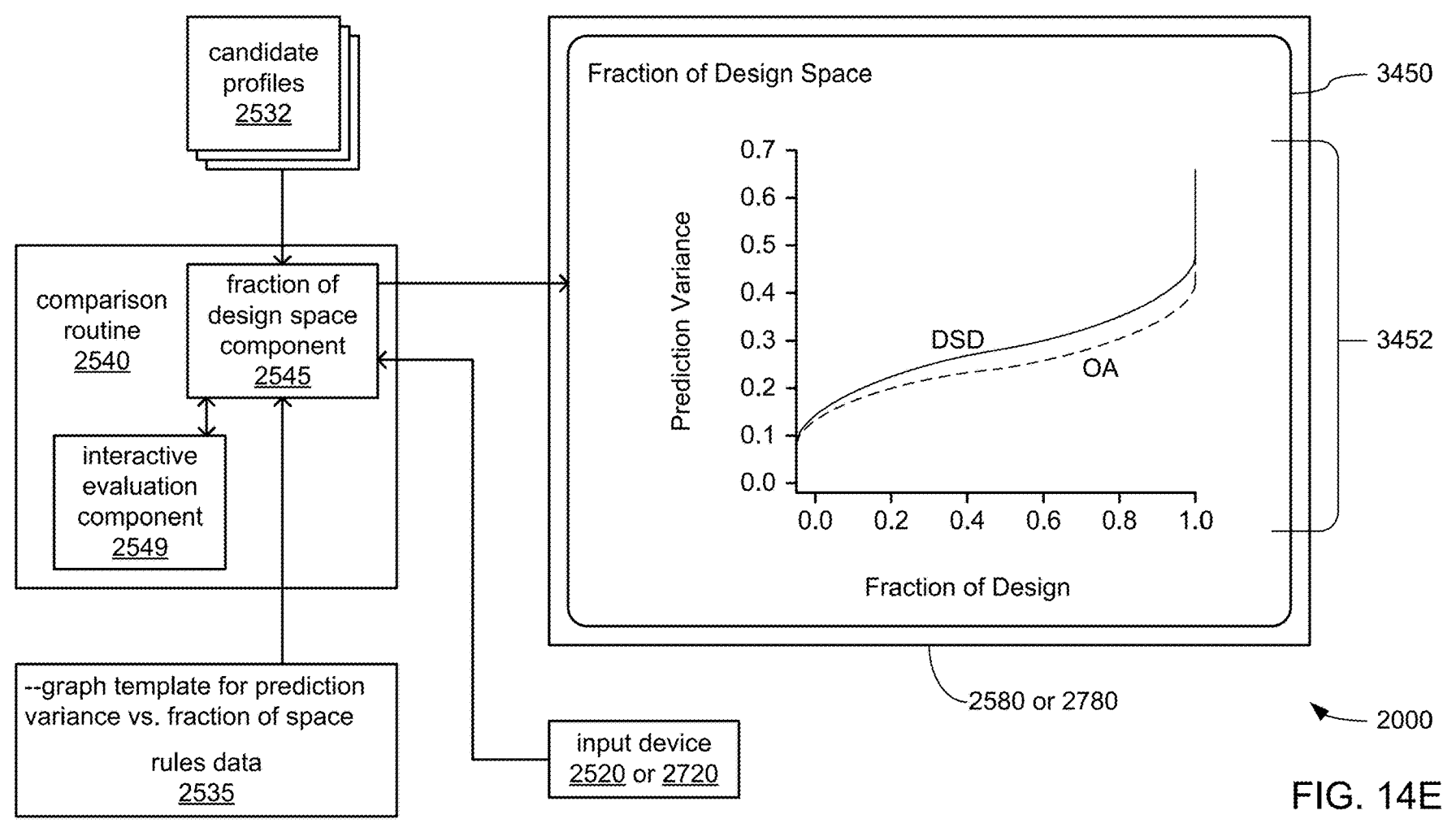

Fraction of Design Space

Prediction Variance 0.7
0.6
0.5
0.4
0.3
0.2
0.1
0.0

DSD

OA 0.0 0.2 0.4 0.6 0.8 1.0

Fraction of Design 2580 or 2780 input device 2520 or 2720 candidate profiles 2532 fraction of design space component 2545 interactive evaluation component 2549 comparison routine 2540

--graph template for prediction variance vs. fraction of space rules data 2535

2000
candidate profiles
2532
interactive evaluation component
2549
comparison routine
2540
statistical correlations component
2546
rules data
2535
--correlation graph template
input device
2520 or 2720
2580 or 2780
Correlations Map
0
1
3460
3462
12 Run
15 Run
18 Run
3464
A
B
C
D
A*B
A*C
A*D
B*C
B*D
C*D

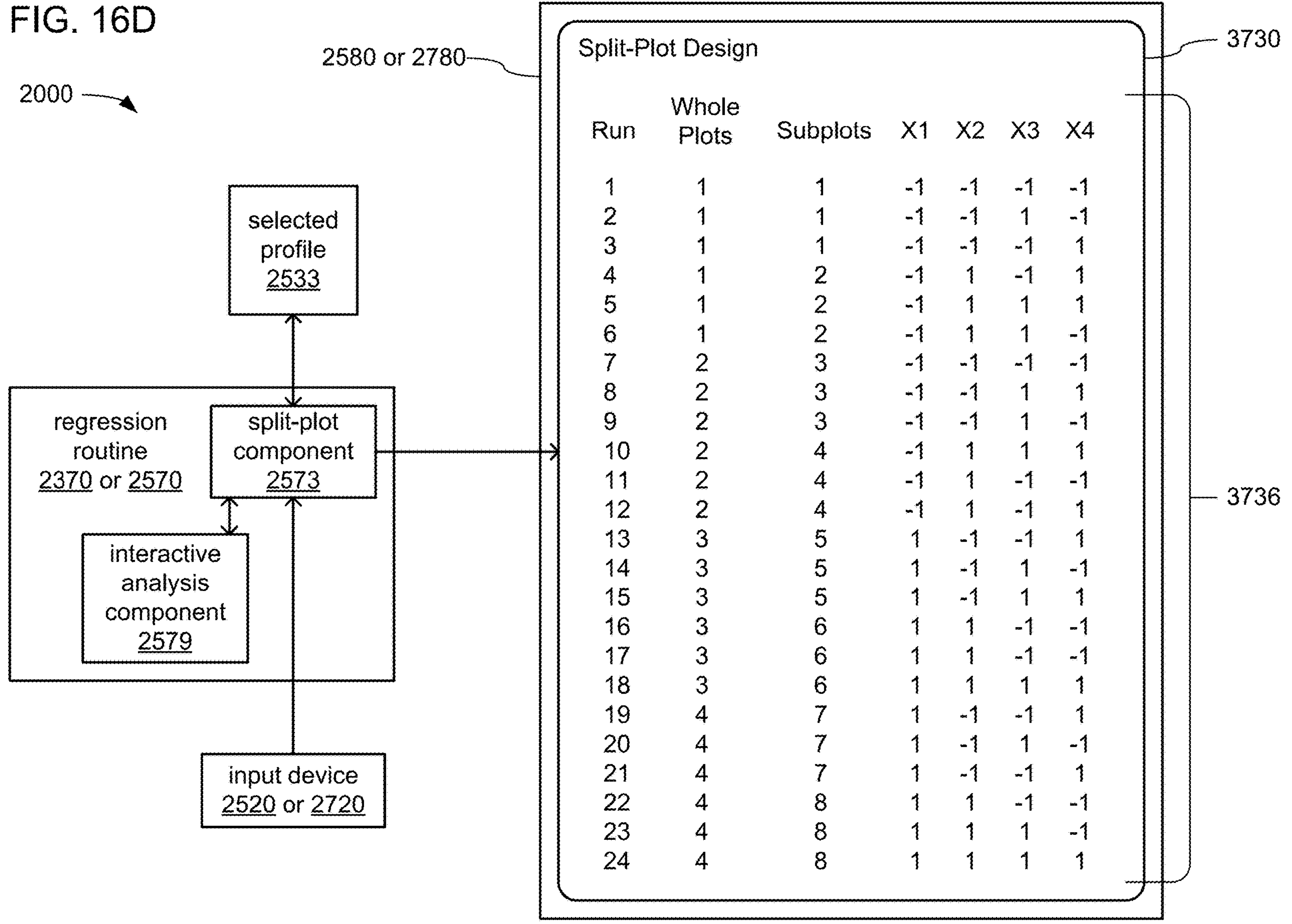
| Run | Whole Plots | Subplots | X1 | X2 | X3 | X4 |
|---|---|---|---|---|---|---|
| 1 | 1 | 1 | -1 | -1 | -1 | -1 |
| 2 | 1 | 1 | -1 | -1 | 1 | -1 |
| 3 | 1 | 1 | -1 | -1 | -1 | 1 |
| 4 | 1 | 2 | -1 | 1 | -1 | 1 |
| 5 | 1 | 2 | -1 | 1 | 1 | 1 |
| 6 | 1 | 2 | -1 | 1 | 1 | -1 |
| 7 | 2 | 3 | -1 | -1 | -1 | -1 |
| 8 | 2 | 3 | -1 | -1 | 1 | 1 |
| 9 | 2 | 3 | -1 | -1 | 1 | -1 |
| 10 | 2 | 4 | -1 | 1 | 1 | 1 |
| 11 | 2 | 4 | -1 | 1 | -1 | -1 |
| 12 | 2 | 4 | -1 | 1 | -1 | 1 |
| 13 | 3 | 5 | 1 | -1 | -1 | 1 |
| 14 | 3 | 5 | 1 | -1 | 1 | -1 |
| 15 | 3 | 5 | 1 | -1 | 1 | 1 |
| 16 | 3 | 6 | 1 | 1 | -1 | -1 |
| 17 | 3 | 6 | 1 | 1 | -1 | -1 |
| 18 | 3 | 6 | 1 | 1 | 1 | 1 |
| 19 | 4 | 7 | 1 | -1 | -1 | 1 |
| 20 | 4 | 7 | 1 | -1 | 1 | -1 |
| 21 | 4 | 7 | 1 | -1 | -1 | 1 |
| 22 | 4 | 8 | 1 | 1 | -1 | -1 |
| 23 | 4 | 8 | 1 | 1 | 1 | -1 |
| 24 | 4 | 8 | 1 | 1 | 1 | 1 |

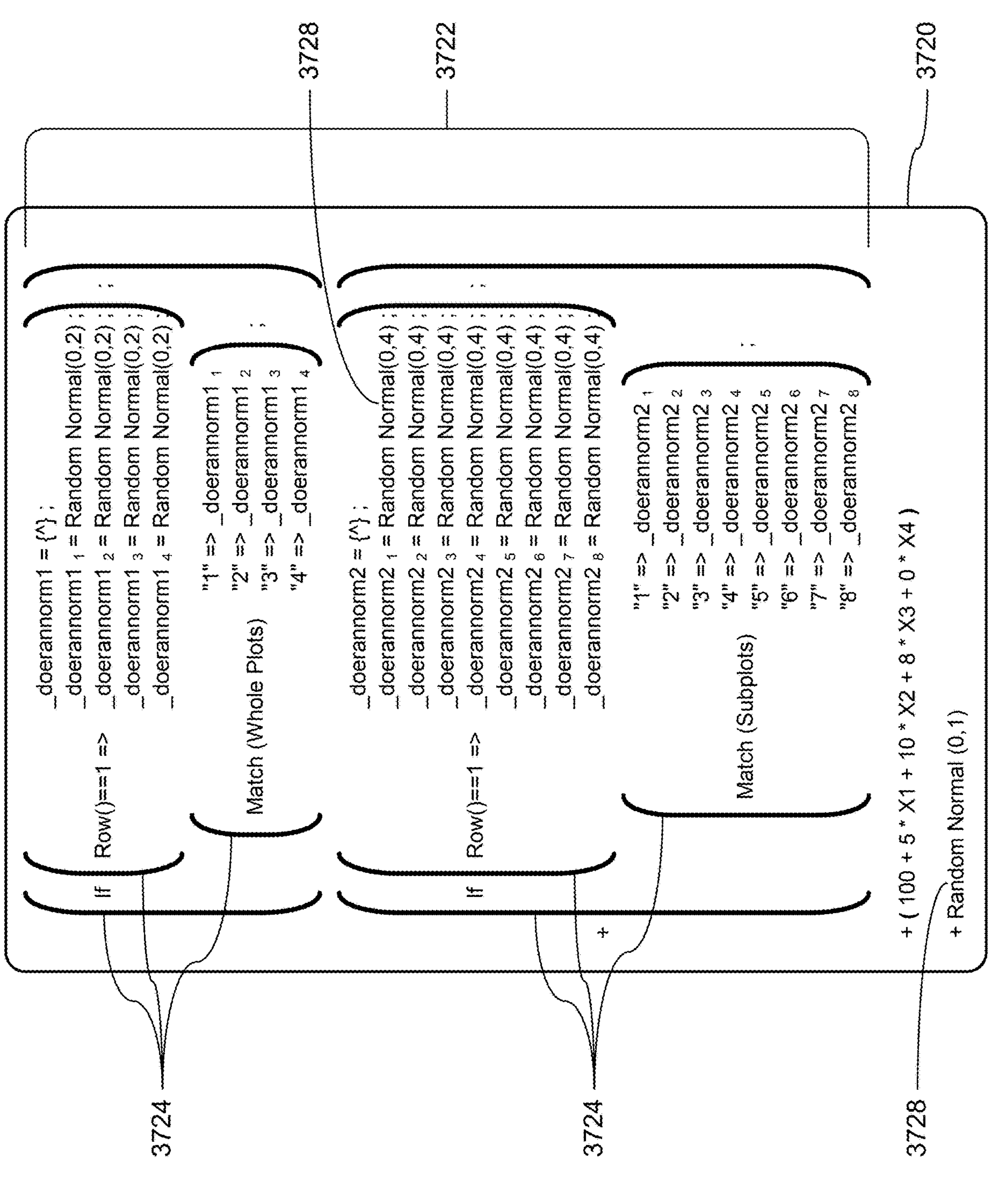
FIG. 16E
2000
3728
3722
3720
3724
3724
3728
If
Row()==1 =>
_doerannorm1 = {^} ;
_doerannorm1 1 = Random Normal(0,2) ;
_doerannorm1 2 = Random Normal(0,2) ;
_doerannorm1 3 = Random Normal(0,2) ;
_doerannorm1 4 = Random Normal(0,2) ;
Match (Whole Plots)
"1" => _doerannorm1 1
"2" => _doerannorm1 2
"3" => _doerannorm1 3
"4" => _doerannorm1 4
;
; ;
If
Row()==1 =>
_doerannorm2 = {^} ;
_doerannorm2 1 = Random Normal(0,4) ;
_doerannorm2 2 = Random Normal(0,4) ;
_doerannorm2 3 = Random Normal(0,4) ;
_doerannorm2 4 = Random Normal(0,4) ;
_doerannorm2 5 = Random Normal(0,4) ;
_doerannorm2 6 = Random Normal(0,4) ;
_doerannorm2 7 = Random Normal(0,4) ;
_doerannorm2 8 = Random Normal(0,4) ;
+
Match (Subplots)
"1" => _doerannorm2 1
"2" => _doerannorm2 2
"3" => _doerannorm2 3
"4" => _doerannorm2 4
"5" => _doerannorm2 5
"6" => _doerannorm2 6
"7" => _doerannorm2 7
"8" => _doerannorm2 8
;
; ;
+ ( 100 + 5 * X1 + 10 * X2 + 8 * X3 + 0 * X4 )
+ Random Normal (0,1)

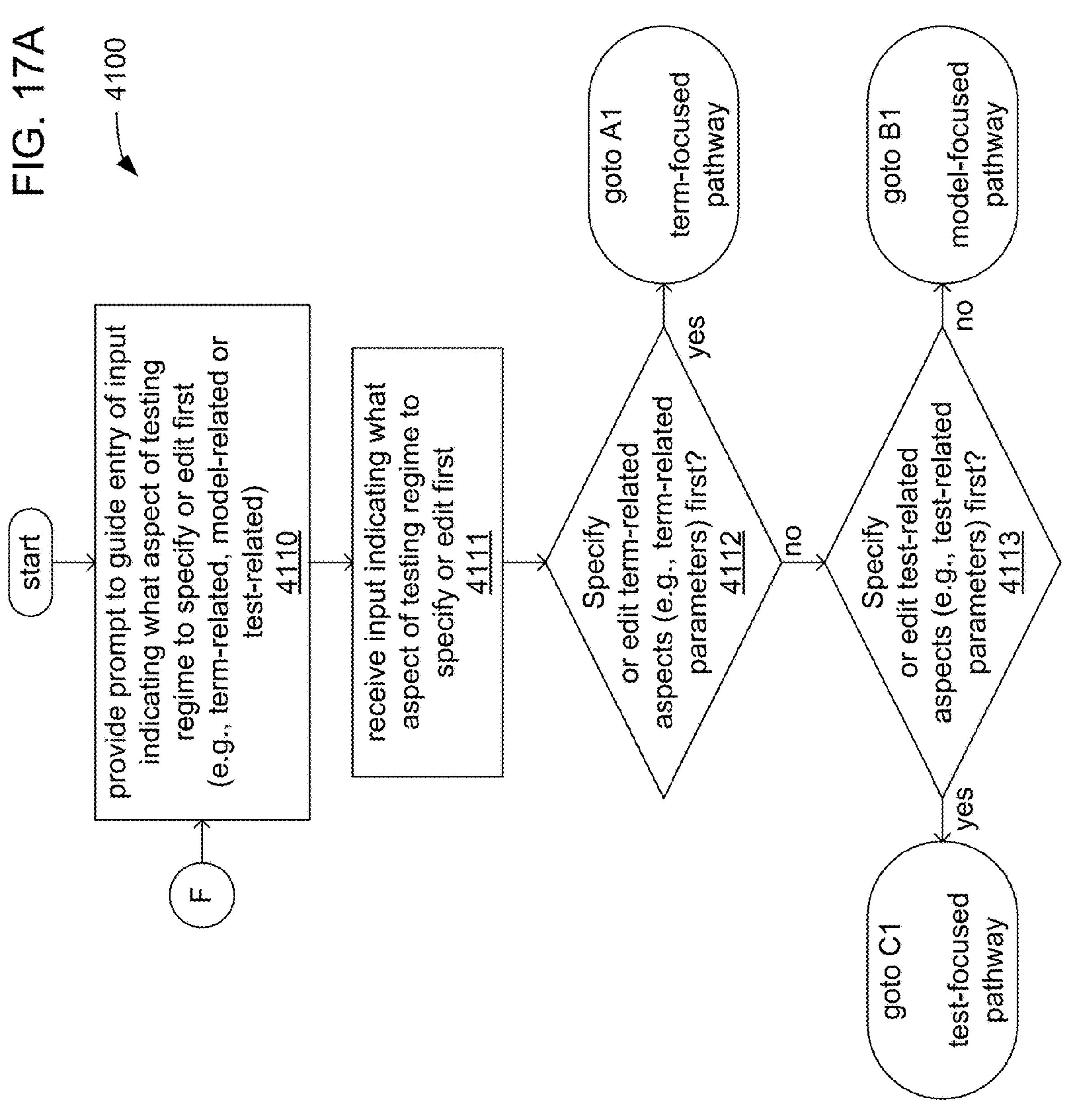
FIG. 17A
4100
start
provide prompt to guide entry of input indicating what aspect of testing regime to specify or edit first (e.g., term-related, model-related or test-related)
4110
F
receive input indicating what aspect of testing regime to specify or edit first
4111
Specify or edit term-related aspects (e.g., term-related parameters) first?
4112
yes
no
goto A1
term-focused pathway
Specify or edit test-related aspects (e.g., test-related parameters) first?
4113
no
yes
goto B1
model-focused pathway
goto C1
test-focused pathway

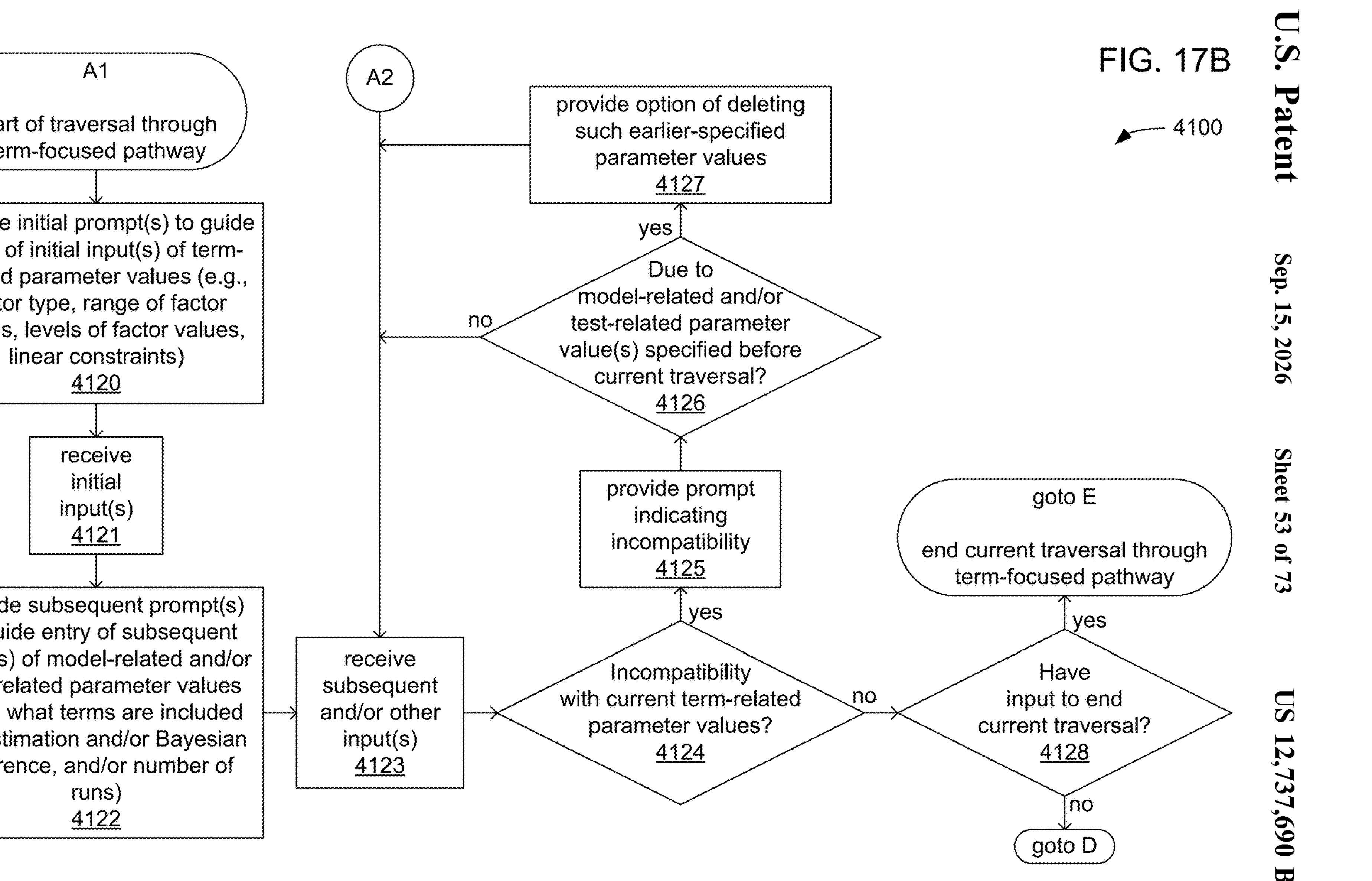
FIG. 17B
4100
A1
start of traversal through term-focused pathway
provide initial prompt(s) to guide entry of initial input(s) of term-related parameter values (e.g., factor type, range of factor values, levels of factor values, linear constraints)
4120
receive initial input(s)
4121
provide subsequent prompt(s) to guide entry of subsequent input(s) of model-related and/or test-related parameter values (e.g., what terms are included for estimation and/or Bayesian inference, and/or number of runs)
4122
A2
receive subsequent and/or other input(s)
4123
Incompatibility with current term-related parameter values?
4124
yes
provide prompt indicating incompatibility
4125
Due to model-related and/or test-related parameter value(s) specified before current traversal?
4126
yes
no
provide option of deleting such earlier-specified parameter values
4127
no
Have input to end current traversal?
4128
yes
goto E
end current traversal through term-focused pathway
no
goto D

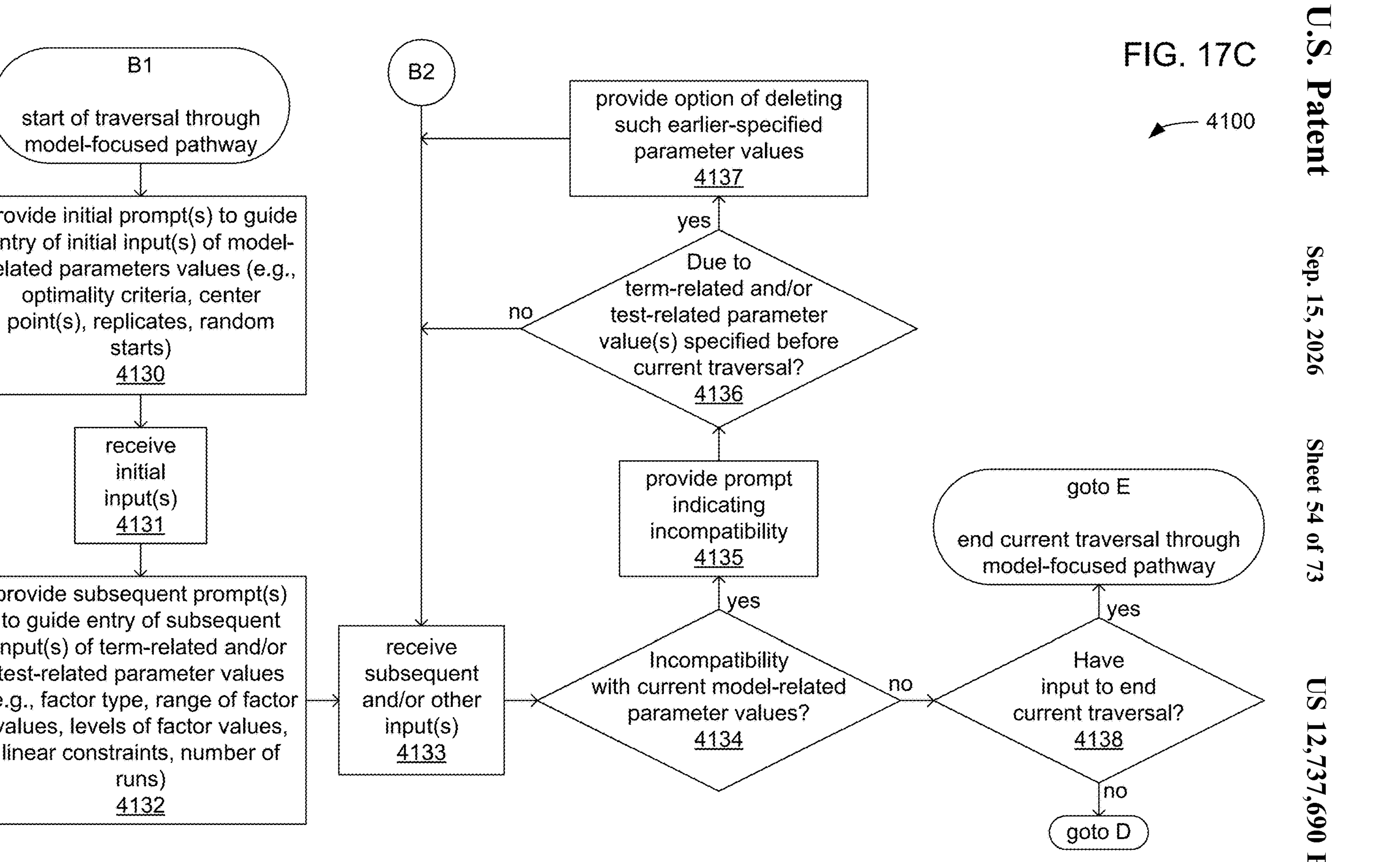
FIG. 17C
4100
B1
start of traversal through model-focused pathway
provide initial prompt(s) to guide entry of initial input(s) of model-related parameters values (e.g., optimality criteria, center point(s), replicates, random starts) 4130
receive initial input(s) 4131
provide subsequent prompt(s) to guide entry of subsequent input(s) of term-related and/or test-related parameter values (e.g., factor type, range of factor values, levels of factor values, linear constraints, number of runs) 4132
B2
receive subsequent and/or other input(s) 4133
Incompatibility with current model-related parameter values? 4134
yes
no
provide prompt indicating incompatibility 4135
Due to term-related and/or test-related parameter value(s) specified before current traversal? 4136
yes
no
provide option of deleting such earlier-specified parameter values 4137
Have input to end current traversal? 4138
yes
no
goto E
end current traversal through model-focused pathway
goto D

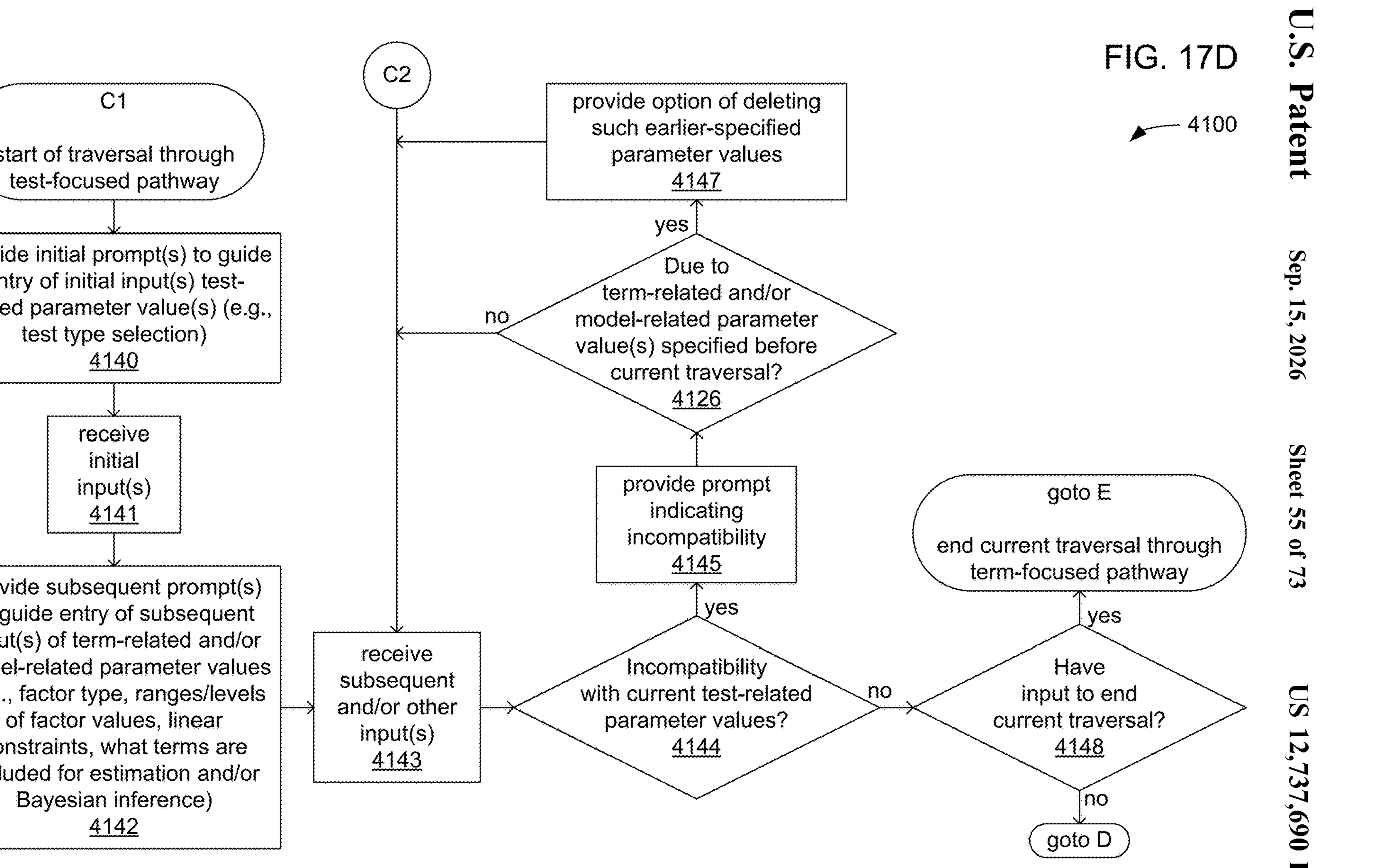
FIG. 17D
4100
C1
start of traversal through test-focused pathway
provide initial prompt(s) to guide entry of initial input(s) test-related parameter value(s) (e.g., test type selection) 4140
receive initial input(s) 4141
provide subsequent prompt(s) to guide entry of subsequent input(s) of term-related and/or model-related parameter values (e.g., factor type, ranges/levels of factor values, linear constraints, what terms are included for estimation and/or Bayesian inference) 4142
C2
receive subsequent and/or other input(s) 4143
Incompatibility with current test-related parameter values? 4144
yes
provide prompt indicating incompatibility 4145
Due to term-related and/or model-related parameter value(s) specified before current traversal? 4126
yes
no
provide option of deleting such earlier-specified parameter values 4147
no
Have input to end current traversal? 4148
yes
goto E
end current traversal through term-focused pathway
no
goto D

D based on currently specified term-related, model-related and/or test-related parameter values, generate set of test types to suggest 4150 remove test types (if any) from set of test types that have already been suggested during current traversal through current pathway 4151

Any remaining test types in set? 4152 no yes organize remaining test types within set into order of preference 4153

Is a particular test type currently specified? 4154 no yes provide prompt suggesting all remaining test types in set in order of preference 4155

Figure 17E:
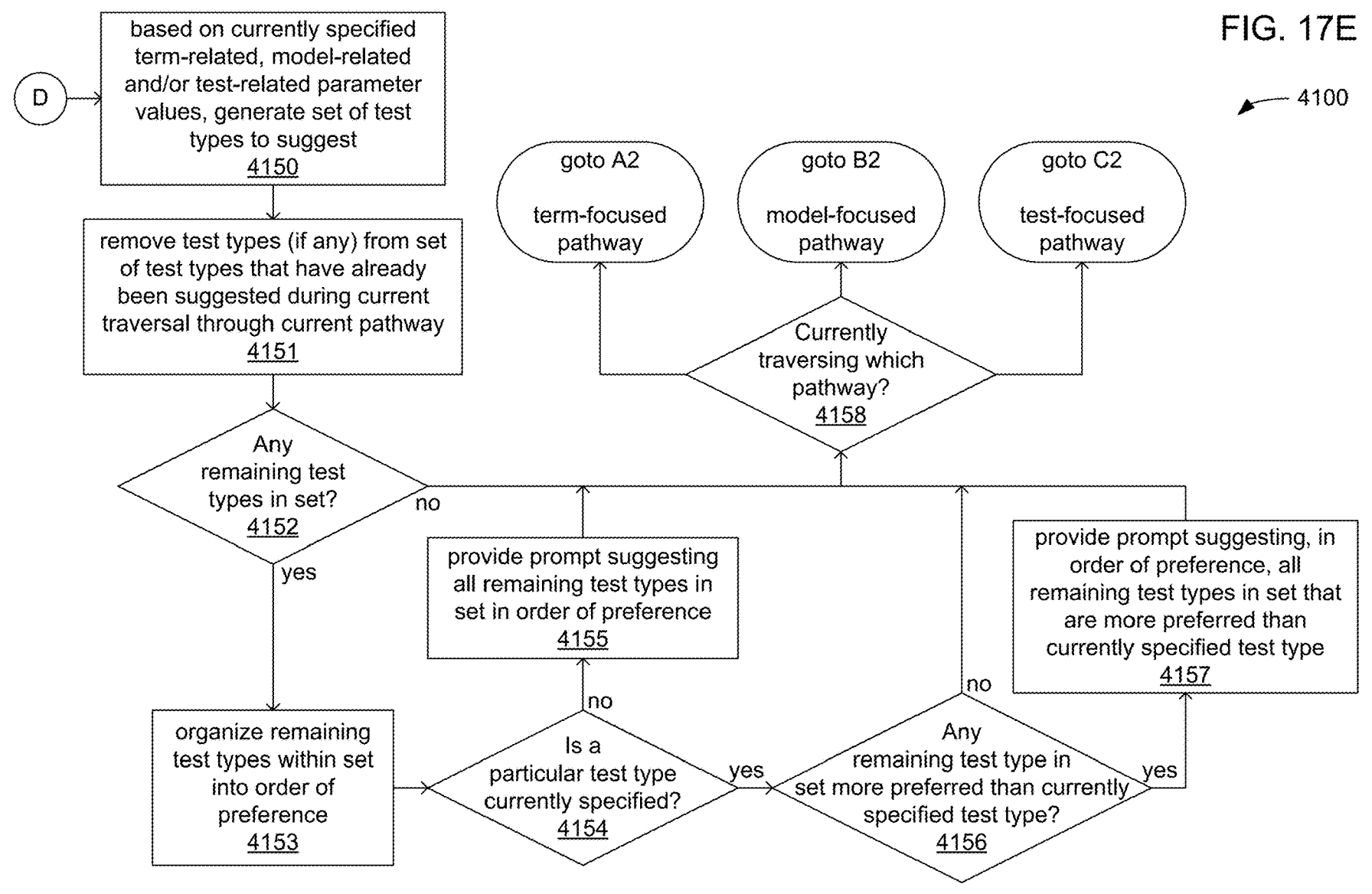

Any remaining test type in set more preferred than currently specified test type? 4156 no yes provide prompt suggesting, in order of preference, all remaining test types in set that are more preferred than currently specified test type 4157

Currently traversing which pathway? 4158 goto A2 term-focused pathway goto B2 model-focused pathway goto C2 test-focused pathway 4100
E
provide prompt for input indicating next action 4160
receive input indicating next action 4161
Editing current testing regime? 4162
yes
goto F
no
store details of current testing regime for future editing and/or for comparison to other testing regimes 4163
end

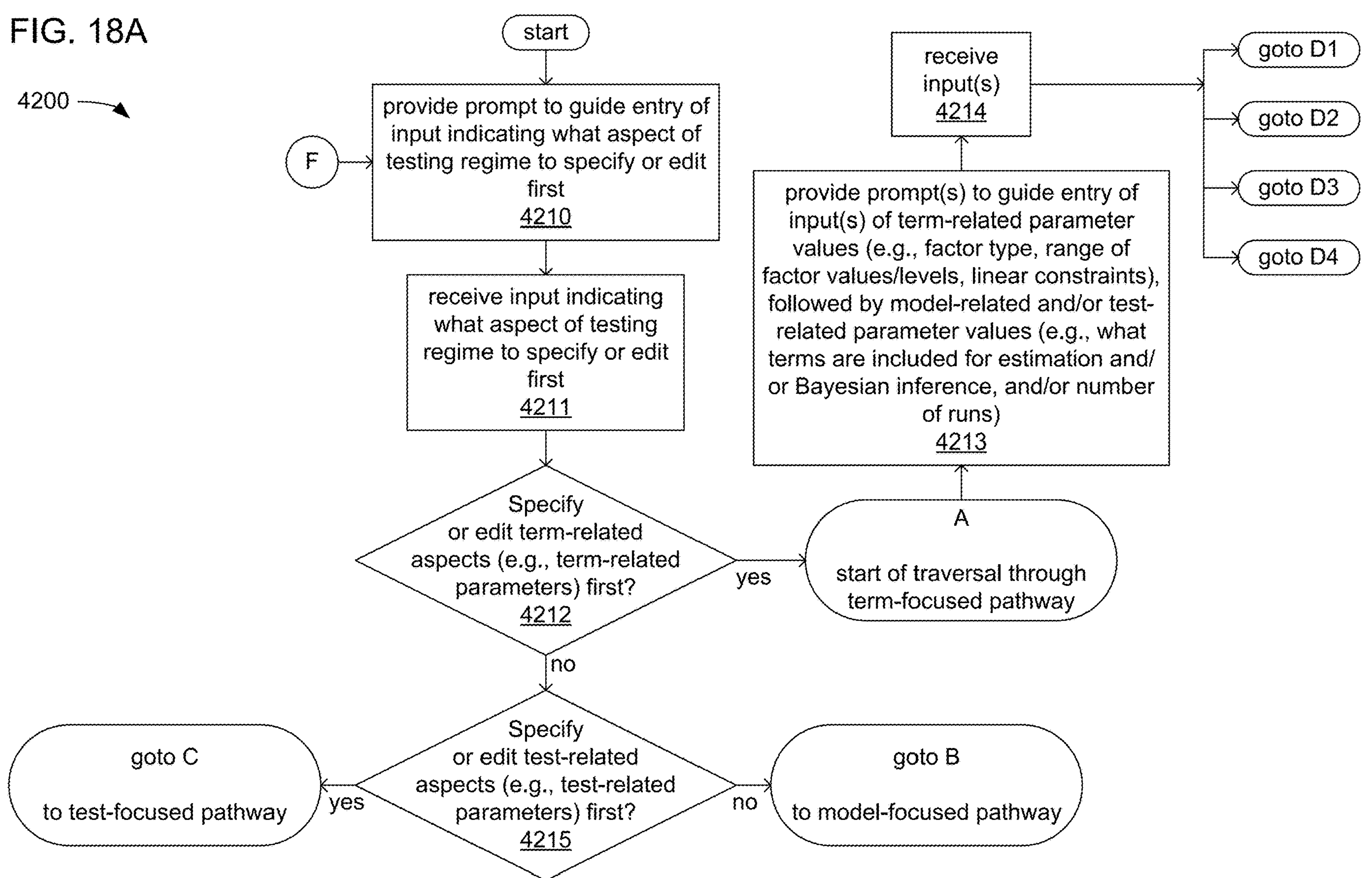
FIG. 18A
4200
start
provide prompt to guide entry of input indicating what aspect of testing regime to specify or edit first
4210
F
receive input indicating what aspect of testing regime to specify or edit first
4211
Specify or edit term-related aspects (e.g., term-related parameters) first?
4212
yes
no
A
start of traversal through term-focused pathway
provide prompt(s) to guide entry of input(s) of term-related parameter values (e.g., factor type, range of factor values/levels, linear constraints), followed by model-related and/or test-related parameter values (e.g., what terms are included for estimation and/or Bayesian inference, and/or number of runs)
4213
receive input(s)
4214
goto D1
goto D2
goto D3
goto D4
Specify or edit test-related aspects (e.g., test-related parameters) first?
4215
yes
no
goto C
to test-focused pathway
goto B
to model-focused pathway 4200
D2
Is there a constraint that values of all factors must add up to 100%? 4225
no
yes
goto E
provide prompt suggesting mixture design (MD) test type 4226

4200
D1
Any linear constraints? 4220
yes
no
Are all factors of continuous type? 4221
yes
no
provide prompt suggesting orthogonal array (OA) as test type 4222
goto E
provide prompt suggesting near orthogonal array (NOA) test type 4223

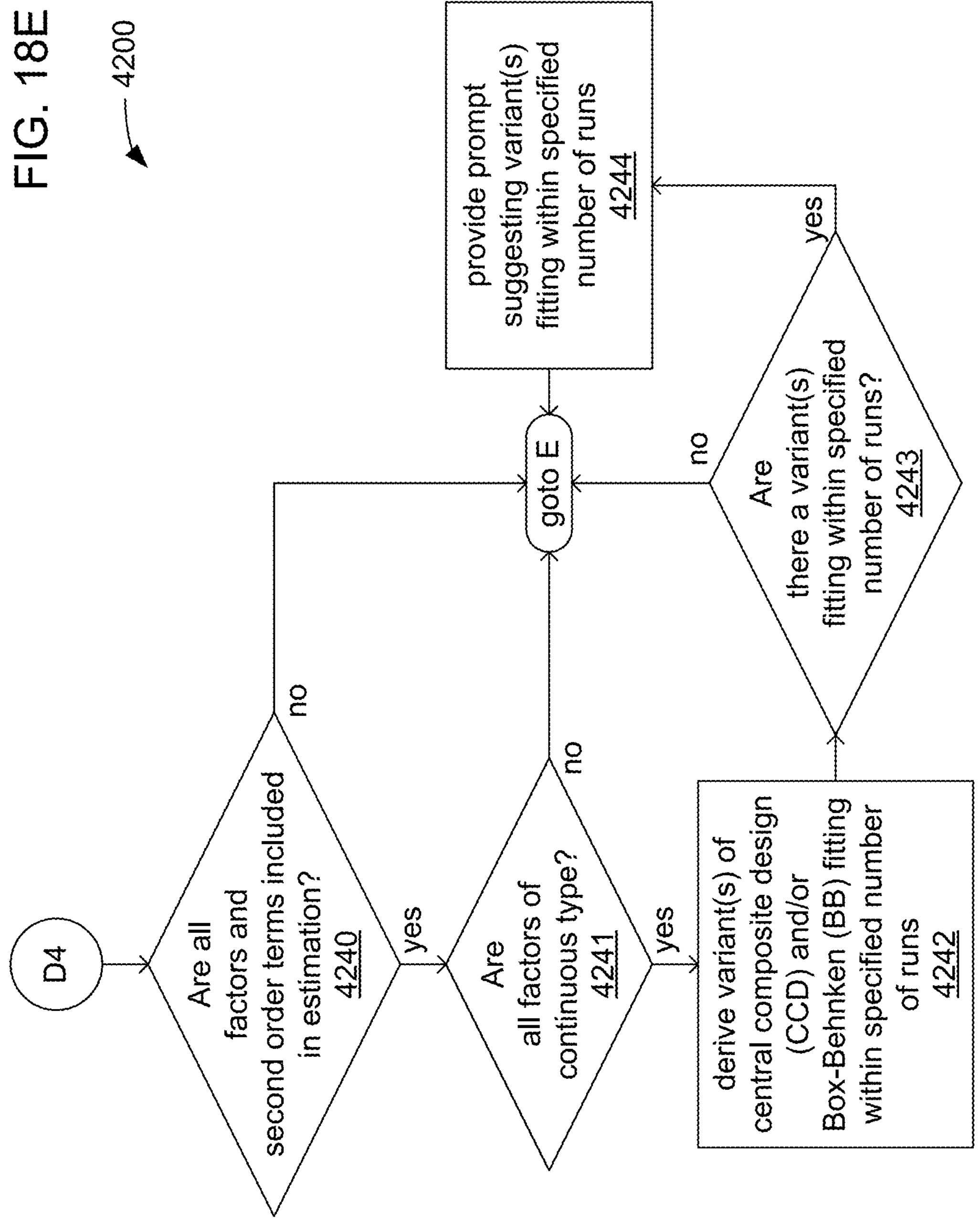
FIG. 18E
4200
D4
Are all factors and second order terms included in estimation? 4240
yes
no
Are all factors of continuous type? 4241
yes
no
derive variant(s) of central composite design (CCD) and/or Box-Behnken (BB) fitting within specified number of runs 4242
Are there a variant(s) fitting within specified number of runs? 4243
yes
no
provide prompt suggesting variant(s) fitting within specified number of runs 4244
goto E

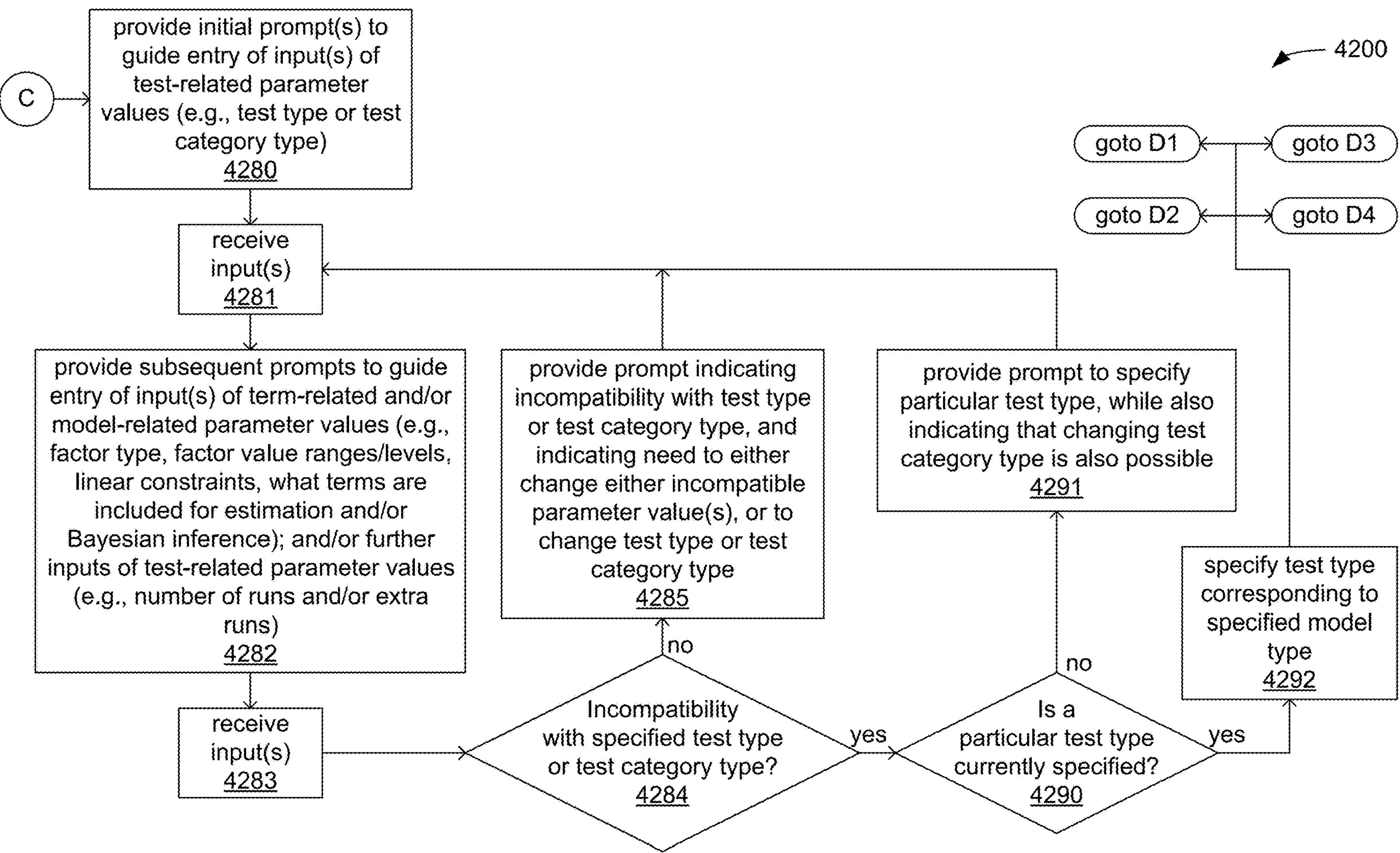
FIG. 18H
4200
C
provide initial prompt(s) to guide entry of input(s) of test-related parameter values (e.g., test type or test category type) 4280
receive input(s) 4281
provide subsequent prompts to guide entry of input(s) of term-related and/or model-related parameter values (e.g., factor type, factor value ranges/levels, linear constraints, what terms are included for estimation and/or Bayesian inference); and/or further inputs of test-related parameter values (e.g., number of runs and/or extra runs) 4282
receive input(s) 4283
Incompatibility with specified test type or test category type? 4284
no
yes
provide prompt indicating incompatibility with test type or test category type, and indicating need to either change either incompatible parameter value(s), or to change test type or test category type 4285
Is a particular test type currently specified? 4290
no
yes
provide prompt to specify particular test type, while also indicating that changing test category type is also possible 4291
specify test type corresponding to specified model type 4292
goto D1
goto D3
goto D2
goto D4

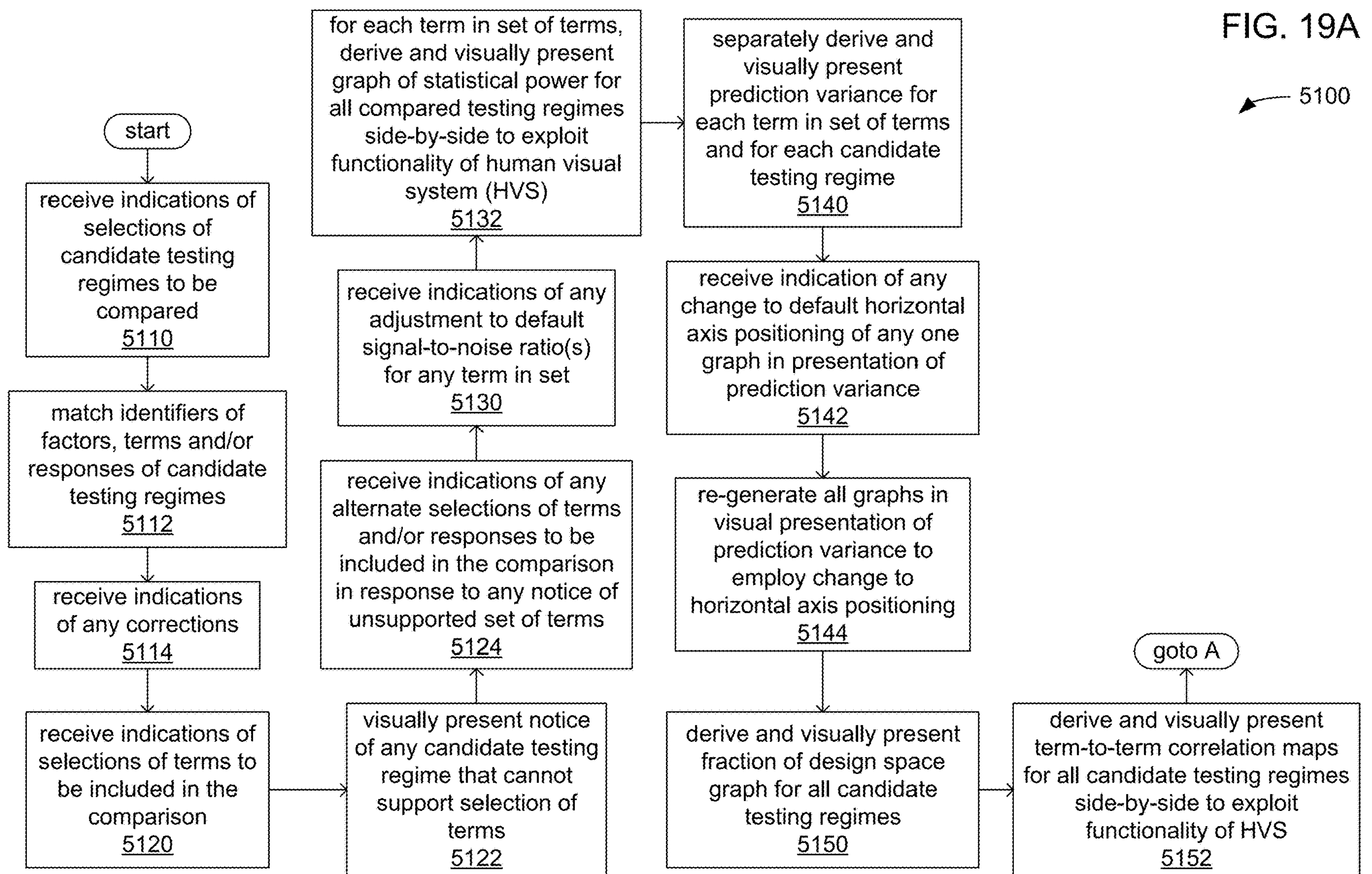
FIG. 19A
5100
start
receive indications of selections of candidate testing regimes to be compared 5110
match identifiers of factors, terms and/or responses of candidate testing regimes 5112
receive indications of any corrections 5114
receive indications of selections of terms to be included in the comparison 5120
visually present notice of any candidate testing regime that cannot support selection of terms 5122
receive indications of any alternate selections of terms and/or responses to be included in the comparison in response to any notice of unsupported set of terms 5124
receive indications of any adjustment to default signal-to-noise ratio(s) for any term in set 5130
for each term in set of terms, derive and visually present graph of statistical power for all compared testing regimes side-by-side to exploit functionality of human visual system (HVS) 5132
separately derive and visually present prediction variance for each term in set of terms and for each candidate testing regime 5140
receive indication of any change to default horizontal axis positioning of any one graph in presentation of prediction variance 5142
re-generate all graphs in visual presentation of prediction variance to employ change to horizontal axis positioning 5144
derive and visually present fraction of design space graph for all candidate testing regimes 5150
derive and visually present term-to-term correlation maps for all candidate testing regimes side-by-side to exploit functionality of HVS 5152
goto A

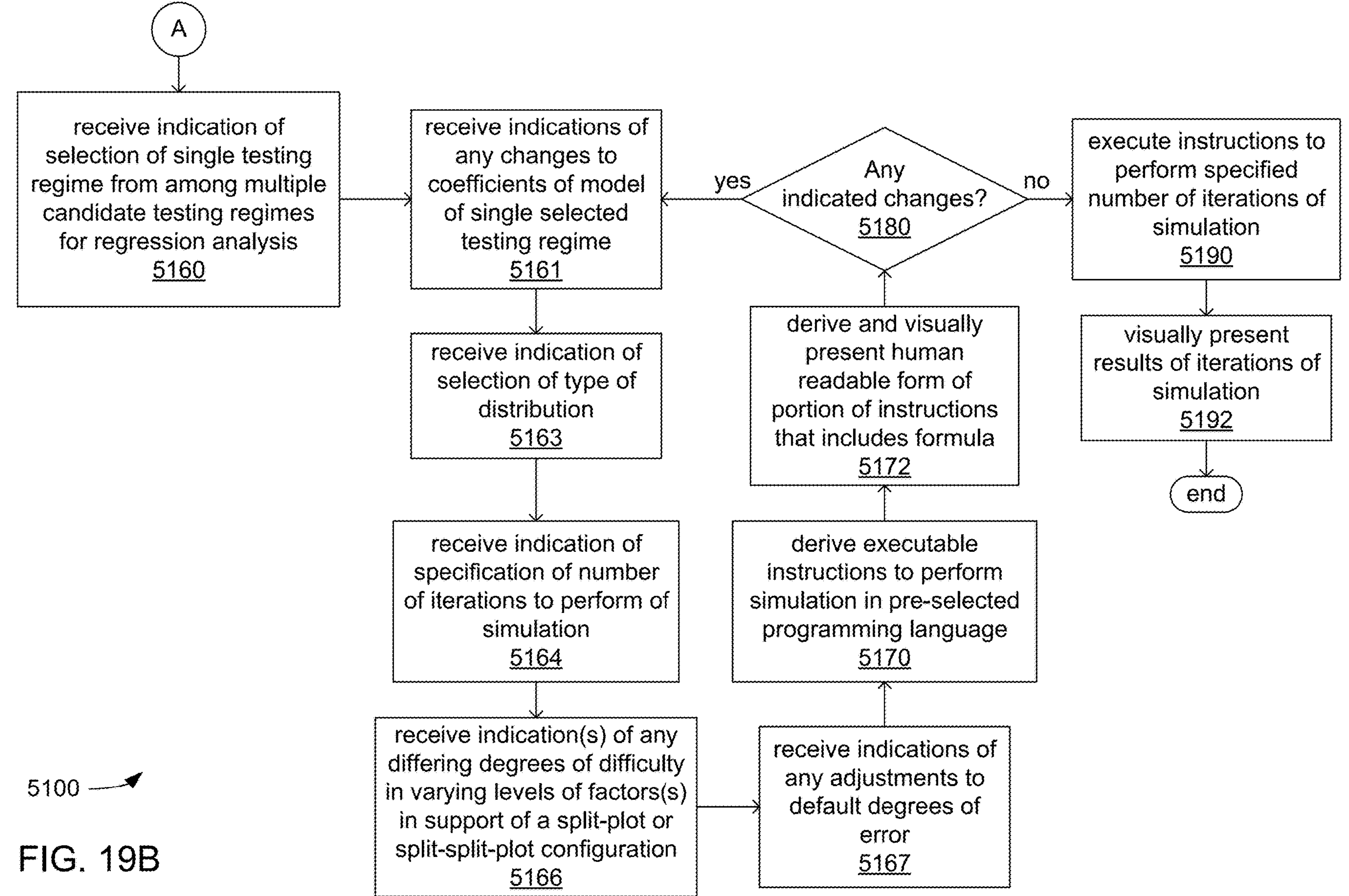
A
receive indication of selection of single testing regime from among multiple candidate testing regimes for regression analysis 5160
receive indications of any changes to coefficients of model of single selected testing regime 5161
receive indication of selection of type of distribution 5163
receive indication of specification of number of iterations to perform of simulation 5164
receive indication(s) of any differing degrees of difficulty in varying levels of factors(s) in support of a split-plot or split-split-plot configuration 5166
receive indications of any adjustments to default degrees of error 5167
derive executable instructions to perform simulation in pre-selected programming language 5170
derive and visually present human readable form of portion of instructions that includes formula 5172
Any indicated changes? 5180
yes
no
execute instructions to perform specified number of iterations of simulation 5190
visually present results of iterations of simulation 5192
end
5100
FIG. 19B

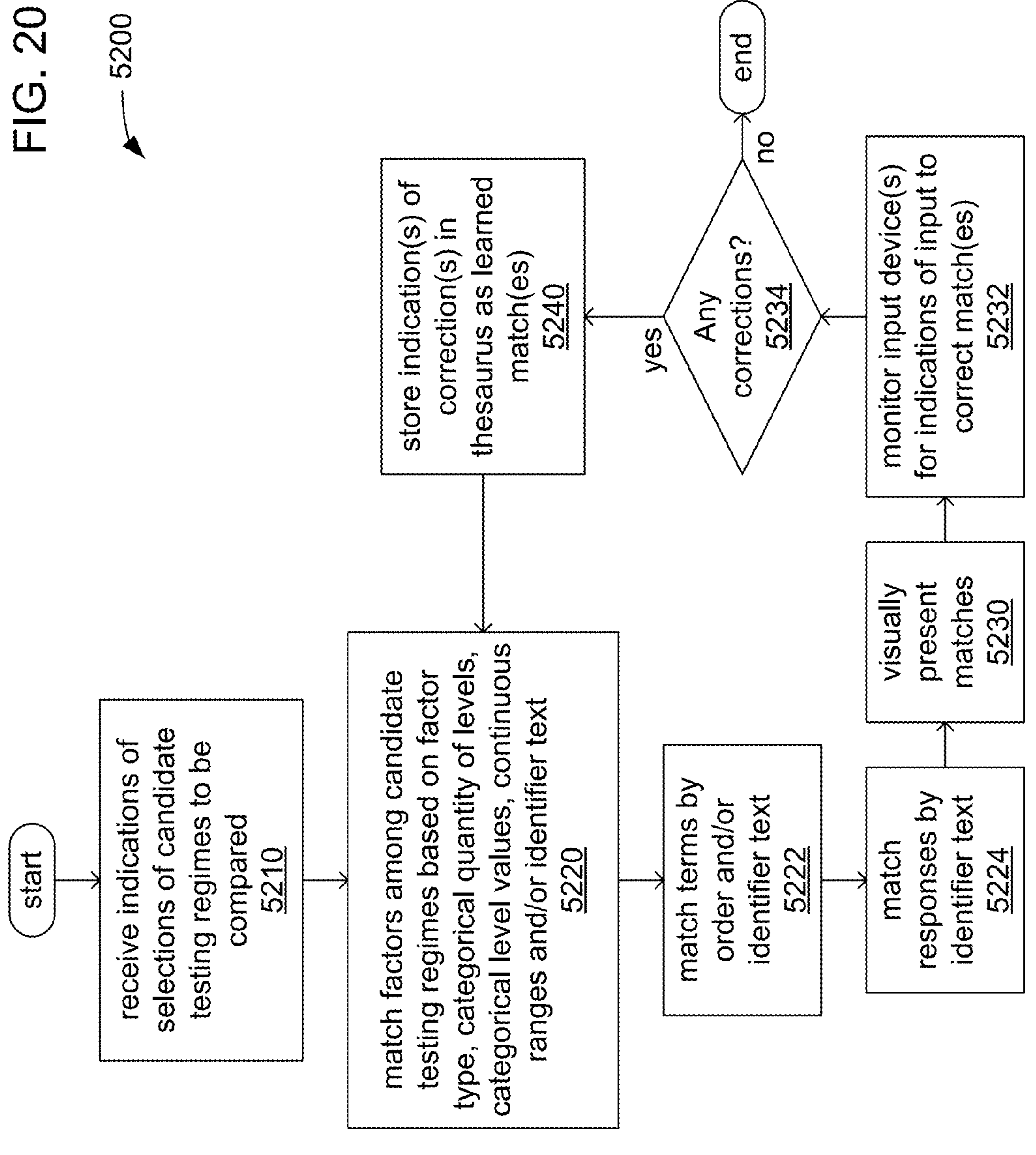
FIG. 20
5200
start
receive indications of selections of candidate testing regimes to be compared
5210
match factors among candidate testing regimes based on factor type, categorical quantity of levels, categorical level values, continuous ranges and/or identifier text
5220
match terms by order and/or identifier text
5222
match responses by identifier text
5224
visually present matches
5230
monitor input device(s) for indications of input to correct match(es)
5232
Any corrections?
5234
yes
no
store indication(s) of correction(s) in thesaurus as learned match(es)
5240
end

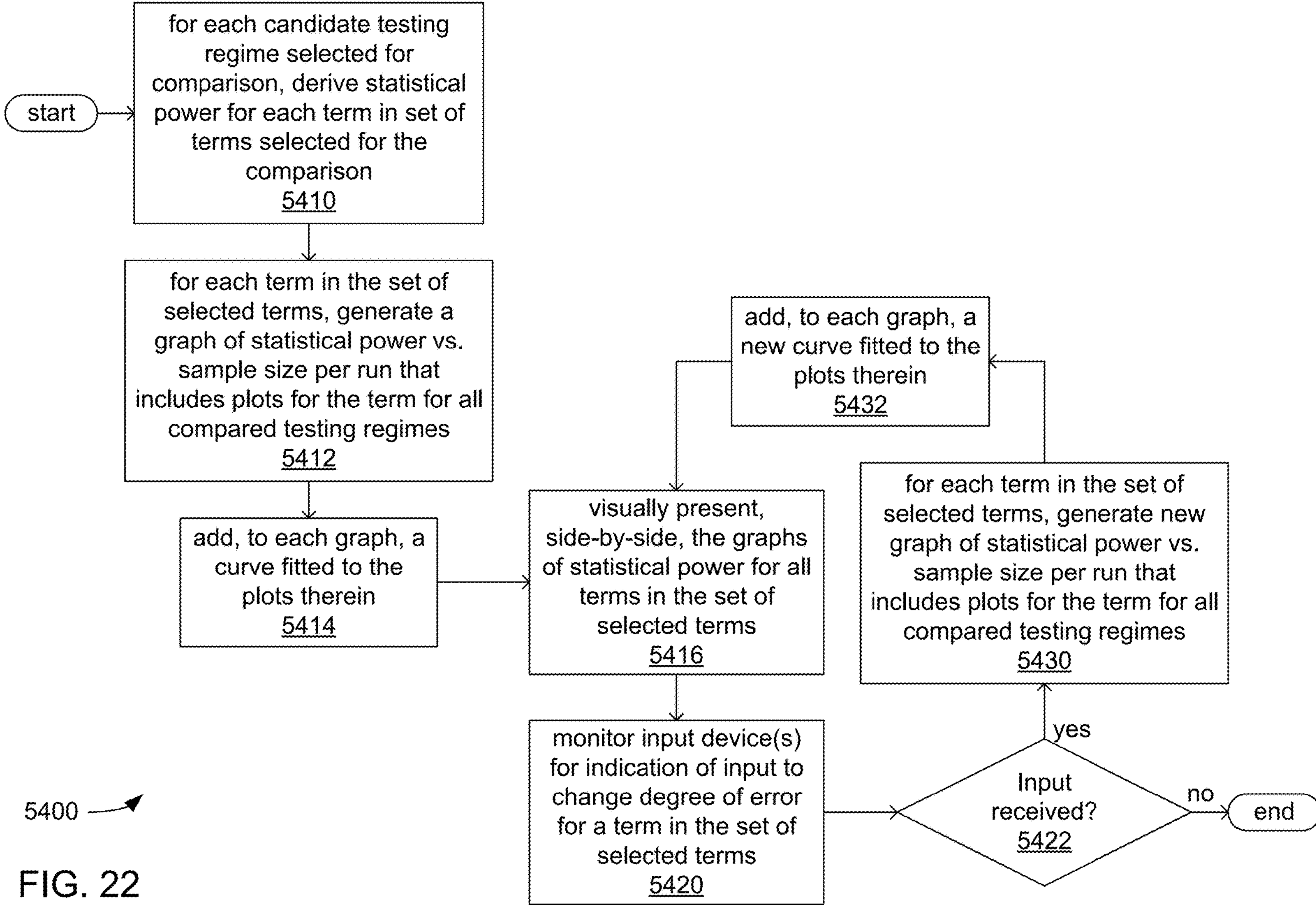
start
for each candidate testing regime selected for comparison, derive statistical power for each term in set of terms selected for the comparison
5410
for each term in the set of selected terms, generate a graph of statistical power vs. sample size per run that includes plots for the term for all compared testing regimes
5412
add, to each graph, a curve fitted to the plots therein
5414
visually present, side-by-side, the graphs of statistical power for all terms in the set of selected terms
5416
monitor input device(s) for indication of input to change degree of error for a term in the set of selected terms
5420
Input received?
5422
yes
no
end
for each term in the set of selected terms, generate new graph of statistical power vs. sample size per run that includes plots for the term for all compared testing regimes
5430
add, to each graph, a new curve fitted to the plots therein
5432
5400
FIG. 22

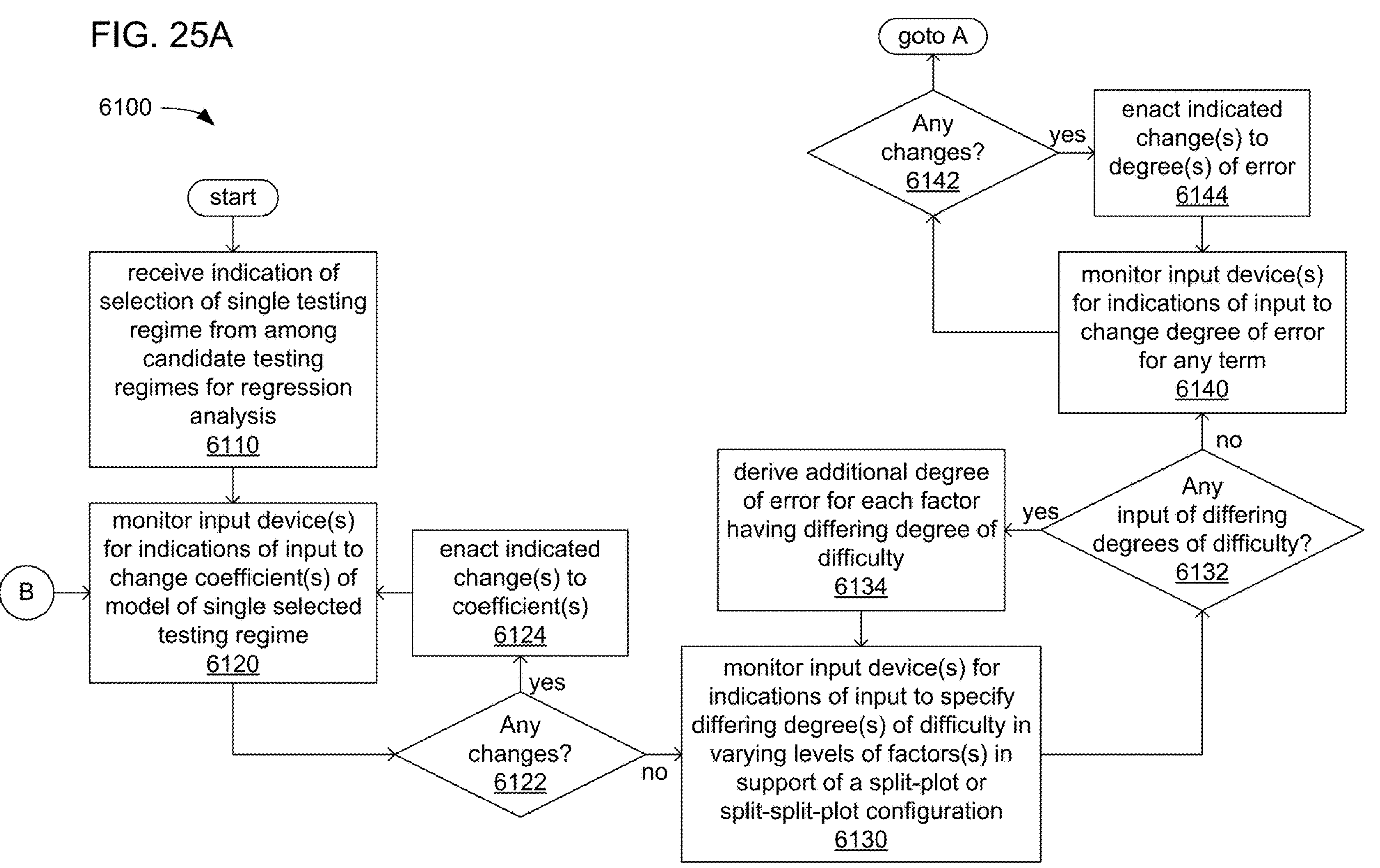
FIG. 25A
6100
start
receive indication of selection of single testing regime from among candidate testing regimes for regression analysis 6110
monitor input device(s) for indications of input to change coefficient(s) of model of single selected testing regime 6120
B
Any changes? 6122
yes
no
enact indicated change(s) to coefficient(s) 6124
monitor input device(s) for indications of input to specify differing degree(s) of difficulty in varying levels of factors(s) in support of a split-plot or split-split-plot configuration 6130
Any input of differing degrees of difficulty? 6132
yes
no
derive additional degree of error for each factor having differing degree of difficulty 6134
monitor input device(s) for indications of input to change degree of error for any term 6140
Any changes? 6142
yes
enact indicated change(s) to degree(s) of error 6144
goto A

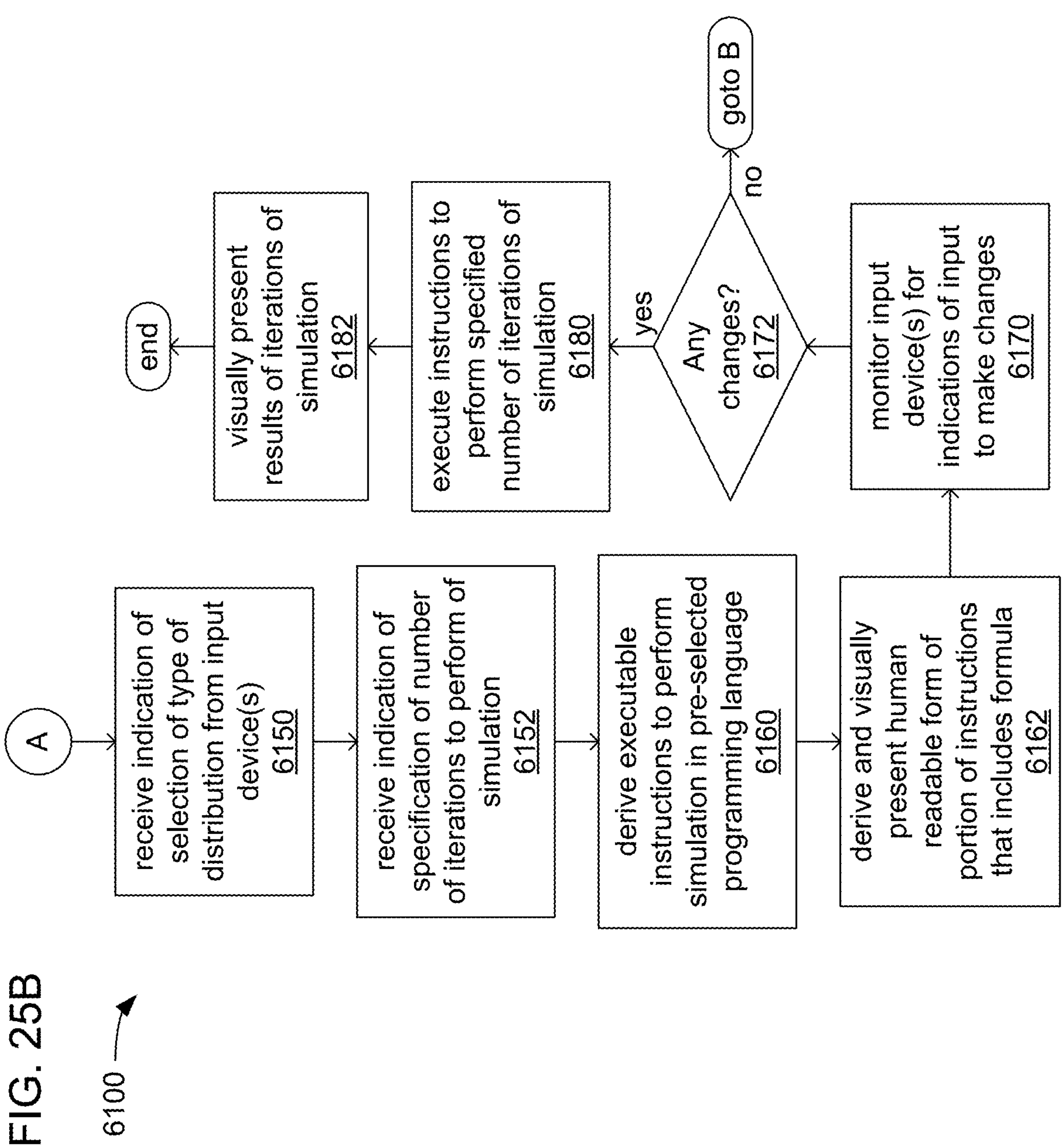
FIG. 25B
6100
A
receive indication of selection of type of distribution from input device(s) 6150
receive indication of specification of number of iterations to perform of simulation 6152
derive executable instructions to perform simulation in pre-selected programming language 6160
derive and visually present human readable form of portion of instructions that includes formula 6162
monitor input device(s) for indications of input to make changes 6170
Any changes? 6172
yes
no
goto B
execute instructions to perform specified number of iterations of simulation 6180
visually present results of iterations of simulation 6182
end

GUIDED TESTING REGIME GENERATION AND SELECTION

CROSS-REFERENCE TO RELATED APPLICATIONS

This application claims the benefit of priority under 35 U.S.C. § 119(e) to U.S. Provisional Application Ser. No. 63/755,845 filed Feb. 7, 2025, and to U.S. Provisional Application Ser. No. 63/768,469 filed Mar. 7, 2025; the entirety of each of which is incorporated herein by reference.

BACKGROUND

It has become increasingly commonplace to use testing regimes as a tool to analyze and arrive at models of complex systems in an effort to identify inputs (commonly referred to as "factors") that explain observed outputs (commonly referred to as "responses"), especially where there is a need to change undesired responses. However, the derivation of a model that provides an understanding of a complex system that is sufficient to explain a linkage between particular factors and particular responses is often a time-consuming task. Particular types of models are often closely associated with a particular types of test, and efforts to confirm whether a correct type of model has been selected often entail having to perform multiple runs of the associated type of test.

Thus, it is often necessary to suffer through a wasteful trial-and-error process in which best efforts to select a type of model that is believed to be capable of providing such a sufficient understanding of a system leads to a choice of a type of test that is later found to be undesirably ineffective in illuminating a linkage between particular factor(s) and response(s). Upon discovery of such deficiencies with one combination of model type and associated test type, another model type and associated test type must be selected and tried. Thus, there may be multiple iterations of selection of a type of model followed by the revelation of the need to make another selection only after an expenditure of considerable time to perform the associated type of test.

Even after the identification of a type of model and associated type of test that at least appears to be sufficiently capable of illuminating a linkage between particular factor(s) and response(s), additional considerable time may be consumed in iteratively deriving coefficients of the model and/or other parameters of the associated test type to derive a sufficiently useful combination of model type and associated test type. Also, practical limitations of cost, availability of materials and/or available time may impose the need to perform the associated test type in a less than technically ideal manner, and such impositions may need to be taken into account in deriving the model.

Hindering all of these efforts is often a lack of background among personnel in how to efficiently arrive at a model type and associated test type. It is not uncommon for such personnel to have some grasp of some aspects of how to do so, while having little or no grasp of other aspects.

SUMMARY

This summary is not intended to identify only key or essential features of the described subject matter, nor is it intended to be used in isolation to determine the scope of the described subject matter. The subject matter should be understood by reference to appropriate portions of the entire specification of this patent, any or all drawings, and each claim.

An apparatus includes at least one processor and a storage to store instructions that, when executed by the at least one processor, cause the at least one processor to perform operations including generate, for visual presentation on a display communicatively coupled to the at least one processor, a prompt for selection of a first pathway of prompts for parameter values of a testing regime to traverse from among a set of pathways including: a test-focused pathway including initial prompts for initial parameter values for test-related parameters of the testing regime, and subsequent prompts for subsequent parameter values for at least one of model-related parameters of a model associated with the testing regime of a system under evaluation, or term-related parameters of terms and responses of the model; a model-focused pathway including initial prompts for initial parameter values for the model-related parameters, and subsequent prompts for subsequent parameter values for at least one of the test-related parameters or the term-related parameters; and a term-focused pathway including initial prompts for initial parameter values for the term-related parameters, and subsequent prompts for subsequent parameter values for at least one of the test-related parameters or the model-related parameters. The at least one processor is further caused to perform operations including: receive, from an input device communicatively coupled to the at least one processor, an indication of the selection of the first pathway to traverse, and in response to the selection of the first pathway, perform operations associated with traversing the first pathway, the operations associated with traversing the first pathway including: visually present, on the display, the initial prompts of the first pathway, followed by the subsequent prompts of the first pathway; and receive, from the input device, at least one indication of specification of an initial parameter value of the first pathway or a subsequent parameter value of the first pathway. The at least one processor is still further caused to perform operations including: in response to completion of the traversal of the first pathway, generate, for visual presentation on the display, a prompt for selection of a second pathway to traverse from among the set of pathways, wherein the second pathway includes a different one of the pathways of the set of pathways from the first pathway; receive, from the input device, an indication of the selection of the second pathway to traverse; and in response to the selection of the second pathway, perform operations associated with traversing the second pathway.

A computer-program product tangibly embodied in a non-transitory machine-readable storage medium includes instructions operable to cause at least one processor to perform operations including generate, for visual presentation on a display communicatively coupled to the at least one processor, a prompt for selection of a first pathway of prompts for parameter values of a testing regime to traverse from among a set of pathways including: a test-focused pathway including initial prompts for initial parameter values for test-related parameters of the testing regime, and subsequent prompts for subsequent parameter values for at least one of model-related parameters of a model associated with the testing regime of a system under evaluation, or term-related parameters of terms and responses of the model; a model-focused pathway including initial prompts for initial parameter values for the model-related parameters, and subsequent prompts for subsequent parameter values for at least one of the test-related parameters or the term-related parameters; and a term-focused pathway including initial prompts for initial parameter values for the term-related parameters, and subsequent prompts for subsequent parameter values for at least one of the test-related parameters or the model-related parameters. The at least one processor is further caused to perform operations including: receive, from an input device communicatively coupled to the at least one processor, an indication of the selection of the first pathway to traverse, and in response to the selection of the first pathway, perform operations associated with traversing the first pathway, the operations associated with traversing the first pathway including: visually present, on the display, the initial prompts of the first pathway, followed by the subsequent prompts of the first pathway; and receive, from the input device, at least one indication of specification of an initial parameter value of the first pathway or a subsequent parameter value of the first pathway. The at least one processor is still further caused to perform operations including: in response to completion of the traversal of the first pathway, generate, for visual presentation on the display, a prompt for selection of a second pathway to traverse from among the set of pathways, wherein the second pathway includes a different one of the pathways of the set of pathways from the first pathway; receive, from the input device, an indication of the selection of the second pathway to traverse; and in response to the selection of the second pathway, perform operations associated with traversing the second pathway.

The operations associated with traversing the first pathway may include determining whether a parameter of one of the subsequent prompts of the first pathway is inapplicable based on the indication, received from the input device, of specification of the initial parameter value or the subsequent parameter value of the first pathway; and visually presenting, on the display, the initial prompts of the first pathway, followed by the subsequent prompts of the first pathway may include presenting the parameter within the one of the subsequent prompts or refraining from presenting the parameter within the one of the subsequent prompts based on the determination of whether the parameter of the one of the subsequent prompts is inapplicable.

At a time prior to receiving the indication of the selection of the first pathway to traverse, the at least one processor may be caused to perform further operations including: visually present, on the display, a prompt for selection of either default parameter values or parameter values of an earlier-generated testing regime to serve as a starting point for the test-related parameters, the model-related parameters and the term-related parameters, wherein at least one parameter value of the default parameter values includes a null value indicative of a lack of specification of the at least one parameter value, and the at least one parameter value includes the null value indicative of a lack of selection of a test type; receive, from the input device, an indication of the selection of either the default parameter values or the parameter values of the earlier-generated testing regime; and based on the indication of the selection, retrieve, from a storage communicatively coupled to the at least one processor, either the default parameter values or the parameter values of the earlier-generated testing regime.

Visually presenting, on the display, the initial prompts of the first pathway, followed by the subsequent prompts of the first pathway may include visually presenting at least one parameter value of either the default parameter values or the parameter values of the earlier-generated testing regime within at least one prompt of the initial prompts or of the subsequent prompts of the first pathway; and receiving, from the input device, the at least one indication of specification of an initial parameter value of the first pathway or a subsequent parameter value of the first pathway may include receiving an indication of use of a navigation control of the first pathway to move past an initial prompt of the first pathway, and interpreting the indication of the use of the navigation control to move past the initial prompt as an indication of acceptance of a parameter value visually presented within the initial prompt as the initial parameter value.

The operations associated with traversing the first pathway may further include: in response to each received indication, of the at least one indication, of the specification of an initial parameter value or a subsequent parameter value of the first pathway, compare the subsequent parameter values to the initial parameter values to determine whether there is an incompatibility between at least one subsequent parameter value and at least one initial parameter value of the first pathway; and in response to there being an incompatibility between at least one subsequent parameter value and at least one initial parameter value of the first pathway, visually present an indication of the incompatibility on the display.

The operations associated with traversing the first pathway may further include: in response to each received indication, of the at least one indication, of the specification of an initial parameter value or a subsequent parameter value of the first pathway, compare at least one of the test-related parameter values, the model-related parameter values or the term-related parameter values of the testing regime to parameter values required for each test type of a set of test types to identify a subset of test types among the set of test types that are compatible with the at least one of the test-related parameter values, the model-related parameter values or the term-related parameter values; and in response to the subset of test types including at least one test type, visually present an indication of the subset of test types on the display.

Visually presenting the indication of the subset of test types may include, prior to visually presenting the indication of the subset of test types, arrange the test types within the subset of test types to follow a predetermined order of preference of test types.

Each pathway of the set of pathways may be associated with a separate predetermined order of preference of test types.

Visually presenting the indication of the subset of test types may include performing operations including analyze the test-related parameter values of the testing regime to determine whether a test type of the testing regime has already been specified and, in response to a test type having already been specified, perform operations including: compare the already specified test type to the predetermined order of preference of test types to determine a degree of preference of each test type of the subset of test types relative to the already specified test type; and remove, from the subset of test types, each test type within the subset of test types that has a lesser degree of preference than the already specified test type.

The operations associated with traversing the second pathway may include: visually present, on the display, the initial prompts of the second pathway, followed by the subsequent prompts of the second pathway, wherein visually presenting, on the display, the initial prompts of the second pathway, followed by the subsequent prompts of the second pathway includes visually presenting at least one parameter value of the testing regime from the input device during the traversal of the first pathway within at least one prompt of the initial prompts or of the subsequent prompts of the second pathway; and receive, from the input device, at least one indication of specification of an initial parameter value of the second pathway or a subsequent parameter value of the second pathway.

A computer-implemented method includes generating, by at least one processor, and for visual presentation on a display communicatively coupled to the at least one processor, a prompt for selection of a first pathway of prompts for parameter values of a testing regime to traverse from among a set of pathways including: a test-focused pathway including initial prompts for initial parameter values for test-related parameters of the testing regime, and subsequent prompts for subsequent parameter values for at least one of model-related parameters of a model associated with the testing regime of a system under evaluation, or term-related parameters of terms and responses of the model; a model-focused pathway including initial prompts for initial parameter values for the model-related parameters, and subsequent prompts for subsequent parameter values for at least one of the test-related parameters or the term-related parameters; and a term-focused pathway including initial prompts for initial parameter values for the term-related parameters, and subsequent prompts for subsequent parameter values for at least one of the test-related parameters or the model-related parameters. The method further includes: receiving, at the at least one processor, and from an input device communicatively coupled to the at least one processor, an indication of the selection of the first pathway to traverse; and in response to the selection of the first pathway, performing, by the at least one processor, operations associated with traversing the first pathway, the operations associated with traversing the first pathway including visually presenting, on the display, the initial prompts of the first pathway, followed by the subsequent prompts of the first pathway, and receiving, from the input device, at least one indication of specification of an initial parameter value of the first pathway or a subsequent parameter value of the first pathway. The method still further includes: in response to the completion of the traversal of the first pathway, generating, by the at least one processor, and for visual presentation on the display, a prompt for selection of a second pathway to traverse from among the set of pathways, wherein the second pathway includes a different one of the pathways of the set of pathways from the first pathway; receiving, at the at least one processor, and from the input device, an indication of the selection of the second pathway to traverse; and in response to the selection of the second pathway, performing, by the at least one processor, operations associated with traversing the second pathway.

The operations associated with traversing the first pathway may include, determine whether a parameter of one of the subsequent prompts of the first pathway is inapplicable based on the indication, received from the input device, of specification of the initial parameter value or the subsequent parameter value of the first pathway; and visually presenting, on the display, the initial prompts of the first pathway, followed by the subsequent prompts of the first pathway may include presenting the parameter within the one of the subsequent prompts or refraining from presenting the parameter within the one of the subsequent prompts based on the determination of whether the parameter of the one of the subsequent prompts is inapplicable.

The method may further include, at a time prior to receiving the indication of the selection of the first pathway to traverse, performing, by the at least one processor, further operations including: visually presenting, on the display, a prompt for selection of either default parameter values or parameter values of an earlier-generated testing regime to serve as a starting point for the test-related parameters, the model-related parameters and the term-related parameters, wherein at least one parameter value of the default parameter values includes a null value indicative of a lack of specification of the at least one parameter value, and the at least one parameter value includes the null value indicative of a lack of selection of a test type; receiving, from the input device, an indication of the selection of either the default parameter values or the parameter values of the earlier-generated testing regime; and based on the indication of the selection, retrieving, from a storage communicatively coupled to the at least one processor, either the default parameter values or the parameter values of the earlier-generated testing regime.

Visually presenting, by the at least one processor, and on the display, the initial prompts of the first pathway, followed by the subsequent prompts of the first pathway may include visually presenting at least one parameter value of either the default parameter values or the parameter values of the earlier-generated testing regime within at least one prompt of the initial prompts or of the subsequent prompts of the first pathway; and receiving, by the at least one processor, and from the input device, the at least one indication of specification of an initial parameter value of the first pathway or a subsequent parameter value of the first pathway may include receiving an indication of use of a navigation control of the first pathway to move past an initial prompt of the first pathway, and interpreting the indication of the use of the navigation control to move past the initial prompt as an indication of acceptance of a parameter value visually presented within the initial prompt as the initial parameter value.

The operations associated with traversing the first pathway may further include: in response to each received indication, of the at least one indication, of the specification of an initial parameter value or a subsequent parameter value of the first pathway, comparing, by the at least one processor, the subsequent parameter values to the initial parameter values to determine whether there is an incompatibility between at least one subsequent parameter value and at least one initial parameter value of the first pathway; and in response to there being an incompatibility between at least one subsequent parameter value and at least one initial parameter value of the first pathway, visually presenting, by the at least one processor, an indication of the incompatibility on the display.

The operations associated with traversing the first pathway further include: in response to each received indication, of the at least one indication, of the specification of an initial parameter value or a subsequent parameter value of the first pathway, comparing, by the at least one processor, at least one of the test-related parameter values, the model-related parameter values or the term-related parameter values of the testing regime to parameter values required for each test type of a set of test types to identify a subset of test types among the set of test types that are compatible with the at least one of the test-related parameter values, the model-related parameter values or the term-related parameter values; and in response to the subset of test types including at least one test type, visually presenting, by the at least one processor, an indication of the subset of test types on the display.

Visually presenting the indication of the subset of test types may include, prior to visually presenting the indication of the subset of test types, arranging, by the at least one processor, the test types within the subset of test types to follow a predetermined order of preference of test types.

Each pathway of the set of pathways may be associated with a separate predetermined order of preference of the test types.

Visually presenting the indication of the subset of test types may include, prior to visually presenting the indication of the subset of test types, performing, by the at least one processor, operations including: analyzing the test-related parameter values of the testing regime to determine whether a test type of the testing regime has already been specified; and in response to a test type having already been specified, performing, by the at least one processor, operations including comparing the already specified test type to the predetermined order of preference of test types to determine a degree of preference of each test type of the subset of test types relative to the already specified test type, and removing, from the subset of test types, each test type within the subset of test types that has a lesser degree of preference than the already specified test type.

The operations associated with traversing the second pathway may include: visually presenting, by the at least one processor, and on the display, the initial prompts of the second pathway, followed by the subsequent prompts of the second pathway, wherein visually presenting, on the display, the initial prompts of the second pathway, followed by the subsequent prompts of the second pathway includes visually presenting at least one parameter value of the testing regime from the input device during the traversal of the first pathway within at least one prompt of the initial prompts or of the subsequent prompts of the second pathway; and receiving, at the at least one processor, and from the input device, at least one indication of specification of an initial parameter value of the second pathway or a subsequent parameter value of the second pathway.

The foregoing, together with other features and embodiments, will become more apparent upon referring to the following specification, claims, and accompanying drawings.

BRIEF DESCRIPTION OF THE DRAWINGS

The present disclosure is described in conjunction with the appended figures:

FIGS. 9A, 9B, 9C, 9D, 9E and 9F, together, illustrate examples of guiding the generation and/or editing of a testing regime with a GUI providing multiple pathways of different sets and/or ordering of prompts.

FIGS. 10A, 10B, 10C, 10D, 10E, 10F, 10G, 10H and 10I, together, illustrate an example term-focused pathway of the multiple pathways of FIGS. 9A-C.

FIGS. 11A, 11B, 11C, 11D, 11E, 11F, 11G and 11H, together, illustrate an example term-focused pathway of the multiple pathways of FIGS. 9A-C.

FIGS. 12A, 12B, 12C, 12D, 12E, 12F and 12G, together, illustrate an example term-focused pathway of the multiple pathways of FIGS. 9A-C.

FIGS. 14A, 14B, 14C, 14D, 14E and 14F, together, illustrate additional details of the guiding the comparison of candidate testing regimes as per FIG. 13.

FIGS. 16A, 16B, 16C, 16D and 16E, together, illustrate additional details of the guidance of performance of the regression analysis of FIG. 15.

FIG. 17A, 17B, 17C, 17D, 17E and 17F, together, illustrate an example embodiment of a logic flow of guiding generation of a testing regime.

FIGS. 18A, 18B, 18C, 18D, 18E, 18F, 18G and 18H, together illustrate another example embodiment of a logic flow of guiding generation of a testing regime.

FIGS. 19A and 19B, together, illustrate an example embodiment of a logic flow of guiding comparison, selection and performances of regression analyses with testing regimes.

FIG. 20 illustrates an example embodiment of a logic flow of matching factors among testing regimes in the guidance of selection of a testing regime.

FIG. 22 illustrates an example embodiment of a logic flow of deriving and presenting statistical power in the guidance of selection of a testing regime.

FIGS. 25A and 25B, together, illustrate an example embodiment of a logic flow of the guidance of performance of a regression analysis.

DETAILED DESCRIPTION

Figure 1:
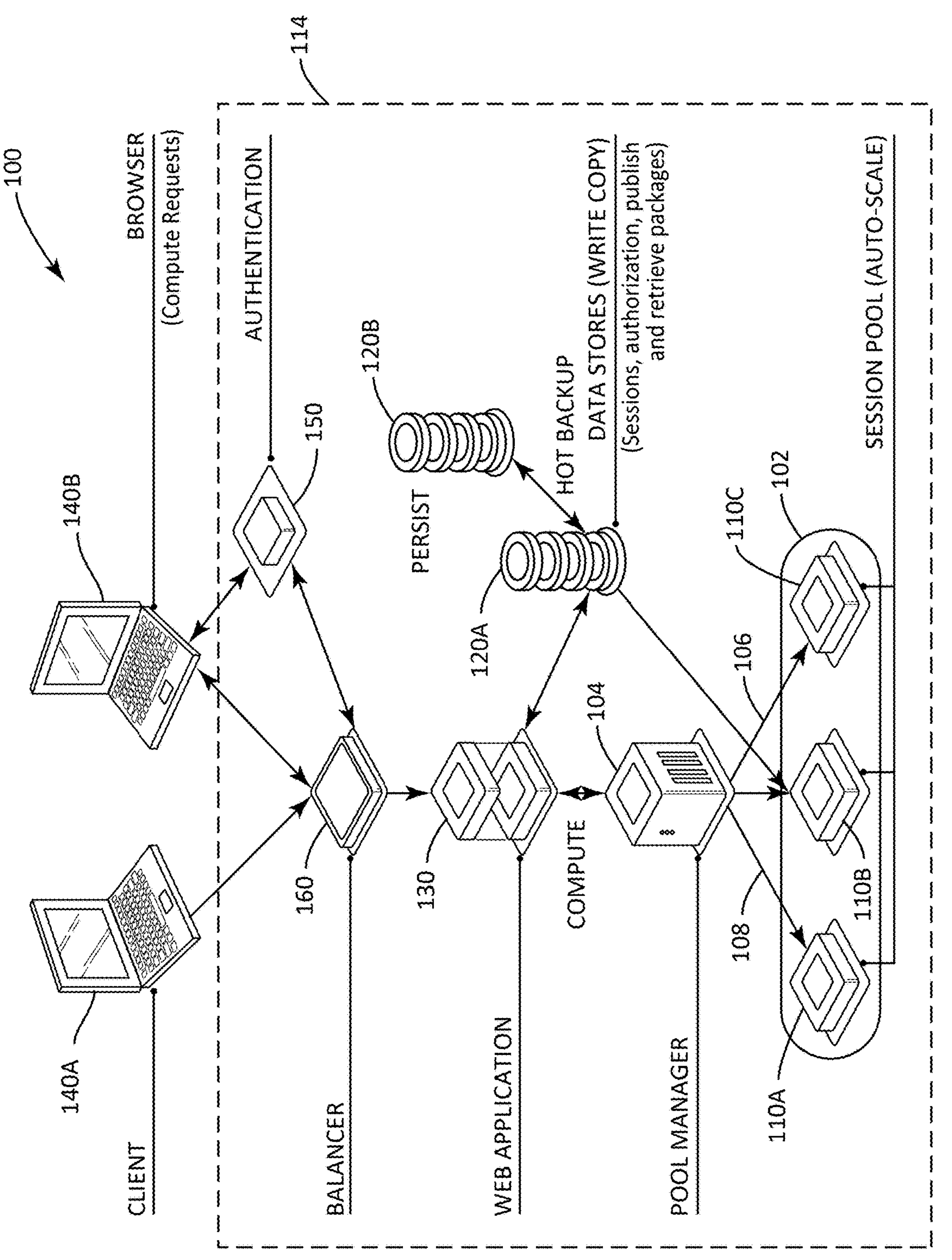
FIG. 1 illustrates an example network including an example set of devices communicating with each other according to some embodiments of present technology.

Various embodiments described herein are generally directed to techniques for guiding and automating various aspects of generating a testing regime by guiding the selection of a model type and associated test type for use in testing a model of a system being studied, as well as the generation of a testing script for execution to perform such testing. More precisely, a generation routine is provided that causes processor(s) to provide an interactive graphical user interface (GUI) that serves to guide the generation of one or more candidate testing regimes. Such a GUI may provide multiple differing pathways. Each such pathway may accommodate different personnel by providing a set of prompts organized in a particular order to enable those personnel to begin with providing testing regime parameters that they are more familiar with, before moving on to providing and/or being guided to testing regime parameters that they are less familiar with.

The variety of studied systems to which these techniques may be applied may include, and not limited to, chemical processes, sub-atomic particle interactions, biomechanical and/or biochemical systems, geological systems, meteorological systems, manufacturing systems, electrical and/or optical networks, group egress behaviors in response to fire emergencies in public spaces, etc. The impetus to apply these techniques may be the observation of one or more undesired responses of a studied system leading to a desire to identify the one or more factors of the studied system that are linked to those undesired response(s). Alternatively or additionally, the impetus may include the desire to derive changes to make to the identified factor(s) that may bring about more desirable responses from the studied system. However, as will be familiar to those skilled in the art, such systems are typically highly complex such that they defy efforts at understanding or addressing undesirable response(s) through intuitive ad hoc trial-and-error experimentation. By way of example, there may simply be too many factors and/or responses to consider, such that the quantity of observation data may be too large to make such unsystematic experimentation practical.

In a distributed processing system that may be employed to generate, refine, analyze, compare and/or perform a testing regime, one or more data devices may store a data set made up of observation data representing captured values of factors and corresponding responses of a studied system. In some embodiments, the one or more data devices may be co-located with and/or directly coupled to the studied system to capture such observation data (e.g., located at a facility to capture observation data from a chemical or manufacturing process that is performed at that facility). In such embodiments, the one or more data devices may incorporate measuring device(s) that may directly capture observation data to thereby generate the stored data set. In other embodiments, the one or more data devices may be storage devices employed to store the data set and/or other information related to the studied system and/or to testing regimes that may be used in developing an understanding of the studied system. In such other embodiments, the one or more data devices may recurringly receive and aggregate observation data that may be captured and transmitted to the one or more data devices by one or more remotely located measuring devices (e.g., measuring devices distributed among medical facilities to capture biomechanical or biochemical data of patients undergoing treatment in a medical study).

A coordinating device of the distributed processing system may provide an interactive generation GUI by which an operator may guided through generating a new testing regime through the manual input of parameters that define it. More specifically, the coordinating device may provide a menu-based and/or step-wise guided generation GUI that enables an operator to specify term-related, model-related and/or test-related parameters of a testing regime. In so doing, the coordinating may provide the operator with a choice of multiple different pathways of prompts by which such guidance is provided, starting with the parameters of a testing regime that the operator may be most familiar and comfortable with. In some embodiments, there may be three of such pathways: 1) a term-focused pathway in which the operator is first guided by initial term-related prompts to provide term-related parameters before being guided by subsequent model-related and/or test-related prompts to provide such other parameters; 2) a model-focused pathway in which the operator is first guided by initial model-related prompts to provide model-related parameters before being guided by subsequent term-related and/or test-related prompts to provide such other parameters; and 3) a test-focused pathway in which the operator is first guided by initial test-related prompts to provide test-related parameters before being guided by subsequent term-related and/or model-related prompts to provide such other parameters.

Following the provision and use of such a generation GUI to generate one or more testing regimes, a comparison GUI may then be provided to guide the operator through evaluating different candidate testing regimes that they may have generated and/or that they may be provided from other sources. More specifically, the coordinating device may provide a comparison GUI by which an operator may be guided through various comparisons of aspects of two or more candidate testing regimes (in situations in which there are multiple candidate testing regimes) to enable the operator to select one of the candidate testing regimes to become the single testing regime that is to be used. The operator may be visually guided through providing various parameters for use in performing the comparisons, including and not limited to, selections of two or more candidate testing regimes to be compared, corrections to one or more automatically derived matches between factors and/or terms of the compared testing regimes, selections of terms and/or responses to be included in the comparisons, signal-to-noise ratios that the selected terms are expected to be subject to, and/or degree(s) of error that the selected terms are expected to be subject to.

During and/or following the provision of such parameters, the operator may be visually presented, via the comparison GUI, with various graphs and/or other visualizations depicting comparisons between aspects of each of the candidate testing regimes. In so doing, graphs and/or other visualizations depicting corresponding aspects of different ones of the candidate testing regimes may be presented at adjacent locations on a display in a manner that advantageously utilizes features of the HVS to enable speedy recognition of degrees of similarity therebetween. More specifically, such graphs and/or other visualizations may be positioned adjacent to each other in a horizontal side-by-side manner that utilizes the generally horizontal binocular placement of the eyes that imparts the typical "landscape" orientation to the field of view (FOV) of the human visual system (HVS). Such visual presentations may be interactive in nature such that depicted numerical values in such visual presentations are dynamically re-derived in response to each new input by an operator to select, specify and/or change a parameter.

The coordinating device may provide yet another interactive GUI by which an operator may be presented with aspects of the manner in which simulated data may be randomly generated during a regression analysis to determine one or more aspects of the model associated with the selected testing regime, such as coefficients and/or statistical power. The operator may be visually guided, via such a regression GUI, through providing various parameters for use in the regression analysis, including and not limited to, values for one or more coefficients and/or changes thereto, degree(s) of difficulty in varying levels of one or more factors, degree(s) of error that one or more terms are expected to be subject to and/or changes thereto, selection of a type of distribution of simulated data to be randomly generated, and/or a number of iterations to perform of the regression analysis and accompanying generation of simulated data.

During and/or following the provision of such parameters, the coordinating device may generate and/or repeatedly regenerate a set of instructions that are executable by one or more processors and/or processor cores to perform the regression analysis and accompanying generation of simulated data. Following such generation or regeneration, the operator may be visually presented, via the regression GUI, with a human readable form of a portion of the executable instructions that includes the presentation of the model in the form of a formula that includes the coefficients and terms, as well as human readable expressions of aspects of randomly generating the simulated data. In situations in which different degrees of difficulty in varying the levels of one or more factors have been specified, such that a split-plot or split-split-plot configuration is thereby specified, the formula visually presented by the regression GUI may include portions separated by bracketing that separately specify the factors for which the varying the levels is more difficult, as well as explicit expressions of the manner in which the varying of levels for those factors are to be minimized (such that the quantity of transitions between levels are minimized for those factors) during generation of the simulated data.

In some embodiments, the generation GUI, the comparison GUI and/or the regression GUI may be visually presented on a display incorporated into or otherwise connected to the coordinating device. Also, one or more input devices, such as a keyboard and/or pointing device, may be monitored for receive inputs from an operator in response to the prompting by one or more of these GUIs, where the one or more input devices may also be incorporated into or otherwise connected to the coordinating device. However, in other embodiments, the display and/or the one or more input devices may be incorporated into and/or otherwise connected to a separate viewing device of the distributed system, thereby enabling a form of remote interaction by the operator with the coordinating device.

In some embodiments, the distributed processing system may incorporate a grid of node devices among which the specified iterations of performances of the regression analysis and associated generation of simulated data may be distributed. More precisely, the coordinating device may distribute the executable instructions for performing the regression analysis, including the random generation of simulated data, among such a grid of node devices. The coordinating device may then coordinate an at least partially parallel performance of the iterations of the regression analysis by the grid of node devices, and aggregate the results thereof. In other embodiments, the coordinating device may, itself, incorporate one or more processors and/or processor cores among which the executable instructions for performing the regression analysis, including the random generation of simulated data, may be distributed. Following such distribution, the coordinating device may then coordinate an at least partially parallel performance of the iterations of the regression analysis by those processors and/or processor cores.

In some embodiments, following the performance of the regression analysis and accompanying generation of simulated data, the distributed processing system may directly perform the selected testing regime. As previously discussed, it may be that the one or more data devices may be co-located with the studied system. In some of such embodiments, the one or more data devices may be capable of controlling the studied system, and therefore, may be capable of actually performing the selected testing regime by directly varying the factors provided to the studied system and capturing the resulting responses thereof. In some of such embodiments, the coordinating device may transmit a testing script and/or other information to the one or more data devices as part of enabling the one or more data devices to perform the testing regime with the studied system.

With general reference to notations and nomenclature used herein, portions of the detailed description that follows may be presented in terms of program procedures executed by a processor of a machine or of multiple networked machines. These procedural descriptions and representations are used by those skilled in the art to most effectively convey the substance of their work to others skilled in the art. A procedure is here, and generally, conceived to be a self-consistent sequence of operations leading to a desired result. These operations are those requiring physical manipulations of physical quantities. Usually, though not necessarily, these quantities take the form of electrical, magnetic or optical communications capable of being stored, transferred, combined, compared, and otherwise manipulated. It proves convenient at times, principally for reasons of common usage, to refer to what is communicated as bits, values, elements, symbols, characters, terms, numbers, or the like. It should be noted, however, that all of these and similar terms are to be associated with the appropriate physical quantities and are merely convenient labels applied to those quantities.

Further, these manipulations are often referred to in terms, such as adding or comparing, which are commonly associated with mental operations performed by a human operator. However, no such capability of a human operator is necessary, or desirable in most cases, in any of the operations described herein that form part of one or more embodiments. Rather, these operations are machine operations. Useful machines for performing operations of various embodiments include machines selectively activated or configured by a routine stored within that is written in accordance with the teachings herein, and/or include apparatus specially constructed for the required purpose. Various embodiments also relate to apparatus or systems for performing these operations. These apparatus may be specially constructed for the required purpose or may include a general purpose computer. The required structure for a variety of these machines will appear from the description given.

Reference is now made to the drawings, wherein like reference numerals are used to refer to like elements throughout. In the following description, for purposes of explanation, numerous specific details are set forth in order to provide a thorough understanding thereof. It may be evident, however, that the novel embodiments can be practiced without these specific details. In other instances, well known structures and devices are shown in block diagram form in order to facilitate a description thereof. The intention is to cover all modifications, equivalents, and alternatives within the scope of the claims.

Systems depicted in some of the figures may be provided in various configurations. In some embodiments, the systems may be configured as a distributed system where one or more components of the system are distributed across one or more networks in a cloud computing system and/or a fog computing system.

In the following description, for the purposes of explanation, specific details are set forth in order to provide a thorough understanding of embodiments of the technology. However, it will be apparent that various embodiments may be practiced without these specific details. The figures and description are not intended to be restrictive.

The ensuing description provides example embodiments only, and is not intended to limit the scope, applicability, or configuration of the disclosure. Rather, the ensuing description of the example embodiments will provide those skilled in the art with an enabling description for implementing an example embodiment. It should be understood that various changes may be made in the function and arrangement of elements without departing from the spirit and scope of the technology as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed but could have additional operations not included in a figure. A process may correspond to a method, a function, a procedure, a subroutine, a subprogram, etc. When a process corresponds to a function, its termination can correspond to a return of the function to the calling function or the main function.

Systems depicted in some of the figures may be provided in various configurations. In some embodiments, the systems may be configured as a distributed system where one or more components of the system are distributed across one or more networks in a cloud computing system.

FIG. 1 illustrates an example network 100 including an example set of devices communicating with each other (e.g., over one or more of an exchange system or a network), according to embodiments of the present technology. Network 100 includes network devices configured to communicate with a variety of types of client devices, for example, client devices 140, over a variety of types of communication channels. A client device 140 may be configured to communicate over a public or private network (e.g., client device 140B is configured to support a browser for computing requests or providing authentication).

Network devices and client devices can transmit a communication over a network 100. Network 100 may include one or more of different types of networks, including a wireless network, a wired network, or a combination of a wired and wireless network. Examples of suitable networks include the Internet, a personal area network, a local area network (LAN), a wide area network (WAN), a wireless local area network (WLAN), cloud network, or a cellular network. A wireless network may include a wireless interface or combination of wireless interfaces. As an example, a network in the one or more networks may include a short-range communication channel, such as a Bluetooth or a Bluetooth Low Energy channel. A wired network may include a wired interface. The wired and/or wireless networks may be implemented using routers, access points, base stations, bridges, gateways, or the like, to connect devices in the network. The one or more networks can be incorporated entirely within or can include an intranet, an extranet, or a combination thereof. In one embodiment, communications between two or more systems and/or devices can be achieved by a secure communications protocol, such as secure sockets layer (SSL) or transport layer security (TLS), or other available protocols such as according to an Open Systems Interaction model. In addition, data and/or transactional details may be encrypted. Networks may include other devices for infrastructure for the network. For example, a cloud network may include cloud infrastructure system on demand. As another example, one or more client devices may utilize an Internet of Things (IoT) infrastructure where things (e.g., machines, devices, phones, sensors) can be connected to networks and the data from these things can be collected and processed within the things and/or external to the things. IoT may be implemented with various infrastructure such as for accessibility (technologies that get data and move it), embed-ability (devices with embedded sensors), and IoT services. Industries in the IoT space may include automotive (connected car), manufacturing (connected factory), smart cities, energy and retail.

Network devices and client devices can be different types of devices or components of devices. For example, client device 140 is shown as a laptop and balancer 160 is shown as a processor. Client devices and network devices could be other types of devices or components of other types of devices such as a mobile phone, laptop computer, tablet computer, temperature sensor, motion sensor, and audio sensor. Additionally, or alternatively, the network devices may be or include sensors that are sensitive to detecting aspects of their environment. For example, the network devices may include sensors such as water sensors, power sensors, electrical current sensors, chemical sensors, optical sensors, pressure sensors, geographic or position sensors (e.g., GPS), velocity sensors, acceleration sensors, and flow rate sensors. Examples of characteristics that may be sensed include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, and electrical current. The sensors may be mounted to various components used as part of a variety of different types of systems (e.g., an oil drilling operation). The network devices may detect and record data related to the environment that it monitors, and transmit that data to network 100.

As noted, one type of system that may include various sensors that collect data to be processed and/or transmitted to a computing environment (not shown) according to certain embodiments includes an oil drilling system. For example, the one or more drilling operation sensors may include, for example, surface sensors that measure a standpipe pressure, a surface torque, and a rotation speed of a drill pipe, and downhole sensors that measure a rotation speed of a bit and fluid densities. Besides the raw data collected directly by the sensors, other data may include parameters either developed by the sensors or assigned to the system by a client or other controlling device. For example, one or more drilling operation control parameters may control settings such as a mud motor speed to flow ratio, a bit diameter, a predicted formation top, seismic data, weather data, etc. Other data may be generated using physical models such as an earth model, a weather model, a seismic model, a bottom hole assembly model, a well plan model, an annular friction model, etc. In addition to sensor and control settings, predicted outputs, of for example, the rate of penetration and pump pressure may also be stored and used for modeling, prediction, or classification.

In another example, another type of system that may include various sensors that collect data to be processed and/or transmitted to a computing environment according to certain embodiments includes a home automation or similar automated network in a different environment, such as an office space, school, public space, sports venue, or a variety of other locations. Network devices in such an automated network may include network devices that allow a user to access, control, and/or configure various home appliances located within the user's home (e.g., a television, radio, light, fan, humidifier, sensor, microwave, iron, and/or the like), or outside of the user's home (e.g., exterior motion sensors, exterior lighting, garage door openers, sprinkler systems, or the like). For example, network device or client device may include a home automation switch that may be coupled with a home appliance. In another embodiment, a network or client device can allow a user to access, control, and/or configure devices, such as office-related devices (e.g., copy machine, printer, or fax machine), audio and/or video related devices (e.g., a receiver, a speaker, a projector, a DVD player, or a television), media-playback devices (e.g., a compact disc player, a CD player, or the like), computing devices (e.g., a home computer, a laptop computer, a tablet, a personal digital assistant (PDA), a computing device, or a wearable device), lighting devices (e.g., a lamp or recessed lighting), devices associated with a security system, devices associated with an alarm system, devices that can be operated in an automobile (e.g., radio devices, navigation devices), and/or the like. Data may be collected from such various sensors in raw form, or data may be processed by the sensors to create parameters or other data either developed by the sensors based on the raw data or assigned to the system by a client or other controlling device.

In another example, another type of system that may include various sensors that collect data to be processed and/or transmitted to a computing environment (e.g., computing environment or another computing environment not shown) according to certain embodiments includes a manufacturing environment (e.g., manufacturing products or energy). A variety of different network devices may be included in an energy pool, such as various devices within one or more power plants, energy farms (e.g., wind farm, and solar farm) energy storage facilities, factories, homes and businesses of consumers. One or more of such devices may include one or more sensors that detect energy gain or loss, electrical input or output or loss, and a variety of other efficiencies. These sensors may collect data to inform users of how the energy pool, and individual devices within the pool, may be functioning and how they may be made more efficient. In a manufacturing environment, image data can be taken of the manufacturing process or other readings of manufacturing equipment. For example, in a semiconductor manufacturing environment, images can be used to track, for example, process points (e.g., movement from a bonding site to a packaging site), and process parameters (e.g., bonding force, electrical properties across a bond of an integrated circuit).

Network device sensors may also perform processing on data it collects before transmitting the data to a computing environment, or before deciding whether to transmit data to a computing environment. For example, network devices may determine whether data collected meets certain rules, for example by comparing data or values calculated from the data and comparing that data to one or more thresholds. The network device may use this data and/or comparisons to determine if the data should be transmitted to a computing environment for further use or processing.

Devices in computing environment 114 may include specialized computers, servers, or other machines that are configured to individually and/or collectively process large amounts of data (e.g., using a session pool 102). The computing environment 114 may also include storage devices (e.g., data stores 120) that include one or more databases of structured data, such as data organized in one or more hierarchies, or unstructured data. The databases may communicate with the processing devices within computing environment 114 to distribute data to them and store data used in the computing environment 114. Computing environment 114 may collect, analyze and/or store data from or pertaining to communications, client device operations, client rules, and/or user-associated actions stored at one or more devices in computing environment 114. Such data may influence communication routing to the devices within computing environment 114, and how data is stored or processed within computing environment 114, among other actions.

Network 100 may also include one or more network-attached data stores 120. Network-attached data stores 120 are used to store data to be processed by the computing environment 114 as well as any intermediate or final data generated by the computing system in non-volatile memory. For instance, data stores 120 can perform functions such as writing and copying data and can provide data storage for network functions such as sessions, authorization, publishing and retrieving packages. In certain embodiments, the configuration of the computing environment 114 allows its operations to be performed such that intermediate and final data results can be stored solely in volatile memory (e.g., RAM), without a requirement that intermediate or final data results be stored to non-volatile types of memory (e.g., disk). This can be useful in certain situations, such as when the computing environment 114 receives ad hoc queries from a user and when responses, which are generated by processing large amounts of data, need to be generated on-the-fly. In this non-limiting situation, the computing environment 114 may be configured to retain the processed information within memory so that responses can be generated for the user at different levels of detail as well as allow a user to interactively query against this information.

Network-attached data stores 120 may store a variety of different types of data organized in a variety of different ways and from a variety of different sources. For example, network-attached data stores 120 may include storage other than primary storage located within computing environment 114 that is directly accessible by processors located therein. Network-attached data stores 120 may include secondary, tertiary, auxiliary, or back-up storage (e.g., data storage 120B), such as large hard drives, servers, and virtual memory, among other types. Storage devices may include portable or non-portable storage devices, optical storage devices, and various other mediums capable of storing and containing data (e.g., computer a machine-readable storage medium or computer-readable storage medium such as computer readable medium 210 in FIG. 2).

Furthermore, the data stores may hold a variety of different types of data. For example, network-attached data stores 120 may hold unstructured (e.g., raw) data, such as manufacturing data (e.g., a database containing records identifying products being manufactured with parameter data for each product, such as performance metrics or criteria) or product sales databases (e.g., a database containing individual data records identifying details of individual product performance).

The unstructured data may be presented to the computing environment 114 in different forms such as a flat file or a conglomerate of data records and may have data values and accompanying time stamps. The computing environment

114 may be used to analyze the unstructured data in a variety of ways to determine the best way to structure (e.g., hierarchically) that data, such that the structured data is tailored to a type of further analysis on the data. For example, after being processed, the unstructured time stamped data may be aggregated by time (e.g., into daily time period units) to generate time series data and/or structured hierarchically according to one or more dimensions (e.g., parameters, attributes, and/or variables). For example, data may be stored in a hierarchical data structure, such as a ROLAP OR MOLAP database, or may be stored in another tabular form, such as in a flat-hierarchy form.

Other devices can further be used to influence communication routing and/or processing between devices within computing environment 114 and with devices outside of computing environment 114. For example, as shown in FIG. 1, computing environment 114 may include a device 130 supporting a web application. Thus, computing environment 114 can retrieve data of interest, such as client information (e.g., product information, client rules, etc.), technical product details, news, current or predicted weather, and so on. Balancer 160 can be used to balance and direct load within the computing environment 114. Authentication device 150 can be used to provide authentication or other security protocols for a client device, user or group accessing computing environment 114.

In addition to computing environment 114 collecting data (e.g., as received from network devices, such as sensors, and client devices or other sources) to be processed as part of a big data analytics project, it may also receive data in real time as part of a streaming analytics environment. As noted, data may be collected using a variety of sources as communicated via different kinds of networks or locally. Such data may be received on a real-time streaming basis. For example, network devices may receive data periodically from sensors as the sensors continuously sense, monitor and track changes in their environments. Devices within computing environment 114 may also perform pre-analysis on data it receives to determine if the data received should be processed as part of an ongoing project. The data received and collected by computing environment 114, no matter what the source or method or timing of receipt, may be processed over a period of time for a client to determine results data based on the client's needs and rules.

FIG. 1 includes a pool of devices with a pool manager 104 and session pool 102. Network 100 includes a variety of pool managers (e.g., pool manager 104) and worker nodes 110 (e.g., devices, servers, or server farms of session pool 102), according to embodiments of the present technology. Devices of session pool 102 are communicatively connected (e.g., via communication path 108 and communication path 106). Therefore, the pool manager may transmit information (e.g., related to the session pool 102 or notifications), to and receive information from each other. Although only one pool manager 104 is shown in FIG. 1, the network 100 may include more pool managers or a different kind of device manager (e.g., a dedicated resource manager).

Session pool 102 includes one or more worker nodes (e.g., worker node 110A). Shown in FIG. 1 are three worker nodes 110A-C merely for illustration, more or less worker nodes could be present. For instance, the pool manager 104 may itself be a worker node and may not need further worker nodes to complete a task. A given worker node could include dedicated computing resources or allocated computing resources as needed to perform operations as directed by the pool manager 104. The number of worker nodes included in a session pool 102 may be dependent, for example, upon how large the project or data set is being processed by the session pool 102, the capacity of each worker node, and the time designated for the session pool 102 to complete the project. Each worker node within the session pool 102 may be connected (wired or wirelessly, and directly or indirectly) to pool manager 104. Therefore, each worker node may receive information from the pool manager 104 (e.g., an instruction to perform work on a project) and may transmit information to the pool manager 104 (e.g., a result from work performed on a project). Furthermore, worker nodes 110 may communicate with each other (either directly or indirectly). For example, worker nodes 110 may transmit data between each other related to a job being performed or an individual task within a job being performed by that worker node. However, in certain embodiments, worker nodes 110 may not, for example, be connected (communicatively or otherwise) to certain other worker nodes. In an embodiment, worker nodes may only be able to communicate with the pool manager 104 that controls it, and may not be able to communicate with other worker nodes in the session pool 102.

The pool manager 104 may connect with other devices of network 100 or an external device (e.g., a pool user, such as a server or computer). For example, a server or computer may connect to pool manager 104 and may transmit a project or job to the node. The project may include a data set. The data set may be of any size. Once the pool manager 104 receives such a project including a large data set, the pool manager 104 may distribute the data set or projects related to the data set to be performed by worker nodes 110. Alternatively, for a project including a large data set, the data set may be received or stored by a machine other than a pool manager 104 or worker node 110 (e.g., a Hadoop data node).

Pool manager may maintain knowledge of the status of the worker nodes 110 in the session pool 102 (i.e., status information), accept work requests from clients, subdivide the work across worker nodes 110, and coordinate the worker nodes 110, among other responsibilities. Worker nodes 110 may accept work requests from a pool manager 104 and provide the pool manager 104 with results of the work performed by the worker nodes 110. A session pool 102 may be started from a single node (e.g., a machine, computer, server, etc.). This first node may be assigned or may start as the primary pool manager 104 that will control any additional nodes that enter the session pool 102.

When a project is submitted for execution (e.g., by a client or a pool manger 104), it may be assigned to a set of nodes. After the nodes are assigned to a project, a data structure (i.e., a communicator) may be created. The communicator may be used by the project for information to be shared between the project code running on each node. A communication handle may be created on each node. A handle, for example, is a reference to the communicator that is valid within a single process on a single node, and the handle may be used when requesting communications between nodes.

A pool manager may be designated as the primary pool manager among multiple pool managers. A server, computer or other external device may connect to the primary pool manager. Once the pool manager receives a project, the primary pool manager may distribute portions of the project to its worker nodes for execution. For example, when a project is initiated on session pool 102, primary pool manager 104 controls the work to be performed for the project to complete the project as requested or instructed. The primary pool manager may distribute work to the worker nodes 110 based on various factors, such as which subsets or portions of projects may be completed most efficiently and in the correct amount of time. For example, a worker node may perform analysis on a portion of data that is already local (e.g., stored on) the worker node. The primary pool manager also coordinates and processes the results of the work performed by each worker node after each worker node executes and completes its job. For example, the primary pool manager may receive a result from one or more worker nodes, and the pool manager may organize (e.g., collect and assemble) the results received and compile them to produce a complete result for the project received from the end user.

Any remaining pool manager (not shown) may be assigned as backup pool manager for the project. In an embodiment, backup pool manager may not control any portion of the project. Instead, backup pool manager may serve as a backup for the primary pool manager and take over as primary pool manager if the primary pool manager were to fail.

To add another node or machine to the session pool 102, the primary pool manager may open a pair of listening sockets, for example. A socket may be used to accept work requests from clients, and the second socket may be used to accept connections from other pool nodes. The primary pool manager may be provided with a list of other nodes (e.g., other machines, computers, servers) that will participate in the pool, and the role that each node will fill in the pool. Upon startup of the primary pool manager (e.g., the first node on the pool), the primary pool manager may use a network protocol to start the server process on every other node in the session pool 102. Command line parameters, for example, may inform each node of one or more pieces of information, such as: the role that the node will have in the pool, the host name of the primary pool manager, and the port number on which the primary pool manager is accepting connections from peer nodes. The information may also be provided in a configuration file, transmitted over a secure shell tunnel, and recovered from a configuration server. While the other machines in the pool may not initially know about the configuration of the pool, that information may also be sent to each other node by the primary pool manager. Updates of the pool information may also be subsequently sent to those nodes.

For any pool manager other than the primary pool manager added to the pool, the pool manager may open multiple sockets. For example, the first socket may accept work requests from clients, the second socket may accept connections from other pool members, and the third socket may connect (e.g., permanently) to the primary pool manager. When a pool manager (e.g., primary pool manager) receives a connection from another pool manager, it first checks to see if the peer node is in the list of configured nodes in the pool. If it is not on the list, the pool manager may clear the connection. If it is on the list, it may then attempt to authenticate the connection. If authentication is successful, the authenticating node may transmit information to its peer, such as the port number on which a node is listening for connections, the host name of the node, and information about how to authenticate the node, among other information. When a node, such as the new pool manager, receives information about another active node, it will check to see if it already has a connection to that other node. If it does not have a connection to that node, it may then establish a connection to that pool manager.

Any worker node added to the pool may establish a connection to the primary pool manager and any other pool manager on the pool. After establishing the connection, it may authenticate itself to the pool (e.g., any pool manager, including both primary and backup, or a server or user controlling the pool). After successful authentication, the worker node may accept configuration information from the pool manager.

When a node joins a session pool 102 (e.g., when the node is powered on or connected to an existing node on the pool or both), the node is assigned (e.g., by an operating system of the pool) an identifier (e.g., a universally unique identifier (UUID)). This identifier may help other nodes and external entities (devices, users, etc.) to identify the node and distinguish it from other nodes. When a node is connected to the pool, the node may share its identifier with the other nodes in the pool. Since each node may share its identifier, each node may know the identifier of every other node on the pool. Identifiers may also designate a hierarchy of each of the nodes (e.g., backup pool manager) within the pool. For example, the identifiers of each of the backup pool manager may be stored in a list of backup pool manager to indicate an order in which the backup pool manager will take over for a failed primary pool manager to become a new primary pool manager. However, a hierarchy of nodes may also be determined using methods other than using the unique identifiers of the nodes. For example, the hierarchy may be predetermined, or may be assigned based on other predetermined factors.

The pool may add new machines at any time (e.g., initiated from any pool manager). Upon adding a new node to the pool, the pool manager may first add the new node to its table of pool nodes. The pool manager may also then notify every other pool manager about the new node. The nodes receiving the notification may acknowledge that they have updated their configuration information.

Primary pool manager 104 may, for example, transmit one or more communications to backup pool manager or other control or worker nodes within the session pool 102). Such communications may be sent using protocols such as periodically, at fixed time intervals, or between known fixed stages of the project's execution. The communications transmitted by primary pool manager 104 may be of varied types and may include a variety of types of information. For example, primary pool manager 104 may transmit snapshots (e.g., status information) of the session pool 102 so that backup pool manager 104 always has a recent snapshot of the session pool 102. The snapshot or pool status may include, for example, the structure of the pool (including, for example, the worker nodes in the pool, unique identifiers of the nodes, or their relationships with the primary pool manager) and the status of a project (including, for example, the status of each worker node's portion of the project). The snapshot may also include analysis or results received from worker nodes in the session pool 102. The backup pool manager may receive and store the backup data received from the primary pool manager. The backup pool manager may transmit a request for such a snapshot (or other information) from the primary pool manager, or the primary pool manager may send such information periodically to the backup pool manager.

As noted, the backup data may allow the backup pool manager to take over as primary pool manager if the primary pool manager fails without requiring the pool to start the project over from scratch. If the primary pool manager fails, the backup pool manager that will take over as primary pool manager may retrieve the most recent version of the snapshot received from the primary pool manager and use the snapshot to continue the project from the stage of the project indicated by the backup data. This may prevent failure of the project as a whole.

A backup pool manager may use various methods to determine that the primary pool manager has failed. In one example of such a method, the primary pool manager may transmit (e.g., periodically) a communication to the backup pool manager that indicates that the primary pool manager is working and has not failed, such as a heartbeat communication. The backup pool manager may determine that the primary pool manager has failed if the backup pool manager has not received a heartbeat communication for a certain predetermined period of time. Alternatively, a backup pool manager may also receive a communication from the primary pool manager itself (before it failed) or from a worker node that the primary pool manager has failed, for example because the primary pool manager has failed to communicate with the worker node.

Different methods may be performed to determine which backup pool manager of a set of backup pool manager will take over for failed primary pool manager 104 and become the new primary pool manager. For example, the new primary pool manager may be chosen based on a ranking or "hierarchy" of backup pool manager based on their unique identifiers. In an alternative embodiment, a backup pool manager may be assigned to be the new primary pool manager by another device in the session pool 102 or from an external device (e.g., a system infrastructure or an end user, such as a server or computer, controlling the session pool 102). In another alternative embodiment, the backup pool manager that takes over as the new primary pool manager may be designated based on bandwidth or other statistics about the session pool 102.

A worker node within the session pool 102 may also fail. If a worker node fails, work being performed by the failed worker node may be redistributed amongst the operational worker nodes. In an alternative embodiment, the primary pool manager may transmit a communication to each of the operable worker nodes still on the session pool 102 that each of the worker nodes should purposefully fail also. After each of the worker nodes fail, they may each retrieve their most recent saved checkpoint of their status and re-start the project from that checkpoint to minimize lost progress on the project being executed.

Figure 2:
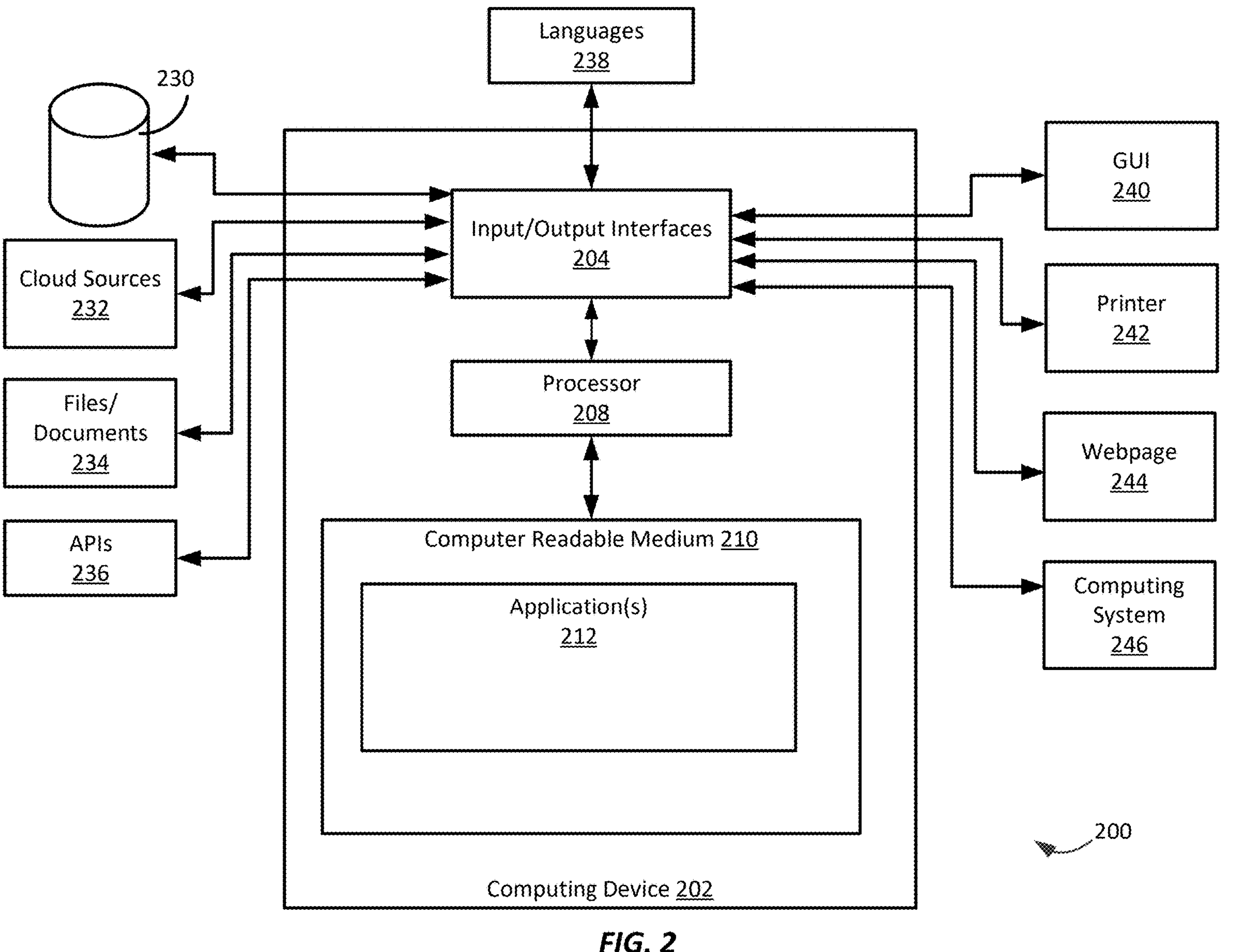
FIG. 2 illustrates a block diagram that provides an illustration of the hardware components of a computing system, according to some embodiments of present technology.

While each device in FIG. 1 is shown as a single device, it will be appreciated that multiple devices may instead be used. FIG. 2 shows an example computing structure for a device in FIG. 2. FIG. 2 includes a computing device 202. The computing device 202 has a computer-readable medium 210 and a processor 208. Computer-readable medium 210 is an electronic holding place or storage for information so the information can be accessed by processor 208. The computer readable medium 210 is a non-transitory medium in which data can be stored and that does not include carrier waves and/or transitory electronic signals. Examples of a non-transitory medium may include, for example, a magnetic disk or tape, optical storage media such as compact disk or digital versatile disk, flash memory, memory or memory devices. A computer-program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including, for example, memory sharing, message passing, token passing, and network transmission. Computer-readable medium 210 can include, but is not limited to, any type of random-access memory (RAM), any type of read only memory (ROM), any type of flash memory, etc. such as magnetic storage devices (e.g., hard disk, floppy disk, magnetic strips), optical disks (e.g., compact disc (CD), digital versatile disc (DVD)), smart cards, flash memory devices, etc.

Processor 208 executes instructions (e.g., stored at the computer-readable medium 210). The instructions can be carried out by a special purpose computer, logic circuits, or hardware circuits. In one or more embodiments, processor 208 is implemented in hardware and/or firmware. Processor 208 executes an instruction, meaning it performs or controls the operations called for by that instruction. The term "execution" is the process of running an application or the carrying out of the operation called for by an instruction. The instructions can be written using one or more programming language, scripting language, assembly language, etc. Processor 208 in one or more embodiments can retrieve a set of instructions from a permanent memory device and copy the instructions in an executable form to a temporary memory device that is generally some form of RAM, for example. Processor 208 operably couples with components of computing device 202 (e.g., input/output interface 204 and with computer readable medium 210) to receive, to send, and to process information.

For instance, in one or more embodiments, computing device 202 sends and/or receives information from one or more of databases 230, cloud sources 232, application programming interfaces 236 (API's), graphical user interfaces 240 (GUIs), printers 242, webpages 244, and computing systems 246. The input/output interface 204 may be configured to receive languages 238 (e.g., to communicate with other computing systems 246) or specific electronic files or documents 234 (e.g., inputs for building models or designing experiments). The input/output interface 204 may be a single interface (e.g., an output interface only to output reports to a printer 242), multiple interface (e.g., a graphical user interface 240 may be interactive and send and receive data over input/output interface 204), or a set of interfaces (e.g., to connect with multiple devices).

In one or more embodiments, computer-readable medium 210 stores instructions for execution by processor 208. In one or more embodiments, one or more applications stored on computer-readable medium 210 are implemented in software (e.g., computer-readable and/or computer-executable instructions) stored in computer-readable medium 210 and accessible by processor 208 for execution of the instructions.

Figure 3:
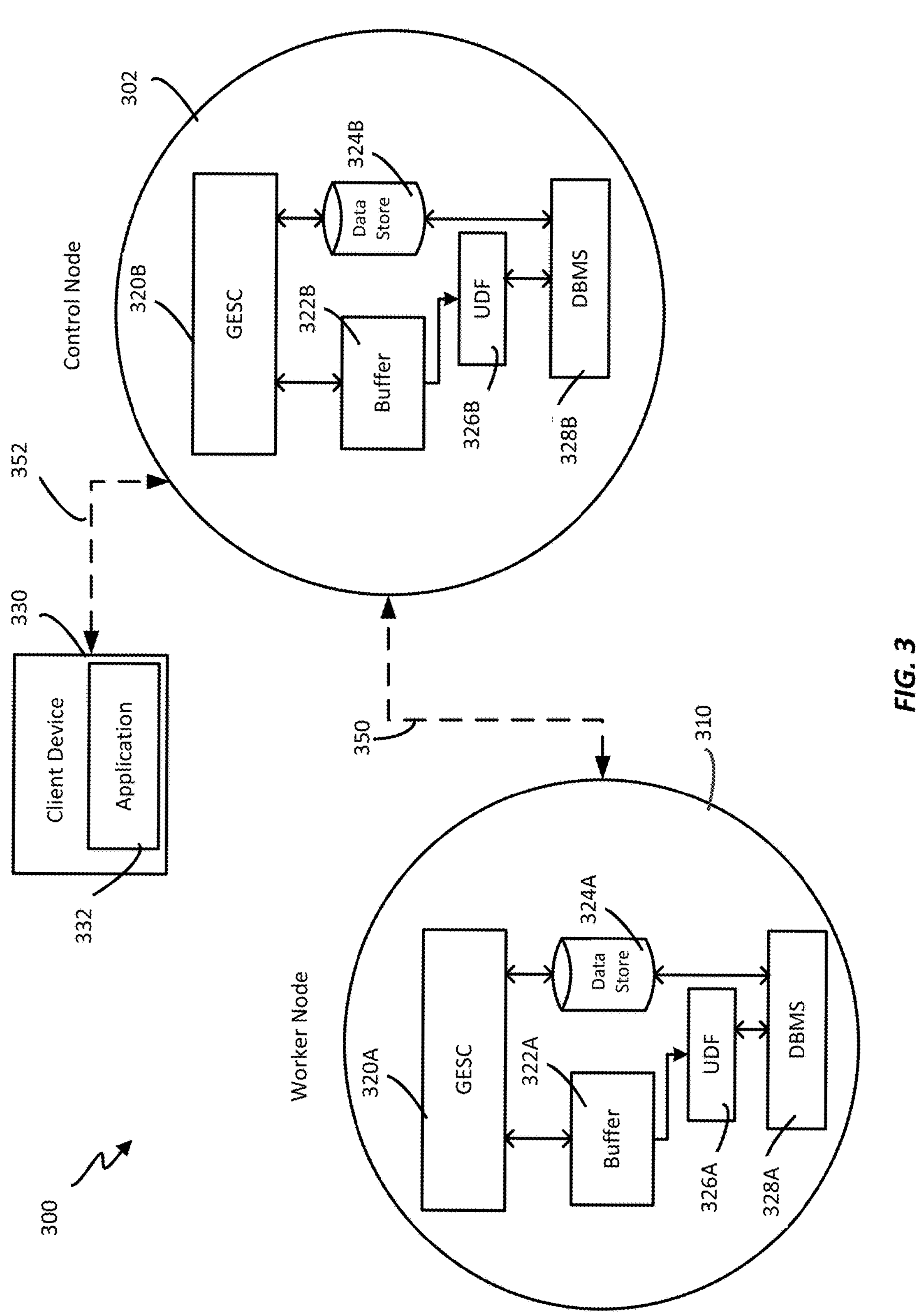
FIG. 3 illustrates a communications grid computing system including a variety of control and worker nodes, according to some embodiments of present technology.

FIG. 3 illustrates a system 300 including a control node (e.g., pool manager 104 of FIG. 1) and a worker node (e.g., worker nodes 110 of FIG. 1), according to embodiments of the present technology. System 300 includes one control node (control node 302) and one worker node (worker node 310) for purposes of illustration but may include more worker and/or control node. The control node 302 is communicatively connected to worker node 310 via communication path 350. Therefore, control node 302 may transmit information (e.g., related to the session pool 102 or notifications), to and receive information from worker node 310 via path 350.

System 300 includes data processing nodes (e.g., control node 302 and worker node 310). Control node 302 and worker node 310 can include multi-core data processors. Each control node 302 and worker node 310 in this example includes a grid-enabled software component (GESC) 320 that executes on the data processor associated with that node and interfaces with buffer memory 322 also associated with that node. Each control node 302 and worker node 310 in this example includes a database management software (DBMS) 328 that executes on a database server (not shown) at control node 302 and on a database server (not shown) at worker node 310.

Each control node 302 and worker node 310 in this example also includes a data storage 324. Data storage 324, similar to network-attached data stores 120 in FIG. 1, are used to store data to be processed by the nodes in the computing environment. Data storage 324 may also store any intermediate or final data generated by the computing system after being processed, for example in non-volatile memory. However, in certain embodiments, the configuration of the system 300 allows its operations to be performed such that intermediate and final data results can be stored solely in volatile memory (e.g., RAM), without a requirement that intermediate or final data results be stored to non-volatile types of memory. Storing such data in volatile memory may be useful in certain situations, such as when the pool receives queries (e.g., ad hoc) from a client device 330 and when responses, which are generated by processing large amounts of data, need to be generated quickly or on-the-fly. In such a situation, the pool may be configured to retain the data within memory so that responses can be generated at different levels of detail and so that a client may interactively query against this information.

Each control node 302 and worker node 310 in this example also includes a user-defined function (UDF) 326. The UDF 326 provides a mechanism for the DBMS 328 to transfer data to or receive data from the database stored in the data storage 324 that are managed by the DBMS. For example, UDF 326 can be invoked by the DBMS 328 to provide data to the GESC 320 for processing. The UDF 326 may establish a socket connection (not shown) with the GESC 320 to transfer the data. Alternatively, the UDF 326 can transfer data to the GESC 320 by writing data to shared memory accessible by both the UDF 326 and the GESC 320.

The GESC 320 at the control node 302 and worker node 310 may be connected via a network. Therefore, control node 302 and worker node 310 can communicate with each other via the network using a predetermined communication protocol such as, for example, the Message Passing Interface (MPI). Each GESC 320 can engage in point-to-point communication with the GESC at another node or in collective communication with multiple GESCs via the network. The GESC 320 at each node may contain identical (or nearly identical) software instructions. Each control node 302 and worker node 310 may be configured to operate as either a pool manager or a worker node. The GESC 320B at the control node 302 can communicate, over a communication path 352, with a client device 330. More specifically, control node 302 may communicate with client application 332 hosted by the client device 330 to receive queries and to respond to those queries after processing large amounts of data.

DBMS 328 may control the creation, maintenance, and use of database or data structure (not shown) within control node 302 and worker node 310. The database may organize data stored in data storage 324. The DBMS 328 at control node 302 may accept requests for data and transfer the appropriate data for the request. With such a process, collections of data may be distributed across multiple physical locations. In this example, each control node 302 and worker node 310 stores a portion of the total data managed by the management system in its associated data storage 324.

Furthermore, the DBMS 328 may be responsible for protecting against data loss using replication techniques. Replication includes providing a backup copy of data stored on one node on one or more other nodes. Therefore, if one node fails, the data from the failed node can be recovered from a replicated copy residing at another node. Data or status information for each node in the session pool 102 may also be shared with each node on the pool.

Figure 4:
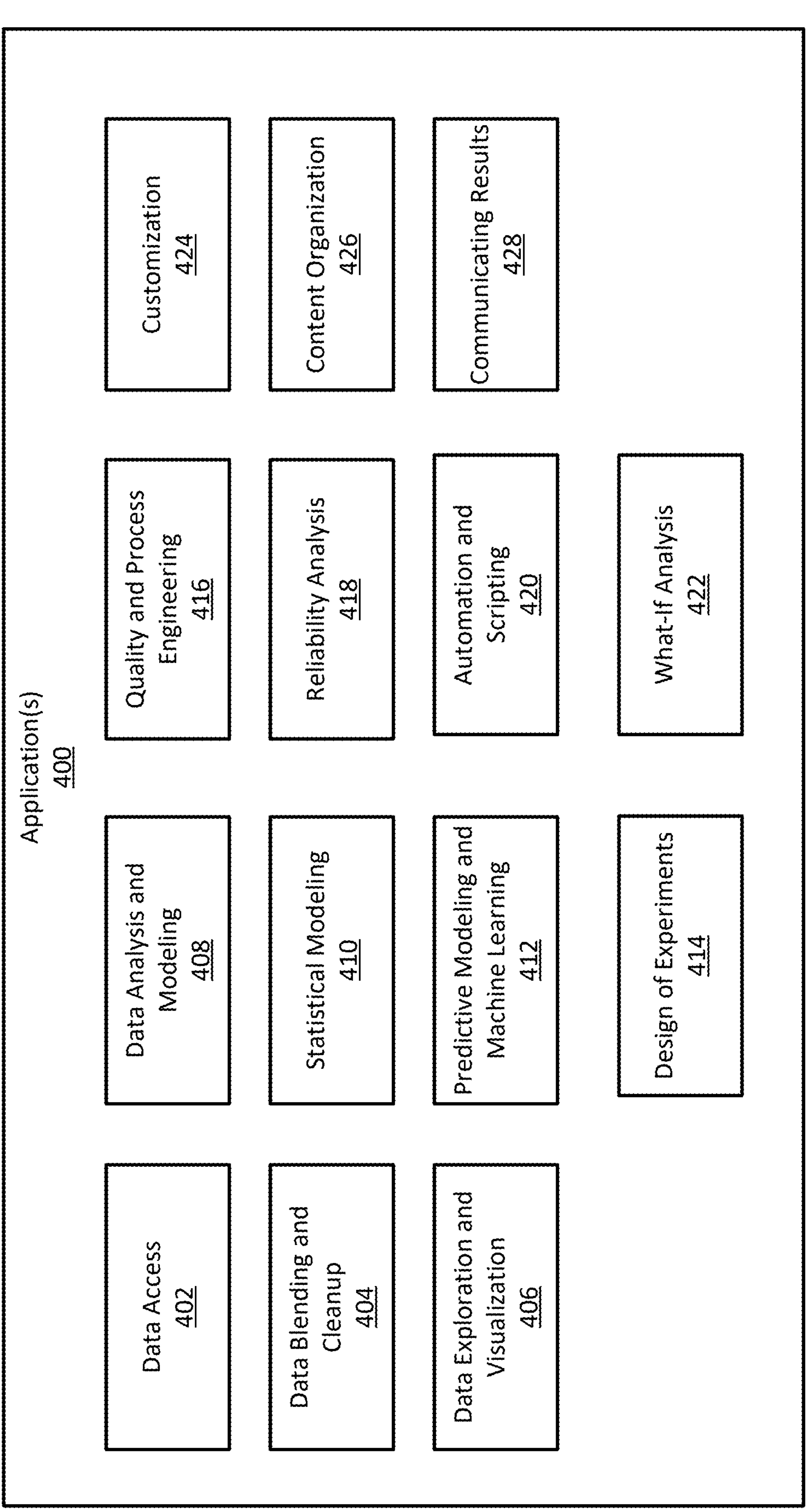
FIG. 4 illustrates application(s) for performing data normalization, visualization and/or analysis task(s)/operation(s), according to some embodiments of present technology.

FIG. 4 provides example applications 400 (e.g., applications executed by a computing device 202, worker node 310, or control node 302) for performing one or more tasks or operations.

For example, data access operations 402 can be used for accessing data from different sources (e.g., importing and/or reading Excel files, flat files, relational databases, APIs, R, Python, and SAS® files and databases). For instance, data can be imported for data visualization, exploration and analysis. Data can be formatted or optimized. For instance, data blending and cleanup operations 404 can be used to remove complexity (e.g., in text, images and functions data) and for screening data (e.g., screening data for outliers, entry errors, missing values and other inconsistencies that can compromise data analysis). This can be useful for visual and interactive tools. Data can also be transformed, blended, grouped, filtered, merged into a single table or into subsets, or otherwise arranged for a particular scenario.

In one or more embodiments, one or more applications 400 include data exploration and visualization operations 406 that can be used to support plot and profiler tools. For instance, plot tools can be used to create data plots (e.g., to plot data to spot patterns and patterns that do not fit a trend). Some example plots include bubble plots, scatter plots (matrix and 3D), parallel plots, cell plots, contour plots, ternary plots, and surface plots. Profilers are tools that can be used to create a specialized set of plots in which changing one plot changes the other plots. For instance, profiling is an approach to generate visualizations of response surfaces by seeing what would happen if a user changed just one or two factors at a time. Profiler tools can be used to create interactive profiles of data (e.g., to explore and graph data dynamically and uncover hidden relationships between graphed data or interface with linked data, to interpret and understand the fit of equations to data, and to find factor values to optimize responses). Some example profiler tools include prediction profiler, contour profiler, surface profiler, mixture profiler, custom profiler, and excel profiler. A prediction profiler can be used to show vertical slices across each factor, holding other factors at a current value. A contour profiler allows horizontal slices showing contour lines for two factors at a time. A surface profiler generates three-dimensional plots for two factors at a time, or contour surface plot for 3 factors at a time. A mixture profiler is a contour profiler for mixture of factors. A custom profiler is a numerical optimizer. An excel profiler allows for visualization of models or formulas stored in electronic worksheets. Accordingly, profiler tools can allow for one or more of simulation, surface visualization, optimization, and desirability studies. Graphs (e.g., from plot or profiler tools) can be exported to electronic or print reports for presenting findings. Further, data exploration and visualization operations 406 can include text exploration such as computer extraction of symbols, characters, words and phrases; or computer visualization such as to organize symbols, characters, words and phrases to uncover information regarding a text or classify the text.

In one or more embodiments, one or more applications 400 include data analysis and modeling operations 408 can be used to analyze one or many variables or factors in linked analysis. Analysis results may be linked with specific graphs designed for different types of data or metrics (e.g., graphs related to histograms, regression modeling and distribution fitting). Data analysis and modeling can be performed real-time (or just-in-time). For instance, applications 400 can included statistical modeling operations 410. For instance, statistical modeling operations 410 can be used for a diversity of modeling tasks such as univariate, multivariate and multifactor. Data can be transformed from its collected form (e.g., text or functional form) and data can be used for building models for better insights (e.g., discovery trends or patterns in data). As another example, one or more applications 400 can include predictive modeling and machine learning operations 412 to build models using predictive modeling techniques, such as regression, neural networks and decision trees. The operations 412 can be used to fit multiple predictive models and determine the best performing model with model screening. Validation (e.g., cross-validation and k-fold cross-validation) can be used (e.g., to prevent over-fitting or to select a best model). Machine learning methods can be used by the user without having to write code and tune algorithms. Examples of machine learning techniques are described in more detail with respect to FIGS. 5 and 6).

In one or more embodiments, one or more applications 400 include design of experiments (DOE) operations 414 used to create designs for experiments that provide test conditions for one or more factors tested in the experiment. For example, the design of experiments operations 414 can be used to create optimally designed experiments, efficient experiments to meet constraints, process limitations and budget, and/or screening designs to untangle important effects between multiple factors. DOE operations 414 can also be used for evaluating designs (e.g., design diagnostic measures such as efficiency metrics).

In one or more embodiments, one or more applications 400 include quality and process engineering operations 416 to track and visualize quality and processes. For instance, the quality and process engineering operations 416 can generate charts to explore root causes of quality or process problems (e.g., causes of variation in manufacturing processes and drill down into problem processes). Additionally, or alternatively, they can be used to generate notifications for metrics that exceed a threshold such as an out-of-control signal or a control chart warning. Additionally, or alternatively, they can be used to study the capability and performance of one or more variables to identify processes that are not meeting user-defined goals. Objective data from processes or consumer data can be used to release better products and react to market trends.

In one or more embodiments, one or more applications 400 include reliability analysis operations 418. For example, in manufacturing, reliability analysis tools can be used to prevent failure, improve warranty or product performance, find and address important design vulnerabilities, and pinpoint defects in materials or processes. Reliability analysis tools can also be used to determine how to reduce or improve these issues (e.g., by identifying trends and outliers in data and model predictions). What-if Analysis operations 422 can be used to demonstrate patterns of predicted responses and the effect of each factor on the response with scenario analysis. For example, a graphical user interface can be used for a user to put in different inputs, assumptions or constraints for a system and observe responses or effects. For instance, in a measurement system analysis analyzing whether parts would be in-specification, different estimated variances between parts and operators testing the parts could be varied to determine the effect on modeled output for the measurement system analysis.

In one or more embodiments, one or more applications 400 include automation and scripting operations 420. For example, automation can allow code-free access for a user to automation routines all the way up to completely customized applications (e.g., code free access to SAS®, MATLAB®, Python® and R routines). For example, a design created for experiments can be automated such that automatic testing is performed for the design.

In one or more embodiments, one or more applications 400 include operations for greater user control and interaction. For instance, customization operations 424 can be used for user customization (e.g., mass customizations, and customizations of graphics, statistics, and default views). As another example, content organization operations 426 can be used to organize data (e.g., translate statistical results to a simplified view to communicate findings and organize, summarize, and document content to better aid the accountability and reproducibility of projects). As another example, the communicating results operations 428 can be used for presentation of results, models, or other output from one or more applications 400 (e.g., presented in print, graphical user interface, or web-based versions).

In one or more embodiments, fewer, different, and additional components can be incorporated into computing device 202. In one or more embodiments, the input/output interface has more than one interface that uses the same or different interface technology.

In one or more embodiments, the one or more applications 400 can be integrated with other analytic or computing tools not specifically shown here. For instance, one or more applications are implemented using or integrated with one or more software tools such as JMP®, Base SAS, SAS® Enterprise Miner™, SAS/STAT®, SAS® High Performance Analytics Server, SAS® Visual Data Mining and Machine Learning, SAS® LASR™ SAS® In-Database Products, SAS® Scalable Performance Data Engine, SAS® Cloud Analytic Services, SAS/OR®, SAS/ETS®, SAS® Inventory Optimization, SAS® Inventory Optimization Workbench, SAS® Visual Analytics, SAS® Viya™, SAS In-Memory Statistics for Hadoop®, SAS® Forecast Server, and SAS/IML®.

Figure 5:
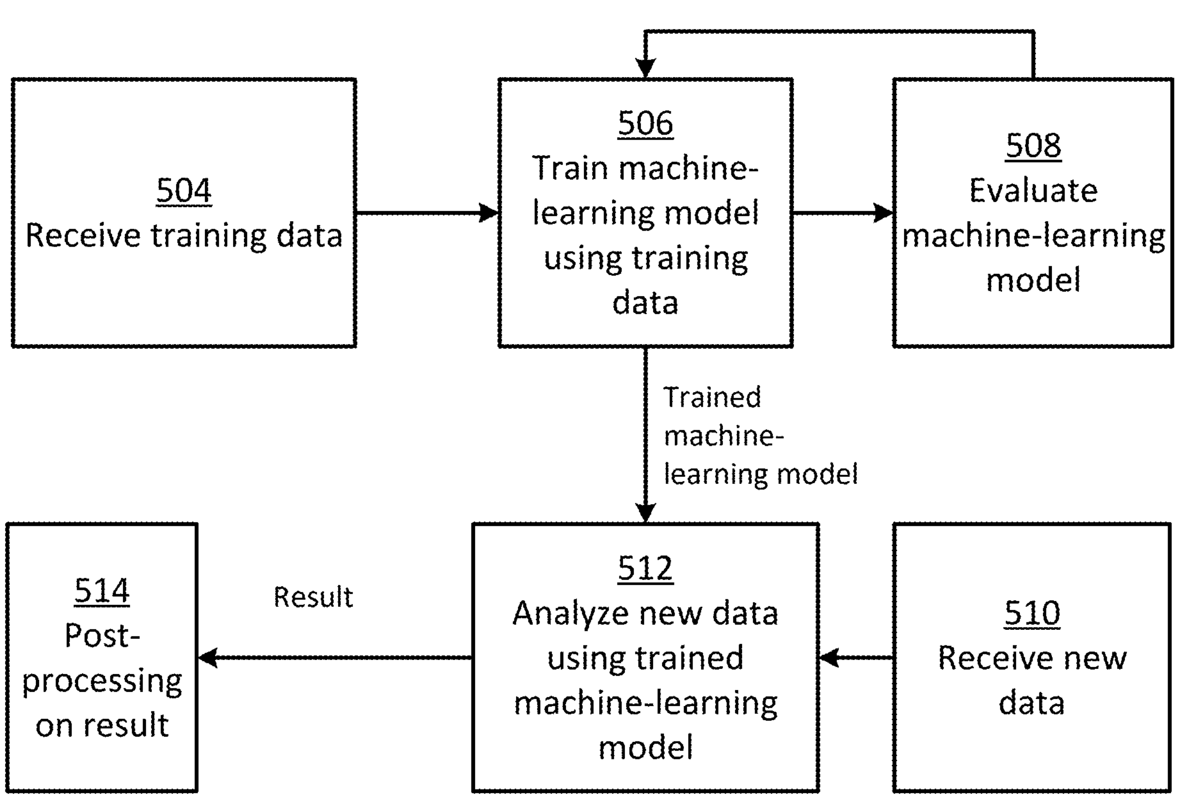
FIG. 5 illustrates a flow chart of an example process of generating and using a machine-learning model according to some aspects.

One or more embodiments are useful for generating and using machine-learning models. FIG. 5 is a flow chart of an example of a process for generating and using a machine-learning model according to some aspects. Machine learning is a branch of artificial intelligence that relates to mathematical models that can learn from, categorize, and make predictions about data. Such mathematical models, which can be referred to as machine-learning models, can classify input data among two or more classes; cluster input data among two or more groups; predict a result based on input data; identify patterns or trends in input data; identify a distribution of input data in a space; or any combination of these. Examples of machine-learning models can include (i) neural networks; (ii) decision trees, such as classification trees and regression trees; (iii) classifiers, such as Naïve bias classifiers, logistic regression classifiers, ridge regression classifiers, random forest classifiers, least absolute shrinkage and selector operator (LASSO) classifiers, and support vector machines; (iv) clusterers, such as k-means clustering, mean-shift clusterers, and spectral clusterers; (v) factorizers, such as factorization machines, principal component analyzers and kernel principal component analyzers; and (vi) ensembles or other combinations of machine-learning models. In some examples, neural networks can include deep neural networks, feed-forward neural networks, recurrent neural networks, convolutional neural networks, radial basis function (RBF) neural networks, echo state neural networks, long short-term memory neural networks, bi-directional recurrent neural networks, gated neural networks, hierarchical recurrent neural networks, stochastic neural networks, modular neural networks, spiking neural networks, dynamic neural networks, cascading neural networks, neuro-fuzzy neural networks, or any combination of these.

Different machine-learning models may be used interchangeably to perform a task. Examples of tasks that can be performed at least partially using machine-learning models include various types of scoring; bioinformatics; cheminformatics; software engineering; fraud detection; customer segmentation; generating online recommendations; adaptive websites; determining customer lifetime value; search engines; placing advertisements in real time or near real time; classifying DNA sequences; affective computing; performing natural language processing and understanding; object recognition and computer vision; robotic locomotion; playing games; optimization and metaheuristics; detecting network intrusions; medical diagnosis and monitoring; or predicting when an asset, such as a machine, will need maintenance.

Any number and combination of tools can be used to create machine-learning models. Examples of tools for creating and managing machine-learning models can include SAS® Enterprise Miner, SAS® Rapid Predictive Modeler, and SAS® Model Manager, SAS Cloud Analytic Services (CAS)®, SAS Viya® of all which are by SAS Institute Inc. of Cary, North Carolina.

Machine-learning models construction can be at least partially automated (e.g., with little or no human involvement) in a training process. During training, input data can be iteratively supplied to a machine-learning model to enable the machine-learning model to identify patterns related to the input data or to identify relationships between the input data and output data. With training, the machine-learning model can be transformed from an untrained state to a trained state. Input data can be split into one or more training sets and one or more validation sets, and the training process may be repeated multiple times. The splitting may follow a k-fold cross-validation rule, a leave-one-out-rule, a leave-p-out rule, or a holdout rule. An overview of training and using a machine-learning model is described below with respect to the flow chart of FIG. 5.

In block 504, training data is received. In some examples, the training data is received from a remote database or a local database, constructed from various subsets of data, or input by a user. The training data can be used in its raw form for training a machine-learning model or pre-processed into another form, which can then be used for training the machine-learning model. For example, the raw form of the training data can be smoothed, truncated, aggregated, clustered, or otherwise manipulated into another form, which can then be used for training the machine-learning model.

In block 506, a machine-learning model is trained using the training data. The machine-learning model can be trained in a supervised, unsupervised, or semi-supervised manner. In supervised training, each input in the training data is correlated to a desired output. This desired output may be a scalar, a vector, or a different type of data structure such as text or an image. This may enable the machine-learning model to learn a mapping between the inputs and desired outputs. In unsupervised training, the training data includes inputs, but not desired outputs, so that the machine-learning model has to find structure in the inputs on its own. In semi-supervised training, only some of the inputs in the training data are correlated to desired outputs.

In block 508, the machine-learning model is evaluated. For example, an evaluation dataset can be obtained, for example, via user input or from a database. The evaluation dataset can include inputs correlated to desired outputs. The inputs can be provided to the machine-learning model and the outputs from the machine-learning model can be compared to the desired outputs. If the outputs from the machine-learning model closely correspond with the desired outputs, the machine-learning model may have a high degree of accuracy. For example, if 90% or more of the outputs from the machine-learning model are the same as the desired outputs in the evaluation dataset, the machine-learning model may have a high degree of accuracy. Otherwise, the machine-learning model may have a low degree of accuracy. The 90% number is an example only. A realistic and desirable accuracy percentage is dependent on the problem and the data.

In some examples, if the machine-learning model has an inadequate degree of accuracy for a particular task, the process can return to block 506, where the machine-learning model can be further trained using additional training data or otherwise modified to improve accuracy. If the machine-learning model has an adequate degree of accuracy for the particular task, the process can continue to block 510.

In block 510, new data is received. In some examples, the new data is received from a remote database or a local database, constructed from various subsets of data, or input by a user. The new data may be unknown to the machine-learning model. For example, the machine-learning model may not have previously processed or analyzed the new data.

In block 512, the trained machine-learning model is used to analyze the new data and provide a result. For example, the new data can be provided as input to the trained machine-learning model. The trained machine-learning model can analyze the new data and provide a result that includes a classification of the new data into a particular class, a clustering of the new data into a particular group, a prediction based on the new data, or any combination of these.

In block 514, the result is post-processed. For example, the result can be added to, multiplied with, or otherwise combined with other data as part of a job. As another example, the result can be transformed from a first format, such as a time series format, into another format, such as a count series format. Any number and combination of operations can be performed on the result during post-processing.

Figure 6:
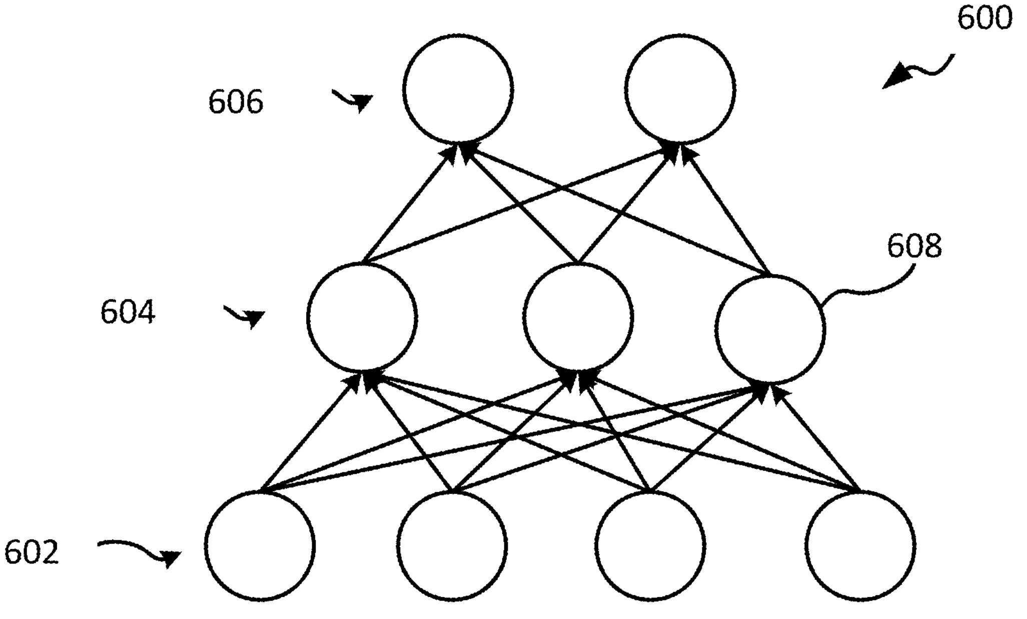
FIG. 6 illustrates an example machine-learning model based on a neural network.

A more specific example of a machine-learning model is the neural network 600 shown in FIG. 6. The neural network 600 is represented as multiple layers of interconnected neurons, such as neuron 608, that can exchange data between one another. The layers include an input layer 602 for receiving input data, a hidden layer 604, and an output layer 606 for providing a result. The hidden layer 604 is referred to as hidden because it may not be directly observable or have its input directly accessible during the normal functioning of the neural network 600. Although the neural network 600 is shown as having a specific number of layers and neurons for exemplary purposes, the neural network 600 can have any number and combination of layers, and each layer can have any number and combination of neurons.

The neurons and connections between the neurons can have numeric weights, which can be tuned during training. For example, training data can be provided to the input layer 602 of the neural network 600, and the neural network 600 can use the training data to tune one or more numeric weights of the neural network 600. In some examples, the neural network 600 can be trained using backpropagation. Backpropagation can include determining a gradient of a particular numeric weight based on a difference between an actual output of the neural network 600 and a desired output of the neural network 600. Based on the gradient, one or more numeric weights of the neural network 600 can be updated to reduce the difference, thereby increasing the accuracy of the neural network 600. This process can be repeated multiple times to train the neural network 600. For example, this process can be repeated hundreds or thousands of times to train the neural network 600.

In some examples, the neural network 600 is a feed-forward neural network. In a feed-forward neural network, every neuron only propagates an output value to a subsequent layer of the neural network 600. For example, data may only move one direction (forward) from one neuron to the next neuron in a feed-forward neural network.

In other examples, the neural network 600 is a recurrent neural network. A recurrent neural network can include one or more feedback loops, allowing data to propagate in both forward and backward through the neural network 600. This can allow for information to persist within the recurrent neural network. For example, a recurrent neural network can determine an output based at least partially on information that the recurrent neural network has seen before, giving the recurrent neural network the ability to use previous input to inform the output.

In some examples, the neural network 600 operates by receiving a vector of numbers from one layer; transforming the vector of numbers into a new vector of numbers using a matrix of numeric weights, a nonlinearity, or both; and providing the new vector of numbers to a subsequent layer of the neural network 600. Each subsequent layer of the neural network 600 can repeat this process until the neural network 600 outputs a final result at the output layer 606. For example, the neural network 600 can receive a vector of numbers as an input at the input layer 602. The neural network 600 can multiply the vector of numbers by a matrix of numeric weights to determine a weighted vector. The matrix of numeric weights can be tuned during the training of the neural network 600. The neural network 600 can transform the weighted vector using a nonlinearity, such as a sigmoid tangent or the hyperbolic tangent. In some examples, the nonlinearity can include a rectified linear unit, which can be expressed using the following equation:

$$y = \max(x, 0)$$

where y is the output and x is an input value from the weighted vector. The transformed output can be supplied to a subsequent layer, such as the hidden layer 604, of the neural network 600. The subsequent layer of the neural network 600 can receive the transformed output, multiply the transformed output by a matrix of numeric weights and a nonlinearity, and provide the result to yet another layer of the neural network 600. This process continues until the neural network 600 outputs a final result at the output layer 606.

Other examples of the present disclosure may include any number and combination of machine-learning models having any number and combination of characteristics. The machine-learning model(s) can be trained in a supervised, semi-supervised, or unsupervised manner, or any combination of these. The machine-learning model(s) can be implemented using a single computing device or multiple computing devices, such as the session pool 102 discussed above.

Implementing some examples of the present disclosure at least in part by using machine-learning models can reduce the total number of processing iterations, time, memory, electrical power, or any combination of these consumed by a computing device when analyzing data. For example, a neural network may more readily identify patterns in data than other approaches. This may enable the neural network to analyze the data using fewer processing cycles and less memory than other approaches, while obtaining a similar or greater level of accuracy.

Some machine-learning approaches may be more efficiently and speedily executed and processed with machine-learning specific processors (e.g., not a generic CPU). Such processors may also provide an energy savings when compared to generic CPUs. For example, some of these processors can include a graphical processing unit (GPU), an application-specific integrated circuit (ASIC), a field-programmable gate array (FPGA), an artificial intelligence (AI) accelerator, a neural computing core, a neural computing engine, a neural processing unit, a purpose-built chip architecture for deep learning, and/or some other machine-learning specific processor that implements a machine learning approach or one or more neural networks using semiconductor (e.g., silicon (Si), gallium arsenide (GaAs)) devices. Furthermore, these processors may also be employed in heterogeneous computing architectures with a number of and a variety of different types of cores, engines, nodes, and/or layers to achieve various energy efficiencies, chip-level thermal processing considerations, processing speed improvements, data communication speed improvements, and/or data efficiency targets and improvements throughout various parts of the system when compared to a homogeneous computing architecture that employs CPUs for general purpose computing.

Figure 7A:
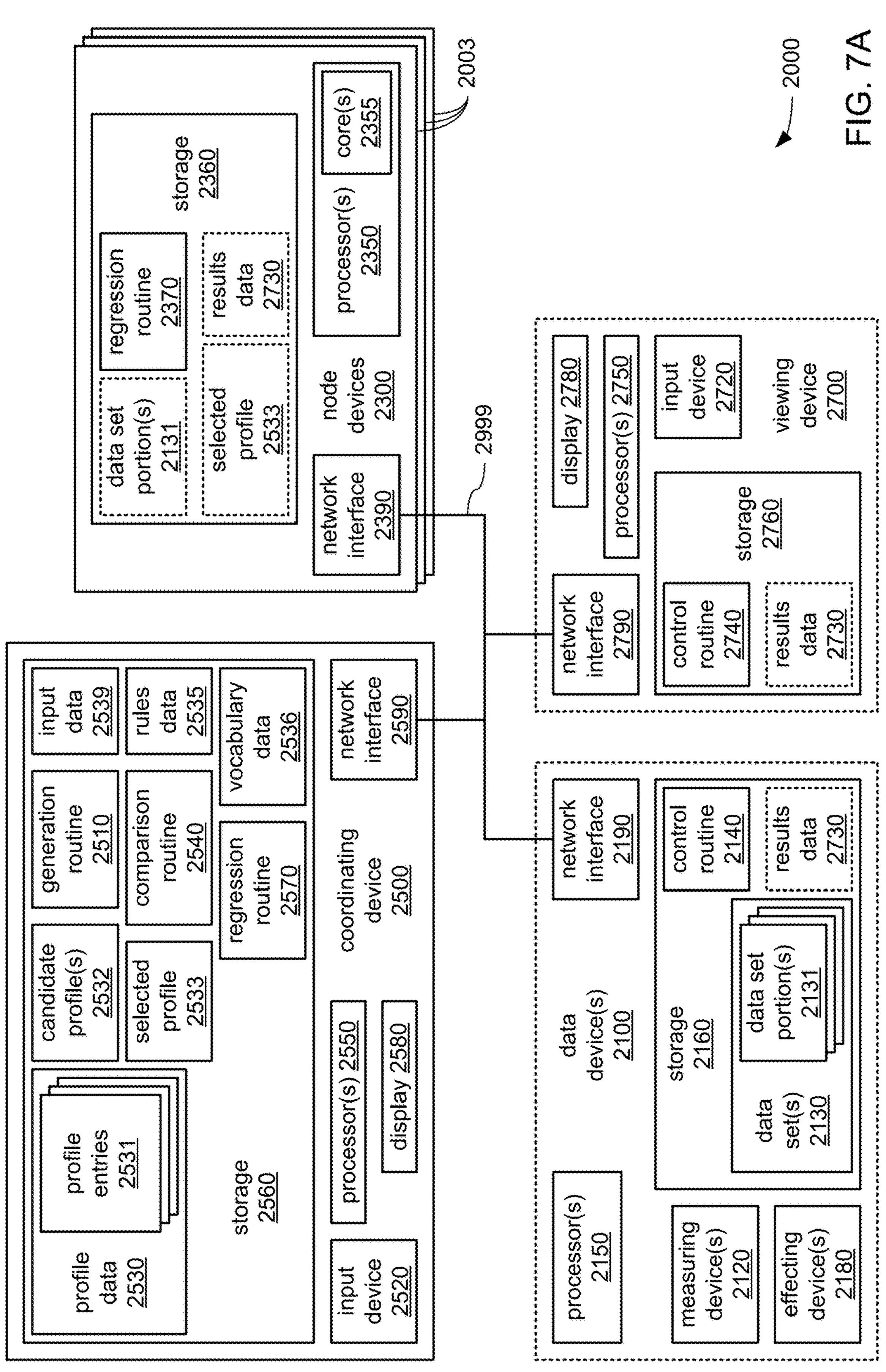
FIGS. 7A and 7B each illustrate an example embodiment of a distributed processing system.
Figure 7B:
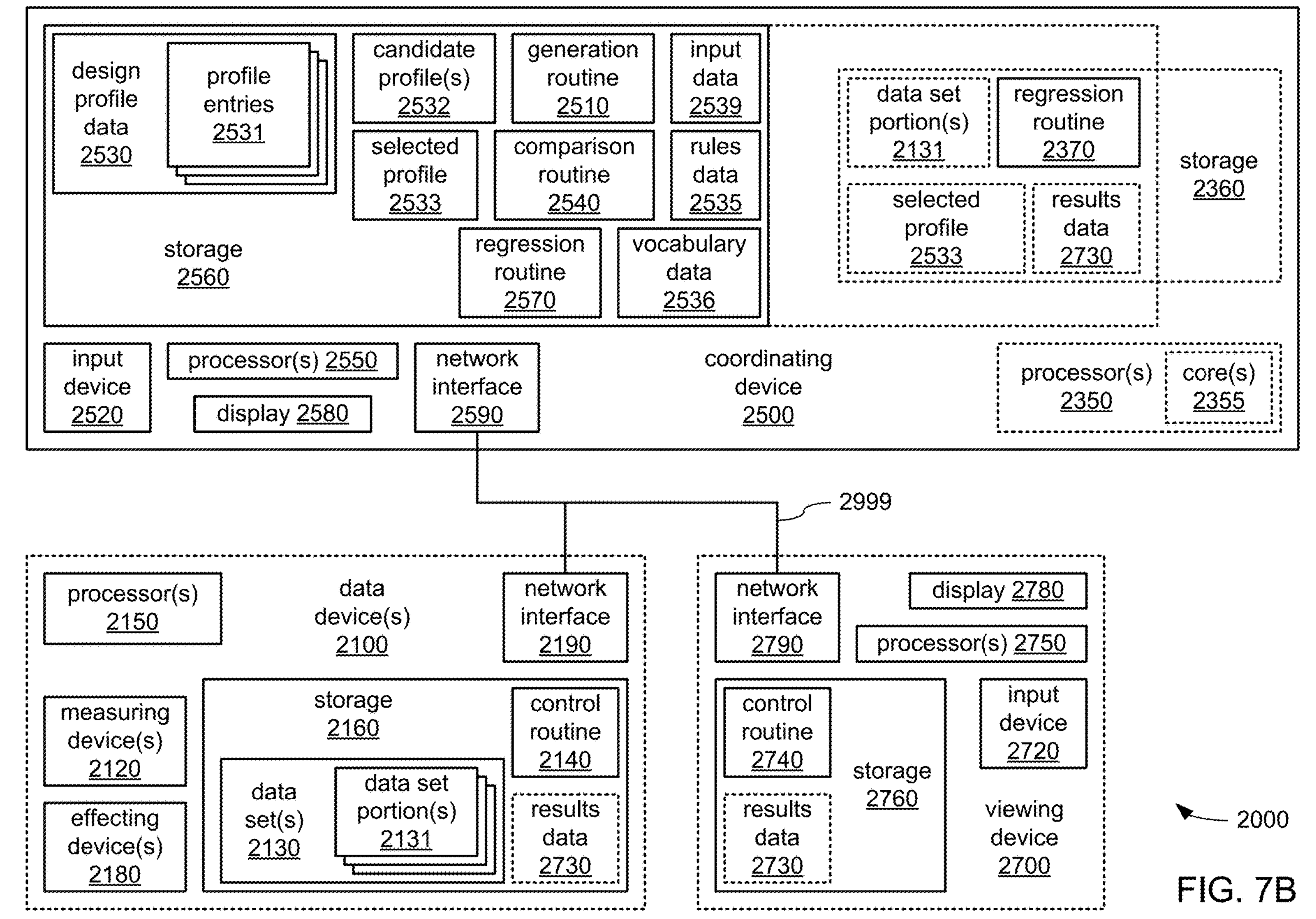

FIG. 7A illustrates a block diagram of an example embodiment of a distributed processing system 2000 incorporating one or more data devices 2100, one or more node devices 2300 that form of a device grid 2003, a coordinating device 2500 and/or a viewing device 2700 coupled by a network 2999. FIG. 7B illustrates a block diagram of an alternate example embodiment of the distributed processing system 2000 in which the coordinating device 2500 may perform the functions of the device grid 2003. In both of the embodiments of FIGS. 7A and 7B, the coordinating device 2500 may provide various GUIs by which an operator may be guided through generating a new testing regime, generating variants of a testing regime, comparing multiple candidate testing regimes, selecting a testing regime from among the candidate testing regimes, performing a regression analysis of the selected testing regime, and/or performing the selected testing regime. In various embodiments, the provision of such GUIs may be performed directly by the coordinating device 2500 or through the viewing device 2700. In various embodiments, the regression analysis (including the generation of simulated data) may be performed by the device grid 2003 or by multiple processors and/or processor cores of the coordinating device 2500. In some embodiments, the one or more data devices may directly perform the selected testing regime with the studied system.

In support of such operations, the devices 2100, 2300, 2500 and/or 2700 may exchange one or more profile entries of parameters concerning one or more testing regimes via the network 2999. In various embodiments, the network 2999 may be a single network that may extend within a single building or other relatively limited area, a combination of connected networks that may extend a considerable distance, and/or may include the Internet. Thus, the network 2999 may be based on any of a variety (or combination) of communications technologies by which communications may be effected, including without limitation, wired technologies employing electrically and/or optically conductive cabling, and wireless technologies employing infrared, radio frequency (RF) or other forms of wireless transmission.

In various embodiments, each of the data devices 2100 may incorporate one or more of a processor 2150, a storage 2160, measuring device(s) 2120, effecting device(s) 2180, and a network interface 2190 to couple each of the data devices 2100 to the network 2999. The storage 2160 may store a control routine 2140, one or more data sets 2130 and/or results data 2730. The control routine 2140 may incorporate a sequence of instructions operative on the processor 2150 of each of the data devices 2100 to implement logic to perform various functions, at least partially in parallel with the processors 2150 of others of the data devices 2100. In executing the control routine 2140, the processor 2150 of each of the data devices 2100 may operate the network interface 2190 thereof to receive items of observation data captured by other devices (not shown) via the network 2999, and may store such items of observation data as one or more of the data sets 2130. Such other devices may include sensors or other forms of measuring device that monitor an aspect of a system under study, and may each transmit captured items of observation data to the one or more data devices 2100 for aggregation and/or storage. Alternatively or additionally, the processor 2150 of each of the data devices 2100 may operate one or more of the measuring devices 2120 that may be incorporated into one or more of the data devices 2100 to more directly capture such items of observation data, and may store such items of observation data as one or more of the data sets 2130.

Each of the measuring devices 2120 that may be incorporated into the one or more data devices 2100, and/or each remote device from which the one or more data devices 2100 may receive captured observation data via the network 2999, may be any of a variety of types of sensor or other data collecting device. Such sensors or other data collection devices may include, and are not limited to, any of a variety of physical and/or chemical sensors that measure aspects of a manufacturing or chemical process; any of a variety of electrical and/or optical energy sensors that measure aspects of transmission and/or reception of electrical and/or optical signals; any of a variety of manual input devices that accept manually entered observations made by personnel; etc. In embodiments in which the one or more data devices 2100 are involved in controlling the studied system such that the one or more data devices 2100 may incorporate one or more of the effecting devices 2180, each of the effecting devices 2180 may be any of a variety of types of controllable output device by which the one or more data devices 2100 may control one or more factors of the studied system. Such controllable output devices may include, and are not limited to, robotic end effectors to manipulate objects (e.g., grips, motors, solenoids, etc.), pumps and/or valves to selectively introduce chemical compounds, electrical and/or optical signal output devices, heaters and/or coolers, vibratory and/or acoustic output devices, radio frequency and/or magnetic emission devices, etc.

Each of the one or more data sets 2130 may include any of a wide variety of types of observation data concerning a studied system, including and not limited to, times, dates and/or locations of operation or use of the studied system; indications of aspects about the studied system that may differentiate the particular studied system from other similar studied systems; and/or captured observations of factors that are inputs to the studied system and responses that are outputs of the studied system. Each of the data sets 2130 may be divided into multiple data set portions 2131 that may each include captured observation data that may be so divided by times, dates and/or locations at which the items of observation data therein were captured. Alternatively or additionally, each of the data sets 2130 may be divided into multiple data set portions 2131 based on random samples taken of items of observation data therefrom to provide smaller, yet statistically representative, portions of each of the data sets 2130 that may be used in as an input to the guidance provided by the coordinating device 2500 in selecting a testing regime and/or in performing a regression test of a selected testing regime.

The studied system may be any of a variety of systems, including and not limited to, chemical processes, sub-atomic particle interactions, biomechanical and/or biochemical systems, geological systems, meteorological systems, manufacturing systems, electrical and/or optical networks, group egress behaviors in response to fire emergencies in public spaces, etc. The impetus to apply these techniques may be the observation of undesired responses of a studied system leading to a desire to identify the one or more factors of the studied system that are linked to those undesired responses. Alternatively or additionally, the impetus may include the desire to derive changes to make to the identified factors that may bring about more desirable responses from the studied system.

Each data set 2130 may be stored as one or more data files, and/or as one or more instances of at least one other type of data structure, in a distributed manner among multiple ones of the data devices 2100. Such distributed storage of a data set 2130 may be carried out to provide redundancy in its storage as a protection against data loss arising from a malfunction or other events associated with one or more of the data devices 2100. Alternatively or additionally, in embodiments in which a data set 2130 is of considerably large size, such distributed storage of a data set 2130 may be carried out to improve the speed and efficiency with which it is able to be accessed and/or exchanged with other devices, including with the coordination device 2500 and/or the multiple node devices 2300 of the node device grid 2003. Indeed, a data set 2130 may be sufficiently large that there may be no single storage device available that has sufficient storage and/or throughput capacity.

In various embodiments, the viewing device 2700 incorporates one or more of a processor 2750, a storage 2760, an input device 2720, a display 2780, and a network interface 2790 to couple the viewing device 2700 to the network 2999. The storage 2760 may store one or both of a control routine 2740 and the results data 2730. The control routine 2740 may incorporate a sequence of instructions operative on the processor 2750 to implement logic to perform various functions. The processor 2750 may be caused by its execution of the control routine 2740 to operate the input device 2720, the display 2780 and/or the network interface 2790 in a manner that causes the viewing device 2700 to enable the coordinating device to remotely provide various GUIs. Alternatively or additionally, the processor 2780 may be caused to operate the network interface 2790 to receive the results data 2730 providing results of a regression analysis of a selected testing regime, may be caused to generate a visualization based on the results data 2730, and/or may be caused to operate the display 2780 to present the visualization on the display 2780.

Turning more specifically to FIG. 7A, each of the node devices 2300 may incorporate one or more of a processor 2350, a storage 2360 and a network interface 2390 to couple each of the node devices 2300 to the network 2999. The processor 2350 of each of the node devices 2300 may incorporate one or more processing cores 2355. The storage 2360 may store one or more of a regression routine 2370, a selected profile 2533, data set portion(s) 2131 and/or the results data 2730. Within each of the multiple node devices 2300, the regression routine 2370 may incorporate a sequence of instructions operative on the processor 2350 to implement logic to perform various functions. The processor 2350 of each of the node devices 2300 may be caused by its execution of the regression routine 2370 to operate the network interface 2390 to receive the selected profile 2533 from the coordinating device 2500 and/or to receive at least one of the data set portions 2131 from the one or more data devices 2100. The processor 2350 of each of the node devices 2300 may then employ the observation data of the studied system within the at least one data set portion 2131 and/or the information about a selected testing regime within the selected profile 2533 to perform a regression analysis with the selected testing regime under the control of the coordinating device 2500. In so doing, the processor 2350 of one or more of the node devices 2300 may generate at least a portion of the results data 2730 providing an indication of the results of the regression analysis, and may operate the network interface 2390 to transmit the results data 2730 to the coordinating device 2500 and/or the viewing device 2700.

In various embodiments, the coordinating device 2500 may incorporate a processor 2550, a storage 2560, an input device 2520, a display 2580, and a network interface 2590 to couple the coordinating device 2500 to the network 2999. The storage 2560 may store one or more of a generation routine 2510, a comparison routine 2540, a regression routine 2570, profile data 2530 that includes one or more profile entries 2531, one or more candidate profiles 2532, the selected profile 2533, rules data 2535, vocabulary data 2536 and input data 2539. Each of the generation routine 2510, the comparison routine 2540 and the regression routine 2570 may incorporate a sequence of instructions operative on the processor 2550 to implement logic to perform various functions.

In executing the generation routine 2510, the processor 2550 may be caused to operate the input device 2520 and/or the display 2580 to locally provide a generation GUI that may provide different pathways to guide an operator through providing parameters to generate a testing regime. A testing regime that is so generated via the generation GUI may be stored within the profile data 2530 as one or more of the profile entries 2531. Alternatively, the processor 2550 may be caused by the generation routine 2510 to operate the network interface 2590 to remotely provide the generation GUI through the network 2999 and another device, such as the viewing device 2700.

Also, in executing the comparison routine 2540, the processor 2550 may be caused to similarly provide a comparison GUI, either locally or remotely, to guide an operator through providing parameters to perform various comparisons between two or more candidate testing regimes, and thereby guide the operator through the consideration of various aspects of the candidate testing regimes in selecting a single testing regime to be used. Further, in executing the regression routine 2570, the processor 2550 may be caused to provide a regression GUI, either locally or remotely, to guide an operator through providing parameters to control aspects of the performance of a regression analysis with the selected testing regime. In so doing, the processor 2550 may be caused to operate the network interface 2590 to distribute and coordinate the performance of the regression analysis among the multiple node devices 2300 through the distribution of the selected profile 2533 thereamong, and may be caused to further operate the network interface 2590 to receive the results data 2730 indicating the results of the regression analysis.

Turning more specifically to FIG. 7B, as an alternative to the multiple node devices 2300 of the embodiment of the distributed processing system 2000 of FIG. 7A, an alternate embodiment of the coordinating device 2500 in the embodiment of the distributed processing system 2000 of FIG. 7B may additionally incorporate one or more of the processors 2350, and/or may incorporate the storage 2360. The storage 2360 may store one or more of the regression routine 2370, the selected profile 2533, the one or more data set portions 2131, and/or the results data 2730. In this alternate embodiment of the coordinating device 2500, each of the one or more processors 2350 may be a graphics processing unit (GPU) incorporating a relatively large quantity of the processing cores 2355 to take the place of the node device grid 2003 in the embodiment of the distributed processing system 2000 of FIG. 7A.

As will be familiar to those skilled in the art, there is an increasingly commonplace trend toward replacing grids of numerous separate computing devices with a single computing device equipped with a relatively small number of GPUs (e.g., under a dozen) to utilize the considerably higher degree of parallelism supported by their internal architectures, including what may be support for dozens, hundreds, thousands, or still greater quantities of threads of execution. Over time, the characteristics of the operations that need to be performed to more quickly render graphical images of ever higher resolutions and color depths have encouraged the development of GPUs that incorporate numerous processing cores that each have relatively limited instruction sets, but which are able to perform those limited instructions in parallel across a relatively large number of threads. It has been found that, where at least a portion of an analysis is amenable to being performed using GPU(s), a considerable increase in speed of performance of such analyses and/or the elimination of the need for a whole grid of separate computing devices may be realized by doing so. Thus, the processor 2550 of the coordinating device may distribute the selected profile **253*e* and/or coordinate the provision of the one or more data set portions 2131 to the storage 2360 for access by the one or more processors 2350** to enable such a widely parallel performance of the regression analysis of a selected testing regime.

Figure 8:
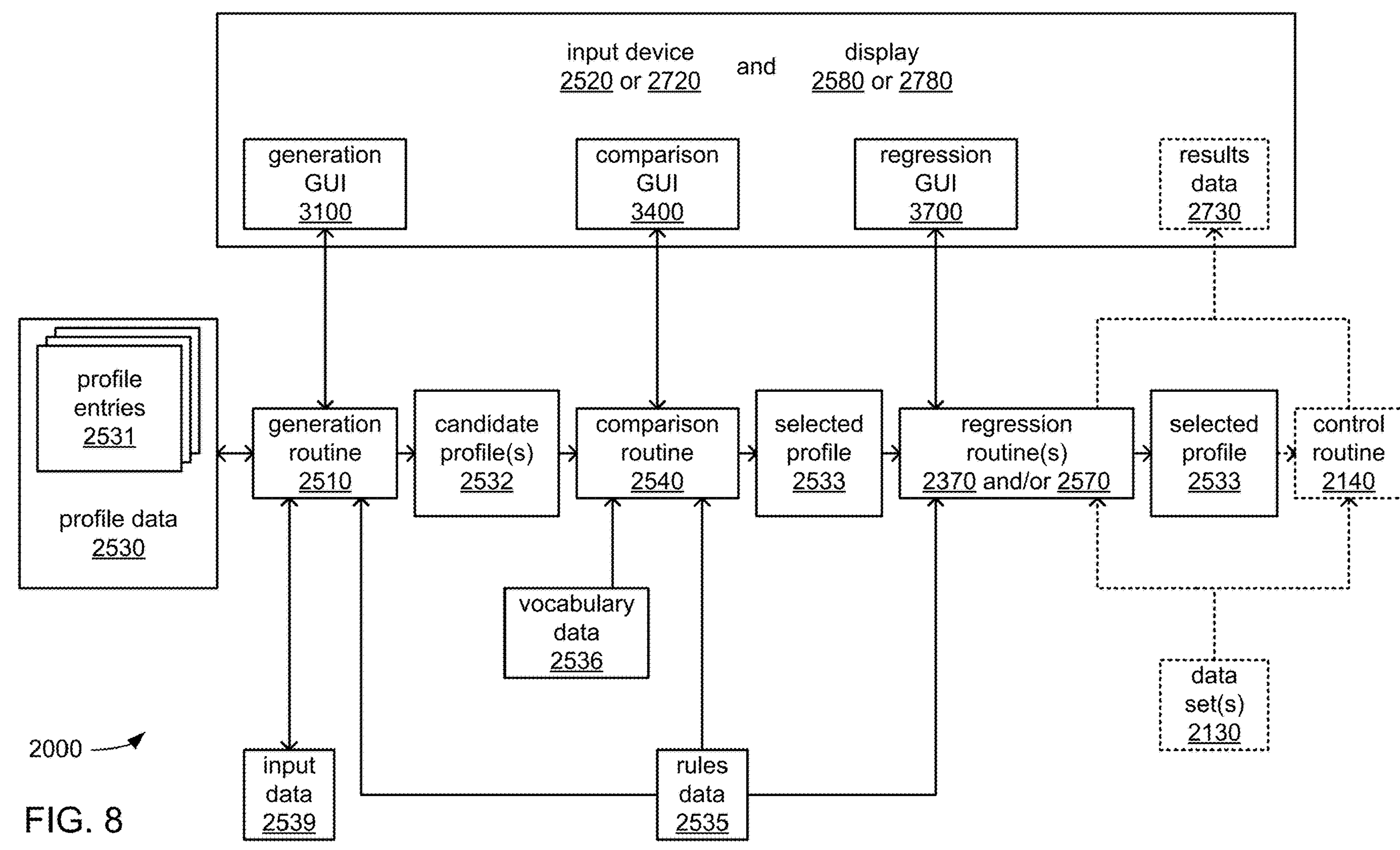
FIG. 8 illustrates an overview of an example of the guided generation, refinement, comparison, selection, regression analysis, and/or use of testing regime(s).

FIG. 8 illustrates an example of performing a combination of generating one or more testing regimes, comparing and selecting from among multiple candidate testing regimes, performing a regression analysis of a selected testing regime, and/or performing the selected testing regime. More specifically, FIG. 8 illustrates aspects of the manner in which the routines 2510, 2540, 2570, 2370 and/or 2140 may be executed cooperatively within embodiments of the distributed processing system 2000 of either of FIG. 7A or 7B to provide a series of GUIs 3100, 3400 and 3700 to visually guide such generation, comparison, selection and/or regression analysis of testing regimes to arrive at a single selected testing regime for use in evaluating and/or understanding aspects of a studied system.

As recognizable to those skilled in the art, each of the control routine 2140, the regression routine 2370, the generation routine 2510, the comparison routine 2540 and the regression routine 2570, including the components of which each may be composed, are selected to be operative on whatever type of processor or processors that are selected to implement applicable ones of the processor(s) 2150, 2350 and/or 2550. In various embodiments, each of these routines may include one or more of an operating system, device drivers and/or application-level routines (e.g., so-called "software suites" provided on disc media, "applets" obtained from a remote server, etc.). Where an operating system is included, the operating system may be any of a variety of available operating systems appropriate for execution by the processor(s) 2150, 2350 and/or 2550. Where one or more device drivers are included, those device drivers may provide support for any of a variety of other components, whether hardware or software components, of the data devices 2100, the node devices 2300 and/or the coordinating device 2500.

As has been discussed, in executing the generation routine 2510, the processor(s) 2550 of the coordinating device 2500 may be caused, either locally through the input device 2520 and/or the display 2580 of the coordinating device 2500, or remotely through the input device 2720 and/or the display 2780 of the viewing device 2700, to provide a generation GUI 3100. The generation GUI 3100 may guide an operator through providing parameters to generate one or more new testing regimes. As will be explained in greater detail, The generation GUI 3100 may provide a choice to traverse one or more pathways of prompts providing guidance through providing input that includes indications of parameter values entered by an operator for term-related, model-related and/or test-related aspects of a new testing regime, thereby accommodating operators of widely differing backgrounds. The processor(s) 2550 may then be caused to store such parameter values of each of those new testing regimes as one of the profile entries 2531 of the profile data 2530 stored within the storage 2560 of the coordinating device 2500.

In executing the comparison routine 2540, the processor(s) 2550 of the coordinating device 2500 may also be caused, either locally or remotely through the viewing device 2700, to similarly provide a comparison GUI 3400 to guide an operator through providing input(s) indicative of selecting a single testing regime for use (or at least for regression testing) from among multiple candidate testing regimes selected and retrieved from corresponding ones of the profile entries 2531. In so doing, and as will be explained in greater detail, following the selection of two or more candidate testing regimes to be so compared, the processor(s) 2550 may be caused to perform an automated matching of terms (e.g., the factors and/or higher order terms) among the candidate testing regimes based on characteristics of the terms, and/or additionally based on the texts of identifiers assigned to each of the terms. This may entail the processor(s) 2550 employing various matching rules retrieved from the rules data 2535 and/or indications of known synonyms retrieved from the vocabulary data 2536.

Also in providing the comparison GUI 3400, the processor(s) 2550 may be caused to guide the operator through providing input indicative of parameters for the performance of the comparison, thereby guiding the operator through the consideration of various aspects of the candidate testing regimes in selecting a single one of the candidate testing regimes to be the selected testing regime that is to be subjected to regression analysis and/or is to be performed. In so doing, the processor(s) 2550 may be caused to employ various templates retrieved from the rules data 2535 to generate and visually present various sets of graphs of corresponding aspects of the candidate testing regimes. One or more of the sets of graphs may advantageously exploit various features of the human visual system (HVS) to improve the ease and/or speed with which similarities and/or differences among the candidate testing regimes are able to be recognized, thereby speeding the selection of one of the candidate testing regimes.

In executing the regression routine 2570, the processor(s) 2550 of the coordinating device 2500 may be caused, either locally or remotely through the viewing device 2700, to similarly provide a regression GUI 3700 to guide an operator through providing input(s) indicative of parameters to control aspects of the performance of a regression analysis with the selected testing regime. With one of the candidate testing regimes having been selected to become the selected testing regime, a single one of the candidate profiles 2532 may be made available to the regression routine 2570 as the single selected profile 2533.

As an operator is so guided through providing parameters for various aspects of performing a regression analysis on the selected testing regime, the processor(s) 2550 may be caused by further execution of the regression routine 2570 to generate a sequence of instructions (e.g., a testing script) executable by the processor(s) 2550 and/or 2350 to cause performance of the regression analysis, and may include such a sequence of instructions in the selected profile 2533 (which may then be stored within a corresponding profile entry 2531 of the profile data 2530). In so generating such executable instructions, the processor(s) 2550 may be caused to employ various templates retrieved from the rules data 2535 to generate and visually present a human readable portion of the executable instructions for performing the regression analysis.

The processor(s) 2550 may then be caused to operate the network interface 2590 to distribute the selected profile 2533, and to coordinate the performance of the regression analysis, among the multiple node devices 2300 (as discussed in reference to FIG. 7A), and may be caused to further operate the network interface 2590 to receive the results data 2730 indicating the results of the regression analysis. The one or more processors 2350 may then be caused by their execution of multiple instances of the regression routine 2370, at least partially in parallel, to perform the regression analysis using simulated data and/or one or more of the data set portions 2131 of a data set 2130.

Following the performance of the regression analysis, the processor(s) 2550 may be further caused to coordinate the presentation of the results data 2730 to the operator. Alternatively or additionally, the processor(s) 2550 may be further caused to operate the network interface 2590 to transmit the selected profile 2533 to the one or more data devices 2100 as part of coordinating a performance of the selected testing regime by the one or more data devices 2100 in embodiments in which the one or more data devices 2100 are capable of controlling the studied system. In such embodiments, each of the processors 2150 may be caused by execution of the control routine 2140 to vary one or more factors provided as inputs to the studied system in accordance with the selected testing regime (e.g., as implemented by executing the testing script), as indicated in the selected profile 2533, such that the one or more processors 2150 of the one or more data devices 2100 may actually perform the selected testing regime on the studied system.

FIGS. 9A, 9B, 9C, 9D, 9E and 9F, taken together, depict higher level aspects of an example of providing the generation GUI 3100 to guide the generation of a new testing regime. As previously discussed, the generation GUI 3100 may be provided through the execution of the generation routine 2510 by the processor(s) 2550 of the coordinating device 2500. Further, FIGS. 9A-F, 10A-G, 11A-G and 12A-G, taken together, depict more detailed aspects of providing GUI portions 3110, 3120, 3130 and 3140 of the generation GUI 3100, respectively.

Turning to FIGS. 9A-B, the generation routine 2510 incorporates one or more GUI components 2511-2514, and one or more of interactive processing components 2518-2519. In executing the GUI components 2511, 2512, 2513 and/or 2514, the processor(s) 2550 are caused to visually present one or more of the GUI portions 3110, 3120, 3130 and/or 3140, respectively, either locally on the display 2580 of the coordinating device 2500 or remotely on the display 2780 of the viewing device 2700, and correspondingly, to receive inputs from an operator either locally via the input device 2520 of the coordinating device 2500 or remotely via the input device 2720 of the viewing device 2700. As those inputs are received, indications of parameters received in those inputs may be stored as part of the input data 2539.

A new testing regime may be generated based on parameters of an existing testing regime with indications of those parameters being retrieved from one of the profile entries 2531. At least some of those parameters are then modified via one or more of the GUI portions 3110-3140 before indications of those parameters, with such modifications, are stored as the new testing regime in a new profile entry 2531. Alternatively, a new testing regime may be an updated or corrected version of an existing testing regime with indications of parameters of that existing testing regime being retrieved from one of the profile entries 2531. At least some of those parameters are then modified via one or more of the GUI portions 3110-3140 before indications of those parameters, with modifications, are stored within the very same profile entry 2531 from which the retrieval occurred. Also alternatively, a new testing regime may be entirely new such that at least some parameters of the new testing regime may be generated via one or more of the GUI portions 3110-3140 based on one or more default values. Then indications of those parameters are stored as the new testing regime in a new profile entry 2531.

The visual presentations of the one or more GUI portions 3110-3140 may serve to provide visual prompts to guide an operator through providing inputs that are indicative of various aspects of a new testing regime, including term-related aspects, model-related aspects and/or test-related aspects. Such prompts may include, and are not limited to, menus, staged pop-up messages, a page-by-page "wizard" or other visual elements to prompt an operator through providing various parameters concerning term-related, model-related and/or test-related aspects of a testing regime. The processor(s) 2550 may be caused to generate the GUI portion 3110 as a result of executing the activity component 2511 of the generation routine 2510. The GUI portion 3110 may provide visual prompts to guide the operator through selecting action(s) to take, including whether to generate a new testing regime based on aspects of an existing testing regime, or not. In so doing, the GUI portion 3110 may also provide visual prompts to guide the operator through selecting one of three different pathways of prompts through which the operator may traverse to be guided through providing inputs indicative of various parameter values (e.g., term-related, model-related, test-related parameter values) of a new testing regime.

As previously discussed, different operators are likely to have different backgrounds, giving each operator a different perspective and/or a different level of understanding of testing regimes. Accordingly, each operator may have a different aspect of testing regimes that they are more familiar with, and thus, more comfortable in specifying (e.g., a different one of term-related aspects, model-related aspects, or test-related aspects). The provision of different pathways of prompts enables an operator to generate of a new testing regime beginning with the parameters for whichever one of such aspects that the operator feels most certain or comfortable about. More specifically, the operator may first be presented with initial prompts for parameters associated with whichever aspects the operator feels most certain or comfortable about, followed by subsequent prompts for parameters associated with other aspects that the operator may feel less certain or comfortable about. As will shortly be explained in greater detail, such initial prompts may be visually presented ahead of the subsequent prompts in a temporal sense (e.g., the initial prompts are visually presented at an earlier time followed by the subsequent prompts being visually presented at a later time) and/or in a spatial sense (e.g., the prompts may be organized spatially such that it is necessary to navigate past the initial prompts to reach the subsequent prompts).

Thus, depending on which pathway is selected via the GUI portion 3110, the processor(s) 2550 may be caused to execute: 1) the term component 2512 to provide a term-focused pathway that begins with initial term-related prompts within the GUI portion 3120 to enable an operator to focus initially on parameters for term-related aspects before moving on to subsequent prompts for model-related and/or test-related aspects; 2) the model component 2513 to provide a model-focused pathway that begins with initial model-related prompts within the GUI portion 3130 to enable an operator to focus initially on parameters for model-related aspects before moving on to subsequent prompts for term-related and/or test-related aspects; or 3) the test component 2514 to provide a test-focused pathway that begins with initial test-related prompts within the GUI portion 3140 to enable an operator to focus initially on parameters for test-related aspects before moving on to subsequent prompts for term-related and/or model-related aspects. Depending on which of the GUI components 2512-2514 is executed, the processor(s) 2550 may be caused to retrieve a corresponding pathway definition from among multiple pathway definitions in the rules data 2535.

Where a new testing regime is to be generated in a manner that is not based on parameter values copied from an existing testing regime retrieved from one of the profile entries 2531, the one or more GUI portions 3120, 3130 and/or 3140 that are used may present default values for various parameters of the new testing regime that may be retrieved from the rules data 2535. It should be noted that at least some of such default values may include indications of no value having been selected or otherwise specified for a one or more parameters (e.g., "null" value(s) or an indication of an "empty set" of values). Alternatively, where the new testing regime is to be generated in a manner that is based on parameter values copied from an existing testing regime retrieved from a profile entry 2531, the one or more GUI portions 3120, 3130 and/or 3140 that are used may present such retrieved parameter values of that existing testing regime as the starting point for the parameters of the new testing regime.

Regardless of which pathway is being traversed, and regardless of whether default values or retrieved values associated with an existing testing regime are used as a starting point for parameters, the processor(s) 2550 may be caused to monitor for the receipt of inputs indicative of selections and/or entry of parameter values for the generation of a testing regime. In some embodiments, a cursor, crosshairs or other visual element (not shown) may be visually presented to provide a visual indication of the current focal point of a corresponding pointing device (e.g., a mouse, trackpad, joystick, etc.) that may be used by an operator to make such selections in a manner that will be familiar to those skilled in the art (e.g., a selection or "clicking" of a virtual button, and/or a selection of one "radio button" from among multiple "radio buttons"). Alternatively or additionally, a text input device (e.g., a keyboard, predictive text keypad, etc.) may be used by an operator to make such selections through entry of text specifying text identifiers, quantities and/or other numerical values. Such inputs provided by the operator may be indicative of modifications to some of such default or retrieved values, while others of such default or retrieved values may remain unmodified. Accordingly, it may be that such default or retrieved values for the parameters are initially stored in the input data 2539, in addition to being initially presented in the prompts that are visually presented within GUI portions 3120, 3130 and/or 3140. As the operator provides inputs indicative of changes to those default or retrieved values, the input data 2539 may then be updated to reflect those changes, in addition to those changes being reflected in the prompts that are visually presented.

It should be noted that the inputs received from the operator may include cursor and/or pointer movements consistent with progressing through prompts (e.g., scrolling through prompts) without making changes to parameters that are visually presented thereat, and it may be that such inputs may be interpreted as indications of a choice to accept those parameters as they currently are, and thus, not modify them. More precisely, it may be that such GUI navigation mechanisms as scrollbars, page tabs, sets of selectable "next" and "back" virtual buttons, etc., may be used to monitor progression through the prompts that are presented while traversing through a selected one of the pathways. Where such navigation mechanisms are used to proceed through currently presented prompt(s) (and onto following prompts), such navigation inputs coupled with the lack of an input indicative of a change being made to a parameter value presented in a currently presented prompt may be interpreted by the processor(s) 2550 as input indicative of selecting/specifying the current value of that parameter.

Following the generation of a new testing regime by traversing at least once through at least one pathway, further prompts may be presented within the GUI portion 3110 to again guide the operator through selecting action(s) to take, including whether to store indications of the parameter values of the new testing regime within a profile entry 2531 for an existing testing regime (thereby replacing the parameter values of that existing testing regime with the parameter values of the new testing regime), or store indications of the parameter values of the new testing regime within a new profile entry 2531.

As depicted, each profile entry 2531 may store parameter values for parameters of term-related aspects, model-related aspects, and/or test-related aspects of a testing regime. Among the parameters for term-related aspects may be names of factors, types of factors (e.g., categorical, discrete or continuous), the quantity and/or names of levels for each categorical or discrete factor, terms formed from factors, the order of each term (e.g., first order, second order, etc.), aspects of derived and/or observed responses to one or more individual factors and/or combinations of factors, constraints (e.g., linear and non-linear constraints), etc. Among the parameters for model-related parameters may be a model type, one or more optimality types, whether each term is included in estimation or Bayesian modification, a coefficient derived for each term, etc. Among the parameters for test-related parameters may be an explicitly specified test type, such as a broader category of test type (e.g., screening design, orthogonal design, response surface design (RSD)); and/or an explicitly specified test type (e.g., definitive screening design (DSD), orthogonal mixed level (OML), Plackett-Burman (PB), orthogonal array (OA), near orthogonal array (NOA), mixture design (MD), Box-Behnken (BB), central composite design (CCD)). Also among the text-related parameters may be a quantity (or quantities) of runs.

It should be noted that, despite this description of the provision and use of GUIs to generate new testing regimes for which parameter values are then stored within profile entries 2531 of the profile data 2530, alternate embodiments are possible in which at least a subset of the profile data 2530 may be provided to the distributed system 2000 with multiple profile entries 2531 already included that store indications of such parameter values for multiple testing regimes. In this way, an operator of the distributed system 2000 may have a larger variety of existing testing regimes to choose from that are not limited to those that were previously generated within the distributed system 2000, itself.

As also depicted, the rules data 2535 may store information controlling various details of generating testing regimes. For the testing regimes, themselves, the rules data 2535 may store: specifications for what parameters are stored within each profile entry 2531 of the profile data 2530, and/or default data values for at least some of such parameters for a new testing regime that is not based on parameter values retrieved from a profile entry 2531 of an existing testing regime. For the GUI portions used in generating new testing regimes (or editing existing testing regimes), the rules data 2535 may store: a pathway definition for each pathway (e.g., state machine, logic tree or other form of logic for generating prompts; text, graphics and/or other content elements for the prompts); and/or order(s) of preference for use in presenting (e.g., in lists, as suggestions, etc.) model types, test types and/or categories of test types.

The rules data 2535 may also store information concerning limitations of compatibility among parameter values. Such information may include specifications of known compatible combinations of parameter values and/or ranges of parameter values for term-related, model-related and/or test-related parameters. Alternatively or additionally, such information may include specifications of known incompatible combinations of parameter values and/or ranges of parameter values for such parameters. Further, such information may include specifications for texts, graphics and/or other content elements for compatibility notices that may provide indications of the limits of compatibility among term-related, model-related and/or test-related parameter values, which may include indications of compatible combinations and/or of incompatible combinations of various parameter values.

In executing the generation routine 2510, the processor(s) 2550 of the coordinating device 2500 may be caused to execute the interactive processing components 2518-2519 in addition to, and at least partially in parallel with, the execution of one of the GUI components 2512-2514. More precisely, the interactive processing components 2518-2519 may be executed in a cooperative manner alongside whichever one of the GUI components 2512, 2513 or 2514 is currently being executed to provide one of the GUI portions 3120, 3130 or 3140, respectively, to provide a corresponding one of the pathways selected by the operator. Indeed, such factors as which one of the GUI portions 3120, 3130 or 3140 (and accordingly, which pathway) is currently being presented, and what inputs are received from the operator through that one of the GUI portions may influence: 1) the content of the prompts to control which options are made available to the operator for specifying parameter values of a new testing regime; 2) the analyses that are performed to identify incompatible combinations of parameter values and/or to identify combinations of parameter values that may trigger the provision of various suggestions; and/or 3) what compatibility notices are provided concerning incompatible combinations and/or the various suggestions.

Regarding the content of prompts, as previously discussed, the content of the initial prompts presented in each of the pathways is based on the focus of that pathway such that the term-focused pathway of the GUI portion 3120 begins with initial prompt(s) focused on term-related aspects, the model-focused pathway of the GUI portion 3130 begins with initial prompt(s) focused on model-related aspects, and the test-focused pathway of the GUI portion 3140 begins with initial prompt(s) focused on test-related aspects. However, the content of the subsequent prompts that are presented after the initial prompts in each of the pathways may be focused on the other aspects that are not the focus of the initial prompts in that pathway, and that content within those subsequent prompts may be at least partially limited by the processor(s) 2550 based on the parameter values that are indicated as selected/specified in/by the initial inputs received from an operator in response to the initial prompts.

More specifically, in executing the interactive conditions component 2518, the processor(s) 2550 may be caused to monitor the input data 2539 for values associated with the parameters presented in the initial prompts, including initial inputs provided by the operator (e.g., input indicative of the operator specifying new/changed parameter value(s)) and/or parameter values already stored within the input data 2539 that are not changed by initial inputs from the operator (e.g., input indicative of the operator choosing to not make a change to a parameter value). The processor(s) 2550 may then use indications retrieved from the rules data 2535 of the limits of compatibility among term-related, model-related and/or test-related parameters of a testing regime to determine what options are to be offered in the subsequent prompts for specifying and/or changing parameter values of parameters. For example, and as will be familiar to those skilled in the art, there may be limits to the quantities and/or types of terms that are compatible with various model types and/or test types such that some combinations of parameter values are simply incompatible. Also for example, there may be minimum and/or maximum quantities of runs that are based on various quantities and/or types of terms, and/or that may be associated with various test types.

Where the specification of a parameter value for one parameter in an initial prompt causes another parameter that might otherwise be presented in a subsequent prompt to become meaningless or otherwise inapplicable (i.e., is caused to serve no function in specifying any aspect of the testing regime), then that other parameter may be presented in that subsequent prompt in a way that makes clear that it is not an option that is able to be specified, or that other parameter may simply not be presented in that subsequent prompt, at all. Also more specifically, where the specification of a value for one parameter in an initial prompt causes one or more values that might otherwise be selected for another parameter in a subsequent prompt to become incompatible, then that other parameter may still be presented in the subsequent prompt, but with the values that are permitted to be specified for it being limited to the values that are compatible. In this way, the responses provided by an operator in initial inputs to the initial prompt(s) focused on a testing regime aspect that the operator is presumably most comfortable about are used as a basis for determining what guidance is to be provided in the subsequent prompts focused on other testing regime aspects that the operator is presumably less comfortable about. Then, in executing the interactive guidance component 2519 (in conjunction with whichever one of the GUI components 2512-2514 is associated with the pathway currently being traversed such that its prompts are currently being presented), the processor(s) 2550 may be caused to present such more limited forms of the subsequent prompts. Stated differently, the parameter values specified by the operator for parameters that are visually presented in the initial prompts serve as a basis for narrowing what parameters may be visually presented in the subsequent prompts and/or for narrowing what parameter values are able to be specified for the parameters that are visually presented in the subsequent prompts.

By way of example, in the term-focused pathway of the GUI portion 3120, the initial prompts are term-related prompts to guide an operator through providing initial term-related inputs that may specify various term-related parameter values, which are stored in the input data 2539. In executing the interactive conditions component 2518, the processor(s) may be caused to use the indications of term-related parameter values present within the input data 2539 as the term-related parameters values specified by the operator in initial inputs in response to those initial term-related prompts to determine what model-related and/or test-related parameters are applicable and/or what model-related and/or test-related parameter values are compatible with those term-related parameter values. Then, in executing the interactive guidance component 2519 in a cooperative manner with the term pathway component 2512, the processor(s) 2550 may be caused to generate the subsequent prompts presented as part of the term-focused pathway of the GUI portion 3120 to correspondingly limit the model-related and/or test-related parameters that are presented, and/or to correspondingly limit the model-related and/or test-related parameter values that are able to be specified. By way of example, in the test-focused pathway of the GUI portion 3140, the initial prompts are test-related prompts to guide an operator through providing test-related inputs that may specify various test-related parameter values. As will later be discussed in greater detail, among such initial prompts may be a prompt that provides the operator with an opportunity to explicitly select a test type. As will be familiar to those skilled in the art, a parameter value unique to the DSD test type is a quantity of extra runs. Thus, where DSD is the specified test type, the quantity of extra runs is applicable. However, if a different test type is specified, then the quantity of extra runs becomes an inapplicable parameter as it has no meaning for other test types. As a result, where DSD is not specified as the test type, then the quantity of extra runs may not be visually presented as a parameter that can be specified in a subsequent prompt, or may be visually presented in a manner that indicates that a value for this parameter cannot be specified. In this way, the operator is guided (to at least some degree) away from providing subsequent inputs for the subsequent prompts that are indicative of specifying inapplicable or incompatible parameter values for the model-related and/or test-related aspects of a new testing regime.

Regarding the analyses that are performed to identify incompatible combinations of parameter values, the focus of the initial prompts in each of the pathways may determine at least some aspects of the analyses that are performed. More specifically, for the term-focused pathway of the GUI portion 3120, the analysis may be a determination of what model-focused and/or test-focused parameter values associated with the subsequent model-focused and test-focused prompts are compatible with the term-focused parameter values that are indicated as specified by initial inputs in response to the initial term-focused prompts; for the model-focused pathway of the GUI portion 3130, the analysis may be a determination of what term-focused and/or test-focused parameter values associated with the subsequent term-focused and test-focused prompts are compatible with the model-focused parameter values that are indicated as specified by initial inputs in response to the initial model-focused prompts; and for the test-focused pathway of the GUI portion 3140, the analysis may be a determination of what term-focused and/or model-focused parameter values associated with the subsequent term-focused and model-focused prompts are compatible with the test-focused parameter values that are indicated as specified by initial inputs in response to the initial term-focused prompts.

Regarding the analyses that are performed to identify combinations of parameter values that may trigger the visual provision of suggestions of test types, the focus of the initial prompts in each of the pathways may determine what test types may be suggested, along with an analysis of what test types are compatible with the other parameter values indicated in the input data 2539 for term-related, model-related and/or test-related aspects (other than a value that may indicate an explicit specification of a particular test type). For example, as more and more term-related parameters are being specified in initial input(s) received in response to initial term-related prompt(s), the processor(s) 2550 may employ such specified term-related parameter values to increasingly narrow the set of test types that are compatible with those parameter values as part of guiding the operator through the selection of a test type. Or, the processor(s) 2550 may employ such term-related parameter values to identify one or more alternative test types to a particular test type that the operator may have already specified as part of providing the operator with guidance concerning what may be a better choice of test type that may lead to a more effective testing regime.

Regarding the compatibility notices that are provided concerning incompatible combinations of parameter values, the focus of the initial prompts in each of the pathways may at least partially determine how an incompatibility is presented and/or the options that are suggested in such notices of what actions to take to resolve an incompatibility. More specifically, for the term-focused pathway of the GUI portion 3120, a compatibility notice may include text that describes an incompatibility as between parameter value(s) of term-related parameter(s) and parameter value(s) of model-related and/or text-related parameter(s); for the model-focused pathway of the GUI portion 3130, a compatibility notice may include test that describes an incompatibility as between parameter value(s) of model-related parameter(s) and parameter value(s) of term-related and/or text-related parameter(s); and for the test-focused pathway of the GUI portion 3140, a compatibility notice may include test that describes an incompatibility as between parameter value(s) of test-related parameter(s) and parameter value(s) of term-related and/or model-related parameter(s).

Further, for the term-focused pathway of the GUI portion 3120, the compatibility notice may include text that suggests altering the parameter value(s) of the model-related and/or test-related parameter(s) that are incompatible with the parameter value(s) of the term-related parameter(s); for the model-focused pathway of the GUI portion 3130, the compatibility notice may include text that suggests altering the parameter value(s) of the term-related and/or test-related parameter(s) that are incompatible with the parameter value(s) of the model-related parameter(s); and for the test-focused pathway of the GUI portion 3140, the compatibility notice may include text that suggests altering the parameter value(s) of the model-related and/or test-related parameter(s) that are incompatible with the parameter value(s) of the test-related parameter(s).

Regarding the suggestion notices that are provided to suggest the specification of particular test-type(s), the focus of the initial prompts in each of the pathways may determine an order of preference for what test types may be suggested. By way of example, it may be that there is a different order of preference for test types for each pathway, and where there are multiple test types to suggest, those multiple test types may be suggested in such an order of preference. Alternatively or additionally, it may be that a determination of whether to suggest a test type is at least partially based on whether it is a more preferred test type than a test type that may have already been explicitly specified.

Still further, it may be that, within a single pathway, there are multiple orders of preference for test types, of which one is automatically selected based on one or more parameter values specified in connection with initial prompts. For example, within the model-focused pathway 3513, the specification of 1) a Response Surface Model as a model type may beget an order of preference for test types (from most to least preferred) of I-optimal design, Central Composite Design and Box-Behnken; 2) main effects with two-factor interactions as required may beget an order of preference for test types (from most to least preferred) of Definitive Screening Design, Orthogonal Array (e.g., Plackett-Burman), A-optimal or D-optimal design(s), Orthogonal Mixed Level and Near-Orthogonal Array; 3) main effects with two-factor interactions as necessary may beget an order of preference for test types (from most to least preferred) of A-optimal design, D-optimal design and I-optimal design; or 4) a mixture design may beget an order of preference for test types (from most to least preferred) of I-optimal design, Simplex Lattice, Simplex Centroid and Extreme Vertices.

However, as another alternative in still other embodiments, it may be that there is a single order of preference for test types that is associated with multiple pathways, if not all pathways. An example of such a single order of preference may be (from most to least preferred): Box-Behnken, Central Composite Design, Definitive Screen Design, Mixture Design, Near Orthogonal Array, Orthogonal Mixed Level, Plackett-Burman.

Regardless of whether there is a single order of preference for all pathways, or different order(s) of preference for each pathway, one(s) of the test types within an order of preference that are not compatible with one or more currently specified parameter values may not be considered and/or utilized for suggestion notices. In effect, an order of preference of test types may be treated as if it does not include test type(s) that are not compatible with currently specified parameter values. Thus, for example, if a number of runs is specified that is not compatible with a test type that requires a specific minimum quantity of runs (e.g., the Definitive Screen Design or the Orthogonal Array), but the currently specified quantity of runs is not high enough to meet such a minimum quantity, then that particular test type would be prevented from being suggested, even if all other parameter values currently specified would be compatible with it.

Also, regardless of the order of preference, or whether there is a single order of preference, differing orders of preference, or no order of preference at all, the processor(s) 2550 may additionally be caused to present, with such suggestion notices, information concerning advantages and/or disadvantages of suggested test type(s), which the processor(s) 2550 may be caused to retrieve from the rules data 2535.

It should be noted that, in situations where the current parameter values for a testing regime provide both a trigger to present a compatibility notice concerning an incompatibility among those values and a trigger to present a suggestion notice to suggest a test type, it may be that the presentation of the compatibility notice is given priority over the presentation of the suggestion notice. This may be done in recognition of the fact that a correction to one or more parameter values that an operator may be prompted to make by a compatibility notice may undo the conditions among the parameter values that would trigger the presentation of the suggestion notice, and/or may bring about other conditions among the parameter values that would trigger the presentation of a different suggestion notice. More broadly, it may be that the processor(s) 2550 are caused to refrain from presenting suggestion notices while an incompatibility among parameter values exists.

Figure 9C:
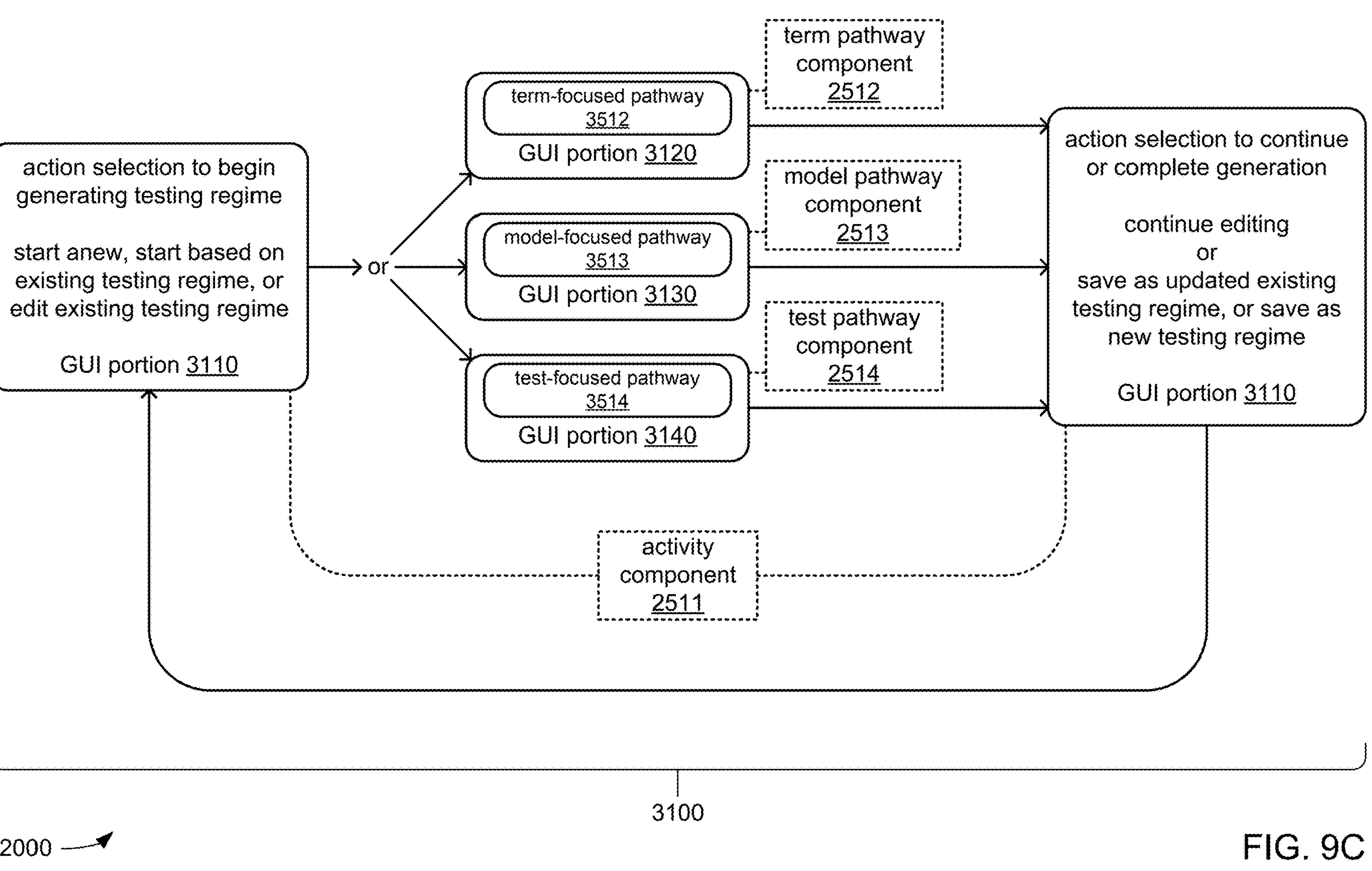

Turning to FIG. 9C, as depicted, the provision of the generation GUI 3100 may begin with the GUI portion 3110 visually presenting options for different courses of action that an operator of the distributed processing system 2000 may choose to generate a new testing regime, or to edit an existing testing regime. Among the options associated with generating a new testing regime may be the option of retrieving and using the parameter values of an existing testing regime as a starting point, or to refrain from doing so such that a set of default parameter values for at least some parameters is used as a starting point. Also among the options associated with generating a new testing regime may be a choice of multiple different pathways of prompts to traverse through, such as the depicted term-focused pathway 3512 of the GUI portion 3120, the depicted model-focused pathway 3513 of the GUI portion 3130, and the depicted test-focused pathway 3514 of the GUI portion 3140.

Upon choosing to traverse through one of such pathways 3512-3514, and upon completing that traversal, it may be that the operator is returned to the GUI portion 3110 where the operator may once again be presented with various options for a course of action. Again, the operator may be presented with various options for storing the parameter values of the new testing regime, including storage within the profile data 2530, either in an entirely new profile entry 2531, or in an existing profile entry 2531 as a replacement for (or updated version of) an existing testing regime. However, it should also be noted that the operator may be presented with the option to further edit a new testing regime to thereby continue the process of generating it, either by traversing again through an already traversed pathway, or by traversing through a different pathway. Either way, as part of continuing the generation a new testing regime, the parameter values that were specified during a prior traversal through one of the pathways 3512-3514 may be preserved and used as the starting point for the new pathway traversal, regardless of which one of the pathways 3512-3514 is now traversed.

The ability to traverse through the same pathway multiple times and/or to traverse through more than one pathway as part of generating a new testing regime may be useful to an operator who initially starts by traversing one pathway that begins with the entry of parameters they feel most certain about, and then later chooses to traverse another pathway that begins with the entry of other parameters that they wish to explore more fully. As previously discussed, the parameter values indicated in initial inputs in response to the initial prompts may influence various aspects of analyses that are performed and what parameter value options are presented and/or accepted for parameters in the subsequent prompts. Thus, it may be that an operator finds the differences in parameter options that may be presented to them in different ones of the pathways 3512-3514 provides them with insights into how various parameters interact across different aspects of a testing regime, and this may inform how the operator chooses ultimately to proceed in generating a new testing regime.

It should be noted that, as a result of the possibility that a traversal through one of the pathways 3512-3514 may be preceded by an earlier traversal through either the same pathway or a different pathway, it may be that the processor(s) 2550 are caused to visually present a compatibility notice concerning an incompatibility among parameters immediately after a change is made to a parameter value associated with one or more of the initial prompts. However, it should also be noted that such an event may, instead, be caused to occur due to the use of parameter values of an existing testing regime as a starting point for generating a new testing regime, even if there has not yet been a traversal through any of the pathways 3512-3514 in connection with generating the new testing regime.

Indeed, and looking briefly ahead, FIGS. 10A-I, 11A-G and 12A-G present examples of the traversal of an example term-focused pathway 3512, an example model-focused pathway 3513 and an example test-focused pathway 3514, respectively, that include examples of incompatible parameters arising from at least one parameter that was either: 1) specified during an earlier traversal through one of these pathways 3512-3514, and then stored within the input data 2539, or 2) retrieved from the parameter values of an existing testing regime as part of using those retrieved parameter values as a starting point for generating a new testing regime. More specifically, FIGS. 10A-B and 10F-G present example situations in which the earlier specification of a model type or a test type, either in an earlier traversal through a pathway or in parameter values retrieved from an existing testing regime, causes various term-related or test-related parameter values to be incompatible with that earlier-specified model type or test type parameter in a current traversal through the example term-focused pathway 3512 of FIGS. 10A-I. Similarly, FIG. 11A presents an example situation in which a quantity of runs that was specified, either in an earlier traversal through a pathway or in parameter values retrieved from an existing testing regime, causes Alias Optimality to be an incompatible model-related parameter value with that earlier-specified test-related parameter in a current traversal through the example model-focused pathway 3513 of FIGS. 11A-G. Also similarly, FIG. 12A presents an example situation in which the specification of term types for the terms, either in an earlier traversal through a pathway or in parameter values retrieved from an existing testing regime, causes the DSD test type to be an incompatible test-related parameter value with those earlier-specified term-related parameters in a later traversal through the example test-focused pathway 3514 of FIGS. 12A-G.

Figure 9D:
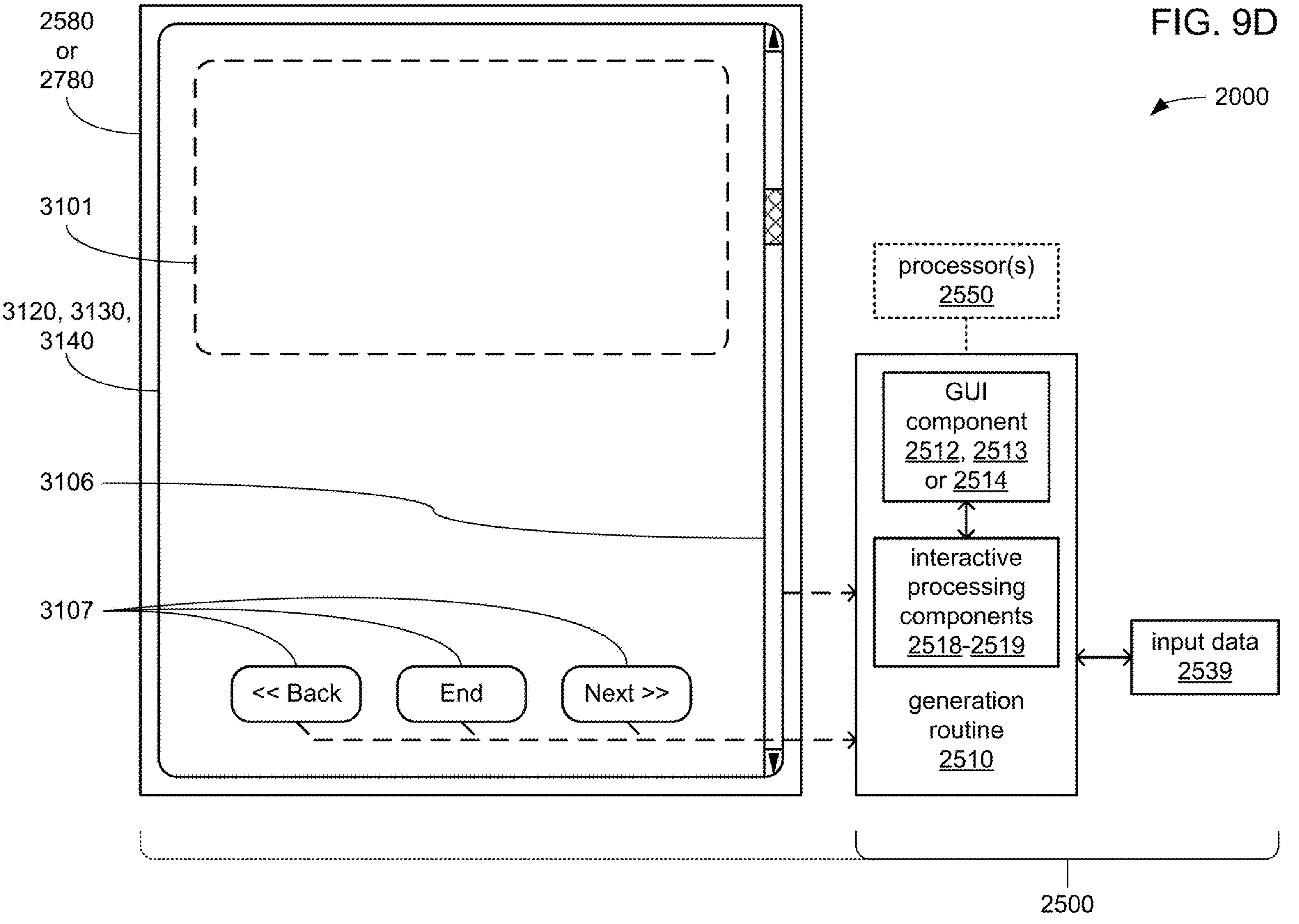

Turning to FIG. 9D, as previously discussed, each of the GUI portions 3120, 3130 and 3140 may present a different pathway 3512, 3513 and 3514, respectively, of prompts that are each organized based on the testing regime aspect that is the focus of that pathway. As also previously discussed, in each pathway, the initial prompts are focused on parameters associated with the testing regime aspect that is the focus of that pathway, while the subsequent prompts address other testing regime aspects. Accordingly, each of the pathways 3512-3514 presents a series of prompts (starting with the initial prompts, and then proceeding to the subsequent prompts) that may likely be too numerous and/or occupy too much display area to all be visually presented on a single display 2580 or 2780, simultaneously. Thus, as depicted, and as previously discussed, various GUI navigation mechanisms may be provided to enable an operator to proceed through such a set of prompts (e.g., multiple ones of the depicted prompt 3101 presented in dashed outline form), such as the depicted scroll bar 3106 and/or the depicted set of navigation buttons 3107 (implemented as virtual buttons visually presented on the display 2580 or 2780).

Again, where such GUI navigation mechanism(s) are used by an operator of the distributed system 2000 to proceed past a prompt 3101 (e.g., operating the scrollbar 3106 to scroll past that prompt 3101, or operating one of the navigation buttons 3107 to proceed past a display page on which that prompt 3101 is presented on the way to another page) without providing input indicative of specifying a parameter value for a parameter thereof (which may include input to change a previously specified parameter value), such use of a navigation mechanism in the absence of other input to proceed past a prompt may be interpreted as input indicative of a choice to accept the current value of that parameter (even if it is a "null" value or an empty set) without alteration. Thus, such input that does not cause a change in a current parameter value may be interpreted as specifying or continuing to specify that current parameter value as is.

It should also be noted that, in some embodiments, where the processor(s) 2550 have been caused to visually present a suggestion notice suggesting a particular test type, an input from the operator to act on that suggestion by selecting that particular test type may also trigger an immediate end to the traversal of the pathway in which that suggestion notice was visually presented. As a result, it may be that one or more further prompts of a pathway are not visually presented, thereby providing no opportunity to specify parameter values for parameters associated with those one or more further prompts, at least during that traversal of that pathway. In such a situation, the processor(s) 2550 may be caused to interpret the resulting lack of input(s) specifying parameter values for those parameters as indicating that the current parameter values for those parameters have been accepted as is (again, even if those parameter value(s) include one or more "null" values and/or empty sets).

Figure 9E:
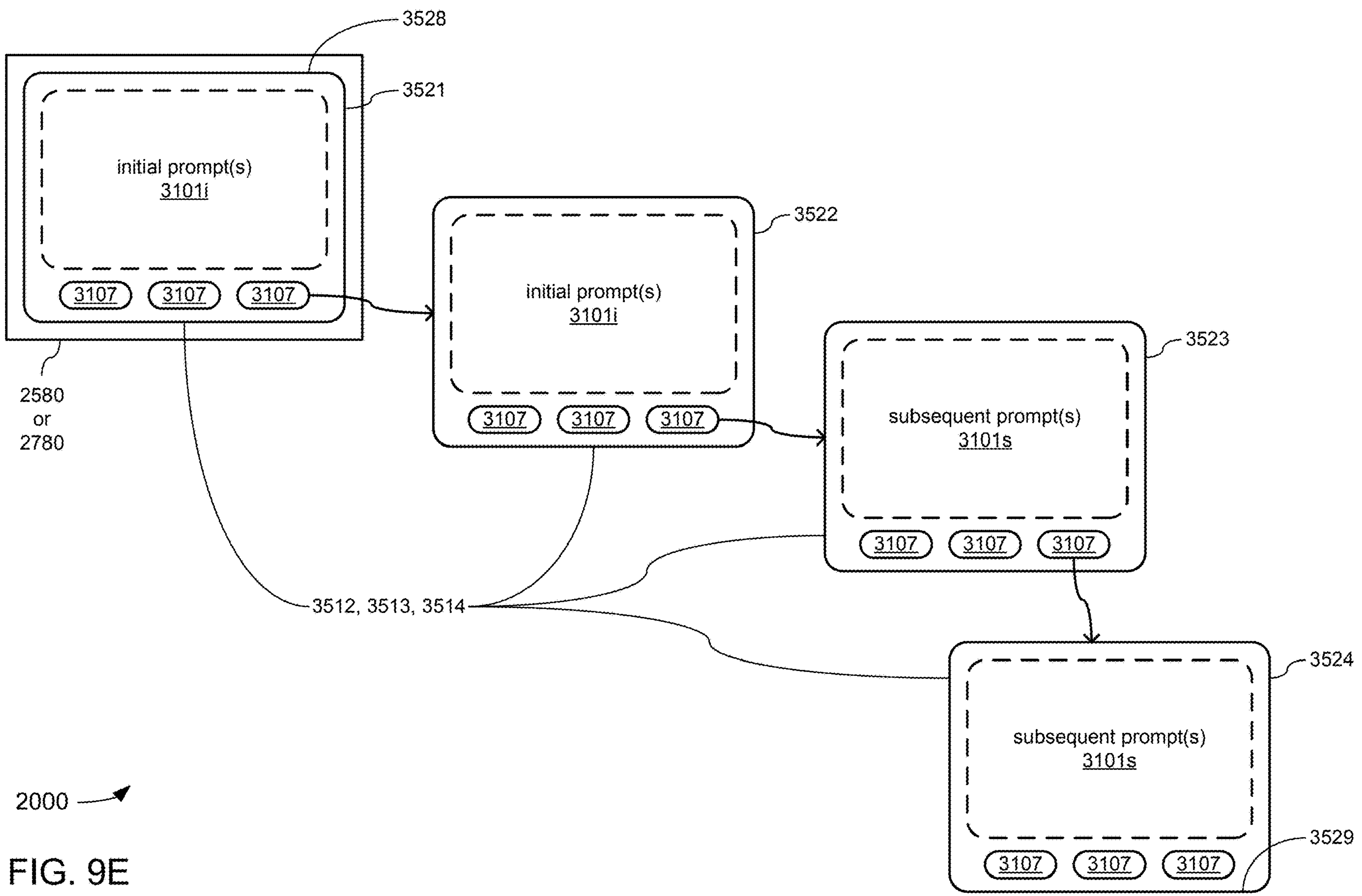
Figure 9F:
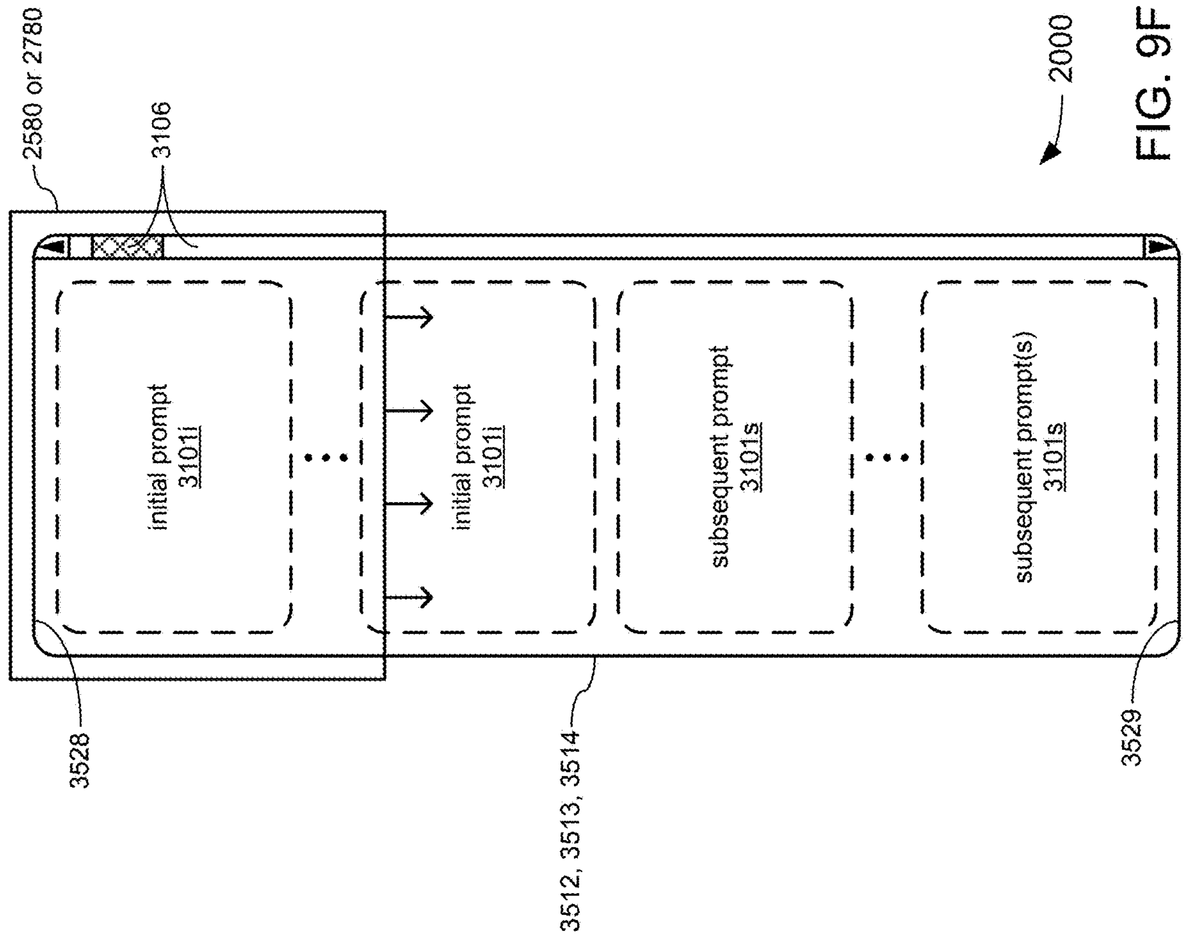

Turning to FIGS. 9E-F, as also previously discussed, the initial prompts of one of the pathways 3512, 3513 or 3514 may be visually presented ahead of the subsequent prompts in a temporal sense (e.g., the initial prompts are visually presented at an earlier time followed by the subsequent prompts being visually presented at a later time) and/or in a spatial sense (e.g., the prompts may be organized spatially such that it is necessary to navigate past the initial prompts to reach the subsequent prompts).

FIG. 9E depicts an example of such a temporally sequential visual presentation of initial prompts 3101*i* of one of the pathways 3512, 3513 or 3514, followed at a later time by the visual presentation of subsequent prompts 3101*s* of that same pathway. More specifically, one of the pathways 3512, 3513 or 3514 may be broken upon into a sequence of pages (e.g., the depicted pages 3521, 3522, 3523 and 3524). Such pages may be visually presented on the display 2580 or 2780, one at a time, starting with the first page at the start 3528 of that pathway (e.g., the depicted page 3521) with one or more initial prompts 3101*i* visually presented therein, before proceeding through one or more further initial prompts 3101*i* visually presented in one or more further pages (e.g., the depicted page 3522), then proceeding through one or more subsequent prompts 3101*s* visually presented in one or more still further pages (e.g., the depicted page 3523), and ending with the last page at the end 3529 of that pathway (e.g., the depicted page 3524) with one or more further subsequent prompts 3101*s* visually presented therein. Moving through those pages, starting at the first page 3521 at the start 3528 of that pathway, proceeding sequentially through intervening pages, and ending at the last page 3524 at the end 3529 of that pathway may be effected through use of such a GUI navigation mechanism as the depicted navigation buttons 3107.

FIG. 9F depicts an example of such a spatially sequential visual presentation of initial prompts 3101*i* of one of the pathways 3512, 3513 or 3514, followed at a later spatial location by the visual presentation of subsequent prompts 3101*s* of that same pathway. More specifically, one of the pathways 3512, 3513 or 3514 may be generated as a sequential set of prompts starting at the start 3528 of that pathway with one or more initial prompts 3101*i* visually presented in a sequential order, and then continuing with one or more subsequent prompts 3101*s* visually presented in a sequential order ending at the end 3529 of that pathway. Moving through the prompts of that pathway, starting at the start 3528 of that pathway, proceeding through the initial prompts 3101*i*, then proceeding through the subsequent prompts 3101*s*, and then reaching the ending 3529 of that pathway may be effected through the use of such a GUI navigation mechanism as the depicted scrollbar 3106. Thus, as will be familiar to those skilled in the art, panning under the control of such a GUI navigation mechanism is used to move through that pathway 3512, 3513 or 3514, starting with the initial prompts 3101*i*, and spatially followed by the subsequent prompts 3101*s*.

Figure 10A:
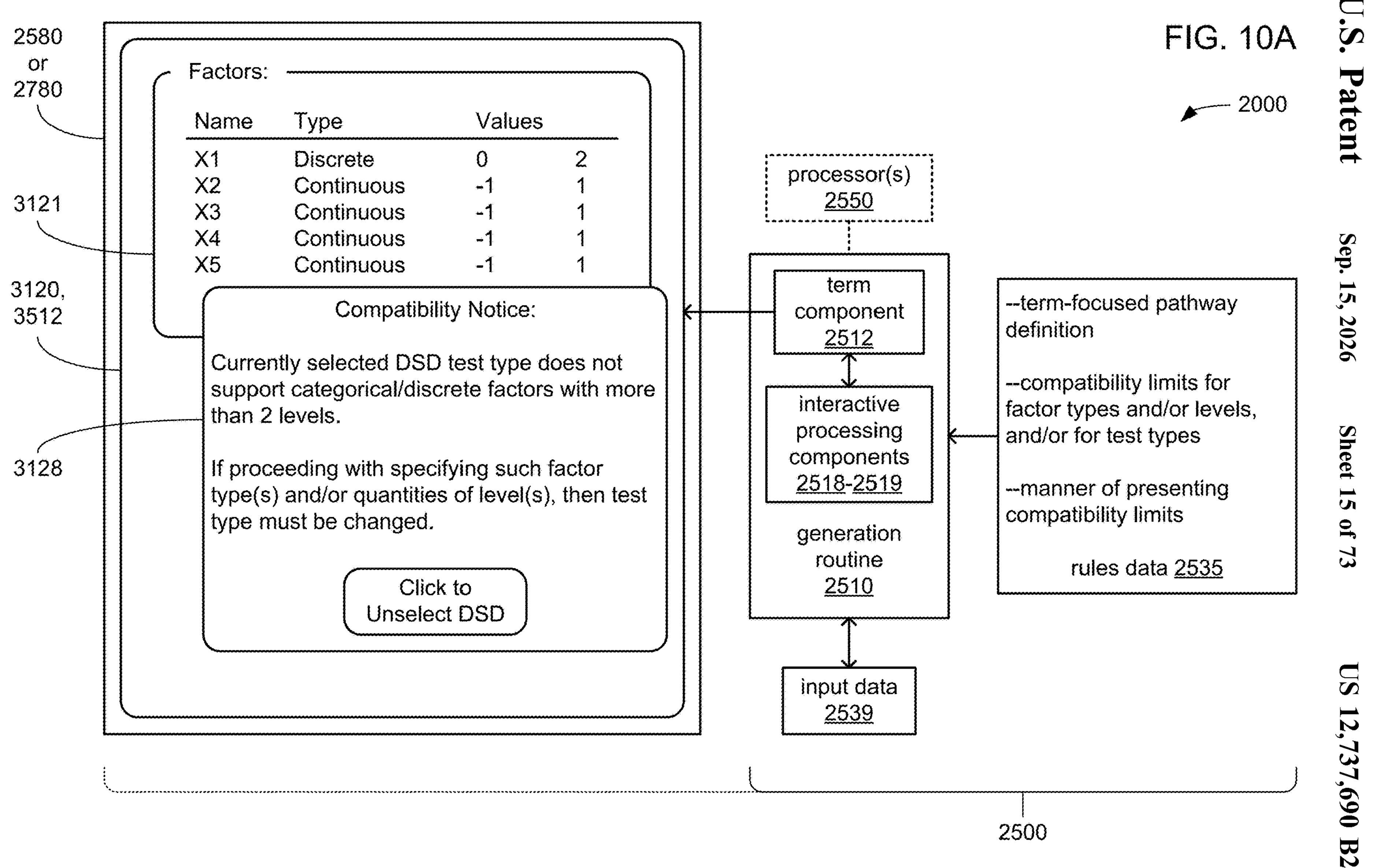

FIGS. 10A, 10B, 10C, 10D, 10E, 10F, 10G, 10H and 10I, taken together, depict, in greater detail, various aspects of traversing through an example term-focused pathway 3512 of prompts of the GUI 3120 that is caused to be visually presented by the processor(s) 2550 as a result of executing the term component 2512 together with the interactive processing components 2518-2519. More specifically, and as discussed above in reference to FIGS. 9A-D, the processor(s) 2550 are initially caused to present one or more initial prompts that focus on term-related parameters of a new testing regime (as depicted in FIGS. 10A-C), before presenting one or more subsequent prompts that focus on model-related and/or test-related parameters thereof (as depicted in FIGS. 10D-10I). Additionally, while the traversal through this term-focused pathway 3512 occurs, the processor(s) 2550 are caused to recurringly analyze the parameter values stored within the input data 2539 (including any default or retrieved parameter values used as a starting point, along with any newly specified and/or newly modified parameter values provide by inputs of the operator), and to selectively present compatibility notices indicating incompatibilities among parameters and/or suggestion notices suggesting test type(s). Further, and as also discussed above in reference to FIGS. 9A-D, one or more of such compatibility notices indicating an incompatibility among parameters may be triggered as a result of this term-focused pathway 3512 being traversed after an earlier traversal of one of the pathways and/or as a result of parameter values of an existing testing regime being used as a starting point (as depicted in FIGS. 10A-B and 10F-G).

Turning to FIG. 10A, as depicted, the processor(s) 2550 may be caused by execution of the term component 2512 to begin the provision of this example term-focused pathway 3512 of prompts of the GUI portion 3120 with the visual presentation of a term-related prompt 3121 as one of the initial prompts. As previously discussed, in so executing the term component 2512, the processor(s) 2550 may be caused to retrieve a definition of the term-focused pathway 3512, including details of what prompts to present, from the rules data 2535. As also depicted, the processor(s) 2550 may be caused by execution of the term component 2512 and the interactive processing components 2518-2519 to also present a compatibility notice 3128 providing an indication of an incompatibility among parameter values. As previously discussed, in so executing the interactive processing components 2518-2519, the processor(s) 2550 may be caused to retrieve, from the rules data 2535, indications of the limits of compatibility of various parameter values for various parameters, including term-related parameter values for such parameters as factor types and/or factor levels, and/or including test-related parameter values for such parameters as test types (including the DSD test type). Additionally, indications of the manner of presenting the term-related prompt 3121 and/or the compatibility notice 3128, including text and/or graphical elements used for each, may also be retrieved from the rules data 2535.

Regarding the term-related prompt 3121, this term-related prompt 3121 serves to guide an operator of the distributed processing system 2000 through providing term-related parameter values for such parameters as the name, type and/or range of values for each factor. As depicted, this prompt takes the form of an editable table of these term-related parameter values. In various embodiments, it may be that the type for each factor may be a continuous type, a categorical type or a discrete type. It may also be that, depending on the type of for each factor, a range of numerical values may be specified. As also depicted, it may be that the parameter values for name, type and range of values for each of multiple factors have already been previously provided. Again, this may be due to parameter values for parameters of an existing testing regime having been retrieved and used as a starting point, and/or this may be due to parameter values for at least some parameters having been provided in operator inputs in one or more previous pathway traversals.

Regarding the compatibility notice 3128, as indicated therein, it may be that the DSD test type was previously specified as a test-related parameter value. As also indicated therein (and as will be familiar to those skilled in the art), factors of the categorical or discrete type that have more than 2 levels are incompatible with the specification of the DSD test type. Thus, as depicted, there are one or more term-related parameter values associated with the term-related prompt 3121 that are not compatible with the test-related parameter value of the DSD test type. As depicted, the compatibility notice 3128 may take the form of a "popup message" that overlaps other prompts so as to set forth this incompatibility in a manner intended to gain the attention of the operator.

As depicted, it may be that the presentation of the compatibility notice 3128 was triggered as a result of the operator having responded to the term-related prompt 3121 with inputs editing the type and/or the range of values for the factor "X1" within the editable table provided in the term-related prompt 3121 to a combination of a discrete type with 3 levels. As previously discussed, before the traversal of this example term-focused pathway 3512 began, previously specified parameter values used as a starting point and/or provided by an operator through one or more previous pathway traversals may be stored within the input data 2539. Indications of changes then made by the operator to the type and/or range of values parameters for the factor "X1" would then be stored within the input data 2539, and would then be used in analyses performed by the processor(s) 2550 to identify such an incompatibility among the parameter values, thereby triggering the presentation of the compatibility notice 3128. While the operator may have the option of returning to the editable table of the term-related prompt 3121 to undo whatever edit(s) were made therein that triggered the compatibility notice 3128, as depicted, the compatibility notice 3128 may directly provide a mechanism by which the operator may alternately resolve this incompatibility by unselecting the DSD test type as a test parameter value (e.g., by clicking the depicted virtual button therein).

Turning to FIG. 10B, as depicted, the processor(s) 2550 may be caused by execution of the term component 2512 to continue the provision of this example term-focused pathway 3512 with the additional visual presentation of another term-related prompt 3122 as another of the initial prompts. As also depicted, the processor(s) 2550 may be caused by the execution of the interactive processing components 2518-2519 to also present a compatibility notice 3128 providing an indication of a different incompatibility among parameter values.

Regarding the term-related prompt 3122, this term-related prompt 3122 serves to guide the operator through providing one or more linear constraints that may be applicable to one or more of the factors displayed in the term-related prompt 3121. As depicted, this prompt takes the form of a virtual button accompanied by explanatory text concerning its function. More specifically, as per the explanatory text, clicking on this virtual button (e.g., with a mouse pointer, not specifically shown) may cause the processor(s) 2550 to present a text entry area (not specifically shown) in which one or more linear constraints may be entered in equation form.

Regarding the compatibility notice 3128, as indicated therein, it may be that the DSD test type was previously specified as a test-related parameter value. As also indicated therein, and as will be familiar to those skilled in the art, linear constraints are incompatible with the specification of the DSD test type. Thus, attempting to provide one or more linear constraints in response to the term-related prompt 3122 is not compatible with the current test-related parameter value of the DSD test type, and it may have been such an attempt to provide one or more linear constraints that triggered the presentation of the compatibility notice 3128.

Again, as depicted, the compatibility notice 3128 may take the form of another "popup message" that overlaps other prompts in a manner intended to gain the attention of the operator. Also again, while the operator may have the option of returning to the term-related prompt 3122 to undo whatever was done to add the linear constraint(s) that triggered the compatibility notice 3128, as depicted, the compatibility notice 3128 may directly provide a mechanism by which the operator may alternately resolve this incompatibility by unselecting the DSD test type as a test parameter value.

Returning to the term-related prompt 3122, it should be noted that, in some embodiments, the processor(s) 2550 may be caused, by execution of the combination of the term component 2512 and the interactive processing components 2518-2519, to visually present the term-related prompt 3122 in a manner that is visually indicative of such an incompatibility arising if a linear constraint were to be added. In some embodiments, such a visual indication may be the presentation of the outline and text of the virtual button, and/or the explanatory text, with gray or other color (as opposed to a more conventional solid black color). Alternatively or additionally, such a visual indication may be the presentation of virtual button colored in with a gray or other color, and/or filed in with a cross-hatch or other pattern. Also, alternatively or additionally, such a visual indication may be the presentation of the virtual button and/or the explanatory text with strike-through and/or cross-out lines. In this way, a visual cue would be provided that there is such a parameter, but that visual cue would be accompanied by another visual cue to the effect that specifying a value for that parameter will create an incompatibility.

Turning to FIG. 10C, as depicted and similar to what was depicted in FIG. 10B, the processor(s) 2550 may be caused by execution of the term component 2512 to continue the provision of this example term-focused pathway 3512 with the visual presentation of the same other term-related prompt 3122. As also depicted, and unlike what was depicted in FIG. 10B, the processor(s) 2550 may be caused by the execution of the interactive processing components 2518-2519 to also present a suggestion notice 3129 providing a suggestion to select a particular test type.

Regarding the term-related prompt 3122, again, this term-related prompt 3122 serves to guide the operator through providing one or more linear constraints that may be applicable to one or more of the factors displayed in the term-related prompt 3121.

Regarding the suggestion notice 3129, as indicated therein, the current parameter values for at least the factors and linear constraints among the term-related parameters may be compatible with the near orthogonal array (NOA) test type. More specifically, and as will those skilled in the art will readily recognize, the NOA test type may be used where all of the factors are of the continuous type, and where no linear constraints have been specified.

As depicted, the suggestion notice 3129 may take the form of another "popup message" that overlaps other prompts in a manner intended to gain the attention of the operator. While the operator may have the option of ignoring the suggestion notice 3129, and either not selecting the NOA test type or selecting the NOA test type at a later time, as depicted, the suggestion notice 3129 may directly provide a mechanism by which the operator may immediately proceed with selecting the NOA test type. As previously discussed, in some embodiments, it may be that selecting a test type that is suggested in such a suggestion notice may bring the current traversal through a pathway to an immediate end. Alternatively, in other embodiments, the current traversal through a pathway may, instead, be allowed to continue to enable the specification of more parameters beyond the suggested test type.

As also depicted, in some embodiments, the suggestion notice 3129 may present some information concerning the suggested test type, such as the depicted text that explains what may be an advantage to using the suggested test type.

Turning to FIG. 10D, as depicted, the processor(s) 2550 may be caused by execution of the term component 2512 to continue the provision of this example term-focused pathway 3512 with the additional visual presentation of a test-related prompt 3123 as a subsequent prompt that follows the two initial prompts 3121 and 3122 of FIGS. 10A-C. As also depicted, and similar to what was depicted in FIG. 10C, the processor(s) 2550 may be caused by the execution of the interactive processing components 2518-2519 to also present a suggestion notice 3129 providing a suggestion to select a particular test type, although the test type that is suggested is different from what was suggested in FIG. 10C.

Regarding the test-related prompt 3123, this test-related prompt 3123 serves to guide the operator through specifying parameter values for the test-related parameters quantity of runs and/or quantity of extra runs. As will be familiar to those skilled in the art, the specification of a quantity of runs and/or of extra runs is often influenced by external factors, such as limitations on available time, budget and/or other resources (e.g., available supplies, available equipment, available personnel, etc.) that are needed to actually perform a test of a system under study in accordance with a testing regime.

Regarding the suggestion notice 3129, as indicated therein, the current parameter values for at least the factors and linear constraints among the term-related parameters, and for at least the quantity of runs among the test-related parameters, may be compatible with the orthogonal mixed level (OML) test type. More specifically, and as those skilled in the art will readily recognize, the OML test type may be used where there are at least 3 factors, where no linear constraints have been specified, and where the specified quantity of runs is large enough.

Again, as depicted, the suggestion notice 3129 may take the form of another "popup message" that overlaps other prompts in a manner intended to gain the attention of the operator. Again, while the operator may have the option of ignoring the suggestion notice 3129, and either not selecting the OML test type or selecting the OML test type at a later time, as depicted, the suggestion notice 3129 may directly provide a mechanism by which the operator may immediately proceed with selecting the OML test type. As previously discussed, in some embodiments, it may be that selecting a test type that is suggested in a suggestion notice may bring the current traversal through a pathway to an immediate end. Alternatively, in other embodiments, the current traversal through a pathway may, instead, be allowed to continue to enable the specification of more parameters beyond the suggested test type.

Again, as also depicted, the suggestion notice 3129 may present some information concerning the suggested test type, such as the depicted text that explains what may be an advantage to using the suggested test type. Alternatively or additionally, and as depicted in FIG. 10E, the suggestion notice 3129 may present a suggestion to select from among multiple test types.

As previously discussed, and regardless of whether a single test type or multiple test types are suggested, the processor(s) 2550 may be caused by execution of the interactive processing components 2518-2519 to retrieve indications of an order of preference for test types from the rules data 2535. It may be that such an order of preference is used to determine whether a test type should be suggested, at all, by comparing its degree of preference in such an order of preference to the degree of preference of an already selected test type. Alternatively or additionally, where there are multiple test types to be suggested, it may be that just the one of those multiple test types with the highest degree of preference is suggested (as may be the case in FIG. 10D), or it may be that the multiple test types to be suggested are visually presented in an order that follows such an order of preference (as may be the case in FIG. 10E).

Turning to FIG. 10F, as depicted and similar to what was depicted in FIGS. 10D-E, the processor(s) 2550 may be caused by execution of the term component 2512 to continue the provision of this example term-focused pathway 3512 with the additional visual presentation of the same test-related prompt 3123 as a subsequent prompt that follows the two initial prompts 3121 and 3122 of FIGS. 10A-E. As also depicted, and unlike what was depicted in FIGS. 10D-E, the processor(s) 2550 may be caused by the execution of the interactive processing components 2518-2519 to also present a compatibility notice 3128 providing an indication of another different incompatibility among parameter values.

Regarding the test-related prompt 3123, again, this test-related prompt 3123 serves to guide the operator through specifying parameter values for the test-related parameters quantity of runs and/or quantity of extra runs.

Regarding the compatibility notice 3128, as indicated therein, it may be that the MD test type was previously specified as a test-related parameter value. As also indicated therein, and as will be familiar to those skilled in the art, extra runs are incompatible with the specification of the MD test type. Thus, attempting to specify a quantity or range of quantities of extra runs in response to the test-related prompt 3123 is not compatible with the current test-related parameter value of the MD test type, and it may have been such an attempt to specify a quantity or range of quantities of extra runs that triggered the presentation of the compatibility notice 3128. Again, as depicted, the compatibility notice 3128 may take the form of another "popup message" that overlaps other prompts in a manner intended to gain the attention of the operator. Also again, while the operator may have the option of returning to the term-related prompt 3122 to undo whatever was done to add the linear constraint(s) that triggered the compatibility notice 3128, as depicted, the compatibility notice 3128 may directly provide a mechanism by which the operator may alternately resolve this incompatibility by unselecting the MD test type as a test-related parameter value.

Returning to the test-related prompt 3123, it should be noted that, in some embodiments, the processor(s) 2550 may be caused, by execution of the combination of the term component 2512 and the interactive processing components 2518-2519, to visually present the test-related prompt 3123 in a manner that is visually indicative of such an incompatibility arising if a quantity or range of quantities of extra runs were to be specified. Again, in some embodiments, such a visual indication may be the presentation of the text, the virtual button and/or the editable fields able to accept numeric values, with gray or other color (as opposed to a more conventional solid black color). Alternatively or additionally, such a visual indication may be the presentation of virtual button and/or the editable fields colored in with a gray or other color, and/or filled in with a cross-hatch or other pattern. Also, alternatively or additionally, such a visual indication may be the presentation of the virtual button and/or the explanatory text with strike-through and/or cross-out lines. Again, in this way, a visual cue would be provided that there is such a parameter, but that visual cue would be accompanied by another visual cue to the effect that specifying value(s) for that parameter will create an incompatibility.

Turning to FIG. 10G, as depicted, the processor(s) 2550 may be caused by execution of the term component 2512 to continue the provision of this example term-focused pathway 3512 with the additional visual presentation of a model-related prompt 3124 as a subsequent prompt that follows the initial prompts 3121-3122 and subsequent prompt 3123 of FIGS. 10D-F. As also depicted, and similar to what was depicted in FIG. 10F, the processor(s) 2550 may be caused by the execution of the interactive processing components 2518-2519 to also present a compatibility notice 3128 providing an indication of still another different incompatibility among parameter values.

Regarding the model-related prompt 3124, this model-related prompt 3124 serves to guide the operator through specifying parameter values for the model-related parameters of which terms are required to be included for estimation. Additionally, and as is more easily seen in FIGS. 10H-I, this model-related prompt 3124 also serves to guide the operator through specifying whether to use Bayesian modification with the terms that are not marked as required for inclusion for estimation.

Regarding the compatibility notice 3128, as indicated therein, it may be that the model type that was previously specified as a model-related parameter value. As also indicated therein, it may be that this specified model type is unable to support having as many of the terms being required to be included for estimation as an operator may have attempted to specify within the editable table provided by the model-related prompt 3124, and it may have been this attempt that triggered the visual presentation of this compatibility notice 3128. Again, as depicted, the compatibility notice 3128 may take the form of another "popup message" that overlaps other prompts in a manner intended to gain the attention of the operator. While the operator may have the option of returning to the model-related prompt 3124 to undo whatever was done to cause too many of the terms to be specified as "necessary" for inclusion for estimation, as depicted, the compatibility notice 3128 may directly provide a mechanism by which the operator may alternately resolve this incompatibility by unspecifying the currently specified model type as a model-related parameter value.

As will be recognizable to those skilled in the art, it is often not possible to use direct analytical approaches based on a model associated with an testing regime to estimate all of the lower order terms (e.g., the factors) and higher order terms that are desired to be evaluated as part of evaluating a testing regime. This may arise from limitations of the model associated with the testing regime, limits in the amount of available observation data for the terms, etc. More specifically, it is frequently possible to estimate all of the first order terms based on a model, but just a subset of the higher order terms. As a result, it is often possible to specify that all of the factors are required to be estimated based on a model in evaluating an associated testing regime, while it may not be possible to similarly require the inclusion of all the higher order terms. However, in some embodiments, there may also be the ability to employ Bayesian modification techniques to augment the analytical analysis that directly employs the model associated with a testing regime with the use of inferences for at least a subset of the higher order terms.

Turning to FIG. 10H, as depicted and similar to what was depicted in FIG. 10G, the processor(s) 2550 may be caused by execution of the term component 2512 to continue the provision of this example term-focused pathway 3512 with the additional visual presentation of the same model-related prompt 3124 as a subsequent prompt that follows the two initial prompts 3121 and 3122 and the subsequent prompt 3123 of FIGS. 10D-G. As also depicted, and unlike what was depicted in FIG. 10G, the processor(s) 2550 may be caused by the execution of the interactive processing components 2518-2519 to also present a suggestion notice 3129 providing a suggestion to select a particular test type.

Regarding the model-related prompt 3124, again, this model-related prompt 3124 serves to guide the operator through specifying parameter values for the model-related parameters of which terms are required to be included for estimation, and whether to use Bayesian modification with the terms that are not marked as required for inclusion for estimation.

Regarding the suggestion notice 3129, as indicated therein, the current parameter values for at least the factors among the term-related parameters, for at least the quantity of runs among the test-related parameters, and for at least which terms are required to be included in estimation and whether to use Bayesian modification, may be compatible with the Box-Behnken (BB) test type. More specifically, and as those skilled in the art will readily recognize, the BB test type may be used where all factors are of the continuous type, and where all factors and all second order terms are included for estimation, and where the specified quantity of runs is large enough.

Again, as depicted, the suggestion notice 3129 may take the form of another "popup message" that overlaps other prompts in a manner intended to gain the attention of the operator. Again, while the operator may have the option of ignoring the suggestion notice 3129, and either not selecting the BB test type or selecting the BB test type at a later time, as depicted, the suggestion notice 3129 may directly provide a mechanism by which the operator may immediately proceed with selecting the BB test type.

Again, as also depicted, the suggestion notice 3129 may present some information concerning the suggested test type, such as the depicted text that explains what may be an advantage to using the suggested test type. Alternatively or additionally, and as depicted in FIG. 10I, the suggestion notice 3129 may present a suggestion to select from among multiple test types.

Again, regardless of whether a single test type or multiple test types are suggested, the processor(s) 2550 may be caused by execution of the interactive processing components 2518-2519 to retrieve indications of an order of preference for test types from the rules data 2535. It may be that such an order of preference is used to determine whether a test type should be suggested, at all, by comparing its degree of preference in such an order of preference to the degree of preference of an already selected test type. Alternatively or additionally, where there are multiple test types to be suggested, it may be that just the one of those multiple test types with the highest degree of preference is suggested (as may be the case in FIG. 10H), or it may be that the multiple test types to be suggested are visually presented in an order that follows such an order of preference (as may be the case in FIG. 10I).

FIGS. 11A, 11B, 11C, 11D, 11E, 11F, 11G and 11H, taken together, depict, in greater detail, various aspects of traversing through an example model-focused pathway 3513 of prompts of the GUI 3130 that is caused to be visually presented by the processor(s) 2550 as a result of executing the model component 2513 together with the interactive processing components 2518-2519. More specifically, and as discussed above in reference to FIGS. 9A-D, the processor(s) 2550 are initially caused to present one or more initial prompts that focus on model-related parameters of a new testing regime (as depicted in FIGS. 11A-B), before presenting one or more subsequent prompts that focus on term-related and/or test-related parameters thereof (as depicted in FIGS. 11C-H). Additionally, while the traversal through this model-focused pathway 3513 occurs, the processor(s) 2550 are caused to recurringly analyze the parameter values stored within the input data 2539 (including any default or retrieved parameter values used as a starting point, along with any newly specified and/or newly modified parameter values provide by inputs of the operator), and to selectively present compatibility notices indicating incompatibilities among parameters and/or suggestion notices suggesting test type(s). Further, and as also discussed above in reference to FIGS. 9A-D, one or more of such compatibility notices indicating an incompatibility among parameters may be triggered as a result of this model-focused pathway 3513 being traversed after an earlier traversal of one of the pathways and/or as a result of parameter values of an existing testing regime being used as a starting point (as depicted in FIG. 11A).

Turning to FIG. 11A, as depicted, the processor(s) 2550 may be caused by execution of the model component 2513 to begin the provision of this example model-focused pathway 3513 of prompts of the GUI portion 3130 with the visual presentation of a model-related prompt 3131 as one of the initial prompts. As previously discussed, in so executing the model component 2513, the processor(s) 2550 may be caused to retrieve a definition of the model-focused pathway 3513, including details of what prompts to present, from the rules data 2535. As also depicted, the processor(s) 2550 may be caused by execution of the model component 2513 and the interactive processing components 2518-2519 to also present a compatibility notice 3138 providing an indication of an incompatibility among parameter values. As previously discussed, in so executing the interactive processing components 2518-2519, the processor(s) 2550 may be caused to retrieve, from the rules data 2535, indications of the limits of compatibility of various parameter values for various parameters, including model-related parameter values for such parameters as model types and/or optimality types, and/or including test-related parameter values for such parameters as quantities of test runs. Additionally, indications of the manner of presenting the model-related prompt 3131 and/or the compatibility notice 3138, including text and/or graphical elements used for each, may also be retrieved from the rules data 2535.

Regarding the model-related prompt 3131, this model-related prompt 3131 serves to guide an operator of the distributed processing system 2000 through providing model-related parameter values for such parameters as a type of model, one or more type(s) of optimality, a quantity of center points, a quantity replicates and/or a quantity of random starts. As depicted, it may be that the type of model is able to be explicitly specified (e.g., via the depicted "RSM" virtual button to specify a response surface model) or may be specified based on which terms and/or what aspects of those terms are to be included in the model (e.g., via the depicted "Main Effects" virtual button to include the factors, and/or the "Power" virtual button to specify which higher order terms to include). As also depicted, it may be that the parameter values for name, type and range of values for each of multiple factors have already been previously provided. Again, this may be due to parameter values for parameters of an existing testing regime having been retrieved and used as a starting point, and/or this may be due to parameter values for at least some parameters having been provided in operator inputs in one or more previous pathway traversals.

Regarding the compatibility notice 3138, as indicated therein, it may be that a quantity of runs was previously specified as a test-related parameter value. As also indicated therein (and as will be familiar to those skilled in the art), the Alias Optimality type can require a greater quantity of runs than other optimality types. Thus, as depicted, there are one or more model-related parameter values associated with the model-related prompt 3131 that are not compatible with the currently specified quantity of runs. As depicted, the compatibility notice 3128 may take the form of a "popup message" that overlaps other prompts so as to set forth this incompatibility in a manner intended to gain the attention of the operator.

As previously discussed, before the traversal of this example model-focused pathway 3513 began, previously specified parameter values used as a starting point and/or provided by an operator through one or more previous pathway traversals may be stored within the input data 2539. Indications of changes then made by the operator to the type of optimality would then be stored within the input data 2539, and would then be used in analyses performed by the processor(s) 2550 to identify such an incompatibility among the parameter values, thereby triggering the presentation of the depicted compatibility notice 3138. While the operator may have the option of returning to the model-related prompt 3131 to undo whatever edit(s) were made therein that triggered the compatibility notice 3138, as depicted, the compatibility notice 3138 may directly provide a mechanism by which the operator may alternately resolve this incompatibility by unspecifying the quantity of runs as a test parameter value (e.g., by clicking the depicted virtual button therein).

Turning to FIG. 11B, as depicted and similar to what was depicted in FIG. 11A, the processor(s) 2550 may be caused by execution of the model component 2513 to continue the provision of this example model-focused pathway 3513 with the visual presentation of the same model-related prompt 3131 as one of the initial prompts. As also depicted, and unlike what was depicted in FIG. 11A, the processor(s) 2550 may be caused by the execution of the interactive processing components 2518-2519 to also present another compatibility notice 3138 providing an indication of incompatibility among parameter values.

Regarding the model-related prompt 3131, again, this model-related prompt 3131 serves to guide an operator of the distributed processing system 2000 through providing model-related parameter values for such parameters as a type of model, one or more type(s) of optimality, a quantity of center points, a quantity replicates and/or a quantity of random starts.

Regarding the compatibility notice 3138, as indicated therein, it may be that a particular type of optimality must be specified to enable a quantity of center points to be specified. As also indicated therein (and as will be familiar to those skilled in the art), the A-Optimality type does not support center points. Again, the compatibility notice 3138 may take the form of a "popup message" that overlaps other prompts so as to set forth this incompatibility in a manner intended to gain the attention of the operator.

Turning to FIG. 11C, as depicted, the processor(s) 2550 may be caused by execution of the model component 2513 to continue the provision of this example model-focused pathway 3513 with the additional visual presentation of a term-related prompt 3132 as a subsequent prompt that follows the initial prompt 3131 of FIGS. 11A-B.

Regarding the term-related prompt 3132, this term-related prompt 3132 serves to guide an operator of the distributed processing system 2000 through providing term-related parameter values for such parameters as the name, type and/or range of values for each factor. As depicted, this prompt takes the form of an editable table of these term-related parameter values. In various embodiments, it may be that the type for each factor may be a continuous type, a categorical type or a discrete type. It may also be that, depending on the type of for each factor, a range of numerical values may be specified. As also depicted, it may be that the parameter values for name, type and range of values for each of multiple factors have already been previously provided. Again, this may be due to parameter values for parameters of an existing testing regime having been retrieved and used as a starting point, and/or this may be due to parameter values for at least some parameters having been provided in operator inputs in one or more previous pathway traversals.

Turning to FIG. 11D, as depicted, the processor(s) 2550 may be caused by execution of the model component 2513 to continue the provision of this example model-focused pathway 3513 with the additional visual presentation of another term-related prompt 3133 as another subsequent prompt that follows the initial prompt 3131 and the subsequent prompt 3132 of FIG. 11C. As also depicted, the processor(s) 2550 may be caused by the execution of the interactive processing components 2518-2519 to also present a suggestion notice 3139 providing a suggestion to select a particular test type.

Regarding the term-related prompt 3133, this term-related prompt 3133 serves to guide the operator through providing one or more linear constraints that may be applicable to one or more of the factors displayed in the term-related prompt 3132 (best seen in FIG. 11C). As depicted, this prompt takes the form of a virtual button accompanied by explanatory text concerning its function. More specifically, as per the explanatory text, clicking on this virtual button (e.g., with a mouse pointer, not specifically shown) may cause the processor(s) 2550 to present a text entry area (not specifically shown) in which one or more linear constraints may be entered in equation form.

Regarding the suggestion notice 3129, as indicated therein, the current parameter values for at least the linear constraints among the term-related parameters may be compatible with the mixture design (MD) test type. More specifically, and as will those skilled in the art will readily recognize, the MD test type may be used where there is a linear constraint that specifies that the values of all of the factors must add up to 100%.

As depicted, the suggestion notice 3129 may take the form of another "popup message" that overlaps other prompts in a manner intended to gain the attention of the operator. While the operator may have the option of ignoring the suggestion notice 3129, and either not selecting the MD test type or selecting the MD test type at a later time, as depicted, the suggestion notice 3129 may directly provide a mechanism by which the operator may immediately proceed with selecting the MD test type. As previously discussed, in some embodiments, it may be that selecting a test type that is suggested in such a suggestion notice may bring the current traversal through a pathway to an immediate end. Alternatively, in other embodiments, the current traversal through a pathway may, instead, be allowed to continue to enable the specification of more parameters beyond the suggested test type.

As also depicted, in some embodiments, the suggestion notice 3129 may present some information concerning the suggested test type, such as the depicted text that explains what may be an advantage to using the suggested test type.

Turning to FIG. 11E, as depicted, the processor(s) 2550 may be caused by execution of the model component 2513 to continue the provision of this example model-focused pathway 3513 with the additional visual presentation of a test-related prompt 3134 as still another subsequent prompt that follows the initial prompts 3131, and the two subsequent prompts 3132 and 3133 of FIG. 11D. As also depicted, and similar to what was depicted in FIG. 11D, the processor(s) 2550 may be caused by the execution of the interactive processing components 2518-2519 to also present a suggestion notice 3139 providing a suggestion to select a particular test type, although the test type that is suggested is different from what was suggested in FIG. 11D.

Regarding the test-related prompt 3134, this test-related prompt 3134 serves to guide the operator through specifying parameter values for the test-related parameters quantity of runs and/or quantity of extra runs. As will be familiar to those skilled in the art, the specification of a quantity of runs and/or of extra runs is often influenced by external factors, such as limitations on available time, budget and/or other resources (e.g., available supplies, available equipment, available personnel, etc.) that are needed to actually perform a test of a system under study in accordance with a testing regime.

Regarding the suggestion notice 3139, as indicated therein, the current parameter values for at least the factors and linear constraints among the term-related parameters, and for at least the quantity of runs among the test-related parameters, may be compatible with the Plackett-Burman (PB) test type. More specifically, and as those skilled in the art will readily recognize, the PB test type may be used where all factors are of the categorical type with just 2 levels, where no linear constraints have been specified, and where the specified quantity of runs is large enough.

Again, as depicted, the suggestion notice 3139 may take the form of another “popup message” that overlaps other prompts in a manner intended to gain the attention of the operator. Again, while the operator may have the option of ignoring the suggestion notice 3139, and either not selecting the PB test type or selecting the PB test type at a later time, as depicted, the suggestion notice 3139 may directly provide a mechanism by which the operator may immediately proceed with selecting the PB test type. Again, in some embodiments, it may be that selecting a test type that is suggested in a suggestion notice may bring the current traversal through a pathway to an immediate end. Alternatively, in other embodiments, the current traversal through a pathway may, instead, be allowed to continue to enable the specification of more parameters beyond the suggested test type.

Again, as also depicted, the suggestion notice 3139 may present some information concerning the suggested test type, such as the depicted text that explains what may be an advantage to using the suggested test type. Alternatively or additionally, and as depicted in FIG. 11F, the suggestion notice 3139 may present a suggestion to select from among multiple test types.

As previously discussed, and regardless of whether a single test type or multiple test types are suggested, the processor(s) 2550 may be caused by execution of the interactive processing components 2518-2519 to retrieve indications of an order of preference for test types from the rules data 2535. It may be that such an order of preference is used to determine whether a test type should be suggested, at all, by comparing its degree of preference in such an order of preference to the degree of preference of an already selected test type. Alternatively or additionally, where there are multiple test types to be suggested, it may be that just the one of those multiple test types with the highest degree of preference is suggested (as may be the case in FIG. 11E), or it may be that the multiple test types to be suggested are visually presented in an order that follows such an order of preference (as may be the case in FIG. 11F).

Turning to FIG. 11G, as depicted, the processor(s) 2550 may be caused by execution of the model component 2513 to continue the provision of this example model-focused pathway 3513 with the additional visual presentation of a model-related prompt 3135 as a subsequent prompt that follows the initial prompt 3131 and subsequent prompts 3132-3134 of FIGS. 11E-F. As also depicted, the processor(s) 2550 may be caused by the execution of the interactive processing components 2518-2519 to also present a compatibility notice 3138 providing an indication of still another different incompatibility among parameter values.

Regarding the model-related prompt 3135, this model-related prompt 3135 serves to guide the operator through specifying parameter values for the model-related parameters of which terms are required to be included for estimation. Additionally, and as is more easily seen in FIG. 11H, this model-related prompt 3135 also serves to guide the operator through specifying whether to use Bayesian modification with the terms that are not marked as required for inclusion for estimation.

Regarding the compatibility notice 3138, as indicated therein, it may be that the model type that was previously specified as a model-related parameter value. As also indicated therein, it may be that this specified model type is unable to support having as many of the terms being required to be included for estimation as an operator may have attempted to specify within the editable table provided by the model-related prompt 3135, and it may have been this attempt that triggered the visual presentation of this compatibility notice 3138. Again, as depicted, the compatibility notice 3138 may take the form of another “popup message” that overlaps other prompts in a manner intended to gain the attention of the operator.

As will be recognizable to those skilled in the art, it is often not possible to use direct analytical approaches based on a model associated with an testing regime to estimate all of the lower order terms (e.g., the factors) and higher order terms that are desired to be evaluated as part of evaluating a testing regime. This may arise from limitations of the model associated with the testing regime, limits in the amount of available observation data for the terms, etc. More specifically, it is frequently possible to estimate all of the first order terms based on a model, but just a subset of the higher order terms. As a result, it is often possible to specify that all of the factors are required to be estimated based on a model in evaluating an associated testing regime, while it may not be possible to similarly require the inclusion of all the higher order terms. However, in some embodiments, there may also be the ability to employ Bayesian modification techniques to augment the analytical analysis that directly employs the model associated with a testing regime with the use of inferences for at least a subset of the higher order terms.

Turning to FIG. 11H, as depicted and similar to what was depicted in FIG. 11G, the processor(s) 2550 may be caused by execution of the model component 2513 to continue the provision of this example model-focused pathway 3513 with the additional visual presentation of the same model-related prompt 3135 as a subsequent prompt that follows initial prompt 3131 and the subsequent prompt 3132-3134 of FIG. 11-G. As also depicted, and unlike what was depicted in FIG. 11G, the processor(s) 2550 may be caused by the execution of the interactive processing components 2518-2519 to also present a suggestion notice 3139 providing a suggestion to select a particular test type.

Regarding the model-related prompt 3135, again, this model-related prompt 3135 serves to guide the operator through specifying parameter values for the model-related parameters of which terms are required to be included for estimation, and whether to use Bayesian modification with the terms that are not marked as required for inclusion for estimation.

Regarding the suggestion notice 3139, as indicated therein, the current parameter values for at least the factors among the term-related parameters, for at least the quantity of runs among the test-related parameters, and for at least which terms are required to be included in estimation and whether to use Bayesian modification, may be compatible with the central composite design (CCD) test type. More specifically, and as those skilled in the art will readily recognize, the CCD test type may be used where all factors are of the continuous type, and where all factors and all second order terms are included for estimation, and where the specified quantity of runs is large enough.

Again, as depicted, the suggestion notice 3139 may take the form of another "popup message" that overlaps other prompts in a manner intended to gain the attention of the operator. Again, while the operator may have the option of ignoring the suggestion notice 3139, and either not selecting the CCD test type or selecting the CCD test type at a later time, as depicted, the suggestion notice 3139 may directly provide a mechanism by which the operator may immediately proceed with selecting the CCD test type.

Again, as also depicted, the suggestion notice 3139 may present some information concerning the suggested test type, such as the depicted text that explains what may be an advantage to using the suggested test type.

FIGS. 12A, 12B, 12C, 12D, 12E, 12F and 12G, taken together, depict, in greater detail, various aspects of traversing through an example test-focused pathway 3514 of prompts of the GUI 3140 that is caused to be visually presented by the processor(s) 2550 as a result of executing the test component 2514 together with the interactive processing components 2518-2519. More specifically, and as discussed above in reference to FIGS. 9A-D, the processor(s) 2550 are initially caused to present one or more initial prompts that focus on test-related parameters of a new testing regime (as depicted in FIG. 12A), before presenting one or more subsequent prompts that focus on term-related and/or model-related parameters thereof (as depicted in FIGS. 12B-G). Additionally, while the traversal through this test-focused pathway 3514 occurs, the processor(s) 2550 are caused to recurringly analyze the parameter values stored within the input data 2539 (including any default or retrieved parameter values used as a starting point, along with any newly specified and/or newly modified parameter values provide by inputs of the operator), and to selectively present compatibility notices indicating incompatibilities among parameters and/or suggestion notices suggesting test type(s). Further, and as also discussed above in reference to FIGS. 9A-D, one or more of such compatibility notices indicating an incompatibility among parameters may be triggered as a result of this test-focused pathway 3514 being traversed after an earlier traversal of one of the pathways and/or as a result of parameter values of an existing testing regime being used as a starting point (as depicted in FIG. 11A).

Turning to FIG. 12A, as depicted, the processor(s) 2550 may be caused by execution of the test component 2514 to begin the provision of this example test-focused pathway 3514 of prompts of the GUI portion 3140 with the visual presentation of a test-related prompt 3141 as one of the initial prompts. As previously discussed, in so executing the test component 2514, the processor(s) 2550 may be caused to retrieve a definition of the test-focused pathway 3514, including details of what prompts to present, from the rules data 2535. As also depicted, the processor(s) 2550 may be caused by execution of the test component 2514 and the interactive processing components 2518-2519 to also present a compatibility notice 3148 providing an indication of an incompatibility among parameter values. As previously discussed, in so executing the interactive processing components 2518-2519, the processor(s) 2550 may be caused to retrieve, from the rules data 2535, indications of the limits of compatibility of various parameter values for various parameters, including test-related parameter values for such parameters as test types and/or test type categories, and/or including term-related parameter values for such parameters as factor types. Additionally, indications of the manner of presenting the test-related prompt 3141 and/or the compatibility notice 3148, including text and/or graphical elements used for each, may also be retrieved from the rules data 2535.

Regarding the test-related prompt 3141, this test-related prompt 3141 serves to guide an operator of the distributed processing system 2000 through specifying either a particular test type or a test category type, where each test category type may encompass multiple particular test types. As depicted, a set of "radio buttons" of which only one is able to be selected at any given time, although in some embodiments, it may be that none may be selected in a situation (and at a time) in which no test type or test category type has yet been selected. As also depicted, it may be that the parameter value for a test type or a test category type has already been previously provided. Again, this may be due to parameter values for parameters of an existing testing regime having been retrieved and used as a starting point, and/or this may be due to parameter values for at least some parameters having been provided in operator inputs in one or more previous pathway traversals.

Regarding the compatibility notice 3148, as indicated therein, it may be that the factor type for each factor was previously specified as a term-related parameter value for the factor type parameter for each factor. As also indicated therein (and as will be familiar to those skilled in the art), factors of the categorical or discrete type that have more than 2 levels are incompatible with the specification of the DSD test type. Thus, as depicted, it may be that an attempt was made to specify the DSD test type with an incompatible factor type for one or more factors having been specified at an earlier time, thereby triggering the visual presentation of the compatibility notice 3148. As depicted, the compatibility notice 3148 may take the form of a "popup message" that overlaps other prompts so as to set forth this incompatibility in a manner intended to gain the attention of the operator.

As previously discussed, before the traversal of this example test-focused pathway 3514 began, previously specified parameter values used as a starting point and/or provided by an operator through one or more previous pathway traversals may be stored within the input data 2539. Indications of changes then made by the operator to the test type or test category type would then be stored within the input data 2539, and would then be used in analyses performed by the processor(s) 2550 to identify such an incompatibility among the parameter values, thereby triggering the presentation of the depicted compatibility notice 3148. While the operator may have the option of returning to the test-related prompt 3141 to undo whatever edit(s) were made therein that triggered the compatibility notice 3148, as depicted, the compatibility notice 3148 may directly provide a mechanism by which the operator may alternately resolve this incompatibility by unspecifying the factor type for each factor as term parameter values (e.g., by clicking the depicted virtual button therein).

Turning to FIG. 12B, as depicted, the processor(s) 2550 may be caused by execution of the test component 2514 to continue the provision of this example test-focused pathway 3514 with the additional visual presentation of a term-related prompt 3142 as a subsequent prompt that follows the initial prompt 3141 of FIG. 12A. As also depicted, and like what was depicted in FIG. 12A, the processor(s) 2550 may be caused by the execution of the interactive processing components 2518-2519 to also present another compatibility notice 3148 providing an indication of a different incompatibility among parameter values.

Regarding the term-related prompt 3142, this term-related prompt 3142 serves to guide an operator of the distributed processing system 2000 through providing term-related parameter values for such parameters as the name, type and/or range of values for each factor. As depicted, this prompt takes the form of an editable table of these term-related parameter values. In various embodiments, it may be that the type for each factor may be a continuous type, a categorical type or a discrete type. It may also be that, depending on the type of for each factor, a range of numerical values may be specified. As also depicted, it may be that the parameter values for name, type and range of values for each of multiple factors have already been previously provided. Again, this may be due to parameter values for parameters of an existing testing regime having been retrieved and used as a starting point, and/or this may be due to parameter values for at least some parameters having been provided in operator inputs in one or more previous pathway traversals.

Regarding the compatibility notice 3148, as indicated therein, it may be that the DSD test type was either previously specified as a test-related parameter value, or was more recently just specified above through use of the associated radio button within the test-related prompt 3141. As also indicated therein (and as will be familiar to those skilled in the art), factors of the categorical or discrete type that have more than 2 levels are incompatible with the specification of the DSD test type. Thus, as depicted, there are one or more term-related parameter values associated with the term-related prompt 3142 that are not compatible with the test-related parameter value of the DSD test type. As depicted, the compatibility notice 3148 may take the form of a "popup message" that overlaps other prompts so as to set forth this incompatibility in a manner intended to gain the attention of the operator.

As depicted, it may be that the presentation of the compatibility notice 3148 was triggered as a result of the operator having responded to the term-related prompt 3142 with inputs editing the type and/or the range of values for the factor "X1" within the editable table provided in the term-related prompt 3142 to a combination of a discrete type with 3 levels. As previously discussed, before the traversal of this example term-focused pathway 3512 began, previously specified parameter values used as a starting point and/or provided by an operator through one or more previous pathway traversals may be stored within the input data 2539. Indications of changes then made by the operator to the type and/or range of values parameters for the factor "X1" would then be stored within the input data 2539, and would then be used in analyses performed by the processor(s) 2550 to identify such an incompatibility among the parameter values, thereby triggering the presentation of the compatibility notice 3148.

Turning to FIG. 12C, as depicted, the processor(s) 2550 may be caused by execution of the test component 2514 to continue the provision of this example test-focused pathway 3514 with the additional visual presentation of another term-related prompt 3143 as another of the subsequent prompts following the test-related initial prompt 3141 and the term-related subsequent prompt 3142 of FIG. 12B. As also depicted, the processor(s) 2550 may be caused by the execution of the interactive processing components 2518-2519 to also present still another compatibility notice 3148 providing an indication of another different incompatibility among parameter values.

Regarding the term-related prompt 3143, this term-related prompt 3143 serves to guide the operator through providing one or more linear constraints that may be applicable to one or more of the factors displayed in the term-related prompt 3142. As depicted, this prompt takes the form of a virtual button accompanied by explanatory text concerning its function. More specifically, as per the explanatory text, clicking on this virtual button (e.g., with a mouse pointer, not specifically shown) may cause the processor(s) 2550 to present a text entry area (not specifically shown) in which one or more linear constraints may be entered in equation form.

Regarding the compatibility notice 3148, again, and as indicated therein, it may be that the DSD test type was either previously specified as a test-related parameter value, or was more recently just specified above through use of the associated radio button within the test-related prompt 3141. As also indicated therein, and as will be familiar to those skilled in the art, linear constraints are incompatible with the specification of the DSD test type. Thus, attempting to provide one or more linear constraints in response to the term-related prompt 3143 is not compatible with the current test-related parameter value of the DSD test type, and it may have been such an attempt to provide one or more linear constraints that triggered the presentation of the compatibility notice 3148. Again, the compatibility notice 3148 may take the form of another "popup message" that overlaps other prompts in a manner intended to gain the attention of the operator.

Returning to the term-related prompt 3143, it should be noted that, in some embodiments, the processor(s) 2550 may be caused, by execution of the combination of the term component 2512 and the interactive processing components 2518-2519, to visually present the term-related prompt 3143 in a manner that is visually indicative of such an incompatibility arising if a linear constraint were to be added. In some embodiments, such a visual indication may be the presentation of the outline and text of the virtual button, and/or the explanatory text, with gray or other color (as opposed to a more conventional solid black color). Alternatively or additionally, such a visual indication may be the presentation of virtual button colored in with a gray or other color, and/or filed in with a cross-hatch or other pattern. Also, alternatively or additionally, such a visual indication may be the presentation of the virtual button and/or the explanatory text with strike-through and/or cross-out lines. In this way, a visual cue would be provided that there is such a parameter, but that visual cue would be accompanied by another visual cue to the effect that specifying a value for that parameter will create an incompatibility.] Turning to FIG. 12D, as depicted and similar to what was depicted in FIG. 12C, the processor(s) 2550 may be caused by execution of the test component 2514 to continue the provision of this example test-focused pathway 3514 with the visual presentation of the same other term-related prompt 3143. As also depicted, and unlike what was depicted in FIG. 12C, the processor(s) 2550 may be caused by the execution of the interactive processing components 2518-2519 to also present a suggestion notice 3149 providing a suggestion to select a particular test type.

Regarding the term-related prompt 3143, again, this term-related prompt 3143 serves to guide the operator through providing one or more linear constraints that may be applicable to one or more of the factors displayed in the term-related prompt 3142.

Regarding the suggestion notice 3149, as indicated therein, the current parameter values for at least the linear constraints among the term-related parameters may be compatible with the mixture design (MD) test type. More specifically, and as will those skilled in the art will readily recognize, the MD test type may be used where there is a linear constraint that specifies that the values of all of the factors must add up to 100%.

As depicted, the suggestion notice 3149 may take the form of another "popup message" that overlaps other prompts in a manner intended to gain the attention of the operator. While the operator may have the option of ignoring the suggestion notice 3149, and either not selecting the MD test type or selecting the MD test type at a later time, as depicted, the suggestion notice 3129 may directly provide a mechanism by which the operator may immediately proceed with selecting the MD test type. As previously discussed, in some embodiments, it may be that selecting a test type that is suggested in such a suggestion notice may bring the current traversal through a pathway to an immediate end. Alternatively, in other embodiments, the current traversal through a pathway may, instead, be allowed to continue to enable the specification of more parameters beyond the suggested test type.

As also depicted, in some embodiments, the suggestion notice 3149 may present some information concerning the suggested test type, such as the depicted text that explains what may be an advantage to using the suggested test type.

Turning to FIG. 12E, as depicted, the processor(s) 2550 may be caused by execution of the test component 2514 to continue the provision of this example test-focused pathway 3514 with the additional visual presentation of a test-related prompt 3144 as still another subsequent prompt that follows the initial prompt 3141, and the two subsequent prompts 3142 and 3143 of FIGS. 12C-D. As also depicted, and similar to what was depicted in FIG. 12D, the processor(s) 2550 may be caused by the execution of the interactive processing components 2518-2519 to also present a suggestion notice 3149 providing a suggestion to select a particular test type, although the test type that is suggested is different from what was suggested in FIG. 12D.

Regarding the test-related prompt 3144, this test-related prompt 3144 serves to guide the operator through specifying parameter values for the test-related parameters quantity of runs and/or quantity of extra runs. As will be familiar to those skilled in the art, the specification of a quantity of runs and/or of extra runs is often influenced by external factors, such as limitations on available time, budget and/or other resources (e.g., available supplies, available equipment, available personnel, etc.) that are needed to actually perform a test of a system under study in accordance with a testing regime.

Regarding the suggestion notice 3149, as indicated therein, the current parameter values for at least the factors and linear constraints among the term-related parameters, and for at least the quantity of runs among the test-related parameters, may be compatible with the definitive screen design (DSD) test type. More specifically, and as those skilled in the art will readily recognize, the DSD test type may be used where all factors are of either the continuous type or the categorical type with just 2 levels, where no linear constraints have been specified, and where the specified quantity of runs is large enough.

Again, as depicted, the suggestion notice 3149 may take the form of another "popup message" that overlaps other prompts in a manner intended to gain the attention of the operator. Again, while the operator may have the option of ignoring the suggestion notice 3149, and either not selecting the DSD test type or selecting the DSD test type at a later time, as depicted, the suggestion notice 3149 may directly provide a mechanism by which the operator may immediately proceed with selecting the DSD test type. Again, in some embodiments, it may be that selecting a test type that is suggested in a suggestion notice may bring the current traversal through a pathway to an immediate end. Alternatively, in other embodiments, the current traversal through a pathway may, instead, be allowed to continue to enable the specification of more parameters beyond the suggested test type.

Again, as also depicted, the suggestion notice 3149 may present some information concerning the suggested test type, such as the depicted text that explains what may be an advantage to using the suggested test type.

Turning to FIG. 12F, as depicted, the processor(s) 2550 may be caused by execution of the test component 2514 to continue the provision of this example test-focused pathway 3514 with the additional visual presentation of a model-related prompt 3145 as another subsequent prompt that follows the initial prompt 3141 and subsequent prompts 3142-3144 of FIG. 12E. As also depicted, the processor(s) 2550 may be caused by the execution of the interactive processing components 2518-2519 to also present a compatibility notice 3148 providing an indication of still another different incompatibility among parameter values.

Regarding the model-related prompt 3145, this model-related prompt 3145 serves to guide the operator through specifying parameter values for the model-related parameters of which terms are required to be included for estimation. Additionally, this model-related prompt 3145 also serves to guide the operator through specifying whether to use Bayesian modification with the terms that are not marked as required for inclusion for estimation.

Regarding the compatibility notice 3148, as indicated therein, it may be that a model type was previously specified as a model-related parameter value. As also indicated therein, it may be that this specified model type is unable to support having as many of the terms being required to be included for estimation as an operator may have attempted to specify within the editable table provided by the model-related prompt 3145, and it may have been this attempt that triggered the visual presentation of this compatibility notice 3148. Again, as depicted, the compatibility notice 3148 may take the form of another "popup message" that overlaps other prompts in a manner intended to gain the attention of the operator. While the operator may have the option of returning to the model-related prompt 3145 to undo whatever was done to cause too many of the terms to be specified as "necessary" for inclusion for estimation, as depicted, the compatibility notice 3148 may directly provide a mechanism by which the operator may alternately resolve this incompatibility by unspecifying the currently specified model type as a model-related parameter value.

As will be recognizable to those skilled in the art, it is often not possible to use direct analytical approaches based on a model associated with an testing regime to estimate all of the lower order terms (e.g., the factors) and higher order terms that are desired to be evaluated as part of evaluating a testing regime. This may arise from limitations of the model associated with the testing regime, limits in the amount of available observation data for the terms, etc. More specifically, it is frequently possible to estimate all of the first order terms based on a model, but just a subset of the higher order terms. As a result, it is often possible to specify that all of the factors are required to be estimated based on a model in evaluating an associated testing regime, while it may not be possible to similarly require the inclusion of all the higher order terms. However, in some embodiments, there may also be the ability to employ Bayesian modification techniques to augment the analytical analysis that directly employs the model associated with a testing regime with the use of inferences for at least a subset of the higher order terms.

Turning to FIG. 12G, as depicted and similar to what was depicted in FIG. 12F, the processor(s) 2550 may be caused by execution of the test component 2514 to continue the provision of this example test-focused pathway 3514 with the additional visual presentation of the same model-related prompt 3145 as a subsequent prompt that follows the initial prompt 3141 and the subsequent prompts 3142-3144. As also depicted, and unlike what was depicted in FIG. 12F, the processor(s) 2550 may be caused by the execution of the interactive processing components 2518-2519 to also present a suggestion notice 3149 providing a suggestion to select a particular test type.

Regarding the model-related prompt 3145, again, this model-related prompt 3145 serves to guide the operator through specifying parameter values for the model-related parameters of which terms are required to be included for estimation, and whether to use Bayesian modification with the terms that are not marked as required for inclusion for estimation.

Regarding the suggestion notice 3139, as indicated therein, the current parameter values for at least the factors among the term-related parameters, for at least the quantity of runs among the test-related parameters, and for at least which terms are required to be included in estimation and whether to use Bayesian modification, may be compatible with the Box-Behnken (BB) test type. More specifically, and as those skilled in the art will readily recognize, the BB test type may be used where all factors are of the continuous type, and where all factors and all second order terms are included for estimation, and where the specified quantity of runs is large enough.

Again, as depicted, the suggestion notice 3149 may take the form of another "popup message" that overlaps other prompts in a manner intended to gain the attention of the operator. Again, while the operator may have the option of ignoring the suggestion notice 3149, and either not selecting the BB test type or selecting the BB test type at a later time, as depicted, the suggestion notice 3149 may directly provide a mechanism by which the operator may immediately proceed with selecting the BB test type.

Again, as also depicted, the suggestion notice 3149 may present some information concerning the suggested test type, such as the depicted text that explains what may be an advantage to using the suggested test type.

Figure 13:
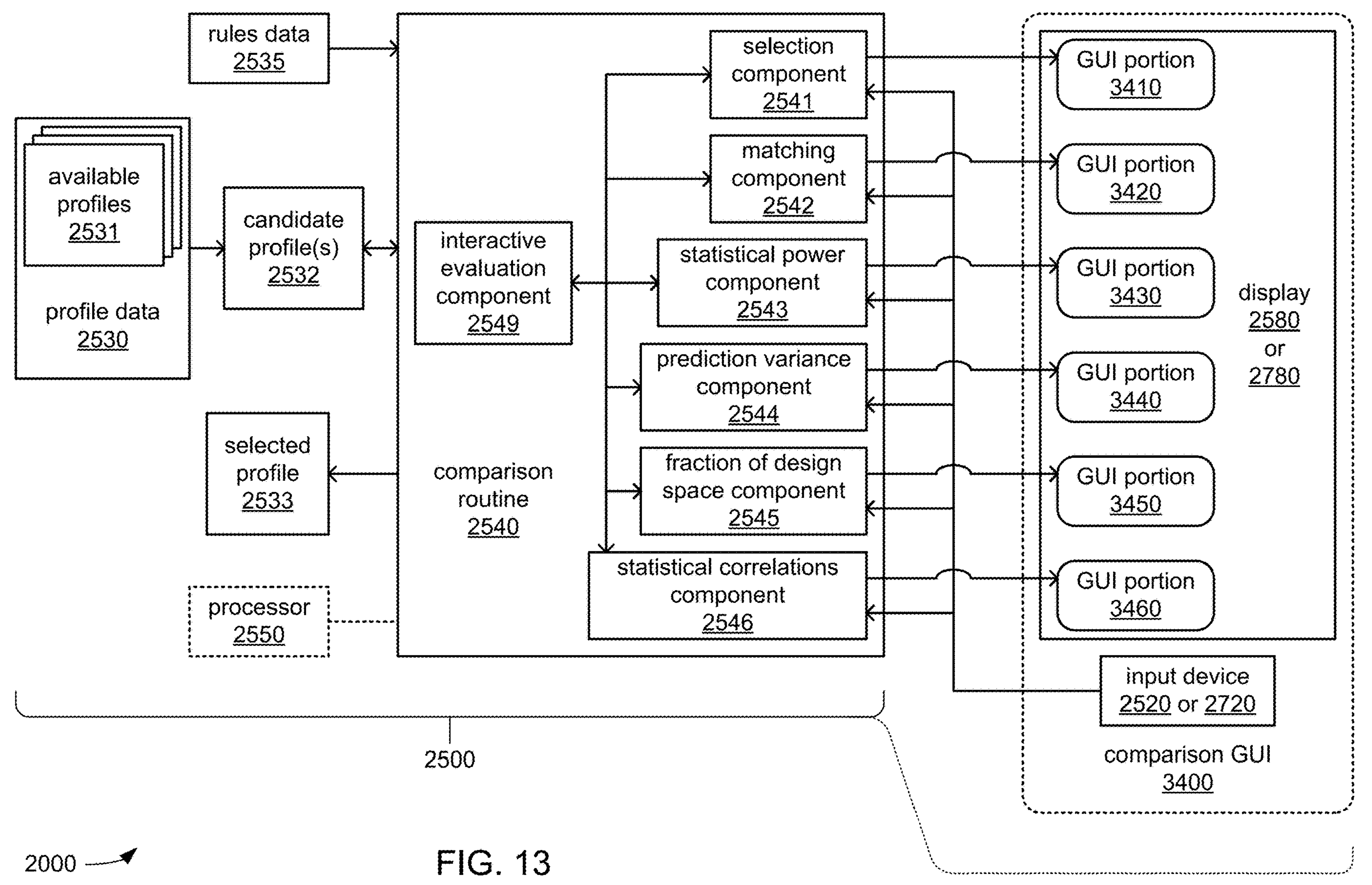
FIG. 13 illustrates an example of guiding the comparison of candidate testing regime(s) to determine which candidate testing regime is to become a selected testing regime.

FIG. 13 depicts aspects of an example of the provision of the GUI 3400 to guide the comparison of two or more candidate testing regimes defined in corresponding candidate profiles 2532. More specifically, FIG. 13 depicts aspects of the execution of the comparison routine 2540 by the processor 2550 of the coordinating device 2500 provides various portions of the comparison GUI 3400, and to perform calculations related to at least a subset of those portions of the comparison GUI 3400. As depicted, the comparison routine 2540 may include a selection component 2541, a matching component 2542, a statistical power component 2543, a prediction variance component 2544, a fraction of design space component 2545, and/or a statistical correlation component 2546 that each cause the provision of a GUI portion 3410, 3420, 3430, 3440, 3450 and/or 3460, respectively. As also depicted, the comparison routine 2540 may include an interactive evaluation component 2549 to cause coordination of the operation of each of the components 2541 through 2546 in performing various calculations and/or in providing their associated GUI portions 3410 through 3460, respectively.

In executing the comparison routine 2540, the processor 2550 may be caused to execute the interactive evaluation component 2549 to recurringly derive numerical values and/or other information as part of providing comparisons between corresponding aspects of each one of multiple candidate testing regimes. Also, the processor 2550 may be caused to do so as those candidate testing regimes are being selected for comparison and/or as various parameters of each of those candidate testing regimes are being provided. Thus, the processor 2550 may be caused to execute the interactive evaluation component 2549 at least partially in parallel with one or more of the other components 2541-2546.

As additionally depicted, and similar to the earlier discussed provision of the generation GUI 3100, the comparison GUI 3400 may be provided either locally via the display 2580 and the input device 2520 of the coordinating device 2500, or remotely through the network 2999 and via the display 2780 and the input device 2720 of the viewing device 2700.

Figure 14A:
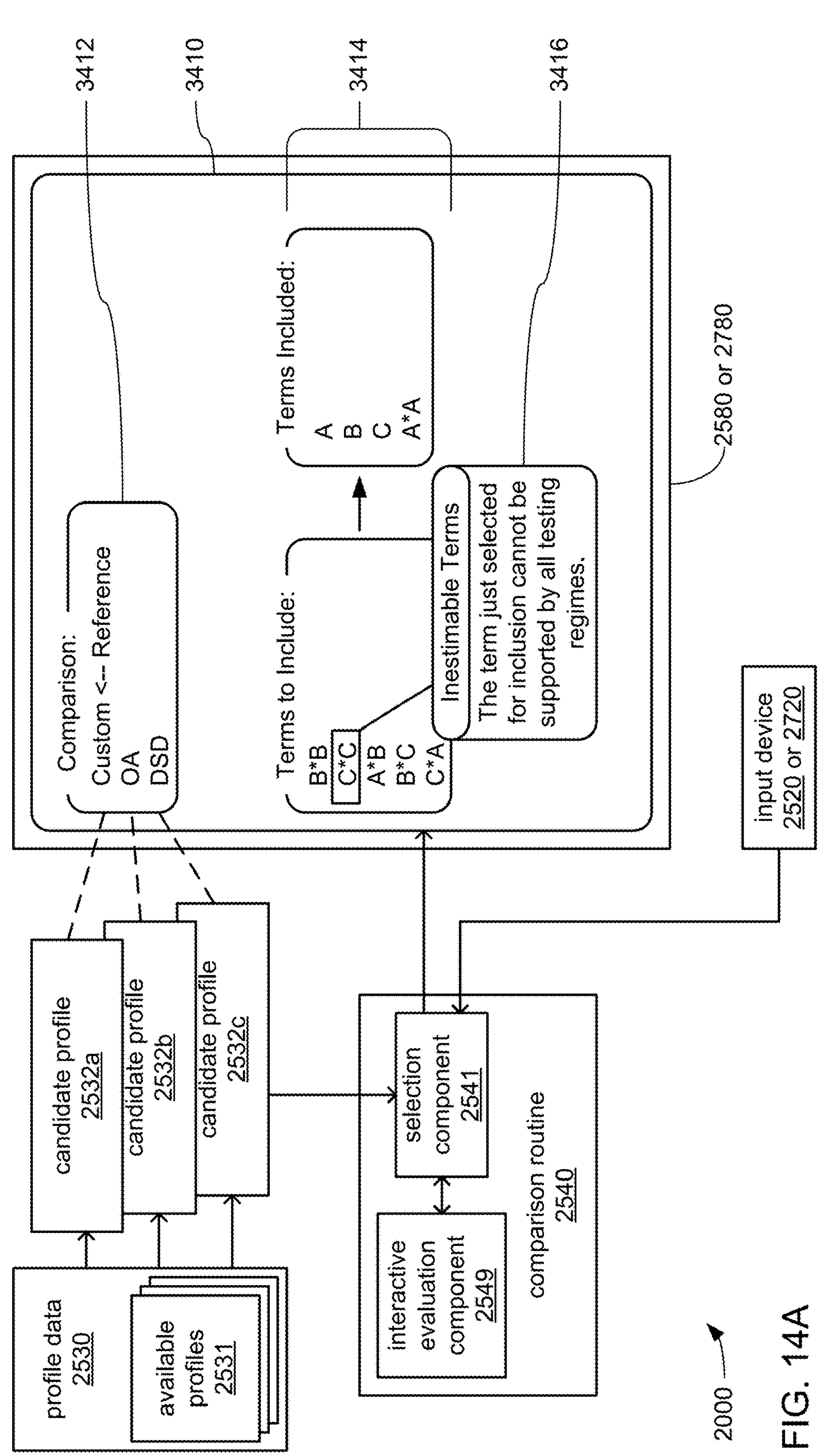

FIG. 14A depicts, in greater detail, aspects of the provision of the GUI portion 3410 to guide the selection of the multiple candidate testing regimes to be compared. In executing the selection component 2541, the processor 2550 may be caused to present a selection list 3412 or other similar visual element in the GUI portion 3410 by which an operator may be guided through selecting two or more candidate testing regimes to be compared. As previously discussed, and as depicted, definitions for testing regimes may be stored as available profiles 2531 within the profile data 2530, thereby enabling definitions of the testing regimes that are selected for comparison to be retrieved by retrieving corresponding ones of the available profiles 2531. More specifically, and as previously discussed, each selection of a testing regime defined within one of the available profiles 2531 may cause the provision of a copy thereof in the form of a corresponding candidate profile 2532 (e.g., the specifically depicted example candidate profiles 2532*a-c*) to the comparison routine 2540. In some embodiments, the selection list 3412 may present each of the available testing regimes with a text identifier given to each one, which as depicted, may be descriptive of the testing regime generation method used in each.

As also depicted, the selection list 3412 in the GUI portion 3410 may include a textual element that indicates which one of the multiple candidate testing regimes that are selected for comparison is designated as a reference. In embodiments in which one of the candidate testing regimes is so designated as a reference, one or more of the comparisons of corresponding aspects the candidate testing regimes may be organized in a manner in which the comparisons are (at least by default) between that reference and each of the other candidate testing regimes that are selected for comparison.

Also in executing the selection component 2541, the processor 2550 may be caused to present side-by-side selection lists 3414 or other similar visual elements in the GUI portion 3410 by which an operator may be guided through selecting terms of the models associated with the candidate testing regime to be included in the comparisons. As depicted, the side-by-side lists 3414 may include a list of terms not yet selected for inclusion in the comparisons, but available for selection, visually presented adjacent to another list of terms that are already in the set of terms selected for inclusion in the comparisons.

Further in executing the selection component 2541, the processor 2550 may be caused to monitor for the receipt of selections of candidate testing regimes for comparison and/or terms to be included in the comparisons made via an input device (e.g., one of the input devices 2520 or 2720). In some embodiments, a cursor, crosshairs or other visual element (not shown) may be presented to provide a visual indication of the current focal point of a corresponding pointing device (e.g., a mouse, trackpad, joystick, etc.) that may be used by an operator to make such selections in a manner that will be familiar to those skilled in the art. Alternatively or additionally, a text input device (e.g., a keyboard, predictive text keypad, etc.) may be used by an operator to make such selections through entry of text identifiers associated with testing regimes and/or terms. Regardless of the exact mechanism by which an operator provides input indicating selections of candidate testing regimes for comparison, the processor 2550 may be caused to respond to such input by retrieving corresponding candidate profile(s) 2532, as just discussed. The processor 2550 may also be caused to respond to input indicating selections of terms for inclusion in the comparisons by retrieving parameters corresponding to those selected terms from the retrieved one or more candidate profiles 2532 (e.g., parameters defining the one or more factors from which each term is formed, etc.).

In executing the interactive evaluation component 2549 at least partially in parallel with the selection component 2541, the processor 2550 may be caused to respond to each selection of a candidate testing regime and each selection of a term to be added to the set of terms to be included in the comparison by recurringly performing an analysis of the set of terms with each of the testing regimes selected for comparison. In so doing, the processor 2550 may be caused to recurringly determine whether the set of terms is unsupportable with any of the candidate testing regimes that have been selected for comparison. If so, then the processor 2550 may be caused to present a notice 3416 that the current set of terms selected for inclusion in the comparisons is not able to be supported by one or more of the candidate testing regimes. More specifically, and where such an unsupportable situation is created by the addition of a particular term to the set, the processor 2550 may be caused to present an embodiment of the notice 3416 that indicates that the term most recently selected for inclusion in the set of terms causes the set of terms to be "inestimable" with one or more of the candidate testing regimes selected for comparison. In some embodiments, the processor 2550 may be caused to await the receipt of input from the operator indicating acknowledgement of the notice 3416, and may respond to such input by removing the most recently selected term from the set. In so doing, the processor 2550 may be caused to modify the presentation of the selection lists 3414 to place the just removed term from the list indicating the set of selected terms and into the list of terms that are available for selection, but not yet selected.

Figure 14B:
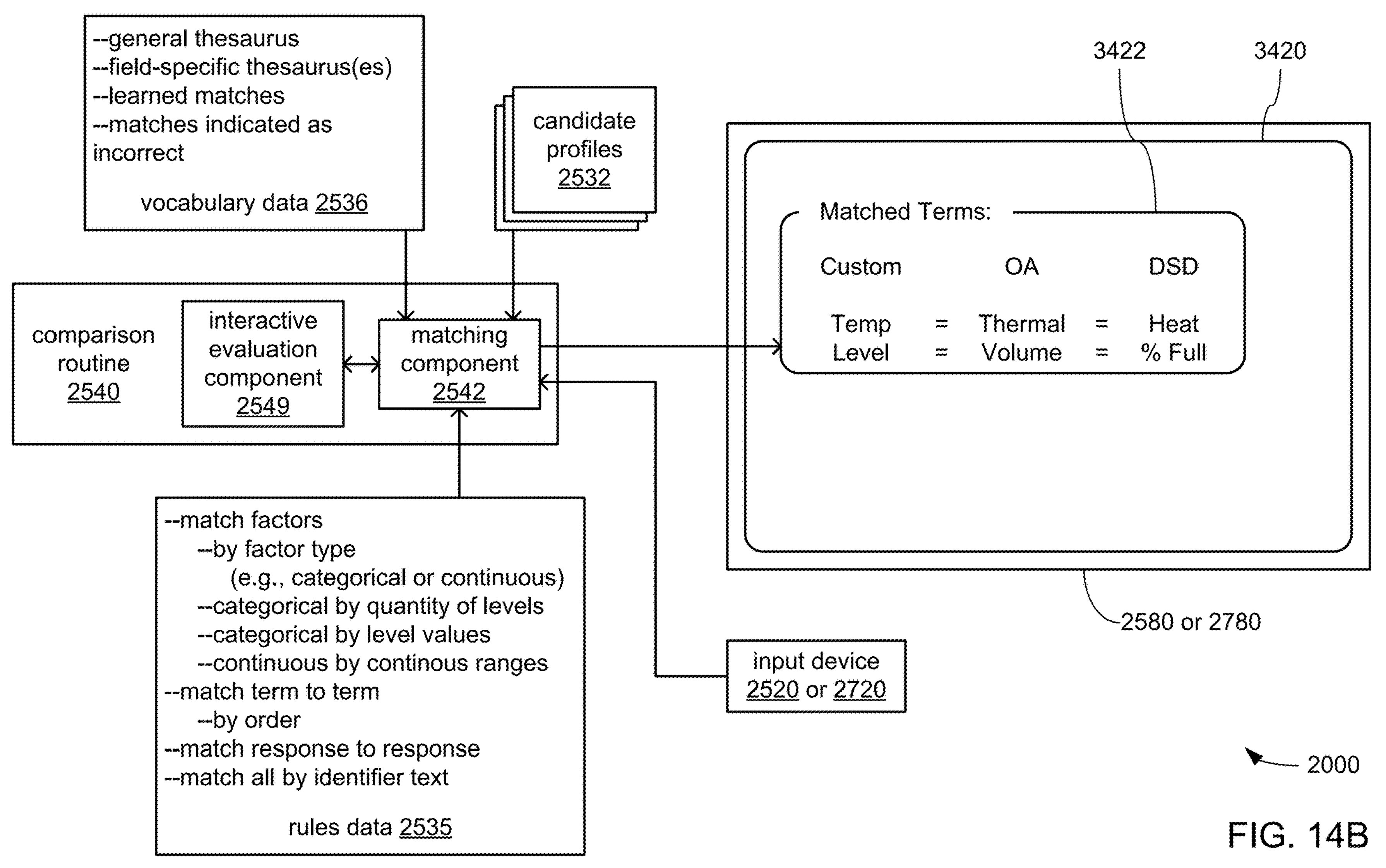

FIG. 14B depicts aspects of the provision of the GUI portion 3420 to guide the generation of matches between terms of the models associated with the multiple candidate testing regimes in greater detail. In executing the matching component 2542, the processor 2550 may be caused to analyze various characteristics of the factors, terms and/or responses of each model associated with one of the candidate testing regimes to identify matches therebetween. Indications of such characteristics may be retrieved by the processor from the candidate profiles 2532 that are associated with the candidate testing regimes. The processor 2550 may also retrieve a set of rules to be followed by the processor 2550 in performing such an analysis and matching from the rules data 2535.

In following such retrieved rules in executing the matching component 2542, the processor 2550 may initially attempt to match factors by the factor type of each factor of each model. By way of example, the processor 2550 may be caused to at least initially identify matches between factors of different models based on whether each factor is of a continuous factor type that may have any value within a continuous range of numerical values, or is of a categorical factor type that may have a value from among a set of discrete values. Following such initial matching of factors by factor type, the processor 2550 may be caused to match factors of the continuous factor type (if there are any) by matching their ranges of values, and/or may be caused to match factors of the categorical type (if there are any) by matching their quantities of levels and/or the values of their levels.

Alternatively or additionally, in following such retrieved rules, the processor 2550 may be caused to identify matches between terms of different models based on their order (e.g., 1st order, 2nd order, 3rd order, etc.). Also alternatively or additionally, the processor 2550 may be caused to identify matches between factors, between terms and/or between responses of different models by matching the texts of their identifiers. By way of example, the processor 2550 may be caused to search and retrieve indications of matches between words based on meaning within the vocabulary data 2536. In some embodiments, the vocabulary data 2536 may include a relatively general thesaurus and/or a field-specific thesaurus (e.g., industry-specific thesaurus, culture-specific thesaurus, technology-specific thesaurus, region-specific thesaurus) that may be deemed to be applicable.

As depicted, upon identifying one or more matches among factors, terms and/or responses, the processor 2550 may be caused by execution of the matching component 2542 to present a listing 3422 or other similar visual element of the identified matches. The processor 2550 may be further caused to monitor for the receipt of input from the operator that indicates that one or more of the matches identified by the processor 2550 is incorrect and/or input from the operator specifying one or more additional matches not successfully made by the processor 2550. In response to such corrective input, the processor 2550 may store indications of matches specified by the operator as learned matches and/or may store indications of incorrect matches made by the processor 2550 within the vocabulary data 2536.

Figure 14C:
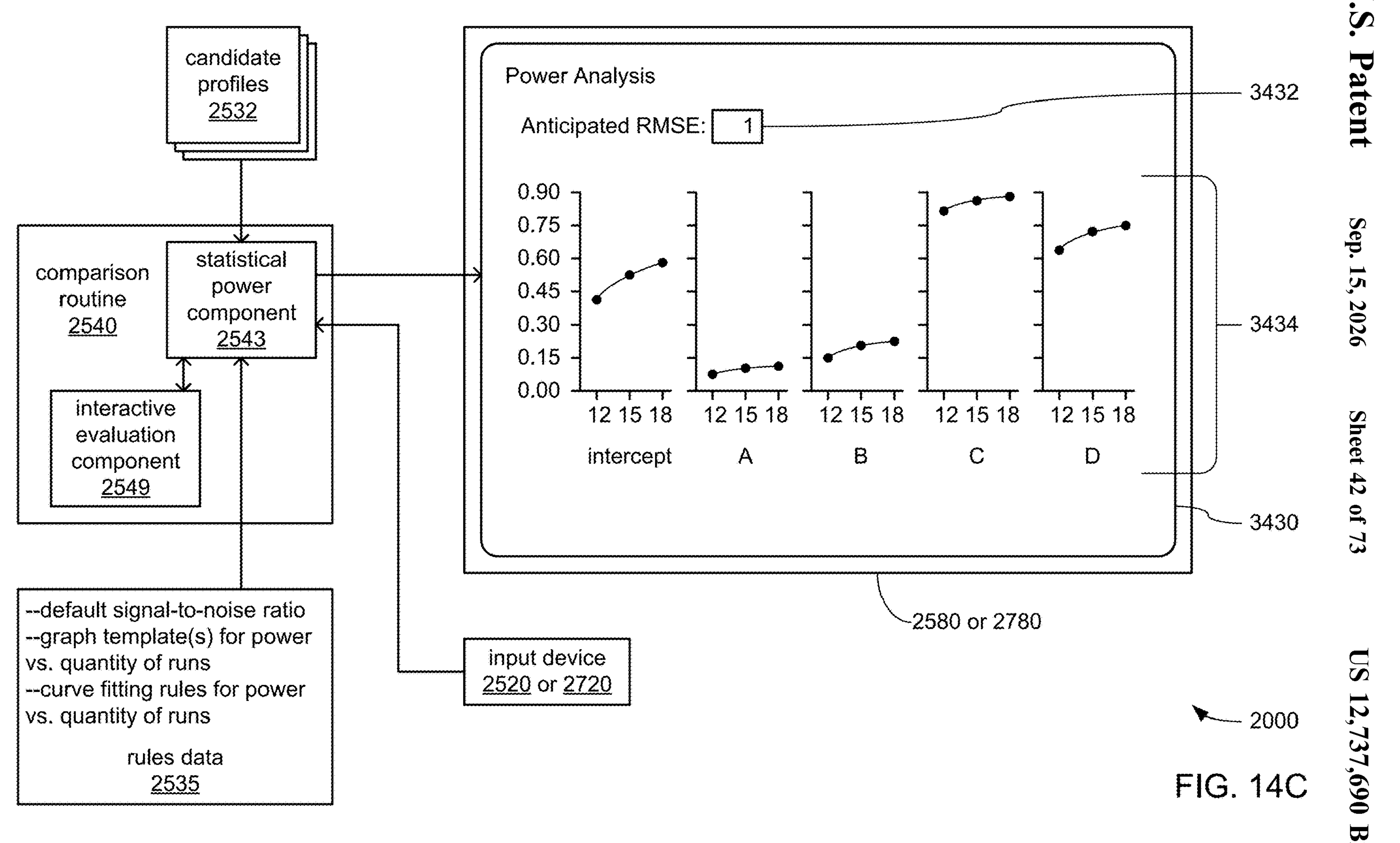

FIG. 14C depicts aspects of the provision of the GUI portion 3430 to guide the generation and consideration of a set of graphs comparing statistical power for terms among the multiple candidate testing regimes in greater detail. In executing the statistical power component 2543, the processor 2550 may be caused to analyze the terms that have been selected for inclusion in the comparisons among the candidate testing regimes, based on a selected signal-to-noise ratio, and may then generate and present a set of comparative graphs based on the analyses. In so doing, the processor 2550 may also retrieve a set of rules to be followed by the processor 2550 in performing such analyses and/or in generating the comparative graphs from the rules data 2535.

In following such retrieved rules in executing the statistical power component 2543, the processor 2550 may employ a predetermined statistical power calculation and/or an initial value for signal-to-noise ratio by default to derive the statistical power of each term of the set of terms selected for inclusion in the comparisons for each of the candidate testing regimes. The processor 2550 may then be caused to generate, for each term of the set of terms, a graph of a set of graphs 3434 of statistical power vs. candidate testing regime. Within each graph of the set of graphs 3434, the statistical power of a term may be plotted as a separate point for each candidate testing regime. In so doing, the processor 2550 may retrieve and employ a template from the rules data 2535 for generating each graph and/or may employ curve-fitting rules for fitting a curve to the plotted points within each graph.

In some embodiments, the rule data 2535 may include a rule that limits the performance of such analyses and the generation of the set of graphs 3434 to situations in which the candidate testing regimes differ only in the quantity of runs. Thus, in such situations, the resulting graphs provide a depiction of statistical power vs. quantity of runs for each term. Such an embodiment of the set of graphs 3434 may be so generated and then presented by the processor 2550 as part of guiding the selection of one of the candidate testing regimes for use by providing a graphical comparison of the relative degree of benefit that may be realized for each higher quantity of runs. Where the testing regime selected as the reference is based on constraints of cost, time and/or availability of materials, and is therefore the candidate testing regime with the lowest quantity of runs, such a visual presentation of fitted curves depicting what is often diminishing returns in statistical power with each increase in the quantity of runs may enable the operator to more quickly identify what may be deemed to be an acceptable tradeoff in incurring an increase in cost, time and/or consumption of available materials to perform a particular quantity of runs that may be greater than the quantity associated with the reference.

As depicted, the processor 2550 may be caused to arrange the set of graphs 3434 adjacent to each other in a horizontally extending manner (i.e., side-by-side in a "landscape" orientation). Such an arrangement of the set of graphs may be deemed desirable to advantageously exploit the "landscape" orientation of the binocular vision of the HVS. As will be familiar to those skilled in the art, it is currently believed that the manner in which the HVS functions to both identify what is in the FOV and perceive stereoscopic depth includes the covering of the FOV of each eye in a two-dimensional array of multiple types of feature detector in which each type of feature detector is implemented with a neuron that is sensitive to the presence of a particular feature within a particular portion of the FOV, such as a simple shape (e.g., a line, curve or corner) formed by one or more transitions between adjacent colors and/or transitions between light and dark. It is also believed that there are multiple layers of such coverage of the FOV of each eye in which a form of averaging is employed to reduce the resolution of the images captured by each eye for each successive layer to allow feature detectors in each of the successive layers to detect features across increasingly larger portions of the FOV of each eye. It is further believed that the perception of stereoscopic vision is based on comparisons between what is detected by the feature detectors at each level between the FOVs of the left and right eyes to identify both similarities and differences therebetween.

Efforts to apply such current theories of how the HVS functions to developing binocular image processing systems to identify objects and perceive depths in machines have met with a considerable degree of success, thereby increasing confidence in the correctness of such theories. Thus, the fitted curve within each of the graphs may advantageously provide a small set of simple shapes that form each of the curves that may be readily detected by a relatively small quantity of adjacent feature detectors within the FOV of each eye. Also, the horizontal or "landscape" orientation of the adjacent placement of the graphs in the set of graphs 3434 may advantageously exploit the left-versus-right feature-to-feature comparison at multiple levels within the HVS to enable speedier recognition of similarities in the fitted curves between adjacent ones of the graphs, thereby enabling a speedier identification of an acceptable tradeoff between quantity of runs to perform and the relative degree of increase in statistical power that may be realized, given the likely diminishing returns of each further increase in the quantity of runs.

As also depicted, the processor 2550 may be caused to present a visual indicator 3432 of the signal-to-noise ratio on which the calculations that derived the statistical power values within the set of graphs 3434 are based. In executing the interactive evaluation component 2549 at least partially in parallel with the statistical power component 2543, the processor 2550 may be caused to await receipt of an indication of input received from an operator that is indicative of a change to the displayed signal-to-noise ratio. The processor 2550 may be caused to respond to each such change by recurringly repeating the calculations that derived the statistical power values within the set of graphs 3434, and recurringly regenerating and re-presenting all of the graphs within the set of graphs 3434 to all reflect the same change in the signal-to-noise ratio. In this way, the operator may be interactively provided with answers to "what-if" questions of what would be the various values of statistical power for different signal-to-noise ratios that may be expected and/or known to be applicable to the studied system.

Figure 14D:
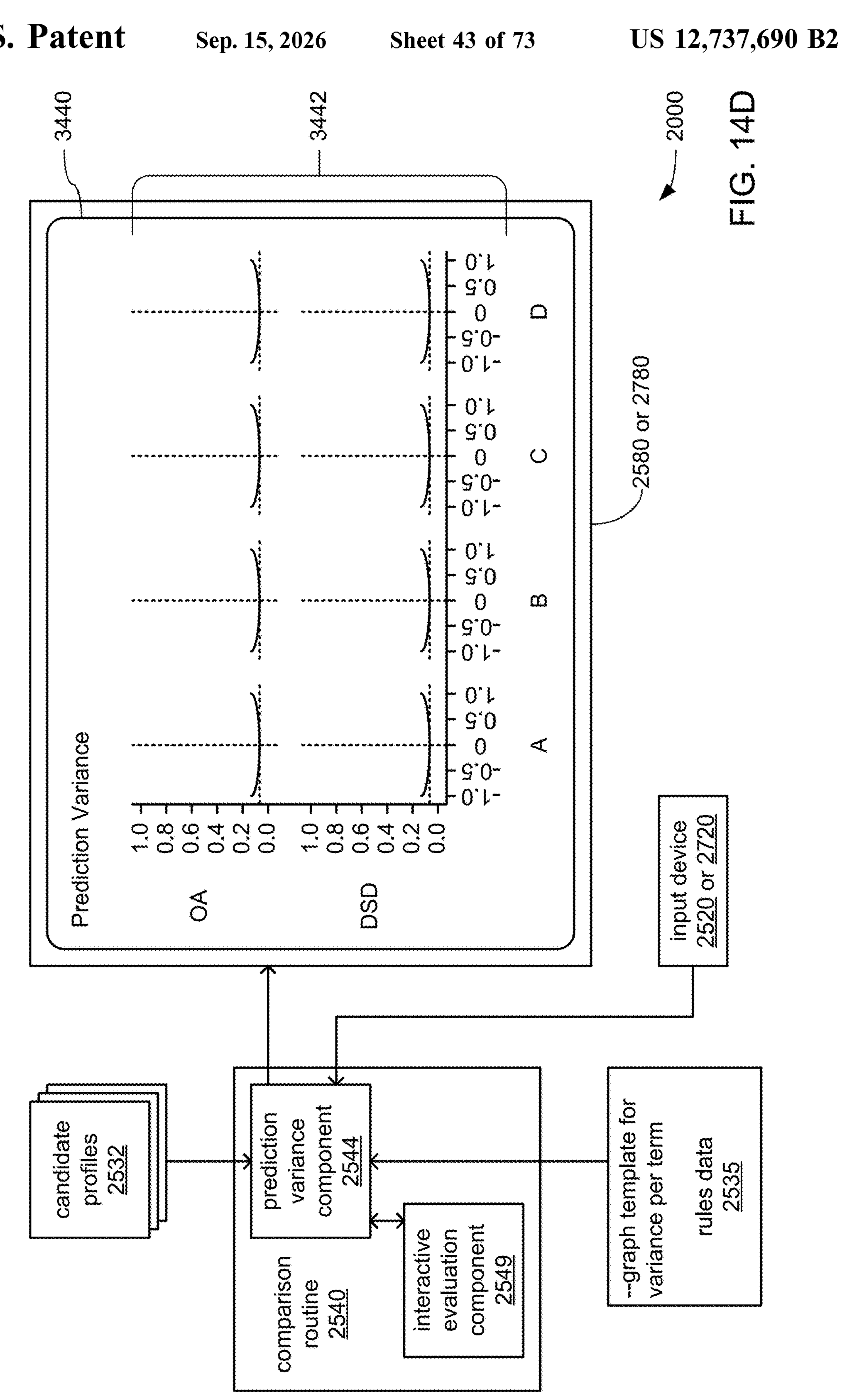

FIG. 14D depicts aspects of the provision of the GUI portion 3440 to guide the generation and consideration of a set of graphs comparing the prediction variance for terms among the multiple candidate testing regimes in greater detail. In executing the prediction variance component 2544, the processor 2550 may be caused to analyze the terms that have been selected for inclusion in the comparisons among the candidate testing regimes, and may then generate and present a set of comparative graphs based on the analyses. In so doing, the processor 2550 may also retrieve a set of rules to be followed by the processor 2550 in performing such analyses and/or in generating the comparative graphs from the rules data 2535.

In following such retrieved rules in executing the prediction variance component 2544, the processor 2550 may employ a predetermined prediction variance calculation to derive the prediction variance of each term of the set of terms selected for inclusion in the comparisons for each of the candidate testing regimes. The processor 2550 may then be caused to generate, for each term of the set of terms and for each of the candidate testing regimes, a graph of a set of graphs 3442 of prediction variance. Within each graph of the set of graphs 3442, a vertical line may be included that may be positioned at a default location at a zero value along the horizontal axis within a single design space that is identical across all of the graphs. In some embodiments, such a default location of the vertical line across all of the graphs may be specified as part of a template for generating the graphs that may be retrieved by the processor 2550 from the rules data 2535.

In executing the interactive evaluation component 2549 at least partially in parallel with the prediction variance component 2544, the processor 2550 may be caused to await receipt of an indication of input received from an operator that is indicative of a change to the displayed position of the vertical line along the horizontal axis in one of the graphs of the set of graphs 3442. The processor 2550 may be caused to respond to each such change by recurringly repeating the calculations that derived the prediction variances for each term for each candidate testing regime, and recurringly regenerating and re-presenting all of the graphs within the set of graphs 3442 to all reflect the same change in the position of the vertical line along the horizontal axis, and the same type of change in all of the resulting depicted curves for prediction variance across the design space.

FIG. 14E depicts aspects of the provision of the GUI portion 3450 to guide the generation and consideration of a combined graph comparing the fraction of design space of each of the candidate testing regimes in greater detail. In executing the fraction of design space component 2545, the processor 2550 may be caused to analyze each of the candidate testing regimes to generate, and then present, a combined graph 3452 of the fraction of design space for all of the candidate testing regimes. In so doing, the processor 2550 may also retrieve a set of rules to be followed by the processor 2550 in performing such analyses and/or in generating the combined graph 3452 from the rules data 2535, including a template.

Figure 14F:
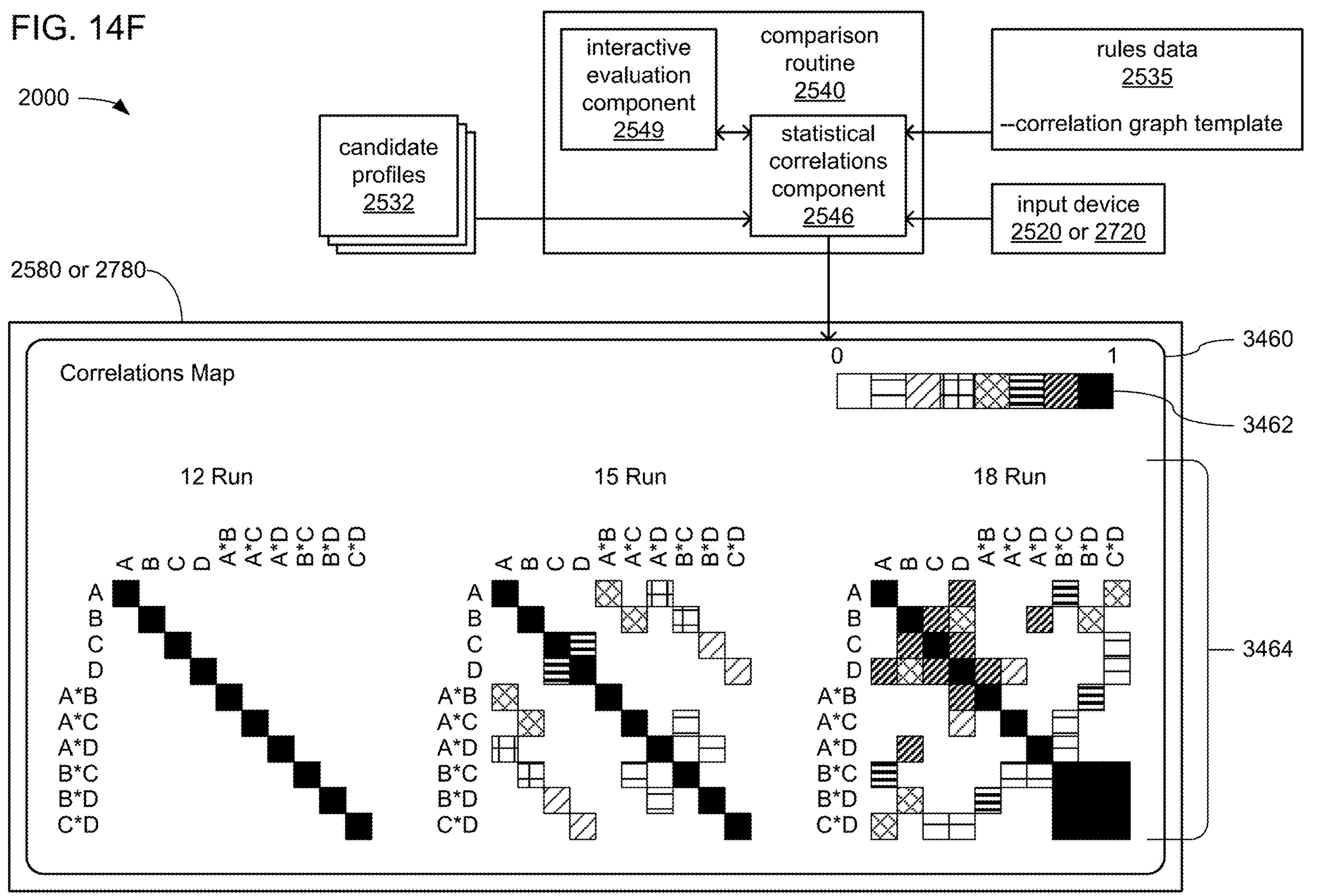

FIG. 14F depicts aspects of the provision of the GUI portion 3460 to guide the generation and consideration of a set of graphs comparing the degree of correlation between terms within each of the candidate testing regimes in greater detail. In executing the statistical correlations component 2546, the processor 2550 may be caused to analyze, within each of the candidate testing regimes, the terms that have been selected for inclusion in the comparisons to derive degrees of correlation between each possible pair of terms. The processor 2550 may then, for each of the candidate testing regimes, generate a correlation graph with all of the terms arranged in the same order along each of the horizontal and vertical axes, and with visual indications at each intersection visually depicting the derived degree of correlation between the terms of the corresponding pair. The processor may then also be caused to visually present the correlation graph so generated for each of the candidate testing regimes adjacent to each other in a set of correlation graphs 3464. Along with the set of correlation graphs 3464, the processor 2550 may additionally be caused to present a scale of the visual indications of the degree of correlation used in the correlation graphs. In so doing, the processor 2550 may also retrieve a set of rules to be followed by the processor 2550 in performing such analyses and/or in generating the correlation graphs from the rules data 2535, including a correlation graph template.

Again, as depicted, the processor 2550 may be caused to arrange the correlation graphs of the set of correlation graphs 3464 adjacent to each other in a horizontally extending manner (i.e., side-by-side in a "landscape" orientation). As discussed earlier, such a horizontally extending adjacent arrangement of the set of correlation graphs 3464 may again be deemed desirable to advantageously exploit the "landscape" orientation of the binocular vision of the HVS, including the stereoscopic comparisons believed to be routinely performed by the HVS at each level of feature detectors between the FOVs of the left and right eyes to identify both similarities and differences therebetween. Stated differently, such a horizontal side-by-side arrangement of such correlation graphs that use such visual indicators of degrees of correlation allow an operator to quickly identify, almost within a single glance, both degrees of similarity and degrees of difference in the visually indicated degrees of correlation among terms within each of the candidate testing regimes.

In some embodiments, the processor 2550 may additionally be caused to present a GUI portion (not shown) that allows for the selection of the scale of visual indicators of degrees of correlation from among multiple different scales of such visual indicators. In some embodiments, different ones of such scales may each include a different form of color coding. Each different form of color coding may include a range of progressively changing proportioned mixtures between two different colors that may, as entirely separate colors, each define one of the minimum and maximum degrees of correlation at the opposite ends of the scale. By way of example, such a scale may include the separate colors red and blue marking the minimum and maximum degrees of correlation, and a progressively changing series of mixtures of different proportions of red and blue forming various different purple colors marking various degrees of correlation between the minimum and maximum degrees of correlation. Alternatively or additionally, different ones of such scales may include different ranges of gray shading of a single color. Also alternatively or additionally, and as specifically depicted, different ones of such scales may include a series of different filling patterns that each provide a different degree of fill of a single color, thereby defining a scale that transitions from no filling to fully filled.

As will be familiar to those skilled in the art, in a testing regime, a high degree of correlation between terms can result in the masking of the influence of a particular factor in controlling one or more responses such that the importance of the particular factor may be overlooked. Alternatively, such a high degree of correlation between terms can cause a misleading inflation of the influence of a particular factor in controlling one or more responses such that valuable time and resources may be wasted in focusing on understanding the particular factor's influence and/or attempting to manipulate the particular factor to control one or more responses. Thus, a testing regime that includes one or more pairs of relatively highly correlated terms may not only provide little or no insight into an important linkage that may exist between factors and responses, but may also provide a misleading impression of there being an important linkage between factors and responses that may not actually exist and/or that may not actually be so important.

The terms may be arranged in the same order along each of the horizontal and vertical axes specifically to cause the diagonal symmetry that can be seen in FIG. 14F in the display of visual indicators of degrees of correlation. One of the results of this diagonal symmetry is the formation of a visually distinct diagonal line of intersections in each graph at which each term is paired with itself, and thus, where it would be expected that there would be complete symmetry. As depicted, each of these intersections along this diagonal line may be marked with an visual indicator that indicates such maximum correlation. Doing so may be deemed desirable to create a simple, easily identified visual reference of the location of each individual correlation graph in relation to the others of the set of correlation graphs 3464 in which the ends of the diagonal line so created denote diagonally opposite corners that quickly define the horizontal and vertical boundaries of each individual correlation graph.

As also depicted, the terms may be arranged along each of the horizontal and vertical axes such that lower order terms are arranged towards one end of the diagonal line and higher order terms are arranged towards the other end of the diagonal line. As will be familiar to those skilled in the art, the fact that many higher order terms are formed by the combining of two or more factors increases the likelihood that higher degrees of correlation will be encountered between higher order terms than between lower order terms. Thus, as depicted, this may produce a region of indications of relatively high degrees of correlation in the corner of one or more of the correlation graphs where the intersections correspond to pairs of higher order terms.

As will be familiar to those skilled in the art, relatively high degrees of correlation between lower order terms that are formed from single factors may be an indication that a testing regime is susceptible to masking and/or misrepresenting the degree of influence that one or more particular factors may have on particular responses, especially if it proves to be the case that a particularly important factor is subject to such high correlation. In contrast, where there is minimal correlation between lower order terms, there is far less risk of not detecting the influence of an important factor or of a factor being given an outsized apparent degree of influence in a testing regime, even if there are higher degrees of correlation between higher order terms.

By arranging the terms along the horizontal and vertical axes based on the order of the terms such that pairs of lower order terms are positioned toward one end of the diagonal line while pairs of higher order terms are positioned toward the other end, the ability is provided to more quickly visually distinguish testing regimes that are more likely to be successful in illuminating linkages between factors and responses from testing regimes that may not be. This also tends to advantageously exploit the aforedescribed multi-layer left-right feature comparisons made by the HVS, since regions of clustered visual indications of high degrees of correlations that appear in one corner corresponding to pairs of lower order terms or in the other corner corresponding to pairs of higher order terms become features that are detected by the feature detectors of the HVS. Such features then feed into left-right comparisons at layers where the feature detectors each cover a larger portion of the FOV of each eye such that there is an ability to relatively speedily detect the difference between a correlation graph that shows such a region in one corner (and towards one of the left or right sides) and another correlation graph that shows such a region in the opposite corner (and towards the other of the left or right sides).

As depicted, the entirety of the rectangular area defined by each of the correlation graphs may be entirely filled in with visual indicators of degrees of correlation such that, except for the pairings of each term to itself along the diagonal line, the presentation of visual indicators of degree of correlation for all possible pairs of terms is actually repeated in a manner that is diagonally mirrored on opposite sides of the diagonal line. Alternate embodiments are possible in which such mirrored repetition is avoided by presenting only one set of such visual indicators in a manner that fills a triangular-shaped portion of the rectangular area of each graph on only one side of the diagonal line. However, it may be deemed desirable to provide such mirrored repetition in the presentation of the visual indicators, since doing so provides a greater volume of such indications, and in a manner that still generally advantageously exploits the innate multilayer left-right feature comparisons of the HVS.

In executing the interactive evaluation component 2549 at least partially in parallel with the statistical correlations component 2546, the processor 2550 may be caused to await receipt of an indication of input received from an operator that is indicative of a change to the set of terms selected to be included in the comparisons of the candidate testing regimes. The processor 2550 may be caused to respond to each such change by recurringly repeating the analyses that derive correlations between terms and/or recurringly repeating the generation and presentation of the set of correlation graphs 3464 to reflect each changed set of terms.

Figure 15:
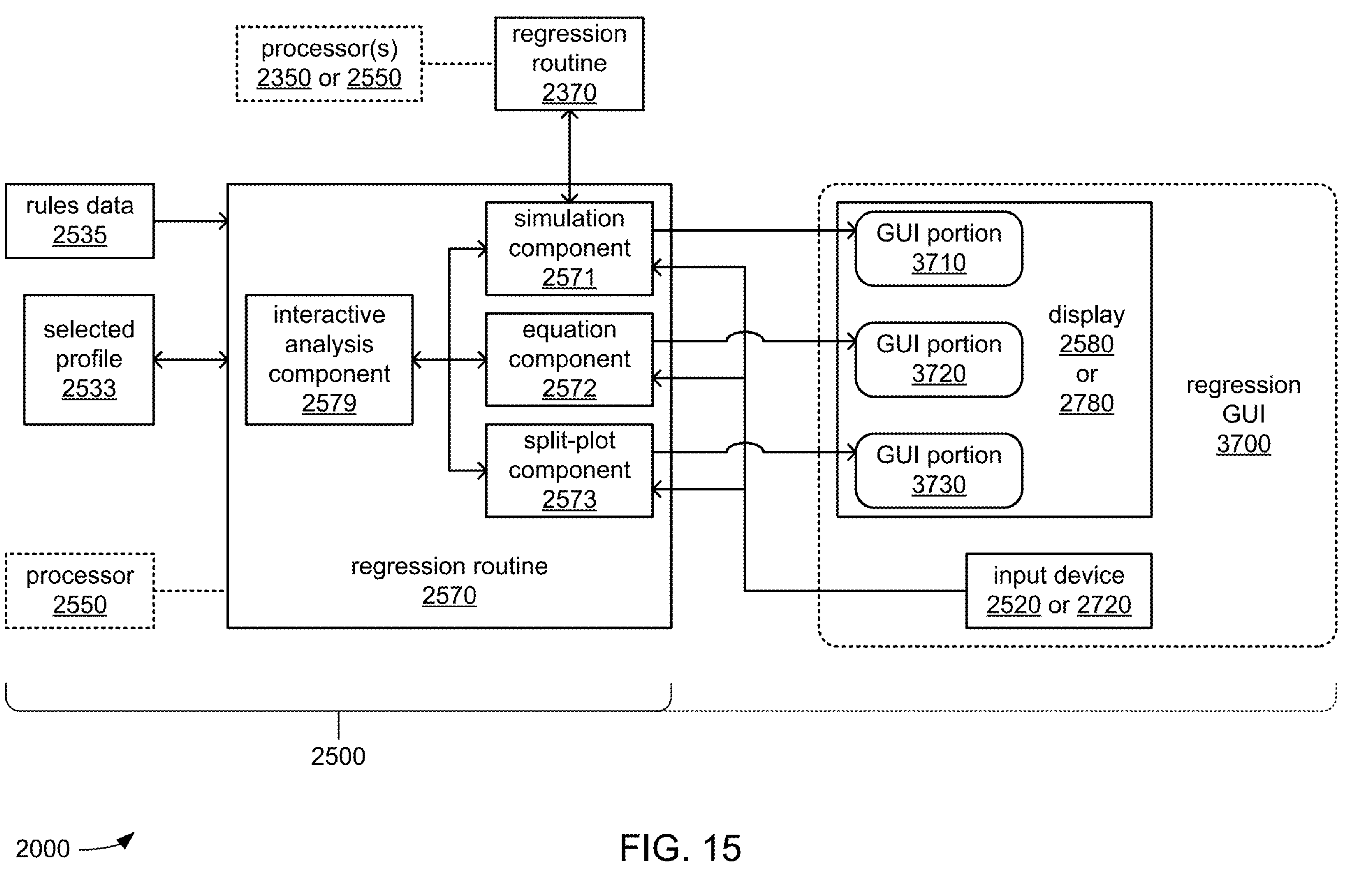
FIG. 15 illustrates an example of guiding the performance of a regression analysis of a selected testing regime.

FIG. 15 depicts aspects of an example of the provision of the regression GUI 3700 to guide the performance of a regression analysis with a selected testing regime (e.g., an testing regime selected from among the candidate testing regimes compared through use of the comparison GUI 3400). More specifically, FIG. 15 depicts aspects of the execution of the regression routine 2570 by the processor 2550 of the coordinating device 2500 to provide the regression GUI 3700. FIG. 15 also depicts aspects of the execution of the regression routine 2370 by at least one processor 2350 of the coordinating device 2500 or of the multiple node devices 2300 to perform the regression analysis, including the generation of simulated data. As depicted, the regression routine 2570 may include a simulation component 2571, an equation component 2572, a split-plot component 2573 and/or an interactive analysis component 2579. As also depicted, and similar to the earlier discussed provision of the generation GUI 3100 and the comparison 3400, the regression GUI 3700 may be provided either locally via the display 2580 and the input device 2520 of the coordinating device 2500, or remotely through the network 2999 and via the display 2780 and the input device 2720 of the viewing device 2700.

In executing the regression routine 2570, the processor 2550 may be caused to execute the interactive analysis component 2579 to recurringly derive numerical values and/or generating executable instructions as part of guiding an operator through preparations for and/or performance of the regression analysis with a selected testing regime. Also, the processor 2550 may be caused to do so as various parameters for the performance of the regression analysis are provided. Thus, the processor 2550 may be caused to execute the interactive analysis component 2579 at least partially in parallel with one or more of the other components 2571-2573.

Figure 16A:
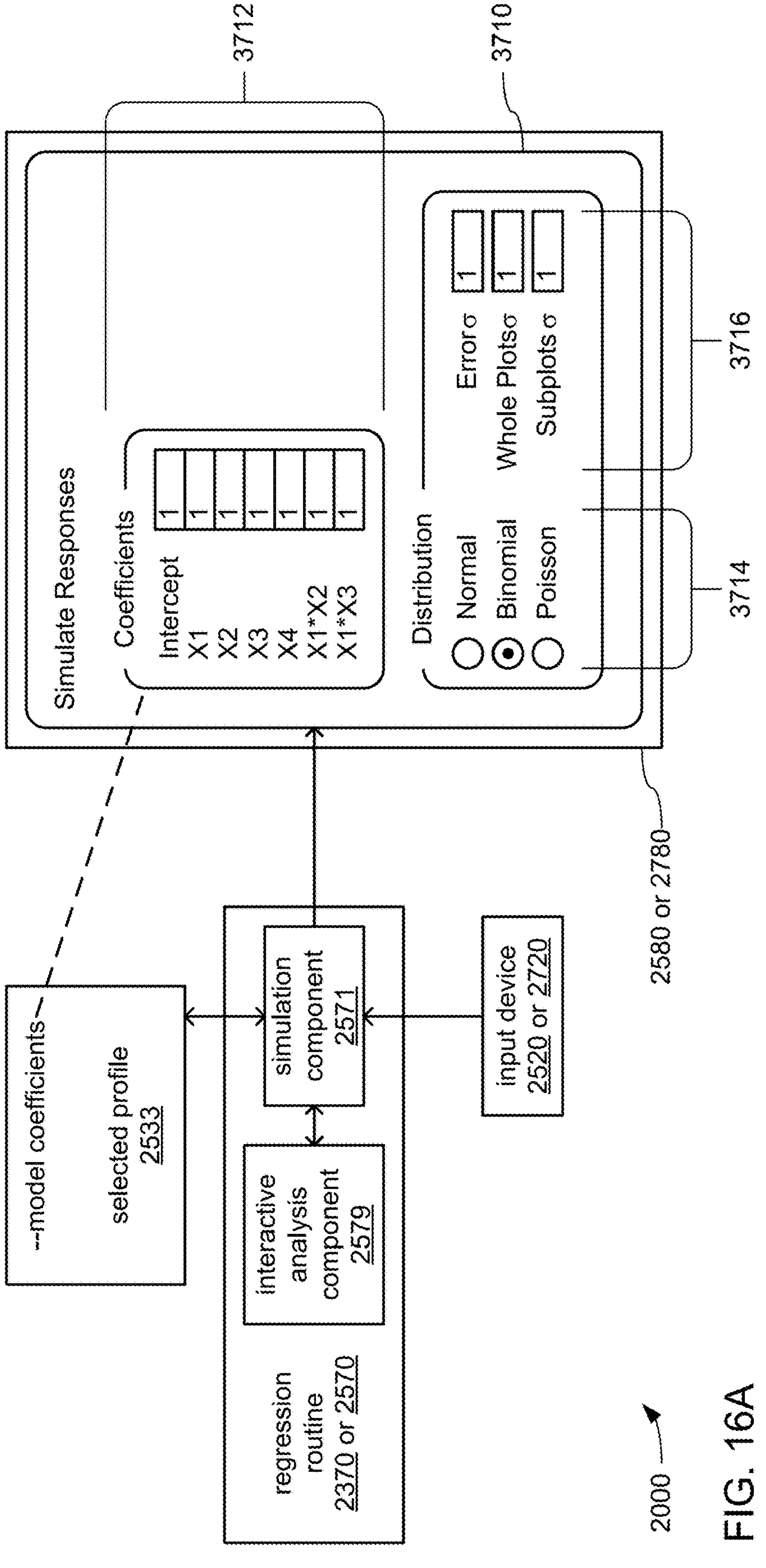

FIG. 16A depicts aspects of the provision of the GUI portion 3710 to guide the provision of various parameters for the performance of the regression analysis with a selected testing regime in greater detail. Where the selected testing regime on which the regression analysis to be performed is a testing regime that was selected from among the earlier discussed candidate testing regimes, the guiding of an operator via the GUI 3400 to select one of the candidate testing regimes for regression analysis may have resulted in the processor 2550 being caused to store various parameters that define the selected testing regime as part of its corresponding candidate profile 2532, and a copy of that candidate profile 2532 may then be provided to the regression routine 2570 as the selected profile 2533. Alternatively or additionally, the processor 2550 may be caused by execution of the regression routine 2570 to provide an opportunity within the regression GUI 3700 for the operator to select a testing regime from among the available testing regimes with the profile data 2530 to become the selected testing regime with which regression is to be performed, and a copy of its corresponding available profile 2531 may then be provided to the regression routine 2570 as the selected profile 2533.

In executing the simulation component 2571, the processor 2550 may be caused to present a set of entry boxes 3712 or other similar visual elements in the GUI portion 3710 in which default coefficients of the model associated with the selected testing regime may be visually presented, and/or by which an operator may provide alternate coefficients. In some embodiments, the default coefficients may be retrieved by the processor 2550 from the selected profile 2533, which may have been copied from one of the candidate profiles 2532, as previously discussed. Thus, the default coefficients may have been introduced during the comparison of the candidate testing regimes, where the same coefficients may have been used across all of the candidate testing regimes. However, as has been discussed, the default coefficients may have been provided through the use of the generation GUI 3100 to enter a definition of the testing regime and its associated model, including the coefficients.

Also in executing the simulation component 2571, the processor 2550 may be caused to present prompts for the provision of various parameters for the generation of simulated data. More specifically, the processor 2550 may be caused to present "radio buttons" 3714 or another type of selectable visual element in the GUI portion 3710 by which one of a list of types of distribution for the generation of the simulated data may be selected. Alternatively or additionally, the processor 2550 may be caused to present one or more entry boxes 3716 or other similar visual elements in the GUI portion 3710 in which default parameters for degree of error may be visually presented, and/or by which an operator may provide alternate parameters for degree of error. As depicted, a single entry box may be presented in which a single error parameter may be specified that may be applicable to all factors, or one or more additional entry boxes may also be presented in which one or more separate additional error parameters may be specified for one or more factors that are indicated as difficult to vary in a split-plot or split-split-plot testing regime.

Figure 16B:
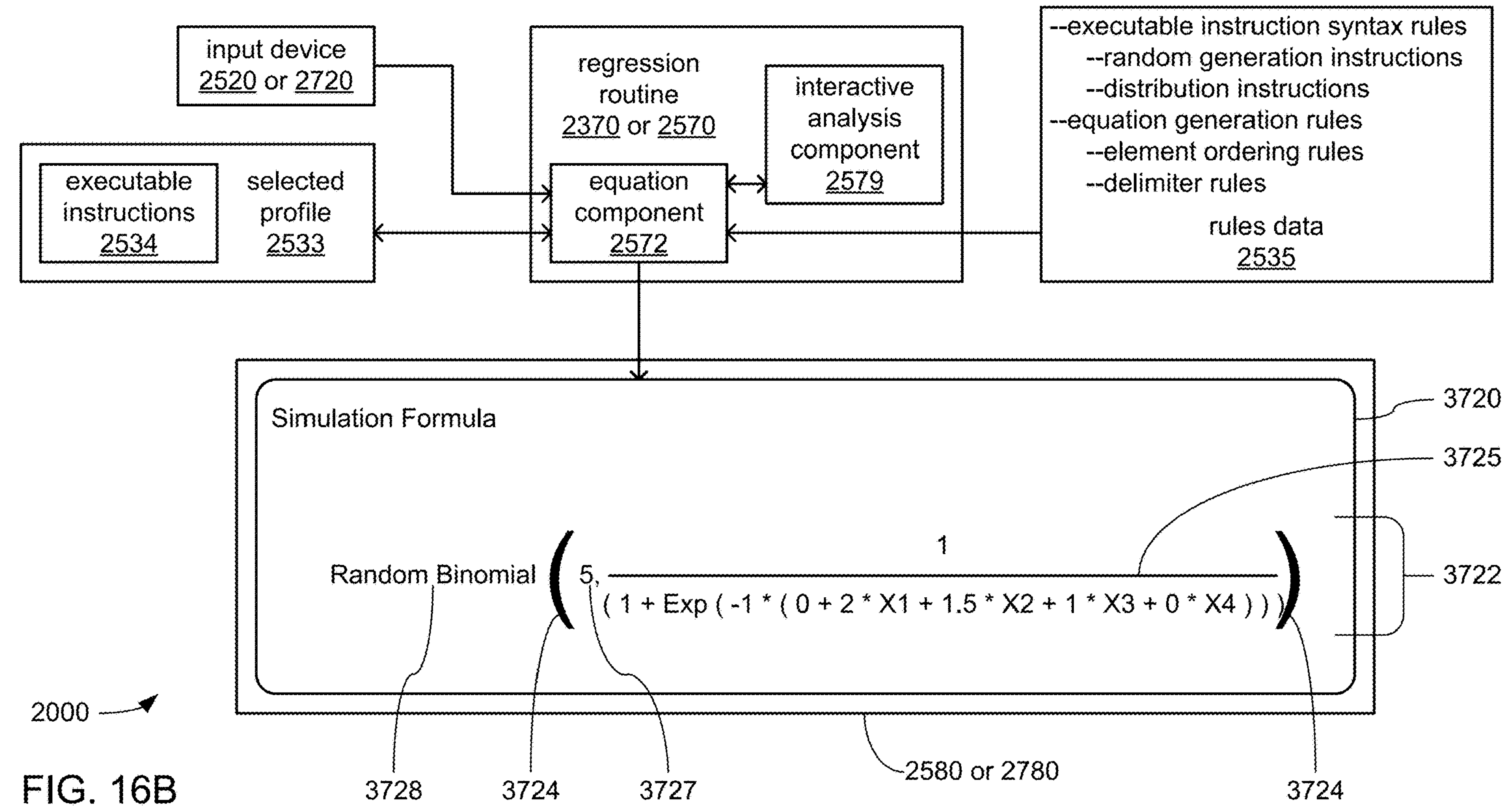

FIG. 16B depicts aspects of the provision of the GUI portion 3720 to guide the generation and consideration of executable instructions that, when executed, control the performance of the regression analysis, including the manner in which simulated data used in the regression analysis is to be generated. In executing the equation component 2572, the processor 2550 may be caused to first generate executable instructions 2534 that may be executed by one or more processors (e.g., the processor 2550 or the one or more processors 2350) to perform the regression analysis with the selected testing regime defined in the selected profile 2533. In generating the executable instructions 2534, the processor 2550 may be caused to retrieve one or more rules from the rules data 2535 that may include syntax rules to be followed in generating the executable instructions 2534, and such rules may be associated with and/or explicitly specify a pre-selected programming language. Alternatively or additionally, the processor 2550 may be caused to retrieve one or more pre-selected algorithms and/or portions of executable instructions that implement one or more pre-selected algorithms for the random generation of simulated data, including doing so in a manner that results in the simulated data having the type of distribution selected via the previously discussed GUI portion 3710. Also, In generating the executable instructions 2534, the processor 2550 may be caused to incorporate various parameters that may be provided to control the performance of the regression analysis, including and not limited to, the terms of the associated model that have been selected for inclusion in the selected testing regime, various characteristics of the factors from which the terms are formed, the coefficients for the terms and any intercept value, various characteristics of the responses, the quantity of runs, input values to be given to the factors, and/or a quantity of iterations to be performed of the regression analysis (including iterations of generating simulated data). Following the generation of the executable instructions 2534, the processor 2550 may be caused to store the executable instructions 2534 as part of the selected profile 2533.

Also in executing the equation component 2572, the processor 2550 may be caused to generate a human readable expression 3722 of a portion of the executable instructions 2534 that includes, and is not limited to including, the terms and/or coefficients of the associated model in mathematical notation, and/or an identifier of the selected type of distribution 3728 for the simulated data and/or of the quantity of iterations 3727 of the regression analysis to be performed. The processor 2550 may then be caused to present the human readable expression 3722. In generating the executable instructions 2534, the processor 2550 may be caused to retrieve one or more rules from the rules data 2535 for generating the human readable expression 3722, such as ordering of various elements, and/or mathematical notation syntax rules concerning delimiters that may be used to separate and organize the various elements. By way of example, in employing mathematical notation syntax rules, the processor 2550 may be caused to separate various elements with pairs of brackets 3724 and/or one or more of a vinculum 3725 (e.g., to separate a numerator from a denominator in expressing a division operation).

In executing the interactive analysis component 2579 at least partially in parallel with the equation component 2742, the processor 2550 may be caused to respond to each provision and/or change in a parameter for performing the regression analysis by recurringly regenerating the executable instructions 2534, and/or by recurringly regenerating and/or re-presenting the human readable expression 3722 of a portion of the executable instructions 2534. The parameters that, upon being provided and/or changed through use of the GUI portion 3710 and/or other GUI portions, may trigger such recurring operations by the processor 2550 may include, and are not limited to, the coefficients, the intercept value, the type of distribution, degree(s) of error and/or the quantity of iterations of the regression to be performed.

Figure 16C:
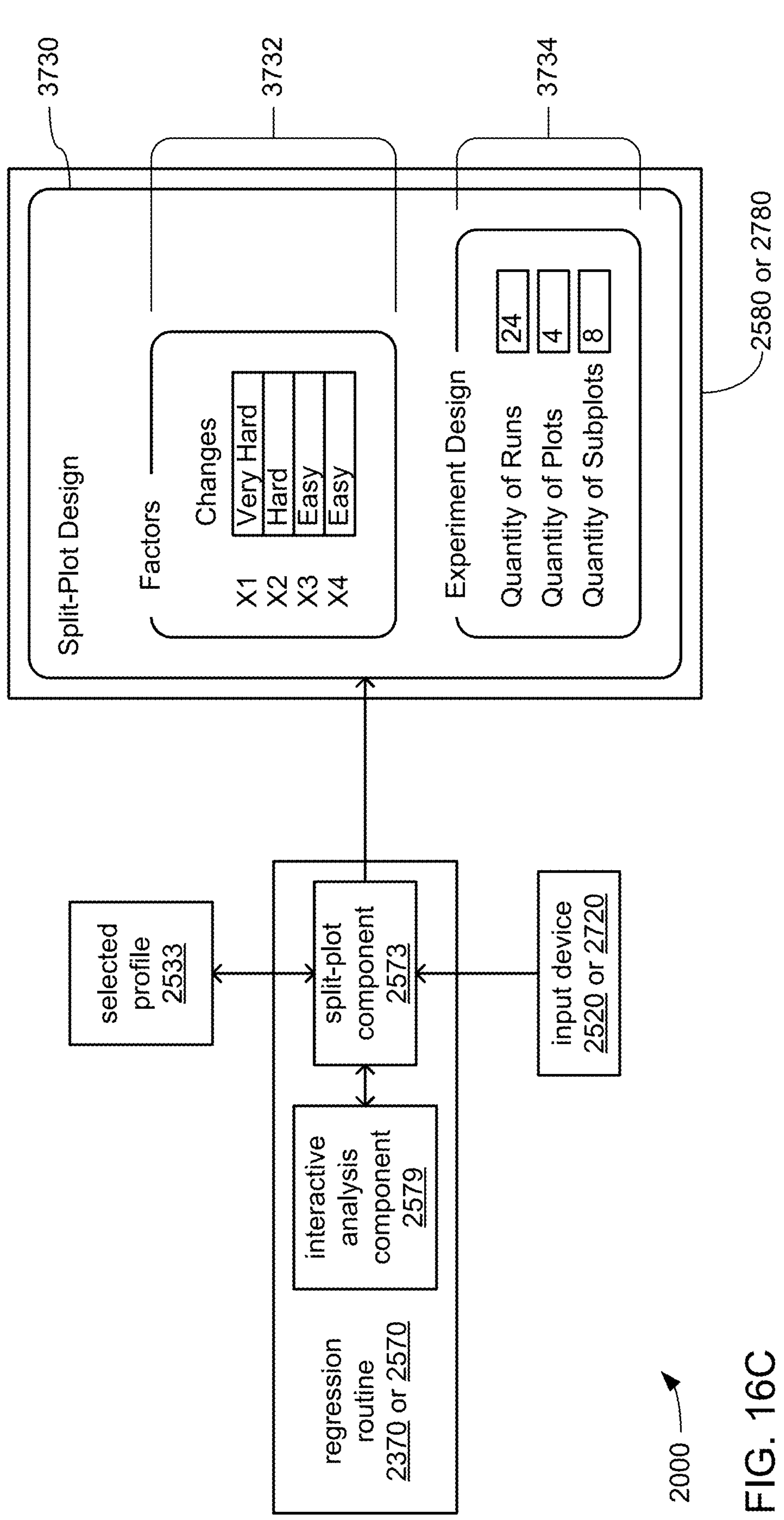

FIGS. 16C and 16D, together, depict aspects of the provision of the GUI portion 3730 to guide the provision of parameters and generation of portions of the executable instructions 2534 associated with the selected testing regime becoming a split-plot or split-split-plot design.

Turning more specifically to FIG. 16C, in executing the split-plot component 2573, the processor 2550 may be caused to present a set of entry boxes 3732 or other similar visual elements in the GUI portion 3730 in which a single default degree of difficulty in varying all factors may be visually presented, but by which an operator may provide one or more alternate indications of degree of difficulty in varying one or more of the factors. Also in executing the split-plot component 2573, the processor 2550 may be caused to present one or more other entry boxes 3734 or other similar visual elements in the GUI portion 3730 in which, at least initially, a default parameter for quantity of runs may be visually presented. However, in response to the entry of one or more degrees of difficulty in varying a factor are entered into one or more of the entry boxes 3732, the processor 2550 may be caused to augment the single entry box 3734 for quantity of runs with one or more additional entry boxes 3734 for quantity of plots and/or subplots, depending on whether the selected testing regime is caused to become a split-plot testing regime or split-split-plot testing regime.

In executing the interactive analysis component 2579 at least partially in parallel with the split-plot component 2743, the processor 2550 may be caused to respond to each provision and/or change in a parameter indicative of a split-plot testing regime or split-split-plot testing regime by recurringly regenerating and re-presenting one or more of the GUI portions 3710, 3720 and 3730 to prompt the operator to provide further parameters. By way of example, the processor 2550 may be caused to regenerate and re-present the GUI portion 3710 with the one or more entry boxes 3716 additionally including an entry box in which a default degree of error for whole plots in at least a split-plot testing regime, and enabling provision of a different degree of error for whole plots by the operator. Also by way of example, the processor 2550 may be caused to augment the GUI portion 3730 to additionally include a table depicting an order in which factors may be varied during the performance of the selected testing regime to minimize the instances in which one or more particular factors may be varied, such as the table 3736 depicted in FIG. 16D.

Alternatively or additionally, in executing the interactive analysis component 2579 at least partially in parallel with the split-plot component 2743, the processor 2550 may be caused to respond to each provision and/or change in a parameter indicative of a split-plot testing regime or split-split-plot testing regime by recurringly regenerating the executable instructions 2534 to accommodate separate degrees of error for each factor indicated as more difficult to vary and/or to accommodate associated changes in the manner in which simulated data is to be generated. Correspondingly, the processor 2550 may be caused to recurringly regenerate and/or re-present the human readable expression 3722 of a portion of the executable instructions 2534.

FIG. 16E depicts an example of an alternate human readable expression 3722 that reflects a change of the selected testing regime to a split-split-plot design. As depicted, multiple pairs of brackets 3724 are used to provide clear visual separation of a portion of the executable instructions that minimizes the varying of one factor in whole plots, from another portion that minimizes the varying of another factor in subplots, and from still other portions that implement fully random varying of the remaining factors. Also again, there are explicit identifiers of the type of distribution 3728 selected for the simulated data.

Following completion of the provision of parameters for the performance of the regression analysis with the selected testing regime, and following the generation of the executable instructions 2534 therefrom, the processor 2550 may be caused by further execution of the regression routine 2570 to distribute the executable instructions 2534 to the one or more processors 2350 to cause performance of the regression analysis. Again, in some embodiments, the executable instructions 2534 may be incorporated into or be other accompanied by the selected profile 2533 such that the selected profile 2533 may be distributed to the one or more processors 2350. In some embodiments, and in addition to the distribution of the executable instructions 2534, the processor 2550 may be further caused to at least coordinate the distribution of one or more of the data set portions 2131 thereamong. Also again, in various embodiments, the one or more processors 2350 may be incorporated into the multiple node devices 2300 or within the coordinating device. Thus, in differing embodiments, the executable instructions 2534 and/or the one or more data set portions 2131 may be distributed among multiple node devices 2300, or among storage locations within storage 2360 for access by the one or more processors 2350 within the coordinating device 2500.

Regardless of the physical location(s) of the one or more processors 2350, in executing the regression routine 2370, each of the one or more processors 2350, and/or each of the processing cores 2355 of each of the one or more processors 2350, may be caused to execute the executable instructions 2534 distributed thereto, and in so doing, perform at least one iteration of the regression analysis with the selected testing regime. The processor 2550 may be caused by its execution of the regression routine 2570 to coordinate the multiple, and at least partially parallel, performances of the regression analysis. As part of each iteration of each such performance, and as per the executable instructions 2534, simulated data is randomly generated in a manner that meets the specified distribution.

From the iterations of the regression analysis, the results data 2730 may be generated to provide an indication of the results of the regression analysis. As previously discussed, the results data 2730 may be presented by the processor 2550 (e.g., through use of the display 2580 or 2780), or may be transmitted to the viewing device 2700 for presentation to the operator via the processor 2750 thereof. Following the performance of the regression analysis, and in embodiments in which the one or more data devices 2100 control the studied system, the selected profile 2533 may be transmitted to the one or more data devices 2100 to enable for use thereby in performing the selected testing regime.

Returning to FIGS. 7A and 7B, in various embodiments, each of the processors 2150, 2350, 2550 and 2750 may include any of a wide variety of commercially available processors. Further, one or more of these processors may include multiple processors, a multi-threaded processor, a multi-core processor (whether the multiple cores coexist on the same or separate dies), and/or a multi-processor architecture of some other variety by which multiple physically separate processors are linked.

However, in a specific embodiment, the processor 2550 of the coordinating device 2500 or the controller 2507 may be selected to efficiently perform an analysis of the multiple testing regimes and/or associated models. Alternatively or additionally, the processor 2350 of each of the node devices 2300 may be selected to efficiently perform a regression analysis while generating simulated data at least partially in parallel. By way of example, the processor 2350 may incorporate a single-instruction multiple-data (SIMD) architecture, may incorporate multiple processing pipelines, and/or may incorporate the ability to support multiple simultaneous threads of execution per processing pipeline.

In various embodiments, each of the routines 2140, 2370, 2510, 2540, 2570 and 2740, including the components of which each is composed, may be selected to be operative on whatever type of processor or processors that are selected to implement applicable ones of the processors 2150, 2350, 2550 and/or 2750 within corresponding ones of the devices 2100, 2300, 2500 and/or 2700. In various embodiments, each of these routines may include one or more of an operating system, device drivers and/or application-level routines (e.g., so-called "software suites" provided on disc media, "applets" obtained from a remote server, etc.). Where an operating system is included, the operating system may be any of a variety of available operating systems appropriate for the processors 2150, 2350, 2550 and/or 2750. Where one or more device drivers are included, those device drivers may provide support for any of a variety of other components, whether hardware or software components, of the devices 2100, 2300, 2500 and/or 2700.

In various embodiments, each of the storages 2160, 2360, 2560 and 2760 may be based on any of a wide variety of information storage technologies, including volatile technologies requiring the uninterrupted provision of electric power, and/or including technologies entailing the use of machine-readable storage media that may or may not be removable. Thus, each of these storages may include any of a wide variety of types (or combination of types) of storage device, including without limitation, read-only memory (ROM), random-access memory (RAM), dynamic RAM (DRAM), Double-Data-Rate DRAM (DDR-DRAM), synchronous DRAM (SDRAM), static RAM (SRAM), programmable ROM (PROM), erasable programmable ROM (EPROM), electrically erasable programmable ROM (EEPROM), flash memory, polymer memory (e.g., ferroelectric polymer memory), ovonic memory, phase change or ferroelectric memory, silicon-oxide-nitride-oxide-silicon (SONOS) memory, magnetic or optical cards, one or more individual ferromagnetic disk drives, non-volatile storage class memory, or a plurality of storage devices organized into one or more arrays (e.g., multiple ferromagnetic disk drives organized into a Redundant Array of Independent Disks array, or RAID array). It should be noted that although each of these storages is depicted as a single block, one or more of these may include multiple storage devices that may be based on differing storage technologies. Thus, for example, one or more of each of these depicted storages may represent a combination of an optical drive or flash memory card reader by which programs and/or data may be stored and conveyed on some form of machine-readable storage media, a ferromagnetic disk drive to store programs and/or data locally for a relatively extended period, and one or more volatile solid state memory devices enabling relatively quick access to programs and/or data (e.g., SRAM or DRAM). It should also be noted that each of these storages may be made up of multiple storage components based on identical storage technology, but which may be maintained separately as a result of specialization in use (e.g., some DRAM devices employed as a main storage while other DRAM devices employed as a distinct frame buffer of a graphics controller).

However, in a specific embodiment, the storage 2360 of one or more of the node devices 2300 that stores one or more of the data set portions 2131 may be implemented with a redundant array of independent discs (RAID) of a RAID level selected to provide fault tolerance to prevent loss of one or more of these datasets and/or to provide increased speed in accessing one or more of these datasets.

In various embodiments, each of the input devices 2520 and 2720 may each be any of a variety of types of input device that may each employ any of a wide variety of input detection and/or reception technologies. Examples of such input devices include, and are not limited to, microphones, remote controls, stylus pens, card readers, finger print readers, virtual reality interaction gloves, graphical input tablets, joysticks, keyboards, retina scanners, the touch input components of touch screens, trackballs, environmental sensors, and/or either cameras or camera arrays to monitor movement of persons to accept commands and/or data provided by those persons via gestures and/or facial expressions. In various embodiments, each of the displays 2580 and 2780 may each be any of a variety of types of display device that may each employ any of a wide variety of visual presentation technologies. Examples of such a display device includes, and is not limited to, a cathode-ray tube (CRT), an electroluminescent (EL) panel, a liquid crystal display (LCD), a gas plasma display, etc. In some embodiments, the display 2580 of the coordinating device 2500 and/or the display 2780 of the viewing device 2700 may be a touchscreen display such that the input device 2520 may be incorporated into the display 2580 and/or the input device 2720 may be incorporated into the display 2780. In such embodiments, the input device 2520 and/or the input device 2720 may be a touch-sensitive component of the display 2580 and/or the display 2780, respectively.

In various embodiments, the network interfaces 2190, 2390, 2590 and 2790 may employ any of a wide variety of communications technologies enabling these devices to be coupled to other devices as has been described. Each of these interfaces includes circuitry providing at least some of the requisite functionality to enable such coupling. However, each of these interfaces may also be at least partially implemented with sequences of instructions executed by corresponding ones of the processors (e.g., to implement a protocol stack or other features). Where electrically and/or optically conductive cabling is employed, these interfaces may employ timings and/or protocols conforming to any of a variety of industry standards, including without limitation, RS-232C, RS-422, USB, Ethernet (IEEE-802.3) or IEEE-1394. Where the use of wireless transmissions is entailed, these interfaces may employ timings and/or protocols conforming to any of a variety of industry standards, including without limitation, IEEE 802.11a, 802.11ad, 802.11ah, 802.11ax, 802.11b, 802.11 g, 802.16, 802.20 (commonly referred to as "Mobile Broadband Wireless Access"); the BLUETOOTH® standard; the ZIGBEE® standard; or a cellular radiotelephone service such as GSM with General Packet Radio Service (GSM/GPRS), CDMA/1×RTT, Enhanced Data Rates for Global Evolution (EDGE), Evolution Data Only/Optimized (EV-DO), Evolution For Data and Voice (EV-DV), High Speed Downlink Packet Access (HSDPA), High Speed Uplink Packet Access (HSUPA), 4G LTE, etc.

However, in a specific embodiment, the network interface 2390 of one or more of the node devices 2300 that stores one or more of the data set portions 2131 may be implemented with multiple copper-based or fiber-optic based network interface ports to provide redundant and/or parallel pathways in exchanging one or more of the data set portions 2131 with the one or more storage devices 2100.

FIGS. 17A, 17B, 17C, 17D, 17E and 17F, together, illustrate an example embodiment of a logic flow 4100. The logic flow 4100 may be representative of some or all of the operations executed by one or more embodiments described herein. More specifically, the logic flow 4100 may illustrate operations performed by the processor(s) 2550, and/or other component(s) of the coordinating device 2500, in executing the generation routine 2510 to guide the generation of a testing regime.

Turning to FIG. 17A, at 4110, processor(s) of a coordinating device of a distributed processing system (e.g., the processor(s) 2550 of the coordinating device 2500 of the distributed processing system 2000) may present a prompt (e.g., a visual prompt, such as a menu, via presentation of the generation GUI 3100 on the display 2580 or 2780) to an operator of the distributed processing system to provide an indication of what aspect of a testing regime is to be specified or edited first. At 4111, the processor(s) may receive input indicating (e.g., manual input via the input device 2520 or 2720 associated with the generation GUI 3100) of that aspect.

As previously discussed, the selection of which aspect of a testing regime to specify or edit first may be implemented as a selection of which pathway of prompts to traverse through in specifying parameters of a testing regime. Again, by providing such multiple pathways, an operator of the system is provided an opportunity to choose to start with the parameters associated with the aspect that they feel most certain about, before moving on to the parameters associated with the other aspects that they feel less certain about. Further, the parameters specified for the aspect that is chosen to start with become the basis for guiding the operator through specifying the other parameters associated with the other aspects that the operator may feel less certain about.

Still more specifically, three pathways may be provided for the operator to choose to traverse through as part of specifying aspects of a testing regime: 1) a term-focused pathway starting with initial prompts for term-related parameters followed by subsequent prompts for model-related and/or test-related parameters; 2) a model-focused pathway starting with initial prompts for model-related parameters followed by subsequent prompts for term-related and/or test-related parameters; and 3) a test-focused pathway starting with initial prompts for test-related parameters followed by subsequent prompts for term-related and/or model-related parameters.

At 4112, the processor(s) may check whether the received input indicates a choice to traverse through a term-focused pathway in which term-related parameters of the testing regime (i.e., parameters concerning the factors and/or the higher order terms) are to be specified or edited first. If at 4112, the received input indicates such a selection of the term-focused pathway, then the processor(s) may begin a traversal through the term-focused pathway at 4120 by providing the initial prompt(s) thereof, as will be described in greater detail.

However, if at 4112, the received input does not indicate such a selection of the term-focused pathway, then at 4113, the processor(s) may check whether the received input indicates a choice to traverse through a test-focused pathway in which the test-related parameters of the testing regime are to be specified or edited first. If at 4113, the received input indicates such a selection of the test-focused pathway, then the processor(s) may begin a traversal through the test-focused pathway at 4140 by providing the initial prompt(s) thereof, as will be described in greater detail.

However, if at 4113, the received input indicates a selection of a model-focused pathway in which model-related parameters of the testing regime are to be specified or edited first, then the processor may begin a traversal through the model-focused pathway at 4130 by providing the initial prompt(s) thereof, as will be described in greater detail.

Turning to FIG. 17B, at 4120, the processor(s) may begin a traversal through the term-focused pathway by providing one or more initial prompts to guide the operator through providing initial inputs indicating the specification or editing of various term-related parameters (e.g., factor types, ranges of values and/or levels for factors, linear constraints, etc.). At 4121, the processor(s) may then receive the initial inputs (if any) conveying indications of the specification of the parameter values prompted for at 4120.

At 4122, following the provision of such initial prompts, the processor(s) may also provide one or more subsequent prompts to guide the operator through providing subsequent inputs indicating the specification or editing of various model-related and/or test-related parameters (e.g., what terms are to be included for estimation and/or Bayesian inference, number of runs, etc.). At 4123, the processor(s) may then receive the subsequent inputs (if any) conveying indications of the specification of the parameter values prompted for at 4122.

At 4124, the processor(s) may check whether current model-related and/or test-related parameter values create an incompatibility with the current term-related parameter values, including any parameter values received either prior to or during the current traversal through the term-focused pathway. It should be noted that, prior to the current traversal through the term-focused pathway, various parameter values may have been provided during previous traversal(s) through one or more pathways, and/or may have been provided as a result of using default parameter values or parameter values of an existing testing regime as a starting point for generating the current testing regime.

If at 4124, there is an incompatibility with the current term-related parameter values, then at 4125, the processor(s) may present a prompt indicating the incompatibility (e.g., a compatibility notice). Then at 4126, the processor(s) may check whether the incompatibility is at least partially caused by earlier model-related and/or test-related parameter values specified prior to the current traversal of the term-focused pathway. If not at 4126, then the processor(s) may return to receiving input(s) at 4123. However, if so at 4126, then at 4127, the processor(s) may provide an additional prompt (either separately, or as part of the prompt provided at 4125) that conveys the option to delete at least some of such earlier-specified parameter values.

However, if at 4124, there is no such incompatibility, then at 4128, the processor(s) may check whether the input(s) received during the current traversal through the term-focused pathway include an indication of a command from the operator of the system to end this current traversal. If not at 4128, then at 4150, the processor(s) may analyze the current parameter values to determine whether to provide prompt(s) suggesting one or more test types (e.g., a suggestion notice 3129). However, if so at 4128, then the processor(s) may end the current traversal through the term-focused pathway, and at 4160, the processor(s) may present a prompt requesting input indicating whether the current testing regime is to be further edited or stored, as will be explained in greater detail.

Turning to FIG. 17C, at 4130, the processor(s) may begin a traversal through the model-focused pathway by providing one or more initial prompts to guide the operator through providing initial inputs indicating the specification or editing of various model-related parameters that, in turn, specify the model type of the current testing regime. At 4131, the processor(s) may then receive the initial inputs (if any) conveying indications of the specification of the parameter values prompted for at 4130.

At 4132, following the provision of such initial prompts, the processor(s) may also provide one or more subsequent prompts to guide the operator through providing subsequent inputs indicating the specification or editing of various term-related and/or test-related parameters (e.g., factor types, ranges of values and/or levels for factors, linear constraints, number of runs, etc.). At 4133, the processor(s) may then receive the subsequent inputs (if any) conveying indications of the specification of the parameter values prompted for at 4132.

At 4134, the processor(s) may check whether current term-related and/or test-related parameter values create an incompatibility with the current model-related parameter values, including any parameter values received either prior to or during the current traversal through the model-focused pathway. It should be noted that, prior to the current traversal through the model-focused pathway, various parameter values may have been provided during previous traversal(s) through one or more pathways, and/or may have been provided as a result of using default parameter values or parameter values of an existing testing regime as a starting point for generating the current testing regime.

If at 4134, there is an incompatibility with the current model-related parameter values, then at 4135, the processor(s) may present a prompt indicating the incompatibility (e.g., a compatibility notice). Then at 4136, the processor(s) may check whether the incompatibility is at least partially caused by earlier term-related and/or test-related parameter values specified prior to the current traversal of the model-focused pathway. If not at 4136, then the processor(s) may return to receiving input(s) at 4133. However, if so at 4136, then at 4137, the processor(s) may provide an additional prompt (either separately, or as part of the prompt provided at 4135) that conveys the option to delete at least some of such earlier-specified parameter values.

However, if at 4134, there is no such incompatibility, then at 4138, the processor(s) may check whether the input(s) received during the current traversal through the model-focused pathway include an indication of a command from the operator of the system to end this current traversal. If not at 4138, then at 4150, the processor(s) may analyze the current parameter values to determine whether to provide prompt(s) suggesting one or more test types (e.g., a suggestion notice 3139). However, if so at 4138, then the processor(s) may end the current traversal through the model-focused pathway, and at 4160, the processor(s) may present a prompt requesting input indicating whether the current testing regime is to be further edited or stored, as will be explained in greater detail.

Turning to FIG. 17D, at 4140, the processor(s) may begin a traversal through the test-focused pathway by providing one or more initial prompts to guide the operator through providing initial inputs indicating the specification or editing of various test-related parameters (e.g., test type, test category type, etc.) of the current testing regime. At 4141, the processor(s) may then receive the initial inputs (if any) conveying indications of the specification of the parameter values prompted for at 4140.

At 4142, following the provision of such initial prompts, the processor(s) may also provide one or more subsequent prompts to guide the operator through providing subsequent inputs indicating the specification or editing of various term-related and/or model-related parameters (e.g., various factor types, ranges of values and/or levels for factors, what terms are to be included for estimation and/or Bayesian inference, etc.). At 4143, the processor(s) may then receive the subsequent inputs (if any) conveying the indications of the specification of the parameter values prompted for at 4142.

At 4144, the processor(s) may check whether current term-related and/or model-related parameter values create an incompatibility with the current test-related parameter values, including any parameter values received either prior to or during the current traversal through the test-focused pathway. It should be noted that, prior to the current traversal through the test-focused pathway, various parameter values may have been provided during previous traversal(s) through one or more pathways, and/or may have been provided as a result of using default parameter values or parameter values of an existing testing regime as a starting point for generating the current testing regime.

If at 4144, there is an incompatibility with the current test-related parameter values, then at 4145, the processor(s) may present a prompt indicating the incompatibility (e.g., a compatibility notice). Then at 4146, the processor(s) may check whether the incompatibility is at least partially caused by earlier term-related and/or model-related parameter values specified prior to the current traversal of the test-focused pathway. If not at 4146, then the processor(s) may return to receiving input(s) at 4143. However, if so at 4146, then at 4147, the processor(s) may provide an additional prompt (either separately, or as part of the prompt provided at 4145) that conveys the option to delete at least some of such earlier-specified parameter values.

However, if at 4144, there is no such incompatibility, then at 4148, the processor(s) may check whether the input(s) received during the current traversal through the test-focused pathway include an indication of a command from the operator of the system to end this current traversal. If not at 4148, then at 4150, the processor(s) may analyze the current parameter values to determine whether to provide prompt(s) suggesting one or more test types (e.g., a suggestion notice 3149). However, if so at 4148, then the processor(s) may end the current traversal through the test-focused pathway, and at 4160, the processor(s) present a prompt requesting input indicating whether the current testing regime is to be further edited or stored, as will be explained in greater detail.

Turning to FIG. 17E, at 4150, the processor(s) may use the current term-related, model-related and/or test-related parameter values as a trigger and/or a basis for generating a set of test types to suggest. Again, these current parameter values may be include: 1) default parameter values used as a starting point for generating a new testing regime with no connection to any existing testing regime; 2) parameter values copied from an existing testing regime and used as a starting point for generating a new testing regime based on that existing testing regime; and/or 3) parameter values received as input(s) to prompt(s) in one or more traversals through one or more pathways.

At 4151, the processor(s) may remove one or more test types from the set of test types (presuming there were any test types in the set) that have already been suggested during the current traversal of whichever one of the pathways is currently being traversed through.

If at 4152, there are no test types remaining in the set of test types, then at 4158, the processor(s) may return to whichever one of the pathways is currently being traversed through. More specifically, if the current pathway being traversed through is the term-focused pathway, then the processor(s) may return to receiving input(s) at 4123; if the current pathway being traversed through is the model-focused pathway, then the processor(s) may return to receiving input(s) at 4133; and if the current pathway being traversed through is the test-focused pathway, then the processor(s) may return to receiving input(s) at 4143.

However, if at 4152, there is at least one test type remaining in the set of test types, then at 4153, the processor(s) may organize those remaining test type(s) into an order that follows an order of preference for test types. Again, in some embodiments, there may be just a single order of preference for test types. Alternatively, in other embodiments, there may be multiple orders of preference for test types based on one or more particular parameters of the current testing regime that may have been specified, and/or based on what pathway is currently being traversed.

At 4154, the processor(s) may check whether there is a currently specified test type. If not at 4154, then at 4155, the processor(s) may present a prompt (e.g., a suggestion notice) suggesting all of the test types that remain within the set in the order of preference into which they were organized at 4153, before returning to whichever one of the pathways is currently being traversed at 4158.

However, if there is a currently specified test type at 4154, then at 4156, the processor(s) may check whether any of the remaining test types in the set is preferred to a greater degree than that currently selected test type. If not at 4156, then the processor(s) may return to whichever one of the pathways is currently being traversed at 4158. However, if there is at least one test type remaining in the set that is more preferred than the currently selected test type, then at 4157, the processor(s) may present a prompt suggesting all of the test types within the set that are more preferred than the currently selected test type, and may do so in the order of preference into which they were organized at 4153, before returning to whichever one of the pathways is currently being traversed at 4158.

Figure 17F:
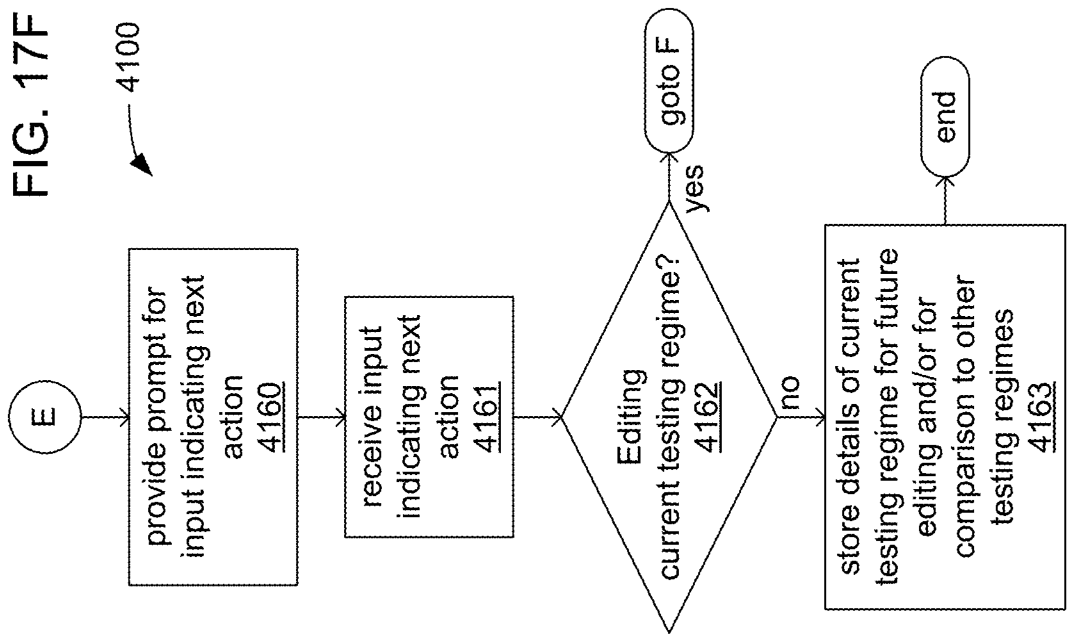

Turning to FIG. 17F, at 4160, the processor(s) may present a prompt requesting input indicating a next course of action. At 4161, the processor(s) may receive the input prompted for at 4160. If at 4162, the next course of action is indicated to be editing the current testing regime for which at least some parameter values have just been specified during a traversal through a pathway, then the processor(s) may return to providing a prompt, at 4110, requesting input indicative of which aspect of the testing regime to specify or edit first. However, if at 4162, the next course of action is not indicated to be editing the current testing regime, then at 4163, the processor(s) may store the details of the current testing regime to enable editing thereof at a later time, and/or to enable the current testing regime to be compared, as a candidate testing regime, to one or more other candidate testing regimes.

FIGS. 18A, 18B, 18C, 18D, 18E, 18F, 18G and 18H, together, illustrate an example embodiment of a logic flow 4200. The logic flow 4200 may be representative of some or all of the operations executed by one or more embodiments described herein. More specifically, the logic flow 4200 may illustrate operations performed by the processor(s) 2550, and/or other component(s) of the coordinating device 2500, in executing the generation routine 2510 to guide the generation of a testing regime.

Turning to FIG. 18A, at 4210, processor(s) of a coordinating device of a distributed processing system (e.g., the processor(s) 2550 of the coordinating device 2500 of the distributed processing system 2000) may visually present a prompt (e.g., a visual prompt, such as a menu, via presentation of the generation GUI 3100 on the display 2580 or 2780) to an operator of the distributed processing system to provide a input indicating what aspect of a testing regime is to be specified or edited first. At 4211, the processor(s) may receive input (e.g., manual input via the input device 2520 or 2720 associated with the generation GUI 3100) indicating that aspect.

As previously discussed, the selection of which aspect of a testing regime to specify or edit first may be implemented as a selection of which pathway of prompts (of multiple path ways of prompts) to traverse through in specifying parameters of a testing regime. Again, by providing such multiple pathways, an operator of the system is provided an opportunity to choose to start with the parameters associated with the testing regime aspect that they feel most certain about, before moving on to the parameters associated with other testing regime aspects that they feel less certain about. Further, the parameters values specified for the aspect that is chosen to start with become the basis for guiding the operator through specifying the other parameter values associated with the other aspects that the operator may feel less certain about.

Still more specifically, three pathways may be provided for the operator to choose to traverse through as part of specifying parameter values of a testing regime: 1) a term-focused pathway starting with initial prompts for term-related parameters followed by subsequent prompts for model-related and/or test-related parameters; 2) a model-focused pathway starting with initial prompts for model-related parameters followed by subsequent prompts for term-related and/or test-related parameters; and 3) a test-focused pathway starting with initial prompts for test-related parameters followed by subsequent prompts for term-related and/or model-related parameters.

At 4212, the processor(s) may check whether the received input indicates a choice to traverse through a term-focused pathway in which term-related parameters of the testing regime (i.e., parameters concerning the factors and/or the higher order terms) are to be specified or edited first.

If at 4212, the received input indicates such a selection of the term-focused pathway, then at 4213, the processor(s) may begin a traversal through the term-focused pathway by presenting one or more initial prompts to guide the operator through providing initial input(s) indicating the specification of parameter values for various term-related parameters (e.g., factor types, ranges of values and/or levels for factors, linear constraints, etc.). Also at 4213, and following the provision of such initial prompts, the processor(s) may also provide one or more subsequent prompts to guide the operator through providing subsequent inputs indicating the specification of parameter values for various model-related and/or test-related parameters (e.g., what terms are to be included for estimation and/or Bayesian inference, number of runs, etc.). At 4214, the processor(s) may then receive the inputs (if any) conveying indications of the specification of the parameter values prompted for at 4213.

However, if at 4212, the received input does not indicate such a selection of the term-focused pathway, then at 4215, the processor(s) may check whether the received input indicates a choice to traverse through a test-focused pathway in which the test-related parameters of the testing regime are to be specified or edited first.

If at 4215, the received input indicates such a selection of the test-focused pathway, then the processor(s) may begin a traversal through the test-focused pathway at 4140 by providing the initial prompt(s) thereof, as will be described in greater detail.

However, if at 4215, the received input indicates a selection of a model-focused pathway in which model-related parameters of the testing regime are to be specified or edited first, then the processor(s) may begin a traversal through the model-focused pathway at 4130 by providing the initial prompt(s) thereof, as will be described in greater detail.

Figure 18C:
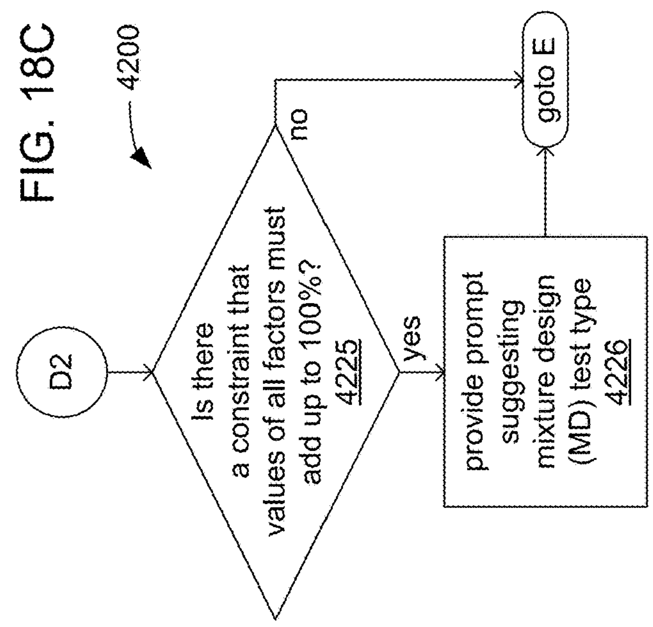
Figure 18B:
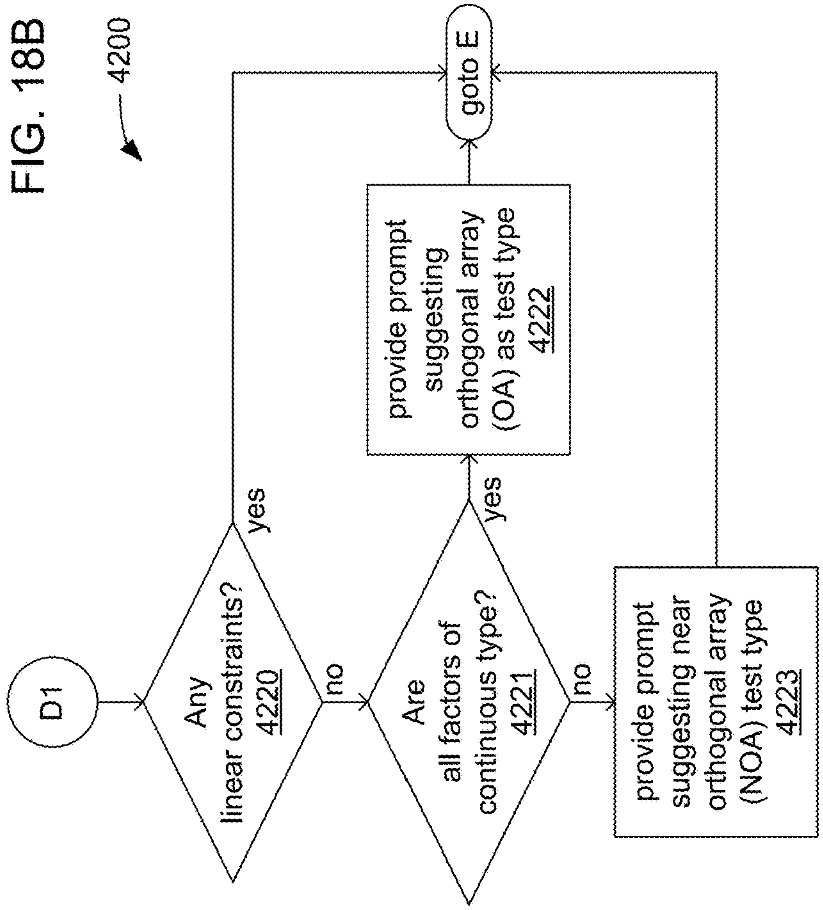

Turning to FIG. 18B, at 4220, the processor(s) may check whether the current parameter values of the current testing regime include the specification of any linear constraints.

If at 4220, one or more linear constraints have been specified among the current parameter values, then at 4250, the processor(s) may check whether the current parameter values include the specification of a particular test type, as will be explained in greater detail.

However, if at 4220, no linear constraints have been specified among the current parameter values, then at 4221, the processor(s) may check whether the current parameter values include a specification that all factors are of the continuous factor type (as opposed to at least a subset of the factors being specified as being of the categorical factor type and/or of the discrete factor type).

If at 4221, all of the factors are specified in the current parameter values to be of the continuous factor type, then at 4222, the processor(s) may present a prompt (e.g., a suggestion notice) suggesting the orthogonal array (OA) test type, before proceeding to checking for the specification of a particular test type at 4250.

However, if at 4221, one or more of the factors are specified in the current parameter values to not be of the continuous factor type, then at 4223, the processor(s) may present a prompt (e.g., a suggestion notice) suggesting the near orthogonal array (NOA) test type, before proceeding to checking for the specification of a particular test type at 4250.

Turning to FIG. 18C, at 4225, the processor(s) may check whether the current parameter values of the current testing regime include a specification of a constraint that the values of all of the factors must add up to 100%.

If at 4225, such a constraint has been specified among the current parameter values, then at 4250, the processor(s) may check whether the current parameter values include the specification of a particular test type.

However, if at 4225, no such constraint has been specified among the current parameter values, then at 4226, the processor(s) may present a prompt suggesting the mixture design (MD) test type (e.g., a suggestion notice0, before proceeding to checking for the specification of a particular test type at 4250.

Figure 18D:
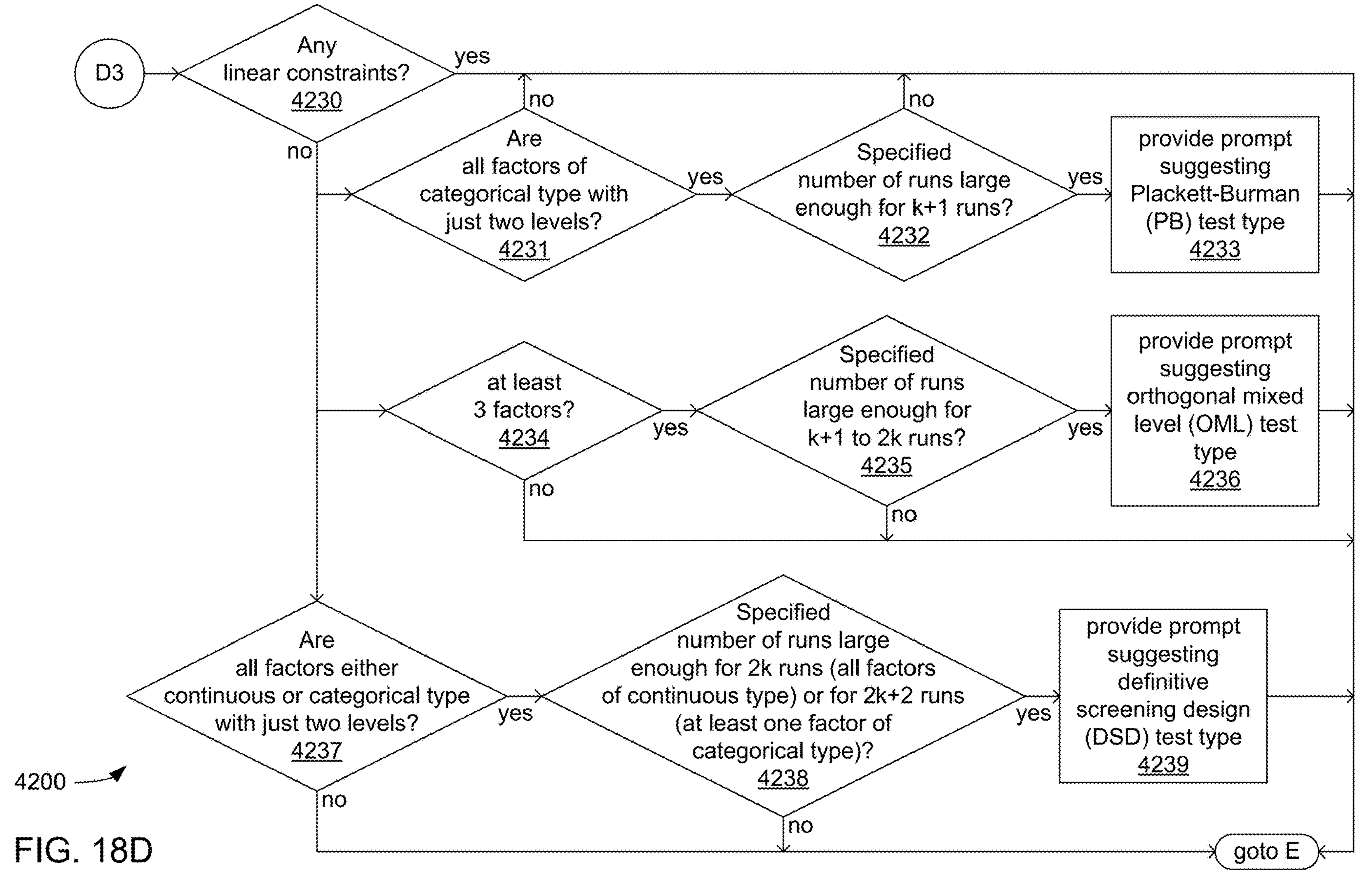

Turning to FIG. 18D, at 4230, the processor(s) may check whether the current parameter values of the current testing regime include the specification of any linear constraints.

If at 4230, one or more linear constraints have been specified among the current parameter values, then at 4250, the processor(s) may check whether the current parameter values include the specification of a particular test type, as will be explained in greater detail.

However, if at 4230, no linear constraints have been specified among the current parameter values, then, starting at 4231, 4234 and 4237, the processor(s) may perform further checks to determine whether to present prompt(s) (e.g., suggestion notices) suggesting one or more test types. Further, it may be that two or more of these further checks are performed at least partially in parallel.

Starting at 4231, the processor(s) may check whether the current parameter values include a specification that all of the factors are of the categorical factor type with just two levels of values. If not at 4231, then at 4250, the processor(s) may check whether the current parameter values include the specification of a particular test type.

However, if so at 4231, then at 4232, the processor(s) may check whether the current parameter values include the specification of a number of runs that is large enough to allow for k+1 runs, where k is the number of factors. If not at 4232, then at 4250, the processor(s) may check whether the current parameter values include the specification of a particular test type.

However, if so at 4232, then at 4233, the processor(s) may present a prompt suggesting the Plackett-Burman (PB) test type, before proceeding to checking for the specification of a particular test type at 4250.

Starting at 4234, the processor(s) may check whether the current parameter values include specification(s) to the effect that there are at least three factors (e.g., specifications of parameter values for at least three factors and/or an explicit specification of a quantity of factors of at least three). If not at 4234, then at 4250, the processor(s) may check whether the current parameter values include the specification of a particular test type.

However, if so at 4234, then at 4235, the processor(s) may check whether the current parameter values include the specification of a number of runs that is large enough to allow for a number of runs in a range from k+1 runs to 2k runs, where k is the number of factors. If not at 4235, then at 4250, the processor(s) may check whether the current parameter values include the specification of a particular test type.

However, if so at 4235, then at 4236, the processor(s) may present a prompt suggesting the orthogonal mixed level (OML) test type, before proceeding to checking for the specification of a particular test type at 4250.

Starting at 4237, the processor(s) may check whether the current parameter values include a specification that all of the factors are either of the continuous factor type or of the categorical factor type with just two levels of values. If not at 4237, then at 4250, the processor(s) may check whether the current parameter values include the specification of a particular test type.

However, if so at 4237, then at 4238, the processor(s) may check whether the current parameter values include specifications of a number of runs that is large enough to allow for either: 2k runs, where k is the number of factors and all of the factors are of the continuous factor type; or s2k+2 runs, where k is the number of factors and at least one factor is of the categorical factor type with values of just two levels. If not at 4238, then at 4250, the processor(s) may check whether the current parameter values include the specification of a particular test type.

However, if so at 4238, then at 4239, the processor(s) may present a prompt suggesting the definitive screen design (DSD) test type, before proceeding to checking for the specification of a particular test type at 4250.

Turning to FIG. 18E, at 4240, the processor(s) may check whether the current parameter values of the current testing regime include a specification that all factors and second order terms are included in estimations.

If at 4240, it is specified in the current parameter values that less than all factors and second order terms are included in estimations, then at 4250, the processor(s) may check whether the current parameter values include the specification of a particular test type.

However, if at 4240, it is specified in the current parameter values that all factors and second order terms are included in estimations, then at 4241, the processor(s) may check whether the current parameter values include a specification that all of the factors are of the continuous factor type (as opposed to at least a subset of the factors being specified as being of the categorical factor type and/or of the discrete factor type).

If at 4241, less than all factors are specified to be of the continuous factor type in the current parameter values, then at 4250, the processor(s) may check whether a particular test type is specified in the current parameter values.

However, if at 4241, all of the factors are so specified to be of the continuous factor type, then at 4242, the processor(s) may derive one or more variants of the central composite design (CCD) test type requiring a number of runs that (if possible) fit within the number of runs specified in the current parameter values for the current testing regime, and/or one or more variants of the Box-Behnken (BB) test type requiring a number of runs that (if possible) fit within the specified number of runs. At 4243, the processor(s) may check whether there are any variants of CCD and/or BB requiring a number of runs that fit within that specified number of runs.

If at 4243, there are no variants of either CCD or BB requiring a number of runs that fit within the specified number of runs, then at 4250, the processor(s) may check whether a particular test type has been specified in the current parameter values.

However, if at 4243, there are one or more variants of CCD and/or BB requiring a number of runs that fit within the specified number of runs, then at 4244, the processor(s) may present a prompt suggesting those variant(s) of CCD and/or BB, before proceeding to checking for the specification of a particular test type at 4250.

Figure 18F:
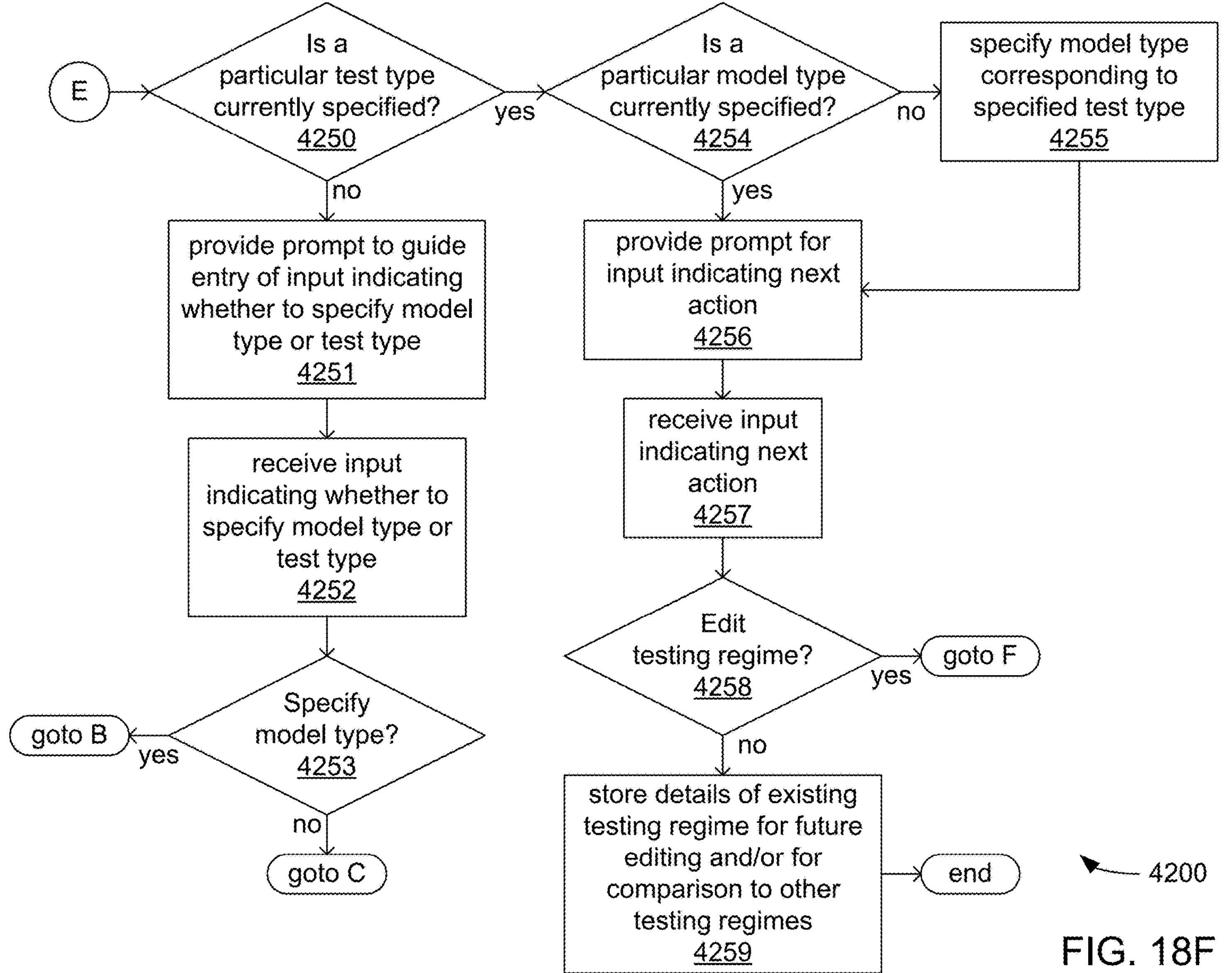

Turning to FIG. 18F, as discussed just above, it may be that two or more portions of the logic flow 4200 that begin at 4220, 4225, 4230 and 4240 may be performed at least partially in parallel. Further, as also discussed just above, it may be that two or more smaller portions of the logic flow 4200 that begin at 4231, 4234 and 4237 may also be performed at least partially in parallel. Regardless of whether there is such parallelism in the performances of these various portions of the logic flow 4200, following the completion of performance of all of these various portions of the logic flow 4200, the aforementioned check of whether a particular test type has been specified in the current parameter values for the current testing regime may then be performed at 4250.

If at 4250, no particular test type is specified in the current parameter values for the current testing regime, then at 4251, the processor(s) may present a prompt to guide the operator through providing input indicating whether the operator wishes to specify a model type or a test type. At 4252, the processor(s) may then receive the input prompted for at 4251, and at 4253, the processor(s) may check whether that input is indicative of a choice to specify a model type. If at 4253, the input indicates such a choice to specify a model type, then starting at 4260, the processor(s) may present one or more prompts to guide the operator through providing inputs indicative of specifying a model type and/or input other model-related parameters. However, if at 4253, the input is not indicative of a choice to specify a model type, then starting at 4280, the processor(s) may present one or more prompts to guide the operator through providing inputs indicative of specifying at least a category of test types, if not a particular test type.

However, if at 4250, a particular test type is specified in the current parameter values for the current testing regime, then at 4254, the processor(s) may check whether a corresponding particular model type is also specified in the current parameter values. If so at 4254, then at 4256, the processor(s) may present a prompt requesting input indicating a next course of action. If not at 4254, then at 4255, the processor(s) may automatically specify a particular model type that corresponds to the particular test type specified in the current parameters before presenting the prompt at 4256. At 4257, the processor may receive the input prompted for at 4256. If at 4258, the input indicates that the next course of action is to edit the current testing regime, then at 4210, the processor may return to presenting a prompt requesting input indicative of which aspect of the testing regime to specify or edit first. However, if at 4258, the input indicates that the next course of action is not to edit the current testing regime, then at 4259, the processor(s) may store the parameter values of the current testing regime to enable editing thereof at a later time, and/or to enable the current testing regime to be compared as a candidate testing regime to one or more other candidate testing regimes.

Figure 18G:
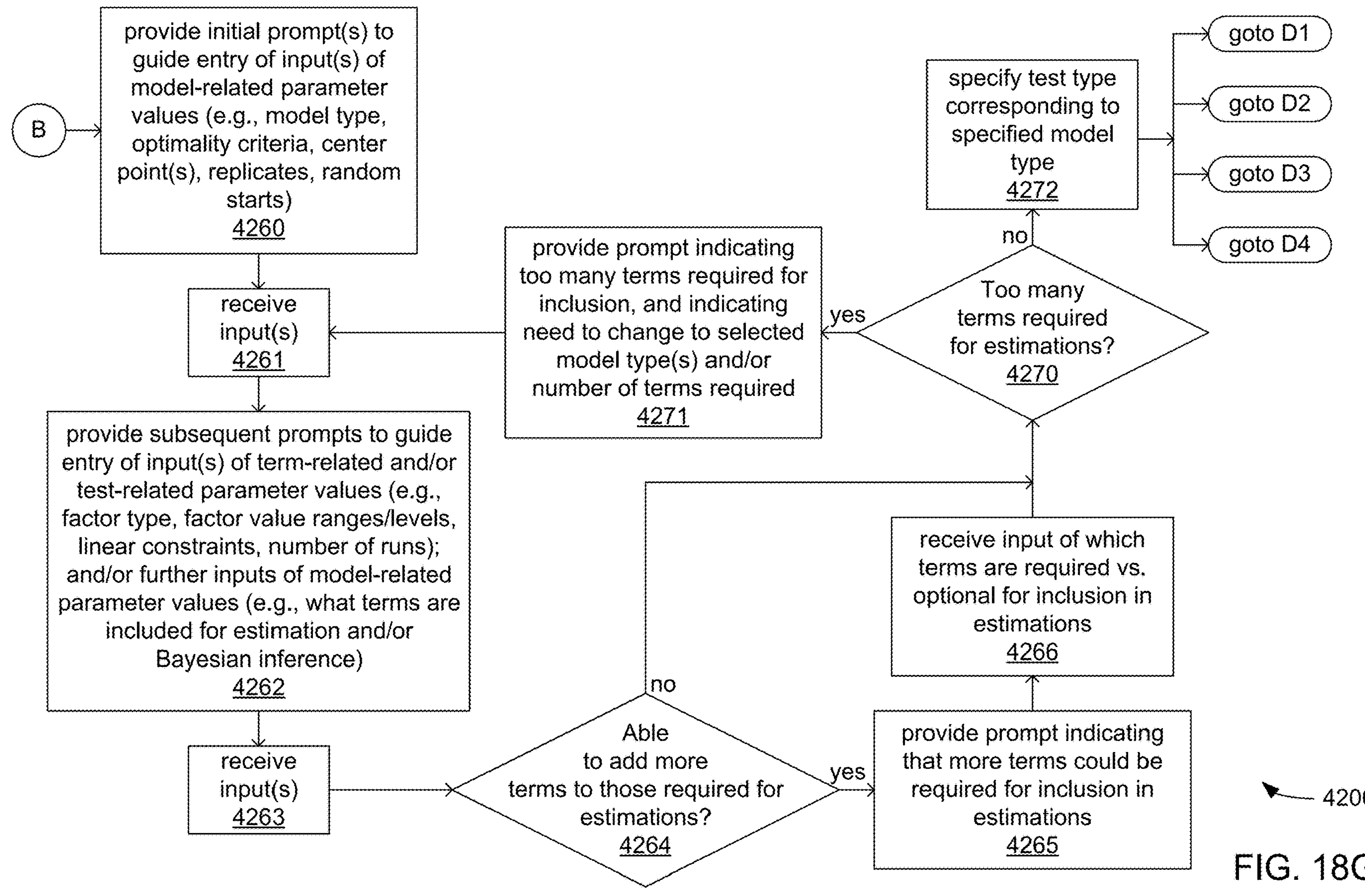

Turning to FIG. 18G, at 4260, the processor(s) may begin a traversal through the model-focused pathway by presenting one or more initial prompts to guide the operator through providing initial input(s) indicating the specification of various model-related parameters that specify a model type (e.g., whether to include factors, whether to include second order terms, optimality criteria, center point(s), replicates, random starts, and/or an explicit specification of a particular model type). At 4261, the processor(s) may receive the initial inputs (if any) conveying indications of the specification of the parameter values prompted for at 4260.

At 4262, the processor(s) may continue the traversal through the model-focused pathway by presenting one or more subsequent prompts to guide the operator through providing subsequent input(s) indicating the specification of various term-related parameters (e.g., factor types, ranges of values for factors and/or value levels for factors, constraints on term values, etc.); and/or by presenting one or more subsequent prompts to guide the operator through providing subsequent input(s) indicating the specification of further model-related parameters and/or various test-related parameters (e.g., what terms are to be included for estimation and/or Bayesian inference, number of runs, etc.). Again, it should be noted that what particular prompts are presented and/or what options are offered for specifying parameters within those prompts may be limited and/or otherwise based on what particular model type is currently specified. At 4263, the processor(s) may then receive the subsequent inputs (if any) conveying indications of the specification of the parameter values prompted for at 4262.

At 4264, the processor may check whether, in view the current parameter values, whether it is possible to add more of the terms to the those already specified as required for inclusion in estimations. If so at 4264, then at 4265, the processor may present a prompt indicating that more terms could be specified as being required for inclusion for estimations. At 4266, the processor may receive input(s) conveying indications of the specification of one more terms as being so required, as prompted for at 4265.

At 4270, the processor may check, again in view of the current parameter values, whether too many terms have been specified as being required for inclusion for estimations. If so at 4270, then at 4271, the processor may present a prompt (e.g., a compatibility notice) indicating that too many terms have been specified as being so required, and that either the number of terms currently specified as being so required must be reduced, or the currently specified model must be changed.

However, if there aren't too many terms that are specified as being so required at 4270, then at 4272, the processor(s) may specify a test type that corresponds to the currently specified model type. Then, starting at 4220, 4225, 4230 and 4240, the processor(s) may perform various checks to determine whether to provide suggestion(s) of one or more testing types to the operator as alternative(s) to the now currently specified test type.

Turning to FIG. 18H, at 4280, the processor(s) may begin a traversal through the test-focused pathway by presenting one or more prompts to guide the operator through providing initial input(s) indicating the specification of a test type or of a test category type. At 4281, the processor(s) may receive the initial inputs (if any) conveying indication of the specification of the parameter values prompted for at 4280.

At 4282, the processor(s) may continue the traversal through the test-focused pathway by presenting one or more subsequent prompts to guide the operator through providing subsequent input(s) indicating the specification of various term-related parameters (e.g., factor types, ranges of values for factors and/or value levels for factors, constraints on term values, etc.); and/or by presenting one or more subsequent prompts to guide the operator through providing subsequent input(s) indicating the specification of various model-related and/or further test-related parameters (e.g., what terms are to be included for estimation and/or Bayesian inference, number of runs, etc.). Again, it should be noted that what particular prompts are presented and/or what options are offered for specifying parameters within those prompts may be limited and/or otherwise based on what test type or what test category type is currently specified. At 4283, the processor(s) may then receive the subsequent inputs (if any) conveying indications of the specification of the parameter values prompted for at 4282.

At 4284, the processor(s) may check whether current term-related and/or model-related parameter values create an incompatibility with the current test-related parameter values (e.g., the currently specified particular test type or the currently specified test category type). If so at 4284, then at 4285, the processor(s) may present a prompt indicating the incompatibility, and suggesting a change be made either what test type or test category type is currently specified, or to incompatible parameter values for one or more other parameters.

However, if there is no such compatibility at 4284, then at 4290, the processor(s) may check whether a particular test type is currently specified (as opposed to the specification of category of test types). If not at 4290, then at 4291, the processor may present a prompt to encourage the specification of a particular test type (although the prompt may also indicate that a change to the test category type could be made in the alternative).

However, if a particular test type is currently specified at 4290, then at 4292, the processor(s) may specify a model type that corresponds to the currently specified test type. Then, starting at 4220, 4225, 4230 and 4240, the processor(s) may perform various checks to determine whether to provide suggestion(s) of one or more testing types to the operator as alternative(s) to the current test type.

FIGS. 19A and 19B, together, illustrate an example embodiment of a logic flow 5100. The logic flow 5100 may be representative of some or all of the operations executed by one or more embodiments described herein. More specifically, the logic flow 5100 may illustrate operations performed by the processor 2550 and/or the one or more processors 2350, and/or performed by other component(s) of each of the coordinating device 2500 and/or the multiple node devices 2300, respectively, in executing corresponding ones of the comparison routine 2540, the regression routine 2570 and/or the regression routine 2370 to guide selection of, and the performance of a regression analysis with, a single testing regime for use.

At 5110, a processor of a coordinating device of a distributed processing system (e.g., the processor 2550 of the coordinating device 2500 of the distributed processing system 2000) may receive indications of selections of two or more candidate testing regimes to be compared. As previously discussed, the processor 2550 may present the GUI portion 3410 (see FIG. 12A) to guide an operator of the coordinating device 2500 (either directly or remotely through another device, such as the viewing device 2700) to provide input indicating such selections.

At 5112, the processor of the coordinating device may employ various characteristics of the factors, terms and/or responses of each of the models associated with one of the candidate testing regimes to identify and present matches thereamong. At 5114, the processor may receive indications from the operator of corrections to one or more of such automatically identified matches. If any such indications are received, the processor may effect such corrections by changing one or more matches so indicated as being in error. As previously discussed, in addition to effecting such corrections, the processor may also be caused to store indications of such corrections by storing indications of learned matches for future use.

At 5120, the processor of the coordinating device may receive indications of selections of terms that are to be included in the set of terms to be used in the comparisons among the candidate testing regimes. At 5122, the processor may be caused to present an indication that the set of terms is not able to be supported by one or more of the candidate testing regimes such that one or more of the terms within the set needs to be removed so that the set is able to be supported. At 5124, where such an indication was presented by the processor, the processor may receive indications of an alternate selection of one or more terms for inclusion in the set of terms for comparison. As previously discussed, the processor 2550 may present the GUI portion 3410 to guide the operator to provide input indicating such selections, including generating and visually presenting the notice 3416 (see FIG. 12A) to the effect that the set of terms current selected is not supportable.

At 5130, the processor of the coordinating device may receive indications of an adjustment to the signal-to-noise ratio(s) to which one or more of the terms may be subject. At 5132, the processor may derive the statistical power of each term and for each of the candidate testing regimes. The processor may then generate a graph, for each term, that plots the statistical power of that term across all of the candidate testing regimes. The processor may further visually present all of the graphs (one per term) adjacent to each other in a manner that may form a horizontally extending row of the graphs (i.e., side-by-side) to exploit the innate left-right feature comparison capabilities of the HVS. As previously discussed, for each such graph of the set of graphs 3434 of statistical power vs. candidate testing regime in GUI portion 3400 (see FIG. 12C), the processor 2550 may be further caused to fit a curve to the plotted points of statistical power vs. candidate testing regime.

At 5140, the processor of the coordinating device may derive the prediction variance of each term and for each of the candidate testing regimes. The processor may then generate a graph, for each term and for each candidate testing regime, that plots the prediction variance, and present those graphs in adjacent to each other in multiple horizontal rows where each row corresponds to one of the candidate testing regimes. At 5142, the processor may receive indications from the operator of a change to the default horizontal positioning within the design space of a vertical line. At 5144, if such an indication is received, the processor may effect such corrections by regenerating all of the graphs to reflect the new horizontal positioning.

At 5150, the processor of the coordinating device may derive and present a combined graph that overlays the fraction of design space for all of the candidate testing regimes. At 5152, the processor may derive the degree of correlation between each possible pair of terms that may be formed from the set of terms selected for use in the comparisons of the candidate testing regimes. The processor may then generate and visually present a correlation graph, one each per candidate testing regime, where all of the terms are arranged in identical order along each of the horizontal and vertical axes, and in which visual indicators are positioned at each intersection within the graph that corresponds to one of the possible pairs of terms. The processor may further present the correlation graphs adjacent to each other and arranged horizontally in a single row (e.g., side-by-side) to exploit the left-right feature comparison capabilities of the HVS. As previously discussed, the visual indicators used may be selected from a scale of visual indicators that may form a scale of progressive transition from one color to another, a progressive transition between light and dark on a grayscale, etc., that may be presented as part of the GUI portion 3460 (see FIG. 12F).

At 5160, the processor of the coordinating device may receive an indication of a selection of a testing regime that may be from among the multiple candidate testing regimes, for regression analysis. At 5161, the processor may receive an indication of a change to default coefficient(s) for one or more of the terms of the model associated with the selected testing regime. At 5163, the processor may receive an indication of a selection of a type of distribution for the random generation of simulated data. At 5164, the processor may receive an indication of a quantity of iterations of the regression analysis to be performed. As previously discussed, the processor 2550 may be caused to present GUI portion 3710 to guide an operator through providing such parameters (see FIG. 14A).

At 5166, the processor of the coordinating device may receive an indication of there being a higher degree of difficulty in varying one or more particular factors than for the other factors. At 5167, the processor may receive an indication of the one or more particular factors having a higher degree of difficulty in being varied also being subject to a different degree of error. As previously discussed, the processor 2550 may be caused to present GUI portion 3730 to guide an operator through providing such parameters (see FIG. 14C). As also previously discussed, following receipt of an indication of there being a different degree of difficulty in varying one or more particular factors, the processor 2550 may be caused to present additional prompts to additionally guide an operator through providing separate additional parameters for whole plots and/or subplots, such as the additional entry boxes 3716 by which separate degrees of error may be provided for whole plots and/or subplots.

At 5170, based on the parameters provided by the operator and/or from any unchanged default parameters, the processor of the coordinating device may be caused to generate a sequence of executable instructions (e.g., the executable instructions 2534) in a pre-selected programming language for performing the regression analysis. At 5172, the processor may also be caused to generate and visually present a human readable form of a portion of the executable instructions that employs the mathematical syntax of a formula to expresses the performance of the regression analysis (e.g., the human readable expression 3722, examples of which are depicted in FIGS. 14B and 14E). As previously discussed, such a human readable expression may include the values of the coefficients and/or any intercept, may specify the selected type of distribution to be achieved in the random generation of simulated data, and/or may specify the quantity of iterations of the regression analysis to be performed.

At 5180, the processor of the coordinating device may check whether any indication has been received of operation of an input device to make changes to one or more of the earlier provided parameters. If so, then the processor may return to receiving and/or acting on the provision of revised versions of various parameters at 5161 through 5167.

However, if at 5180, there are no such indications of changes to parameters, then at 5190, the processor of the coordinating device may proceed with either directly executing the executable instructions to perform the specified quantity of iterations of the regression analysis, or may coordinate the distribution and performance of the iterations of the regression analysis by multiple other processors and/or processor cores (e.g., the one or more processors 2350 and/or processor cores 2355). As previously discussed, such other processors and/or processor cores may be incorporated into multiple node devices with which the coordinating device may communicate via a network (e.g., the multiple node devices 2300 via the network 2999). Alternatively, and as also previously discussed, such other processor(s) and/or processor cores may be incorporated into the coordinating device (e.g., as one or more GPUs).

Upon completion of the specified quantity of iterations of the regression analysis, the processor of the coordinating device may visually present the results thereof at 5192.

FIG. 20 illustrates an example embodiment of a logic flow 5200. The logic flow 5200 may be representative of some or all of the operations executed by one or more embodiments described herein. More specifically, the logic flow 5200 may illustrate operations performed by the processor 2550, and/or performed by other component(s) of the coordinating device 2500 in executing the comparison routine 2540 to guide selection of a single testing regime for use.

At 5210, a processor of a coordinating device of a distributed processing system (e.g., the processor 2550 of the coordinating device 2500 of the distributed processing system 2000) may receive indications of selections of two or more candidate testing regimes to be compared. Again, as previously discussed, the processor 2550 may present the GUI portion 3410 (see FIG. 12A) to guide an operator of the coordinating device 2500 to provide input indicating such selections.

At 5220, the processor of the coordinating device may employ various characteristics of the factors of each of the models associated with one of the candidate testing regimes to identify matches thereamong. Among the characteristics that the processor may be caused to use, at least initially, may include, and are not limited to, type of factor (e.g., continuous or categorical), quantities of levels and/or values of the levels for each categorical factor (if any), ranges of values (e.g., the minimum and maximum values of the range of values) for each continuous factor (if any). Where there remain factors yet to be matched, or where there is otherwise remaining uncertainty in the identification of matches between factors, the processor may also employ the texts and/or the meanings of the texts of the identifiers given to each factor. As has been discussed, the processor may employ vocabulary data that may include a thesaurus (e.g., the vocabulary data 2536) in such text-based identification of matches.

At 5222, the processor of the coordinating device may employ various characteristics of the terms of the models associated with one of the candidate testing regimes to identify matches thereamong, including and not limited to, the order of each term (e.g., first order, second order, third order, etc.). Where there remain terms yet to be matched, or where there is otherwise remaining uncertainty in the identification of matches between terms, the processor may also employ the texts and/or the meanings of the texts of the identifiers given to each term.

At 5224, the processor of the coordinating device may employ at least the texts and/or the meanings of the texts of the identifiers given to each response to identify matches thereamong.

At 5230, the processor of the coordinating device may present the matches identified by the processor among factors, terms and/or responses. As previously discussed, the processor 2550 may present such matches through the presentation of the GUI portion 3420 (see FIG. 12B) as part of guiding an operator of the coordinating device 2500 (either directly or remotely through another device, such as the viewing device 2700) to provide input indicating such selections. At 5232, the processor of the coordinating device may monitor one or more input devices for indications of entry of input conveying one or more corrections to the matches identified by the processor at 5220-5224.

At 5234, if such input is received, then the processor of the coordinating device may store an indication of the correction along with and/or as part of the thesaurus. The processor may then repeat some or all of the work of identifying matches at 5220-5224.

Figure 21:
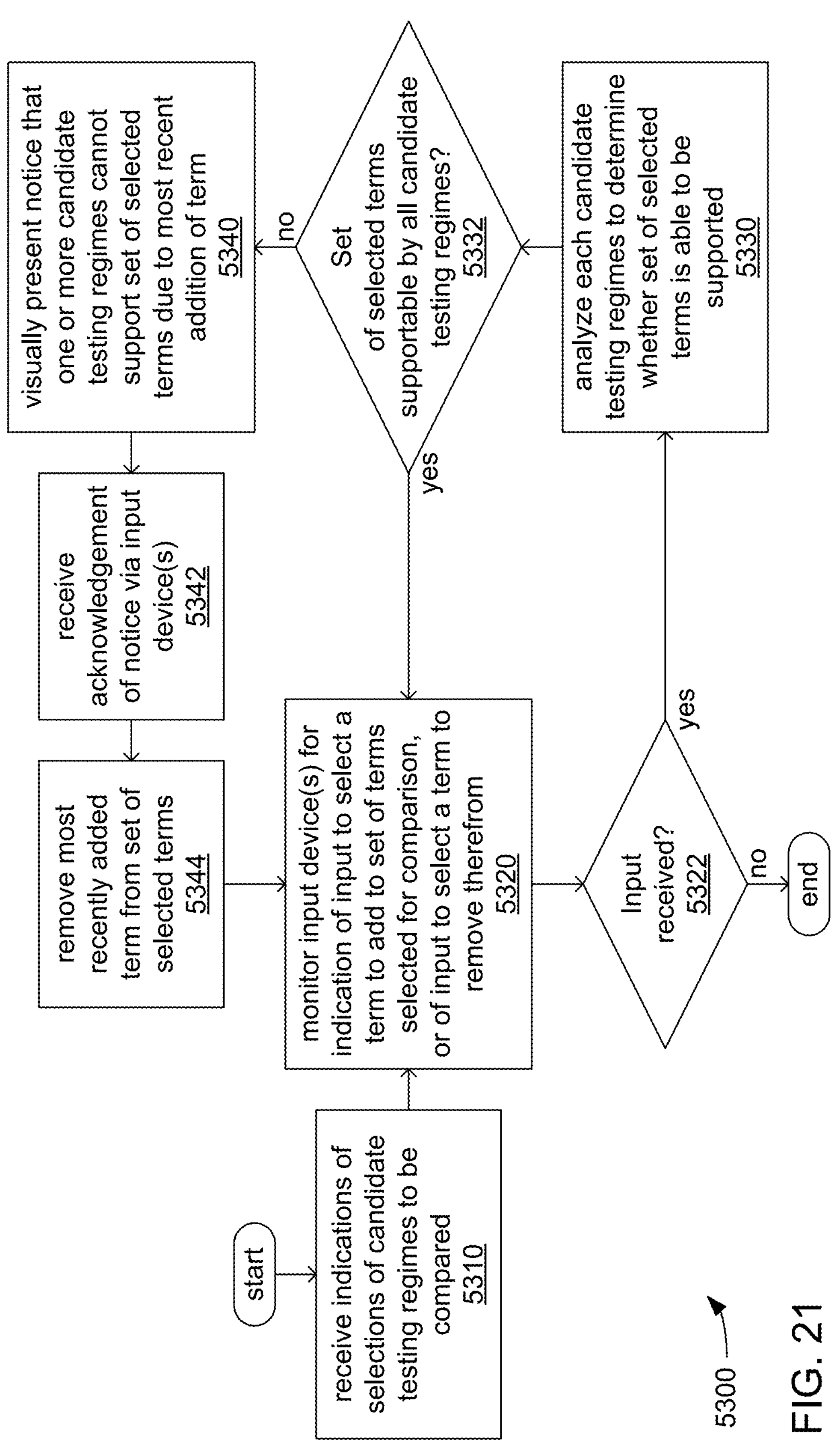
FIG. 21 illustrates an example embodiment of a logic flow of guiding selection of terms in the guidance of selection of a testing regime.

FIG. 21 illustrates an example embodiment of a logic flow 5300. The logic flow 5300 may be representative of some or all of the operations executed by one or more embodiments described herein. More specifically, the logic flow 5300 may illustrate operations performed by the processor 2550, and/or performed by other component(s) of the coordinating device 2500 in executing the comparison routine 2540 to guide selection of a selected testing regime for use.

At 5310, a processor of a coordinating device of a distributed processing system (e.g., the processor 2550 of the coordinating device 2500 of the distributed processing system 2000) may receive indications of selections of two or more candidate testing regimes to be compared. Again, as previously discussed, the processor 2550 may present the GUI portion 3410 (see FIG. 12A) to guide an operator of the coordinating device 2500 to provide input indicating such selections.

At 5320, the processor of the coordinating device may monitor one or more input devices for indications of entry of input indicative of a selection of a term to add to the set of terms to be included in the comparison.

At 5322, if such input is received, then at 5330, the processor of the coordinating device may analyze each of the candidate testing regimes to determine whether one or more of them are unable to support the set of terms selected for inclusion in the comparison following the addition of the just selected term to the set. If, at 5332, the resulting set of terms is supportable by all of the candidate testing regimes, then the processor may return to monitoring one or more input devices at 5320.

However, if at 5332, the set of terms selected for inclusion in the comparison is not supportable by all of the candidate testing regimes, then at 5340, the processor may be caused to present a notice that the set of terms is not able to be supported by one or more of the candidate testing regimes. At 5342, the processor may receive an indication of reception of input indicating an acknowledgement of the notice. In response, the processor may remove the term most recently selected for addition to the set at 5344, and return to monitoring one or more input devices at 5320.

FIG. 22 illustrates an example embodiment of a logic flow 5400. The logic flow 5400 may be representative of some or all of the operations executed by one or more embodiments described herein. More specifically, the logic flow 5400 may illustrate operations performed by the processor 2550, and/or performed by other component(s) of the coordinating device 2500 in executing the comparison routine 2540 to guide selection of a single testing regime for use.

At 5410, a processor of a coordinating device of a distributed processing system (e.g., the processor 2550 of the coordinating device 2500 of the distributed processing system 2000) may derive a statistical power for each term in a set of terms to be included in a comparison of multiple candidate testing regimes, and separately for each one of the candidate testing regimes. At 5412, the processor may then generate, for each term of the set of terms, a graph that plots the statistical power of that term across all of the candidate testing regimes. At 5414, within each of the graphs, the processor may then fit a curve to the plots of the corresponding term for all of the candidate testing regimes. At 5416, the processor may visually present all of the graphs (again, each one corresponding to one of the terms of the set) adjacent to each other in a manner that may form a horizontally extending row of the graphs (i.e., side-by-side) to exploit the innate left-right feature comparison capabilities of the HVS.

At 5420, the processor of the coordinating device may monitor one or more input devices for indications of entry of input indicative of a change to a degree of error for a term in the set of terms. If, at 5422, such input is received, then at 5430, the processor may generate, for each term of the set of terms, a new graph that plots the statistical power of that term across all of the candidate testing regimes. At 5432, within each of the new graphs, the processor may then fit a new curve to the new plots of the corresponding term for all of the candidate testing regimes.

Figure 23:
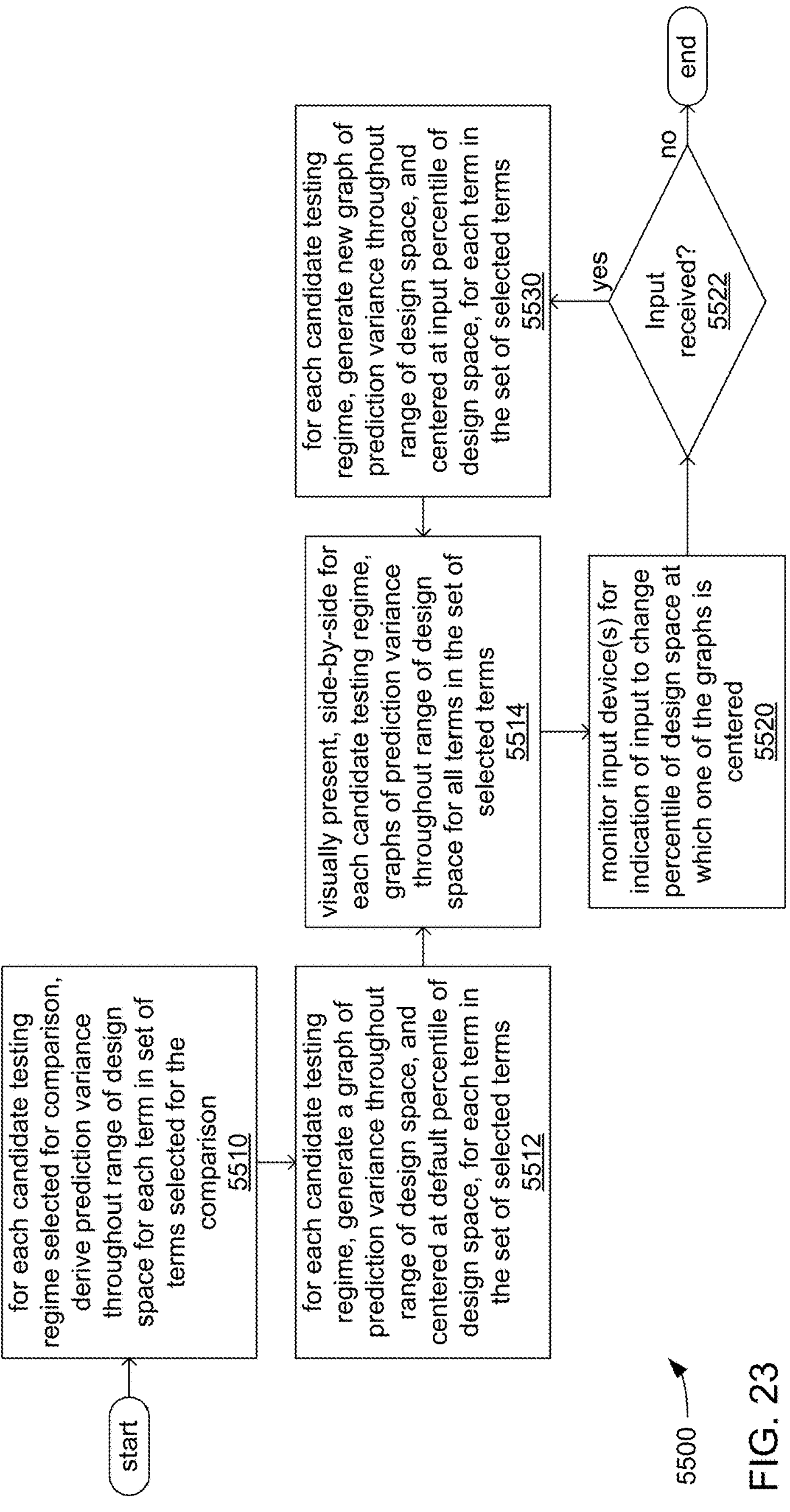
FIG. 23 illustrates an example embodiment of a logic flow of deriving and presenting prediction variance in the guidance of selection of a testing regime.

FIG. 23 illustrates an example embodiment of a logic flow 5500. The logic flow 5500 may be representative of some or all of the operations executed by one or more embodiments described herein. More specifically, the logic flow 5500 may illustrate operations performed by the processor 2550, and/or performed by other component(s) of the coordinating device 2500 in executing the comparison routine 2540 to guide selection of a single testing regime for use.

At 5510, a processor of a coordinating device of a distributed processing system (e.g., the processor 2550 of the coordinating device 2500 of the distributed processing system 2000) may derive a prediction variance for each term in a set of terms to be included in a comparison of multiple candidate testing regimes, and separately for each one of the candidate testing regimes. At 5512, the processor may then generate, for each term and for each candidate testing regime, a graph of the prediction variance throughout the range of design space, and centered at a default percentile of the design space that may be marked by a vertical line positioned along the horizontal axis. At 5514, the processor may present those graphs in adjacent to each other in multiple horizontal rows where each row corresponds to one of the candidate testing regimes.

At 5520, the processor of the coordinating device may monitor one or more input devices for indications of entry of input indicative of a change in the percentile of the design space at which the graph is centered. As previously discussed, such an indication may be as a result of use of a pointing device to horizontally change the position of the vertical line along the horizontal axis. If, at 5522, such input is received, then at 5530, the processor may generate, for each term and for each candidate testing regime, a new graph of the prediction variance throughout the range of design space, and centered at a new percentile of the design space that may be marked by the vertical line at a new position along the horizontal axis. At 5514, the processor may present the new graphs in adjacent to each other in multiple horizontal rows where each row corresponds to one of the candidate testing regimes.

Figure 24:
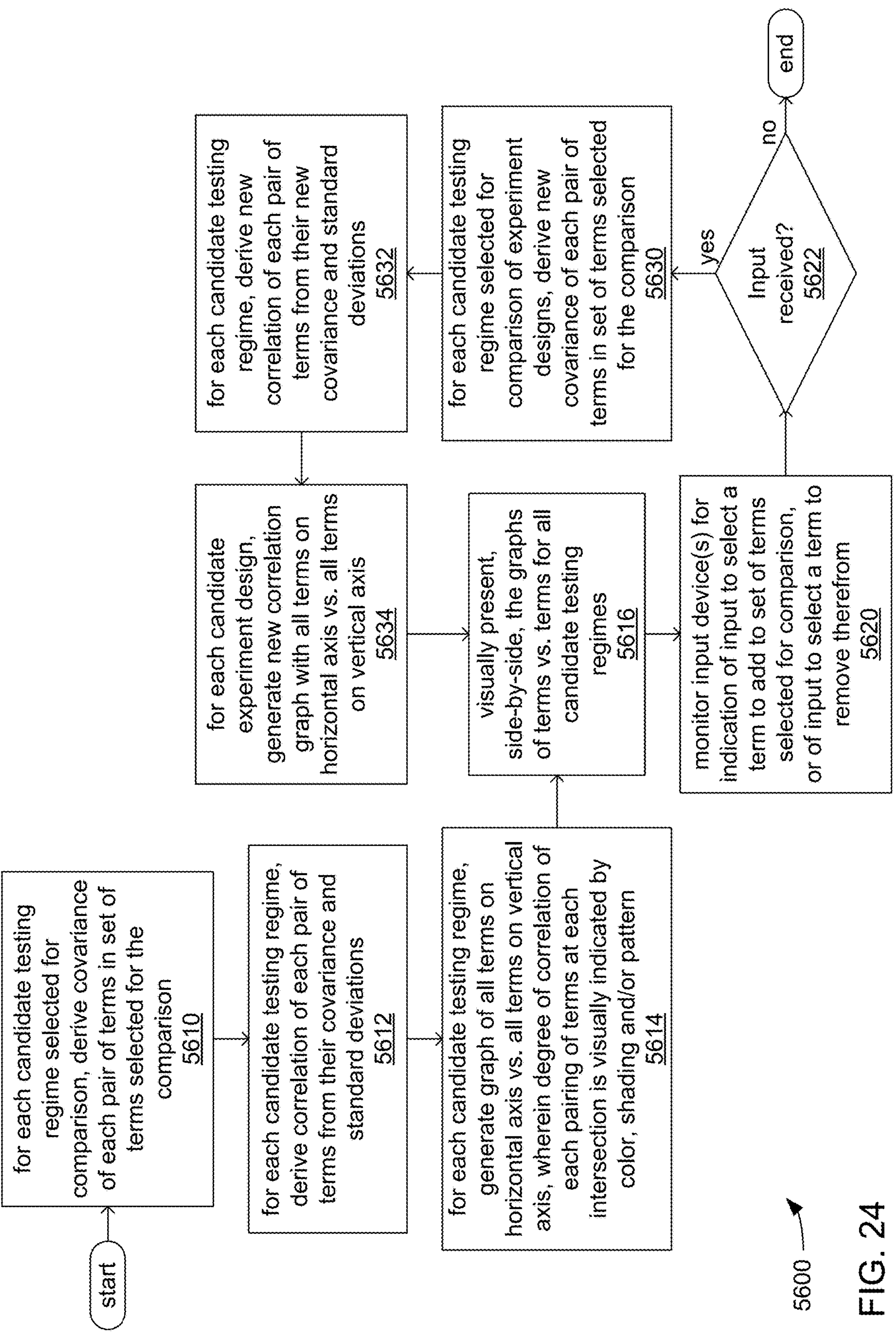
FIG. 24 illustrates an example embodiment of a logic flow of deriving and presenting correlations between terms in the guidance of selection of a testing regime.

FIG. 24 illustrates an example embodiment of a logic flow 5600. The logic flow 5600 may be representative of some or all of the operations executed by one or more embodiments described herein. More specifically, the logic flow 5600 may illustrate operations performed by the processor 2550, and/or performed by other component(s) of the coordinating device 2500 in executing the comparison routine 2540 to guide selection of a single testing regime for use.

At 5610 and 5612, a processor of a coordinating device of a distributed processing system (e.g., the processor 2550 of the coordinating device 2500 of the distributed processing system 2000) may derive the degree of correlation between each possible pair of terms that may be formed from a set of terms to be included in a comparison of multiple candidate testing regimes. More specifically, in some embodiments, the processor may derive the covariance of each possible pair of terms, and then derive the degree of correlation for each of those pairs based on their derived covariance and standard deviations.

At 5614, the processor of the coordinating device may then generate a correlation graph, one each per candidate testing regime, where all of the terms are arranged in identical order along each of the horizontal and vertical axes, and in which visual indicators are positioned at each intersection within the graph that corresponds to one of the possible pairs of terms. As previously discussed, the visual indicators used may be selected from a scale of visual indicators that may form a scale of progressive transition from one color to another, a progressive transition between light and dark on a grayscale, and/or a progressive transition through a series of patterns that transition between no fill and being fully filled in. At 5616, the processor may further present the correlation graphs adjacent to each other and arranged horizontally in a single row (e.g., side-by-side) to exploit the left-right feature comparison capabilities of the HVS.

At 5620, the processor of the coordinating device may monitor one or more input devices for indications of entry of input indicative of a change to the set of terms to either add a term thereto or remove a term therefrom. If, at 5622, such input is received, then at 5630 and 5632, the may again derive the degree of correlation between each possible pair of terms that may be formed from the set of terms. Again, more specifically in some embodiments, the processor may derive the covariance of each possible pair of terms, and then derive the degree of correlation for each of those pairs based on their derived covariance and standard deviations.

At 5634, the processor of the coordinating device may generate a new correlation graph, one each per candidate testing regime, where all of the terms are arranged in identical order along each of the horizontal and vertical axes, and in which visual indicators are positioned at each intersection within the graph that corresponds to one of the possible pairs of terms. At 5616, the processor may then present the new correlation graphs adjacent to each other and arranged horizontally in a single row (e.g., side-by-side) to exploit the left-right feature comparison capabilities of the HVS.

FIGS. 25A and 25B, together, illustrate an example embodiment of a logic flow 6100. The logic flow 6100 may be representative of some or all of the operations executed by one or more embodiments described herein. More specifically, the logic flow 6100 may illustrate operations performed by the processor 2550 and/or the one or more processors 2350, and/or performed by other component(s) of each of the coordinating device 2500 and/or the multiple node devices 2300, respectively, in executing corresponding ones of the regression routines 2570 and/or 2370 to guide the performance of a regression analysis with, a single testing regime for use.

At 6110, a processor of a coordinating device of a distributed processing system (e.g., the processor 2550 of the coordinating device 2500 of the distributed processing system 2000) may receive an indication of a selection of a single testing regime (which may be selected from among multiple previously compared candidate testing regimes) for regression analysis.

At 6120, the processor of the coordinating device may monitor one or more input devices for indications of entry of input indicative of a change to default coefficient(s) for one or more of the terms of the model associated with the selected testing regime. If, at 6122, such input is received, then at 6124, the processor may enact such change(s) to the default coefficient(s), and may return to monitoring for more of such input at 6120.

At 6130, the processor of the coordinating device may monitor the one or more input devices for indications of entry of input indicative of there being a higher degree of difficulty in varying one or more particular factors than for the other factors such that the processor receives an indication that the selected testing regime is to have a split-plot or a split-split-plot configuration. If, at 6132, such input is received, then at 6134, the processor may derive an additional degree of error to which each such factor is to be subject, may present an indication of the additional default degree of error to prompt input indicating a change thereto, and may return to monitoring for more of such input at 6130. Again, as also previously discussed, following receipt of an indication of there being a different degree of difficulty in varying one or more particular factors, the processor 2550 may be caused to present additional prompts to additionally guide an operator through providing separate additional parameters for whole plots and/or subplots, such as the additional entry boxes 3716 by which separate degrees of error may be provided for whole plots and/or subplots.

At 6140, the processor of the coordinating device may monitor the one or more input devices for indications of entry of input indicative of a change to default a degree of error to which one or more of the factors may be subject, such as the separate degree of error that one or more factors indicated as being more difficult to vary may be subject. If, at 6142, such input is received, then at 6144, the processor may enact such change(s) to default degree(s) of error, and may return to monitoring for more of such input at 6140.

At 6150, the processor of the coordinating device may receive an indication of a selection of a type of distribution for the random generation of simulated data. At 6152, the processor may receive an indication of a quantity of iterations of the regression analysis, including the generation of simulated data, is to be performed.

At 6160, based on the parameters provided by the operator and/or from any unchanged default parameters, the processor of the coordinating device may be caused to generate a sequence of executable instructions (e.g., the executable instructions 2534) in a pre-selected programming language for performing the specified quantity of iterations of the regression analysis. At 6162, the processor may also be caused to generate and visually present a human readable form of a portion of the executable instructions that employs mathematical notation to expresses the performance of the regression analysis (e.g., the human readable expression 3722). As previously discussed, such a human readable expression may include the values of the coefficients and/or any intercept, may specify the selected type of distribution to be achieved in the random generation of simulated data, and/or may specify the quantity of iterations of the regression analysis to be performed.

At 6170, the processor of the coordinating device may monitor the one or more input devices for indications of entry of input indicative of a change to one or more of the parameters and/or default parameters upon which the generation of the executable instructions was based. If, at 6172, such input is received, then the processor may return to receiving and/or acting on the provision of revised ones of those parameters at 6120 through 6152.

However, if at 6172, there are no such input, then at 6180, the processor of the coordinating device may proceed with either directly executing the executable instructions to perform the specified quantity of iterations of the regression analysis, or may coordinate the distribution and performance of the iterations of the regression analysis by multiple other processors and/or processor cores (e.g., the one or more processors 2350 and/or processor cores 2355). As previously discussed, such other processors and/or processor cores may be incorporated into multiple node devices with which the coordinating device may communicate via a network (e.g., the multiple node devices 2300 via the network 2999). Alternatively, and as also previously discussed, such other processor(s) and/or processor cores may also be incorporated into the coordinating device (e.g., as one or more GPUs).

Upon completion of the specified quantity of iterations of the regression analysis, the processor of the coordinating device may visually present the results thereof at 6182.

In various embodiments, the division of processing and/or storage resources among the devices, and/or the API architectures supporting communications among the devices, may be configured to and/or selected to conform to any of a variety of standards for distributed processing, including without limitation, IEEE P2413, the ALLJOYN® standard, the IOTIVITY™ standard, etc. By way of example, a subset of API and/or other architectural features of one or more of such standards may be employed to implement the relatively minimal degree of coordination described herein to provide greater efficiency in parallelizing processing of data, while minimizing exchanges of coordinating information that may lead to undesired instances of serialization among processes. However, it should be noted that the parallelization of storage, retrieval and/or processing of data set portions of data set(s) are not dependent on, nor constrained by, existing API architectures and/or supporting communications protocols. More broadly, there is nothing in the manner in which data set(s) may be organized in storage, transmission and/or distribution via a network that is bound to existing API architectures or protocols.

Some systems may use the HADOOP® framework, an open-source framework for storing and analyzing big data in a distributed computing environment. Some systems may use cloud computing, which can enable ubiquitous, convenient, on-demand network access to a shared pool of configurable computing resources (e.g., networks, servers, storage, applications and services) that can be rapidly provisioned and released with minimal management effort or service provider interaction. Some grid systems may be implemented as a multi-node HADOOP® cluster, as understood by a person of skill in the art. The APACHE™ HADOOP® framework is an open-source software framework for distributed computing.

Implementing some examples at least in part by using machine-learning models can reduce the total number of processing iterations, time, memory, electrical power, or any combination of these consumed by a computing device when analyzing data. Some machine-learning approaches may be more efficiently and speedily executed and processed with machine-learning specific processors (e.g., not a generic CPU). For example, some of these processors can include a graphical processing unit (GPU), an application-specific integrated circuit (ASIC), a field-programmable gate array (FPGA), a Tensor Processing Unit (TPU) by Google, and/or some other machine-learning specific processor that implements one or more neural networks using semiconductor (e.g., silicon (Si), gallium arsenide (GaAs)) devices.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

The invention claimed is:

1. An apparatus comprising at least one processor and a storage to store instructions that, when executed by the at least one processor, cause the at least one processor to perform operations comprising:

generate, for visual presentation on a display communicatively coupled to the at least one processor, a prompt for selection of a first pathway of prompts for parameter values of a testing regime to traverse from among a set of pathways comprising:

a test-focused pathway comprising initial prompts for initial parameter values for test-related parameters of the testing regime, and subsequent prompts for subsequent parameter values for at least one of:

model-related parameters of a model associated with the testing regime of a system under evaluation; or term-related parameters of terms and responses of the model;

a model-focused pathway comprising initial prompts for initial parameter values for the model-related parameters, and subsequent prompts for subsequent parameter values for at least one of the test-related parameters or the term-related parameters; and a term-focused pathway comprising initial prompts for initial parameter values for the term-related parameters, and subsequent prompts for subsequent parameter values for at least one of the test-related parameters or the model-related parameters;

receive, from an input device communicatively coupled to the at least one processor, an indication of the selection of the first pathway to traverse;

in response to the selection of the first pathway, perform operations associated with traversing the first pathway, the operations associated with traversing the first pathway comprising:

visually present, on the display, the initial prompts of the first pathway, followed by the subsequent prompts of the first pathway; and receive, from the input device, at least one indication of specification of an initial parameter value of the first pathway or a subsequent parameter value of the first pathway;

in response to completion of the traversal of the first pathway, generate, for visual presentation on the display, a prompt for selection of a second pathway to traverse from among the set of pathways, wherein the second pathway comprises a different one of the pathways of the set of pathways from the first pathway;

receive, from the input device, an indication of the selection of the second pathway to traverse; and in response to the selection of the second pathway, perform operations associated with traversing the second pathway.

2. The apparatus of claim 1, wherein:

the operations associated with traversing the first pathway comprise determining whether a parameter of one of the subsequent prompts of the first pathway is inapplicable based on the indication, received from the input device, of specification of the initial parameter value or the subsequent parameter value of the first pathway; and visually presenting, on the display, the initial prompts of the first pathway, followed by the subsequent prompts of the first pathway comprises visually presenting the parameter within the one of the subsequent prompts or refraining from presenting the parameter within the one of the subsequent prompts based on the determination of whether the parameter of the one of the subsequent prompts is inapplicable.

3. The apparatus of claim 1, wherein, at a time prior to receiving the indication of the selection of the first pathway to traverse, the at least one processor is caused to perform further operations comprising:

visually present, on the display, a prompt for selection of either default parameter values or parameter values of an earlier-generated testing regime to serve as a starting point for the test-related parameters, the model-related parameters and the term-related parameters, wherein:

at least one parameter value of the default parameter values comprises a null value indicative of a lack of specification of the at least one parameter value; and the at least one parameter value includes the null value indicative of a lack of selection of a test type;

receive, from the input device, an indication of the selection of either the default parameter values or the parameter values of the earlier-generated testing regime; and based on the indication of the selection, retrieve, from a storage communicatively coupled to the at least one processor, either the default parameter values or the parameter values of the earlier-generated testing regime.

4. The apparatus of claim 3, wherein:

visually presenting, on the display, the initial prompts of the first pathway, followed by the subsequent prompts of the first pathway comprises visually presenting at least one parameter value of either the default parameter values or the parameter values of the earlier-generated testing regime within at least one prompt of the initial prompts or of the subsequent prompts of the first pathway; and receiving, from the input device, the at least one indication of specification of an initial parameter value of the first pathway or a subsequent parameter value of the first pathway comprises receiving an indication of use of a navigation control of the first pathway to move past an initial prompt of the first pathway, and interpreting the indication of the use of the navigation control to move past the initial prompt as an indication of acceptance of a parameter value visually presented within the initial prompt as the initial parameter value.

5. The apparatus of claim 1, wherein, the operations associated with traversing the first pathway further comprise:

in response to each received indication, of the at least one indication, of the specification of an initial parameter value or a subsequent parameter value of the first pathway, compare the subsequent parameter values to the initial parameter values to determine whether there is an incompatibility between at least one subsequent parameter value and at least one initial parameter value of the first pathway; and in response to there being an incompatibility between at least one subsequent parameter value and at least one initial parameter value of the first pathway, visually present an indication of the incompatibility on the display.

6. The apparatus of claim 1, wherein, the operations associated with traversing the first pathway further comprise:

in response to each received indication, of the at least one indication, of the specification of an initial parameter value or a subsequent parameter value of the first pathway, compare at least one of the test-related parameter values, the model-related parameter values or the term-related parameter values of the testing regime to parameter values required for each test type of a set of test types to identify a subset of test types among the set of test types that are compatible with the at least one of the test-related parameter values, the model-related parameter values or the term-related parameter values; and in response to the subset of test types including at least one test type, visually present an indication of the subset of test types on the display.

7. The apparatus of claim 6, wherein visually presenting the indication of the subset of test types comprises, prior to visually presenting the indication of the subset of test types, arrange the test types within the subset of test types to follow a predetermined order of preference of test types.

8. The apparatus of claim 7, wherein each pathway of the set of pathways is associated with a separate predetermined order of preference of test types.

9. The apparatus of claim 7, wherein visually presenting the indication of the subset of test types comprises performing operations comprising:

analyze the test-related parameter values of the testing regime to determine whether a test type of the testing regime has already been specified; and in response to a test type having already been specified, perform operations comprising:

compare the already specified test type to the predetermined order of preference of test types to determine a degree of preference of each test type of the subset of test types relative to the already specified test type; and remove, from the subset of test types, each test type within the subset of test types that has a lesser degree of preference than the already specified test type.

10. The apparatus of claim 1, wherein the operations associated with traversing the second pathway comprise:

visually present, on the display, the initial prompts of the second pathway, followed by the subsequent prompts of the second pathway, wherein visually presenting, on the display, the initial prompts of the second pathway, followed by the subsequent prompts of the second pathway comprises visually presenting at least one parameter value of the testing regime from the input device during the traversal of the first pathway within at least one prompt of the initial prompts or of the subsequent prompts of the second pathway; and receive, from the input device, at least one indication of specification of an initial parameter value of the second pathway or a subsequent parameter value of the second pathway.

11. A computer-program product tangibly embodied in a non-transitory machine-readable storage medium, the computer-program product including instructions operable to cause at least one processor to perform operations comprising:

generate, for visual presentation on a display communicatively coupled to the at least one processor, a prompt for selection of a first pathway of prompts for parameter values of a testing regime to traverse from among a set of pathways comprising:

a test-focused pathway comprising initial prompts for initial parameter values for test-related parameters of the testing regime, and subsequent prompts for subsequent parameter values for at least one of:

model-related parameters of a model associated with the testing regime of a system under evaluation; or term-related parameters of terms and responses of the model;

a model-focused pathway comprising initial prompts for initial parameter values for the model-related parameters, and subsequent prompts for subsequent parameter values for at least one of the test-related parameters or the term-related parameters; and a term-focused pathway comprising initial prompts for initial parameter values for the term-related parameters, and subsequent prompts for subsequent parameter values for at least one of the test-related parameters or the model-related parameters;

receive, from an input device communicatively coupled to the at least one processor, an indication of the selection of the first pathway to traverse;

in response to the selection of the first pathway, perform operations associated with traversing the first pathway, the operations associated with traversing the first pathway comprising:

visually present, on the display, the initial prompts of the first pathway, followed by the subsequent prompts of the first pathway; and receive, from the input device, at least one indication of specification of an initial parameter value of the first pathway or a subsequent parameter value of the first pathway;

in response to completion of the traversal of the first pathway, generate, for visual presentation on the display, a prompt for selection of a second pathway to traverse from among the set of pathways, wherein the second pathway comprises a different one of the pathways of the set of pathways from the first pathway;

receive, from the input device, an indication of the selection of the second pathway to traverse; and in response to the selection of the second pathway, perform operations associated with traversing the second pathway.

12. The computer-program product of claim 11, wherein:

the operations associated with traversing the first pathway comprise determining whether a parameter of one of the subsequent prompts of the first pathway is inapplicable based on the indication, received from the input device, of specification of the initial parameter value or the subsequent parameter value of the first pathway; and visually presenting, on the display, the initial prompts of the first pathway, followed by the subsequent prompts of the first pathway comprises visually presenting the parameter within the one of the subsequent prompts or refraining from presenting the parameter within the one of the subsequent prompts based on the determination of whether the parameter of the one of the subsequent prompts is inapplicable.

13. The computer-program product of claim 11, wherein, at a time prior to receiving the indication of the selection of the first pathway to traverse, the at least one processor is caused to perform further operations comprising:

visually present, on the display, a prompt for selection of either default parameter values or parameter values of an earlier-generated testing regime to serve as a starting point for the test-related parameters, the model-related parameters and the term-related parameters, wherein:

at least one parameter value of the default parameter values comprises a null value indicative of a lack of specification of the at least one parameter value; and the at least one parameter value includes the null value indicative of a lack of selection of a test type;

receive, from the input device, an indication of the selection of either the default parameter values or the parameter values of the earlier-generated testing regime; and based on the indication of the selection, retrieve, from a storage communicatively coupled to the at least one processor, either the default parameter values or the parameter values of the earlier-generated testing regime.

14. The computer-program product of claim 13, wherein:

visually presenting the initial prompts of the first pathway, followed by the subsequent prompts of the first pathway comprises visually presenting at least one parameter value of either the default parameter values or the parameter values of the earlier-generated testing regime within at least one prompt of the initial prompts or of the subsequent prompts of the first pathway; and receiving, from the input device, the at least one indication of specification of an initial parameter value of the first pathway or a subsequent parameter value of the first pathway comprises receiving an indication of use of a navigation control of the first pathway to move past an initial prompt of the first pathway, and interpreting the indication of the use of the navigation control to move past the initial prompt as an indication of acceptance of a parameter value visually presented within the initial prompt as the initial parameter value.

15. The computer-program product of claim 11, wherein, the operations associated with traversing the first pathway further comprise:

in response to each received indication, of the at least one indication, of the specification of an initial parameter value or a subsequent parameter value of the first pathway, compare the subsequent parameter values to the initial parameter values to determine whether there is an incompatibility between at least one subsequent parameter value and at least one initial parameter value of the first pathway; and in response to there being an incompatibility between at least one subsequent parameter value and at least one initial parameter value of the first pathway, visually present an indication of the incompatibility on the display.

16. The computer-program product of claim 11, wherein, the operations associated with traversing the first pathway further comprise:

in response to each received indication, of the at least one indication, of the specification of an initial parameter value or a subsequent parameter value of the first pathway, compare at least one of the test-related parameter values, the model-related parameter values or the term-related parameter values of the testing regime to parameter values required for each test type of a set of test types to identify a subset of test types among the set of test types that are compatible with the at least one of the test-related parameter values, the model-related parameter values or the term-related parameter values; and in response to the subset of test types including at least one test type, visually present an indication of the subset of test types on the display.

17. The computer-program product of claim 16, wherein visually presenting the indication of the subset of test types comprises, prior to visually presenting the indication of the subset of test types, arrange the test types within the subset of test types to follow a predetermined order of preference of test types.

18. The computer-program product of claim 17, wherein each pathway of the set of pathways is associated with a separate predetermined order of preference of the test types.

19. The computer-program product of claim 17, wherein visually presenting the indication of the subset of test types comprises, prior to visually presenting the indication of the subset of test types, perform operations comprising:

analyze the test-related parameter values of the testing regime to determine whether a test type of the testing regime has already been specified; and in response to a test type having already been specified, perform operations comprising:

compare the already specified test type to the predetermined order of preference of test types to determine a degree of preference of each test type of the subset of test types relative to the already specified test type; and remove, from the subset of test types, each test type within the subset of test types that has a lesser degree of preference than the already specified test type.

20. The computer-program product of claim 11, wherein the operations associated with traversing the second pathway comprise:

visually present, on the display, the initial prompts of the second pathway, followed by the subsequent prompts of the second pathway, wherein visually presenting, on the display, the initial prompts of the second pathway, followed by the subsequent prompts of the second pathway comprises visually presenting at least one parameter value of the testing regime from the input device during the traversal of the first pathway within at least one prompt of the initial prompts or of the subsequent prompts of the second pathway; and receive, from the input device, at least one indication of specification of an initial parameter value of the second pathway or a subsequent parameter value of the second pathway.

21. A computer-implemented method comprising:

generating, by at least one processor, and for visual presentation on a display communicatively coupled to the at least one processor, a prompt for selection of a first pathway of prompts for parameter values of a testing regime to traverse from among a set of pathways comprising:

a test-focused pathway comprising initial prompts for initial parameter values for test-related parameters of the testing regime, and subsequent prompts for subsequent parameter values for at least one of:

model-related parameters of a model associated with the testing regime of a system under evaluation; or term-related parameters of terms and responses of the model;

a model-focused pathway comprising initial prompts for initial parameter values for the model-related parameters, and subsequent prompts for subsequent parameter values for at least one of the test-related parameters or the term-related parameters; and a term-focused pathway comprising initial prompts for initial parameter values for the term-related parameters, and subsequent prompts for subsequent parameter values for at least one of the test-related parameters or the model-related parameters;

receiving, at the at least one processor, and from an input device communicatively coupled to the at least one processor, an indication of the selection of the first pathway to traverse;

in response to the selection of the first pathway, performing, by the at least one processor, operations associated with traversing the first pathway, the operations associated with traversing the first pathway comprising:

visually presenting, on the display, the initial prompts of the first pathway, followed by the subsequent prompts of the first pathway; and receiving, from the input device, at least one indication of specification of an initial parameter value of the first pathway or a subsequent parameter value of the first pathway;

in response to the completion of the traversal of the first pathway, generating, by the at least one processor, and for visual presentation on the display, a prompt for selection of a second pathway to traverse from among the set of pathways, wherein the second pathway comprises a different one of the pathways of the set of pathways from the first pathway;

receiving, at the at least one processor, and from the input device, an indication of the selection of the second pathway to traverse; and in response to the selection of the second pathway, performing, by the at least one processor, operations associated with traversing the second pathway.

22. The computer-implemented method of claim 21, wherein:

the operations associated with traversing the first pathway comprise determining whether a parameter of one of the subsequent prompts of the first pathway is inapplicable based on the indication, received from the input device, of specification of the initial parameter value or the subsequent parameter value of the first pathway; and visually presenting, on the display, the initial prompts of the first pathway, followed by the subsequent prompts of the first pathway comprises visually presenting the parameter within the one of the subsequent prompts or refraining from presenting the parameter within the one of the subsequent prompts based on the determination of whether the parameter of the one of the subsequent prompts is inapplicable.

23. The computer-implemented method of claim 21, further comprising, at a time prior to receiving the indication of the selection of the first pathway to traverse, performing, by the at least one processor, further operations comprising:

visually presenting, on the display, a prompt for selection of either default parameter values or parameter values of an earlier-generated testing regime to serve as a starting point for the test-related parameters, the model-related parameters and the term-related parameters, wherein;

at least one parameter value of the default parameter values comprises a null value indicative of a lack of specification of the at least one parameter value; and the at least one parameter value includes the null value indicative of a lack of selection of a test type;

receiving, from the input device, an indication of the selection of either the default parameter values or the parameter values of the earlier-generated testing regime; and based on the indication of the selection, retrieving, from a storage communicatively coupled to the at least one processor, either the default parameter values or the parameter values of the earlier-generated testing regime.

24. The computer-implemented method of claim 23, wherein:

visually presenting, by the at least one processor, and on the display, the initial prompts of the first pathway, followed by the subsequent prompts of the first pathway comprises visually presenting at least one parameter value of either the default parameter values or the parameter values of the earlier-generated testing regime within at least one prompt of the initial prompts or of the subsequent prompts of the first pathway; and receiving, by the at least one processor, and from the input device, the at least one indication of specification of an initial parameter value of the first pathway or a subsequent parameter value of the first pathway comprises receiving an indication of use of a navigation control of the first pathway to move past an initial prompt of the first pathway, and interpreting the indication of the use of the navigation control to move past the initial prompt as an indication of acceptance of a parameter value visually presented within the initial prompt as the initial parameter value.

25. The computer-implemented method of claim 21, wherein, the operations associated with traversing the first pathway further comprise:

in response to each received indication, of the at least one indication, of the specification of an initial parameter value or a subsequent parameter value of the first pathway, comparing, by the at least one processor, the subsequent parameter values to the initial parameter values to determine whether there is an incompatibility between at least one subsequent parameter value and at least one initial parameter value of the first pathway; and in response to there being an incompatibility between at least one subsequent parameter value and at least one initial parameter value of the first pathway, visually presenting, by the at least one processor, an indication of the incompatibility on the display.

26. The computer-implemented method of claim 21, wherein, the operations associated with traversing the first pathway further comprise:

in response to each received indication, of the at least one indication, of the specification of an initial parameter value or a subsequent parameter value of the first pathway, comparing, by the at least one processor, at least one of the test-related parameter values, the model-related parameter values or the term-related parameter values of the testing regime to parameter values required for each test type of a set of test types to identify a subset of test types among the set of test types that are compatible with the at least one of the test-related parameter values, the model-related parameter values or the term-related parameter values; and in response to the subset of test types including at least one test type, visually presenting, by the at least one processor, an indication of the subset of test types on the display.

27. The computer-implemented method of claim 26, wherein visually presenting the indication of the subset of test types comprises, prior to visually presenting the indication of the subset of test types, arranging, by the at least one processor, the test types within the subset of test types to follow a predetermined order of preference of test types.

28. The computer-implemented method of claim 27, wherein each pathway of the set of pathways is associated with a separate predetermined order of preference of the test types.

29. The computer-implemented method of claim 27, wherein visually presenting the indication of the subset of test types comprises, prior to visually presenting the indication of the subset of test types, performing, by the at least one processor, operations comprising:

analyzing the test-related parameter values of the testing regime to determine whether a test type of the testing regime has already been specified; and in response to a test type having already been specified, performing, by the at least one processor, operations comprising:

comparing the already specified test type to the predetermined order of preference of test types to determine a degree of preference of each test type of the subset of test types relative to the already specified test type; and removing, from the subset of test types, each test type within the subset of test types that has a lesser degree of preference than the already specified test type.

30. The computer-implemented method of claim 21, wherein the operations associated with traversing the second pathway comprise:

visually presenting, by the at least one processor, and on the display, the initial prompts of the second pathway, followed by the subsequent prompts of the second pathway, wherein visually presenting, on the display, the initial prompts of the second pathway, followed by the subsequent prompts of the second pathway comprises visually presenting at least one parameter value of the testing regime from the input device during the traversal of the first pathway within at least one prompt of the initial prompts or of the subsequent prompts of the second pathway; and receiving, at the at least one processor, and from the input device, at least one indication of specification of an initial parameter value of the second pathway or a subsequent parameter value of the second pathway.

* * * * *